US007846671B2

(12) United States Patent
Cockett et al.

(10) Patent No.: US 7,846,671 B2
(45) Date of Patent: Dec. 7, 2010

(54) METHODS OF SCREENING FOR AGENTS THAT MODULATE THE INTERACTION OF RGS AND GαQ AND URINARY INCONTINENCE

(75) Inventors: Mark Cockett, Newtown, PA (US); Chandra S. Ramanathan, Wallingford, CT (US); Nicholas J. Lodge, Madison, CT (US); Kevin Fitzgerald, Lambertville, NJ (US); Terry Stouch, West Windsor, NJ (US); Lisa Moore, San Francisco, CA (US); Rachel M. Kindt, San Carlos, CA (US); Jenny Kopczynski, Chapel Hill, NC (US); Stephen Kohl Doberstein, Pasadena, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1126 days.

(21) Appl. No.: 10/352,843

(22) Filed: Jan. 27, 2003

(65) Prior Publication Data

US 2004/0014135 A1 Jan. 22, 2004

Related U.S. Application Data

(60) Provisional application No. 60/352,720, filed on Jan. 28, 2002.

(51) Int. Cl.
*G01N 33/53* (2006.01)
(52) U.S. Cl. .............................. 435/7.1; 435/7.8; 800/3
(58) Field of Classification Search ...................... None
See application file for complete search history.

(56) References Cited

U.S. PATENT DOCUMENTS

| 4,522,811 | A | 6/1985 | Eppstein et al. |
| 5,846,780 | A | 12/1998 | Levinson et al. |
| 5,869,509 | A | 2/1999 | Romine et al. |
| 6,069,296 | A | 5/2000 | Horvitz et al. |
| 6,077,861 | A | 6/2000 | Romine et al. |
| 6,410,240 | B1 | 6/2002 | Hodge et al. |
| 6,551,786 | B2 * | 4/2003 | Manfredi .................. 435/6 |
| 6,613,786 | B2 | 9/2003 | Hewawasam et al. |
| 2003/0144333 | A1 | 7/2003 | Hewawasam et al. |
| 2007/0065883 | A1 | 3/2007 | Cockett et al. |

FOREIGN PATENT DOCUMENTS

| EP | 1276371 A2 | 11/2001 |
| WO | WO 98/06737 | 2/1998 |
| WO | WO 99/66324 | 12/1999 |
| WO | WO 01/19984 | 3/2001 |
| WO | WO 01/44197 | 6/2001 |
| WO | WO 01/83514 | 11/2001 |
| WO | WO 01/84921 | 11/2001 |
| WO | WO 01/85769 | 11/2001 |
| WO | WO 02/50104 | 6/2002 |

OTHER PUBLICATIONS

Cunningham et al. Protein kinase C phosphorylates RGS2 and modulates its capacity for negative regulation of Galpha 11 signaling. J Biol Chem. Feb. 23, 2001;276(8):5438-44. Epub Nov. 3, 2000.*
Dowal et al. Determination of the contact energies between a regulator of G protein signaling and G protein subunits and phospholipase C beta 1. Biochemistry. Jan. 16, 2001; 40(2): 414-21.*
Ogura et al. Block and modified gating of cardiac calcium channel currents by terodiline. Br J Pharmacol. Aug. 1999; 127(8): 1837-45).*
Mickle et al. Genotype-phenotype relationships in cystic fibrosis. Med Clin North Am. May 2000;84(3):597-607.*
Voet et al. Biochemistry. 1990. John Wiley & Sons, Inc. 126-129 and 228-234.*
Yan et al. Two-amino acid molecular switch in an epithelial morphogen that regulates binding to two distinct receptors. Science 290: 523-527, 2000.*
De Vries et al. The regulator of G protein signaling family. Annu Rev Pharmacol Toxicol. 2000;40:235-71.*
Heximer et al. RGS2/G0S8 is a selective inhibitor of Gqalpha function. Proc Natl Acad Sci U S A. Dec. 23, 1997;94(26):14389-93.*
Hegde et al. Peripheral 5-HT4 receptors. FASEB J. Oct. 1996;10(12):1398-407.*
Berridge, et al., "The Versatility and Universatility of Calcium Signalling", *Nature*, (2000), 1, pp. 11-21.
Brenner, "The Genetics of *Caenorhabditis elegans*", *Genetics*, (1974), 77, pp. 71-94.
Janetopoulous, et al., "Receptor-Mediated Activation of Heterotrimeric G-Proteins in Living Cells" *Science*, (2001), 291, pp. 2408-2410.
Malkowicz, et al., "Acute Biochemical and Functional Alterations in the Partially Obstructed Rabbit Urinary Bladder", *J. Urol.*, (1986), 136, pp. 1324-1329.
Meng, et al., "Automated Docking With Grid-Based Energy Evaluation", *J. Comp. Chem.*, (1992), 13, pp. 505-524.
Moy, et al., "NMR Structure of Free RGS4 Reveals an Induced Conformational Change Upon Binding Gα," *Biochem.*, (2000), 39(24), pp. 7063-7073.
Razvi, E.S., "Industry Trends in High-Throughput Screening," *Drug & Market Development Publications*, (2000).
Razvi, E.S., "High-Throughput Screening—Where Are We Today?" *Drug & Market Development Publications*, (1999).
Slep, et al., "Structural Determinants for Regulation of Phospodiesterase by a G-Protein at 2.0 .," *Nature*, (2001), 409, 1071.
Tesmer, et al., "Structure of RGS4 Bound to ALF4(-)-Activated G(I Alpha1): Stabilization of The transition State for GTP Hydrolysis," *Cell*, (1997), pp. 251-261.
Tesmer, et al., "Molecular Basis for P-Site Inhibition of Adenlyl Cyclase," *Biochem.*, (2000), 39, 14464.
Weber, "Ion Currents of *Xenopus laevis* Oocytes: State of Art", *Biochim. Biophys. Acta*, (1999), 1421, pp. 213-233.
Zhong, et al., "Regulator of G Protein Signalling Proteins: Novel Multifunctional Drug Targets", *Perspectives in Pharmacology*, (2001), 297, pp. 837-845.

(Continued)

*Primary Examiner*—Daniel E Kolker
*Assistant Examiner*—Gregory S Emch
(74) *Attorney, Agent, or Firm*—Stephen C. D'Amico

(57) ABSTRACT

The present invention provides methods that are useful for the treatment or prevention of smooth muscle disorders such as urinary incontinence and compounds that are useful in such methods.

6 Claims, 27 Drawing Sheets

OTHER PUBLICATIONS

Figure 3A:
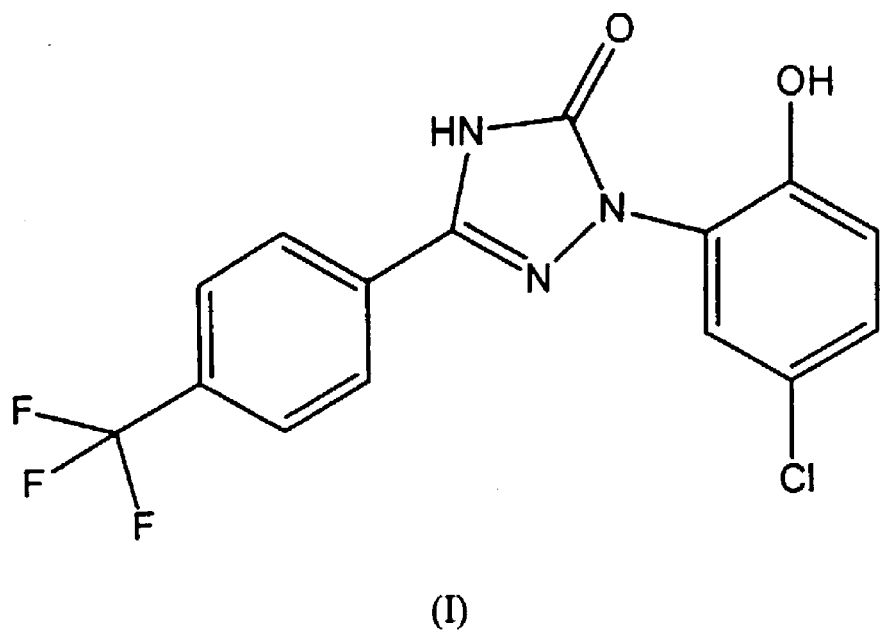

Zhu, et al., "Receptor-Activated Ca$^{2+}$Infux Via Human Trp3 Stably Expressed in Human Embryonic Kidney (HEK) 293 Cells" *J Biol. Chem.*, 273, pp. 133-142.

NCBI Entrez Accession No. gi|AAB04059, Brudage, L. et al., Jul. 18, 1996.

NCBI Entrez Accession No. gi|XM_001330, NCBI Annotation Project, Oct. 16, 2001.

NCBI Entrez Accession No. gi|XM_002185, NCBI Annotation Project, May 8, 2002.

NCBI Entrez Accession No. gi|XM_005324, NCBI Annotation Project, Oct. 16, 2001.

NCBI Entrez Accession No. gi|XM_010645, NCBI Annotation Project, May 13, 2002.

NCBI Entrez Accession No. gi|XM_027292, NCBI Annotation Project, Oct. 16, 2001.

NCBI Entrez Accession No. gi|XM_027524, NCBI Annotation Project, Oct. 16, 2001.

NCBI Entrez Accession No. gi|XM_027525, NCBI Annotation Project, Oct. 16, 2001.

NCBI Entrez Accession No. gi|XM_029884, NCBI Annotation Project, May 8, 2002.

NCBI Entrez Accession No. gi|XM_032141, NCBI Annotation Project, May 13, 2002.

NCBI Entrez Accession No. gi|XM_034023, NCBI Annotation Project, May 8, 2002.

NCBI Entrez Accession No. gi|XM_046463, NCBI Annotation Project, Dec. 11, 2001.

NCBI Entrez Accession No. gi|1181671, Dong, Q. et al., Feb. 7, 1996.

NCBI Entrez Accession No. gi|1354761, Brundage, L. et al., Jul. 19, 1996.

NCBI Entrez Accession No. gi|2398571, Barlow, K., Dec. 3, 2003.

NCBI Entrez Accession No. gi|8394182, Garnier, M. et al., Oct. 5, 2003.

NCBI Entrez Accession No. gi|12620875, Gabbeta, J. et al., Jan. 31, 2001.

Abagyan, R. et al., "Biased Probability Monte Carlo Conformational Searches and Electrostatic Calculations for Peptides and Proteins," J. Mol. Biol., vol. 235, pp. 983-1002 (1994).

Abagyan, R. et al., "ICM—A New Method for Protein Modeling and Design: Applications to Docking and Structure Prediction from the Distorted Native Conformation," Journal of Computational Chemistry, vol. 15, No. 5, pp. 488-506 (1994).

Ausubel, F.M. et al., eds., Current Protocols in Molecular Biology, vols. 1-4, John Wiley & Sons, Inc., publ., pp. 1-11 (table of contents) (1994).

Bartlett, P.A. et al., "CAVEAT: A Program to Facilitate the Structure-derived Design of Biologically Active Molecules," Molecular Recognition: Chemical and Biochemical Problems, The Proceedings of an International Symposium, University of Exeter, Special Publ. No. 78, pp. 182-196 (Apr. 1989).

Böhm, H.-J., "The computer program LUDI: A new method for the de novo design of enzyme inhibitors," Journal of Computer-Aided Molecular Design, vol. 6, pp. 61-78 (1992).

Bowen, J.P. et al., Chapter 3: "Molecular Mechanics: The Art and Science of Parameterization," Reviews in Computational Chemistry II, VCH Publishers, Inc., publ., Lipkowitz, K.B. et al., eds., pp. 81-97 (1991).

Brooks, B.R. et al., "CHARMM: A Program for Macromolecular Energy, Minimization, and Dynamics Calculations," Journal of Computational Chemistry, vol. 4, No. 2, pp. 187-217 (1983).

Brundage, L. et al., "Mutations in a *C. elegans* G$_q$α Gene Disrupt Movement, Egg Laying, and Viability," Neuron, vol. 16, pp. 999-1009 (1996).

Cohen, N.C. et al., "Molecular Modeling Software and Methods for Medicinal Chemistry," Journal of Medicinal Chemistry, vol. 33, No. 3, pp. 883-894 (1990).

Creighton, T.E., Proteins: Structures and Molecular Principles, W.H. Freeman and Company, publ., pp. v-viii (table of contents) (1984).

Dalby, A. et al., "Description of Several Chemical Structure File Formats Used by Computer Programs Developed at Molecular Design Limited," J. Chem. Inf. Comput. Sci., vol. 32, pp. 244-255 (1992).

Fingl, E. et al., Chapter 1: "General Principles," The Pharmacological Basis of Therapeutics, 5$^{th}$ Ed., Macmillan Publishing Co., Inc., publ., Goodman, L.S. et al., eds., pp. 1-46 (1975).

Goodford, P.J., "A Computational Procedure for Determining Energetically Favorable Binding Sites on Biologically Important Macromolecules," J. Med. Chem., vol. 28, pp. 849-857 (1985).

Goodsell, D.S. et al., "Automated Docking of Substrates to Proteins by Simulated Annealing," PROTEINS: Structure, Function, and Genetics, vol. 8, pp. 195-202 (1990).

Gundertofte, K. et al., "A Comparison of Conformational Energies Calculated by Several Molecular Mechanics Methods," Journal of Computational Chemistry, vol. 17, No. 4, pp. 429-449 (1996).

Heiden, W. et al., "A new approach to analysis and display of local lipophilicity/hydrophilicity mapped on molecular surfaces,"-Journal of Computer-Aided Molecular Design, vol. 7, pp. 503-514 (1993).

Johnson, M.A. et al., eds., Concepts and Applications of Molecular Similarity, John Wiley & Sons, Inc., publ., pp. x-xix (table of contents) (1990).

Jones, G. et al., "Molecular Recognition of Receptor Sites using a Genetic Algorithm with a Description of Desolvation," J. Mol. Biol., vol. 245, pp. 43-53 (1995).

Kong, J. et al., "Q-Chem 2.0: A High-Performance Ab Initio Electronic Structure Program Package," Journal of Computational Chemistry, vol. 21, No. 16, pp. 1532-1548 (2000).

Kuntz, I.D. et al., "A Geometric Approach to Macromolecule-Ligand Interactions," J. Mol. Biol., vol. 161, pp. 269-288 (1982).

Levitt, M., "Accurate Modeling of Protein Conformation by Automatic Segment Matching," J. Mol. Biol., vol. 226, pp. 507-533 (1992).

Levitt, M., "Protein Folding by Restrained Energy Minimization and Molecular Dynamics," J. Mol. Biol., vol. 170, pp. 723-764 (1983).

Li, Q. et al., Chapter 6: "Assays for Measuring Receptor-G Protein Coupling," Regulation of G Protein-Coupled Receptor Function and Expression, Wiley-Liss, Inc., publ., Benovic, J.L., ed., pp. 119-132 (2000).

MacKerell, Jr., A.D. et al., "CHARMM: The Energy Function and Its Parameterization," Encyclopedia of Computational Chemistry, vol. 1 (A-D), John Wiley & Sons Ltd., publ., von Rague Schleyer, P., ed., pp. 271-277 (1998).

Martin, Y.C., "3D Database Searching in Drug Design," Journal of Medicinal Chemistry, vol. 35, No. 12, pp. 2145-2154 (1992).

Miranker, A. et al., "Functionality Maps of Binding Sites: A Multiple Copy Simultaneous Search Method," PROTEINS: Structure, Function, and Genetics, vol. 11, pp. 29-34 (1991).

Navia, M.A. et al., "Use of structural information in drug design," Current Opinion in Structural Biology, vol. 2, pp. 202-210 (1992).

Nicholls, A. et al., "Protein Folding and Association: Insights From the Interfacial and Thermodynamic Properties of Hydrocarbons," PROTEINS: Structure, Function, and Genetics, vol. 11, pp. 281-296 (1991).

Nishibata, Y. et al., "Automatic Creation of Drug Candidate Structures Based on Receptor Structure. Starting Point for Artificial Lead Generation," Tetrahedron, vol. 47, No. 43, pp. 8985-8990 (1991).

Sambrook, J. et al., Molecular Cloning: A Laboratory Manual, 2nd Ed., Cold Spring Harbor Laboratory Press, publ., pp. xi-xxi (table of contents) (1989).

Siani, M.A. et al., "CHUCKLES: A Method for Representing and Searching Peptide and Peptoid Sequences on Both Monomer and Atomic Levels," J. Chem. Inf. Comput. Sci., vol. 34, pp. 588-593 (1994).

Sutcliffe, M.J. et al., "Knowledge based modelling of homologous proteins, part I: three-dimensional frameworks derived from the simultaneous superposition of multiple structures," Protein Engineering, vol. 1, No. 5, pp. 377-384 (1987).

Weininger, D., "SMILES, a Chemical Language and Information System. 1. Introduction to Methodology and Encoding Rules," J. Chem. Inf. Comput. Sci., vol. 28, pp. 31-36 (1988).

Wood, W.B. et al., eds., The Nematode *Caenorhabditis elegans*, Cold Spring Harbor Laboratory, publ., pp. v-vi (table of contents) (1988).

Zheng, B. et al., "Divergence of RGS proteins: evidence for the existence of six mammalian RGS subfamilies," TIBS, vol. 24, pp. 411-414 (1999).

Kwok, Pui-Yan, "High-Throughput Genotyping Assay Approaches" *Pharmacogenomics*, (2000), 1(1), pp. 95-100.

"Regulation of G Protein-Coupled Receptor Function and Expression," ed. Benovic, J.L., pp. 119-132 (2000), Wiley-Liss, New York.

International Search Report of PCT/US03/02452, Oct. 12, 2004, PCT.

Nilvebrant et al., 1997, "Tolterodine—A New Bladder-Selective Antimuscarinic Agent," *European Journal of Pharmacology*, 327: 195-207.

Robatzek et al., 2001, "Eat-11 Encodes GPB-2, a $G\beta_5$ Ortholog that Interacts with $G_o$ $\alpha$ and $G_q$ $\alpha$ to Regulate *C. elegans* Behavior," *Current Biology*, 11(4):288-293.

European Search Report of EP 03 71 3302, May 29, 2006, EPO.

Wehrens, et al., *Science*, 304: 292-296 (2004).

Fitzgerald et al., "Chemical Genetics Reveals an RGS/G-Protein Role in the Action of a Compound", PLoS Genetics, 2(4):0425-0437 (Apr. 2006).

Roman et al., "Identification of Small Molecule Inhibitors of Regulator of G-Protein Signaling 4 (RGS4) Using a High Throughput Flow Cytometry Protein Interaction Assay (FCPIA)", American Society for Pharmacology and Experimental Therapeutics, MOL #28670, pp. 1-31 (Sep. 29, 2006).

\* cited by examiner

FIG. 1A

```
RGS7       MAQGNNYGQTSNGVADESPNMLVYRKMEDVIARMQDEKNGIPIRTVKSFLSKIPSVFSGS
EGL-10     MALPRLRVNASNEERLVHPNHMVYRKMEMLVNQMLDAEAGVPIKTVKSFLSKVPSVFTGQ
RGS11      MAAG--PAPPPGRPRAQMP-HL--RKMERVVVSMQDPDQGVKMRSQRLLVTVIPHAVTGS
EAT-16     ----------------MMP-PL--TKIEVLAKRVME---GAQLKTHKYFRIAVPHAITGQ
RGS9       -------MTIRHQGQQYRPRMAFLQKIEALVKDMQNPETGVRMQNQRVLVTSVPHAMTGS
consensus  ma                P  l  rKmE lv  mqd e Gv irt k  fls vPhavtGs RGS7       DIVQWLIKNLTIEDPVEALHLGTLMAAHGYFFPISD-HVLTLKDDGTFYRFQTPYFWPSN
EGL-10     DLIGWIMKNLEMTDLSDALHLAHLIASHGYLFQIDD-HVLTVKNDGTFYRFQTPYFWPSN
RGS11      DVVQWLAQKFCVSEE-EALHLGAVLVQHGYIYPLRDPRSLMLRPDETPYRFQVRLGG---
EAT-16     QLIALVLERGAPDDEAEASHLASLLLHHGYMFPVIE-HGQPFKDDGTLYRLQRPYFWPSQ
RGS9       DVLQWIVQRLWISSL-EAQNLGNFIVRYGYIYPLQDPKNLILKPDGSLYRFQTPYFWPTQ
consensus  divqwli kl itd  eAlhLg lmv hGYlfpi d h l lk Dgt YRfQtpyfwpsn RGS7       CWEPENTDYAVYLCKRTMQNKARLELADYEAESLARLQRAFARKWEFIFMQAEAQKVDK
EGL-10     CWDPENTDYAVYLCKRTMQNKAHLELEDFEAENLAKLQKMFSRKWEFVFMQAEAQYKVDK
RGS11      --------AAIYLAKKNIRKKG--TLVDYEKDCYDRLHKKINHAWDLVLMQAREQLRAAK
EAT-16     AELVPDVEYAIYLNKRLLRNEQKHGLEEDEVESFNRLADVLAHMWAFIVQQSELQLKQQK
RGS9       QWPAEDTDYAIYLAKRNIKKKG--ILEEYEKENYNFLNQKMNYKWDFVIMQAKEQYRAGK
consensus    w  e tdyAiYL Kr mrnka   LedyE e y rLqr i  kWefvlmQae Q k  K RGS7       KRDKIERKILDSQERAFWDVHRPVPGCVNTTEVDIKKSSRMRNP----------------
EGL-10     KRDRQERQILDSQERAFWDVHRPVPGCVNTTEVDFRKLSRSGRPKYSSGGHAALAASTSG
RGS11      QRSKGDRLVIACQEQTYWLVNRPPPGAPDVLE-------Q--GP----------------
EAT-16     EKKKVDKVVFDSEERAFWKIRKPSRGGPNFLE----------DP----------------
RGS9       ERNKADRYALDCQEKAYWLVHRCPPGMDNVLDYG---LDRVTNP----------------
consensus    r k dr ildsqErafW vhrp pG n le         r   P RGS7       -------------HKTRKSVY-G-----LQNDIR------SHSP-----------THTPT
EGL-10     IGCTQYSQSVAAAHASLPSTSNGSATSPRKNDQEPSTSSGGESPSTSSAAAGTATTSAPS
RGS11      ---------------------G---------R-------GSCA------------ASRV
EAT-16     ------------------------------------------YMK------------IEKK
RGS9       ----------------------------------------NE------------VKV
consensus                      g                                  r RGS7       PETKPP-----T---------------------EDELQQQIKYWQIQLD-RHRLKMSKV
EGL-10     TSTPPVTTITATINAGSFRNNYYTRPGLRRCTQVQDTLKLEIVQLNSRLS-KNVLRTSKV
RGS11      LMTKSA---------------------------DFHKREIEYFRKALG-RTRVKSSVC
EAT-16     IRRQNA---------------------------QGYRCLMDRLRFAIKTKPWLKALKA
RGS9       NQKQTV---------------------------VAVKKEIMYYQQALM-RSTVKSSVS
consensus    t                              d lk ei ywq al   r  lktsk RGS7       ADSLLSYTEQYLEYDPFLLPP----DPS----NPWLSDDTTFWELEASK----EPSQQRV
EGL-10     VENYLAYYEQRRVFDPLLTPPGSQADPFQSQPNPWINDTVDFWQHDKITG---DIQTRRL
RGS11      LEAYLSFCGQRGPHDPLVSGC----LPS----NPWISDNDAYWVMNAPTV--AAPTKLRV
EAT-16     SDTMVTWVDQRAEFDPFLHPP----QPS----NPWISDEASFWNQPTDTSSAEIPTEKRV
RGS9       LGGIVKYSEQFSSNDAIMSGC----LPS----NPWITDDTQFWDLNAKLV--EIPTKMRV
consensus  vd llsy eQr  yDplltpp     Ps    NPWisDd  fW l a t    pt  Rv RGS7       KRWGFGMDEALKDPVGREQFLKFLESEFSSENLRFWLAVEDLKKRPIKEVPSRVQEIWQE
EGL-10     KLWEDSFEELLADSLGRETLQKFLDKEYSGENLRFWWEVQKLRKCSSRMVPVMVTEIYNE
RGS11      ERWGFSFRELLEDPVGRAHFMDFLGKEFSGENLSFWEACEELRYGAQAVPTLVDAVYEQ
EAT-16     KRWGLSVQELVKDPIGRQVLETFLESEFSSENIRFWIAIQDLKYAPNEQIYKAERIREE
RGS9       ERWAFNFSELIRDPKGRQSFQYFLKKEFSGENLGFWEACEDLKYGDQSKVKEKAEEIYKL
consensus  krWgfsf EllkDpvGR  f  FLekEfSgENlrFW avedLkyg q  vp rvdeiy e
```

FIG. 1A (Continued)

```
RGS7      FLAP-GAPSAINLDSKSYDKTTQNVKEPG-----RYTFEDAQEHIYKLMKSDSYPRFIRS
EGL-10    FIDTNAATSPVNVDCKVMEVTEDNLKNPN-----RWSFDEAADHIYCLMKNDSYQRFLRS
RGS11     FLAP-GAAHWVNIDSRTMEQTLEGLRQPH-----RYVLDDAQLHIYMLMKKDSYPRFLKS
EAT-16    FLAQ-GAPAQVNVDNRTLDQTLECISKAKDASQMRFAFYHSEEHVFTLMAKDSYPRFVRS
RGS9      FLAP-GARRWINIDGKTMDITVKGLKHPH-----RYVLDAAQTHIYMLMKKDSYARYLKS
consensus Flap gA   vNlD ktmd Tld lk p       Ry fddaqeHiy LMkkDSYpRflrS RGS7      SAYQELLQAK----------------KKG-------------------------KS
EGL-10    EIYKDLVLQS----------------RK--------------------------KV
RGS11     DMYKALLAEAGIPLEMKRRVFPFTWRPRHSSPS----------------------PA
EAT-16    QIYKAVLTAAQQHG--TKRLGWRNFVFNMGTTK----------------------KP
RGS9      PIYKDMLAKAIEPQETTKKSSTLPFMRRHLRSSPSPVILRQLEEEAKAREAANTVDITQP
consensus  iYkell  a          rr     w   r                          k RGS7      LTSKRLTS-----LAQSY-------------------------------------
EGL-10    SLNCSFSI-----FAS---------------------------------------
RGS11     LLPTPVEP-----TAACGPGGGD--------------------------------
EAT-16    ATSKPAKPQDSIGTGQVLPKQLSS--------------------------DSLPV
RGS9      GQHMAPSPHLTVYTGTCMPPSPSSPFSSSCRSPRKPFASPSRFIRRPSTTICPSPIRVAL
consensus        tp    ta  p RGS7      -------------------------------------------------------
EGL-10    -------------------------------------------------------
RGS11     ----GVA------------------------------------------------
EAT-16    RQAHGVKPDPE--------------------------------------------
RGS9      ESSSGLEQKGECSGSMAPRGPSVTESSEASLDTSWPRSRPRAPPKARMALSFSRFLRRGC
consensus     gv RGS7      -------------------------------------------------------
EGL-10    -------------------------------------------------------
RGS11     -------------------------------------------------------
EAT-16    -------------------------------------------------------
RGS9      LASPVFARLSPKCPAVSHGRVQPLGDVGQQLPRLKSKRVANFFQIKMDVPTGSGTCLMDS
consensus RGS7      ------------------------
EGL-10    ------------------------
RGS11     ------------------------
EAT-16    ------------------------
RGS9      EDAGTGESGDRATEKEVICPWESL
consensus
```

FIG. 1B

```
EGL-30     ---------------MACCLSE--------EAREQKRINQEIEKQLQRDKRNARRELKLLL
G(q)       ---------------MACCLSE--------EAKEARRINDEIERQLRRDKRDARRELKLLL
G(i)       ---------------MGCTLSA--------EDKAAVERSKMIDRNLREDGEKAAREVKLLL
G(t)       ---------------MGAGASA--------EEKHSRE----LEKKLKEDAEKDARTVKLLL
G(o)       ---------------MGCTLSA--------EERAALERSKAIEKNLKEDGISAAKDVKLLL
G(x)       ---------------MGCRQSS--------EEKEAARRSRRIDRHLRSESQRQRREIKLLL
G(s)       ------------MGCLGNSKTEDQRNEEKAQREANKKIEKQLQKDKQVYRATHRLLL
G(13)      MADFLPSRSVLSVCFPGCLLTSG------EAEQQRK-SKEIDKCLSREKTYVKRLVKILL
consensus                 mgc ls         Eakearr nkeiekqlrrdk  arrelklLL EGL-30     LGTGESGKSTFIKQMRIIHGQGYSEE--------------DKRAHIRLVYQNVFMAIQS
G(q)       LGTGESGKSTFIKQMRIIHGSGYSDE--------------DKRGFTKLVYQNIFTAMQA
G(i)       LGAGESGKSTIVKQMKIIHEAGYSEE--------------ECKQYKAVVYSNTIQSIIA
G(t)       LGAGESGKSTIVKQMKIIHQDGYSLE--------------ECLEFIAIIYGNTLQSILA
G(o)       LGAGESGKSTIVKQMKIIHEDGFSGE--------------DVKQYKPVVYSNTIQSLAA
G(x)       LGTSNSGKSTIVKQMKIIHSGGFNLE--------------ACKEYKPLIIYNAIDSLTR
G(s)       LGAGESGKSTIVKQMRILHVNGFNGEGGEEDPQAARSNSDGEKATKVQDIKNNLKEAIET
G(13)      LGAGESGKSTFLKQMRIIHGQDFDQR--------------AREEFRPTIYSNVIKGMRV
consensus  LG geSGKST vKQMrIiHg gysde              dkr f  lvyqNii am a EGL-30     MIRAMDTLDIKFGNESEELQEKAAVVREVDFESVTS------FEEPYVSYIKELWEDSGI
G(q)       MIRAMDTLKIPYK--YEHNKAHAQLVREVDVEKVSA------FENPYVDAIKSLWNDPGI
G(i)       IIRAMGRLKIDFGDSARADDARQLFVLAGAAEEGF-------MTAELAGVIKRLWKDSGV
G(t)       IVRAMTTLNIQYGDSARQDDARKLMHMADTIEEGT-------MPKEMSDIIQRLWKDSGI
G(o)       IVRAMDTLGIEYGDKERKADAKMVCDVVSRMEDTEP------FSAELLSAMMRLWGDSGI
G(x)       IIRALAALRIDFHNPDRAYDAVQLFALTGPAESKGE------ITPELLGVMRRLWADPGA
G(s)       IVAAMSNLVPPVELANPENQFRVDYILSVMNVPDFD------FPPEFYEHAKALWEDEGV
G(13)      LVDAREKLHIPWGDNSNQQHGDKMMSFDTRAPMAAQGMVETRVFLQYLPAIRALWADSGI
consensus  iirAmdtLki yg         ak llvm v e  s      f  eyv aik LW DsGi EGL-30     QECYDRRREYQLTDSAKYYLSDLRRLAVPDYLPTEQDILRVRVPTTGIIEYPFDLEQIIF
G(q)       QECYDRRREYQLSDSTKYYLNDLDRVADPAYLPTQQDVLRVRVPTTGIIEYPFDLQSVIF
G(i)       QACFNRSREYQLNDSAAYYLNDLDRIAQPNYIPTQQDVLRTRVKTTGIVETHFTFKDLHF
G(t)       QACFERASEYQLNDSAGYYLSDLERLVTPGYVPTEQDVLRSRVKTTGIIETQFSFKDLNF
G(o)       QECFNRSREYQLNDSAKYYLDSLDRIGAADYQPTEQDILRTRVKTTGIVETHFTFKNLHF
G(x)       QACFSRSSEYHLEDNAAYYLNDLERIAAADYIPTVEDILRSRDMTTGIVENKFTFKELTF
G(s)       RACYERSNEYQLIDCAQYFLDKIDVIKQADYVPSDQDLLRCRVLTSGIFETKFQVDKVNF
G(13)      QNAYDRRREFQLGESVKYFLDNLDKLGEPDYIPSQQDILLARRPTKGIHEYDFEIKNVPF
consensus  qecydRrrEyqL dsakYyL dldrva pdYlPteqDiLr RvpTtGIiEy Fdlk v F EGL-30     RMVDVGGQRSERRKWIHCFENVTSIMFLVALSEYDQVLVECDNENRMEESKALFRTIITY
G(q)       RMVDVGGQRSERRKWIHCFENVTSIMFLVALSEYDQVLVESDNENRMEESKALFRTIITY
G(i)       KMFDVGGQRSERKKWIHCFEGVTAIIFCVALSDYDLVLAEDEEMNRMHESMKLFDSICNN
G(t)       RMFDVGGQRSERKKWIHCFEGVTCIIFIAALSAYDMVLVEDDEVNRMHESLHLFNSICNH
G(o)       RLFDVGGQRSERKKWIHCFEDVTAIIFCVALSGYDQVLHEDETTNRMHESLMLFDSICNN
G(x)       KMVDVGGQRSERKKWIHCFEGVTAIIFCVELSGYDLKLYEDNQTSRMAESLRLFDSICNN
G(s)       HMFDVGGQRDERRKWIQCFNDVTAIIFVVASSSYNMVIREDNQTNRLQEALNLFKSIWNN
G(13)      KMLDVGGQRSERKRWFECFDSVTSILFLVSSSEFDQVLMEDRLTNRLTESLNIFETIVNN
consensus  rmvDVGGQRsERrkWihCFe VTsIiFlvalSeydqvlvEddn nRm Esl lFrtIinn
```

FIG. 1B (Continued)

```
EGL-30     PWFTNSSVILFLNKKDLLEEKILY--SHLADYFPEYDG-PPRDPIAAR------------
G(q)       PWFQNSSVILFLNKKDLLEEKIMY--SHLVDYFPEYDG-PQRDAQAAR------------
G(i)       KWFTDTSIILFLNKKDLFEEKIKK--SPLTICYPEYAG-SNTYEEAA-------------
G(t)       RYFATTSIVLFLNKKDVFFEKIKK--AHLSICFPDYDG-PNTYEDAG-------------
G(o)       KFFIDTSIILFLNKKDLFGEKIKK--SPLTICFPEYTG-PNTYEDAA-------------
G(x)       NWFINTSLILFLNKKDLLAEKIRR--IPLTICFPEYKG-QNTYEEAA-------------
G(s)       RWLRTISVILFLNKQDLLAEKVLAGKSKIEDYFPEFAR-YTTPEDATPEPGEDPRVTRAK
G(13)      RVFSNVSIILFLNKTDLLEEKVQI--VSIKDYFLEFEGDPHCLRDVQ-------------
consensus  kwf nsSviLFLNKkDlleEKim   shl dyfpeydg pqt eeaa EGL-30     EFILKMFVDLNPDADK---IIYSHFTCATDTENIRFVFAAVKDTILQHNLKEYNLV
G(q)       EFILKMFVDLNPDSDK---IIYSHFTCATDTENIRFVFAAVKDTILQLNLKEYNAV
G(i)       AYIQCQFEDLNKRKDT--KEIYTHFTCATDTKNVQFVFDAVTDVIIKNNLKDCGLF
G(t)       NYIKVQFLELNMRRDV--KEIYSHMTCATDTQNVKFVFDAVTDIIIKENLKDCGLF
G(o)       AYIQAQFESKN-RSPN--KEIYCHMTCATDTNNIQVVFDAVTDIIIANNLRGCGLY
G(x)       VYIQRQFEDLNRNKET--KEIYSHFTCATDTSNIQFVFDAVTDVIIQNNLKYIGLC
G(s)       YFIRDEFLRISTASGDGRHYCYPHFTCAVDTENIRRVFNDCRDIIQRMHLRQYELL
G(13)      KFLVECFRNKRRDQQQ--KPLYHHFTTAINTENIRLVFRDVKDTILHDNLKQLMLQ
consensus   filk Fvdln dsd   k iYsHfTcAtdTeNirfVF avkDtIlq nLkey lv
```

Figure 2A (wt egl-30)

```
  1 GTACACACACACCCGCCACCACCACATTTCCACCAACAGAGAGGCATCCCTGTGCGTTGT 60

61 TGTGTTGTTGTTTTTTTGTGATGTTTATAACTTGACGCCCTCAATCGTCCCACCGAAATA 120

121 CAAAAATTGCATCGAACTTCTATCCTCGCTCTAGCGTGTTCTTCTTGTTCTATTCGCTGG 180

181 CTTCATCTGCGGCCTTGGTGGCACCTTTTCGGCCGCCATGGCCTGCTGTTTATCCGAAGA 240
  1                                        M  A  C  C  L  S  E  E   8

241 GGCTCGCGAGCAGAAGCGAATAAATCAAGAAATTGAGAAGCAGCTTCAGCGTGACAAAAG 300
  8  A  R  E  Q  K  R  I  N  Q  E  I  E  K  Q  L  Q  R  D  K  R  28

301 AAATGCTCGACGAGAACTCAAACTTCTTTTATTGGGGACTGGAGAGTCCGGCAAGTCAAC 360
 28  N  A  R  R  E  L  K  L  L  L  L  G  T  G  E  S  G  K  S  T  48

361 GTTCATCAAGCAGATGCGAATTATCCACGGTCAGGGATATTCGGAAGAGGACAAGCGAGC 420
 48  F  I  K  Q  M  R  I  I  H  G  Q  G  Y  S  E  E  D  K  R  A  68

421 ACACATTCGACTTGTCTATCAGAACGTGTTTATGGCCATACAGTCTATGATACGAGCGAT 480
 68  H  I  R  L  V  Y  Q  N  V  F  M  A  I  Q  S  M  I  R  A  M  88

481 GGACACATTAGATATAAAGTTTGGTAACGAATCAGAGGAGCTGCAGGAGAAGGCGGCTGT 540
 88  D  T  L  D  I  K  F  G  N  E  S  E  E  L  Q  E  K  A  A  V 108

541 GGTGCGGGAAGTGGATTTCGAGTCGGTGACGTCTTTCGAGGAACCCTACGTGTCGTATAT 600
108  V  R  E  V  D  F  E  S  V  T  S  F  E  E  P  Y  V  S  Y  I 128

601 CAAAGAGCTATGGGAGGATTCTGGTATTCAGGAATGTTATGATAGGAGGCGAGAATATCA 660
128  K  E  L  W  E  D  S  G  I  Q  E  C  Y  D  R  R  R  E  Y  Q 148
```

Figure 2A (Con'd)

```
 661 GCTCACCGATTCAGCCAAATACTATCTCTCCGATCTCCGACGGCTGGCGGTGCCAGACTA  720
 148   L  T  D  S  A  K  Y  Y  L  S  D  L  R  R  L  A  V  P  D  Y  168

721 TCTGCCAACCGAGCAGGACATTCTGCGTGTTCGTGTGCCAACCACTGGTATCATTGAATA  780
 168   L  P  T  E  Q  D  I  L  R  V  R  V  P  T  T  G  I  I  E  Y  188

781 TCCATTTGATTTGGAGCAGATCATCTTTCGAATGGTGGACGTCGGAGGTCAGCGATCAGA  840
 188   P  F  D  L  E  Q  I  I  F  R  M  V  D  V  G  G  Q  R  S  E  208

841 AAGGCGGAAGTGGATCCACTGTTTCGAAAATGTCACCTCAATCATGTTCCTGGTGGCGCT  900
 208   R  R  K  W  I  H  C  F  E  N  V  T  S  I  M  F  L  V  A  L  228

901 TTCCGAGTATGATCAGGTGTTGGTCGAGTGTGACAACGAGAACCGAATGGAAGAATCGAA  960
 228   S  E  Y  D  Q  V  L  V  E  C  D  N  E  N  R  M  E  E  S  K  248

961 AGCTCTGTTCCGAACGATCATCACGTACCCATGGTTCACCAACTCATCGGTCATTCTATT 1020
 248   A  L  F  R  T  I  I  T  Y  P  W  F  T  N  S  S  V  I  L  F  268

1021 CCTGAACAAGAAGGATCTGCTCGAGGAGAAGATTCTGTACTCGCATCTCGCTGACTACTT 1080
 268   L  N  K  K  D  L  L  E  E  K  I  L  Y  S  H  L  A  D  Y  F  288

1081 TCCCGAATATGACGGACCCCCACGCGATCCGATCGCCGCCCGCGAGTTTATTCTCAAAAT 1140
 288   P  E  Y  D  G  P  P  R  D  P  I  A  A  R  E  F  I  L  K  M  308

1141 GTTTGTCGACTTGAATCCGGACGCCGACAAGATTATCTACTCTCATTTTACGTGCGCGAC 1200
 308   F  V  D  L  N  P  D  A  D  K  I  I  Y  S  H  F  T  C  A  T  328

1201 TGATACGGAAAACATTCGGTTCGTGTTCGCCGCCGTCAAAGACACAATTCTACAGCATAA 1260
 328   D  T  E  N  I  R  F  V  F  A  A  V  K  D  T  I  L  Q  H  N  348
```

Figure 2A (Con'd)

```
1261 TCTGAAGGAGTACAACTTGGTGTAAGAAGAAAGTCGCATGTCGGATTGGATGATGATGAT 1320
 348  L  K  E  Y  N  L  V  *                                    355

1321 GATGATCCATCTCTCTCTCTCTCTCTCTCACTGGGTCGAGTGAGACACCACCACCTAA 1380

1381 ACCTAGGAAACATTTTCTTGTACTCCTTCTAATTTTTGTTTTTTTTTTGCAAAAAACTTT 1440

1441 CTCTCTCTGTCTGTCTCTCTCTCCATCTCTTCCTTATTTTCTTATTTTCTCATTTTCCTC 1500

1501 CCTAAAACAAATGCTCCTCCCGAATATTCTTTCCATATAAGCACTTTTTTCTTCTTTTTT 1560

1561 TGGATGTGCTTTCTGATATAGCTAATGCAAAAAAAAAAAACGG 1603
```

Figure 2B (mutant egl-30)

```
  1 GTACACACACACCCGCCACCACCACATTTCCACCAACAGAGAGGCATCCCTGTGCGTTGT  60

61 TGTGTTGTTGTTTTTTTGTGATGTTTATAACTTGACGCCCTCAATCGTCCCACCGAAATA 120

121 CAAAAATTGCATCGAACTTCTATCCTCGCTCTAGCGTGTTCTTCTTGTTCTATTCGCTGG 180

181 CTTCATCTGCGGCCTTGGTGGCACCTTTTCGGCCGCCATGGCCTGCTGTTTATCCGAAGA 240
  1                                         M  A  C  C  L  S  E  E   8

241 GGCTCGCGAGCAGAAGCGAATAAATCAAGAAATTGAGAAGCAGCTTCAGCGTGACAAAAG 300
  8  A  R  E  Q  K  R  I  N  Q  E  I  E  K  Q  L  Q  R  D  K  R  28

301 AAATGCTCGACGAGAACTCAAACTTCTTTTATTGGGGACTGGAGAGTCCGGCAAGTCAAC 360
 28  N  A  R  R  E  L  K  L  L  L  G  T  G  E  S  G  K  S  T  48

361 GTTCATCAAGCAGATGCGAATTATCCACGGTCAGGGATATTCGGAAGAGGACAAGCGAGC 420
 48  F  I  K  Q  M  R  I  I  H  G  Q  G  Y  S  E  E  D  K  R  A  68

421 ACACATTCGACTTGTCTATCAGAACGTGTTTATGGCCATACAGTCTATGATACGAGCGAT 480
 68  H  I  R  L  V  Y  Q  N  V  F  M  A  I  Q  S  M  I  R  A  M  88

481 GGACACATTAGATATAAAGTTTGGTAACGAATCAGAGGAGCTGCAGGAGAAGGCGGCTGT 540
 88  D  T  L  D  I  K  F  G  N  E  S  E  E  L  Q  E  K  A  A  V 108

541 GGTGCGGGAAGTGGATTTCGAGTCGGTGACGTCTTTCGAGGAACCCTACGTGTCGTATAT 600
108  V  R  E  V  D  F  E  S  V  T  S  F  E  E  P  Y  V  S  Y  I 128

601 CAAAGAGCTATGGGAGGATTCTGGTATTCAGGAATGTTATGATAGGAGGCGAGAATATCA 660
128  K  E  L  W  E  D  S  G  I  Q  E  C  Y  D  R  R  R  E  Y  Q 148
```

Figure 2B (Con'd)

```
661 GCTCACCGATTCAGCCAAATACTATCTCTCCGATCTCCGACGGCTGGCGGTGCCAGACTA 720
148  L  T  D  S  A  K  Y  Y  L  S  D  L  R  R  L  A  V  P  D  Y  168

721 TCTGCCAACCGAGCAGGACATTCTGCGTGTTCGTGTGCCAACCACTGGTATCATTGAATA 780
168  L  P  T  E  Q  D  I  L  R  V  R  V  P  T  T  G  I  I  E  Y  188

781 TCCATTTGATTTGGAGCAGATCATCTTTCGAATGGTGGACGTCGGAGGTCAGCGATCAGA 840
188  P  F  D  L  E  Q  I  I  F  R  M  V  D  V  G  G  Q  R  S  E  208

841 AAGGCGGAAGTGGATCCACTGTTTCGAAAATGTCACCTCAATCATGTTCCTGGTGGCGCT 900
208  R  R  K  W  I  H  C  F  E  N  V  T  S  I  M  F  L  V  A  L  228

901 TTCCGAGTATGATCAGGTGTTGGTCGAGTGTGACAACGAGAACCGAATAGAAGAATCGAA 960
228  S  E  Y  D  Q  V  L  V  E  C  D  N  E  N  R  I  E  E  S  K  248

961 AGCTCTGTTCCGAACGATCATCACGTACCCATGGTTCACCAACTCATCGGTCATTCTATT 1020
248  A  L  F  R  T  I  I  T  Y  P  W  F  T  N  S  S  V  I  L  F  268

1021 CCTGAACAAGAAGGATCTGCTCGAGGAGAAGATTCTGTACTCGCATCTCGCTGACTACTT 1080
268  L  N  K  K  D  L  L  E  E  K  I  L  Y  S  H  L  A  D  Y  F  288

1081 TCCCGAATATGACGGACCCCCACGCGATCCGATCGCCGCCCGCGAGTTTATTCTCAAAAT 1140
288  P  E  Y  D  G  P  P  R  D  P  I  A  A  R  E  F  I  L  K  M  308

1141 GTTTGTCGACTTGAATCCGGACGCCGACAAGATTATCTACTCTCATTTTACGTGCGCGAC 1200
308  F  V  D  L  N  P  D  A  D  K  I  I  Y  S  H  F  T  C  A  T  328

1201 TGATACGGAAAACATTCGGTTCGTGTTCGCCGCCGTCAAAGACACAATTCTACAGCATAA 1260
328  D  T  E  N  I  R  F  V  F  A  A  V  K  D  T  I  L  Q  H  N  348
```

Figure 2C  (wt eat-16)

```
  1 ATGATGCCACCGTTGACCAAGATCGAGGTGCTCGCGAAGCGAGTGATGGAAGGTGCGCAA  60
  1 M  M  P  P  L  T  K  I  E  V  L  A  K  R  V  M  E  G  A  Q   20

61 TTGAAAACGCATAAATACTTCCGGATCGCCGTGCCTCATGCCATCACCGGTCAGCAATTG 120
 21 L  K  T  H  K  Y  F  R  I  A  V  P  H  A  I  T  G  Q  Q  L   40

121 ATAGCTCTCGTTCTTGAGCGAGGTGCTCCTGACGATGAGGCTGAAGCGAGTCATCTGGCA 180
 41 I  A  L  V  L  E  R  G  A  P  D  D  E  A  E  A  S  H  L  A   60

181 AGTTTGTTACTTCACCACGGTTACATGTTTCCAGTTATCGAACATGGCCAACCTTTCAAA 240
 61 S  L  L  L  H  H  G  Y  M  F  P  V  I  E  H  G  Q  P  F  K   80

241 GACGATGGAACGTTATACAGGCTTCAAAGGCCGTATTTTTGGCCTTCACAGGCTGAACTG 300
 81 D  D  G  T  L  Y  R  L  Q  R  P  Y  F  W  P  S  Q  A  E  L  100

301 GTTCCGGATGTTGAATATGCCATTTACCTCAACAAGCGATTGCTCCGAAATGAGCAAAAA 360
101 V  P  D  V  E  Y  A  I  Y  L  N  K  R  L  L  R  N  E  Q  K  120

361 CACGGGTTAGAAGAAGATGAAGTTGAGTCATTCAACAGACTTGCCGATGTTCTCGCACAC 420
121 H  G  L  E  E  D  E  V  E  S  F  N  R  L  A  D  V  L  A  H  140

421 ATGTGGGCTTTCATCGTTCAACAGTCTGAGCTTCAATTGAAGCAGCAAAAAGAAAAAAAG 480
141 M  W  A  F  I  V  Q  Q  S  E  L  Q  L  K  Q  Q  K  E  K  K  160

481 AAAGTGGACAAGGTAGTGTTCGATTCAGAAGAACGAGCGTTTTGGAAGATACGAAAACCA 540
161 K  V  D  K  V  V  F  D  S  E  E  R  A  F  W  K  I  R  K  P  180
```

Figure 2C (Con'd)

```
541 AGTCGTGGTGGACCAAATTTCCTAGAGGACCCTTATATGAAAATAGAAAAGAAAATACGA 600
181  S   R   G   G   P   N   F   L   E   D   P   Y   M   K   I   E   K   K   I   R  200

601 CGGCAGAATGCACAAGGTTATAGATGTCTTATGGATCGATTACGATTTGCAATCAAGACA 660
201  R   Q   N   A   Q   G   Y   R   C   L   M   D   R   L   R   F   A   I   K   T  220

661 AAGCCATGGCTAAAAGCATTAAAAGCATCGGATACAATGGTGACGTGGGTTGACCAAAGA 720
221  K   P   W   L   K   A   L   K   A   S   D   T   M   V   T   W   V   D   Q   R  240

721 GCTGAATTCGATCCATTCCTTCACCCTCCACAACCATCCAATCCATGGATCAGTGATGAA 780
241  A   E   F   D   P   F   L   H   P   P   Q   P   S   N   P   W   I   S   D   E  260

781 GCTTCATTTTGGAATCAGCCTACTGACACGTCAAGTGCCGAGATCCCTACCGAGAAACGG 840
261  A   S   F   W   N   Q   P   T   D   T   S   S   A   E   I   P   T   E   K   R  280

841 GTAAAACGATGGGGACTTTCTGTTCAAGAGCTTGTGAAAGATCCTATAGGACGGCAAGTG 900
281  V   K   R   W   G   L   S   V   Q   E   L   V   K   D   P   I   G   R   Q   V  300

901 CTCGAAACATTTTTAGAATCCGAATTTTCGTCGGAAAATATACGGTTCTGGATAGCGATA 960
301  L   E   T   F   L   E   S   E   F   S   S   E   N   I   R   F   W   I   A   I  320

961 CAAGATTTGAAATATGCACCGAATGAGCAGATATACCAGAAAGCTGAAAGAATACGAGAA 1020
321  Q   D   L   K   Y   A   P   N   E   Q   I   Y   Q   K   A   E   R   I   R   E  340
```

Figure 2C (Con'd)

```
1021 GAATTTTTGGCTCAAGGAGCACCTGCACAAGTAAATGTAGACAATAGAACCCTCGATCAG 1080
 341 E   F   L   A   Q   G   A   P   A   Q   V   N   V   D   N   R   T   L   D   Q    360

1081 ACATTGGAGTGTATTTCGAAAGCGAAAGATGCTTCACAAATGAGATTCGCATTCTATCAT 1140
 361 T   L   E   C   I   S   K   A   K   D   A   S   Q   M   R   F   A   F   Y   H    380

1141 TCTGAAGAGCACGTGTTCACATTGATGGCAAAGGATTCATATCCACGTTTCGTCCGATCC 1200
 381 S   E   E   H   V   F   T   L   M   A   K   D   S   Y   P   R   F   V   R   S    400

1201 CAAATCTACAAAGCAGTATTGACAGCAGCGCAACAGCACGGAACAAAGCGACTCGGGTGG 1260
 401 Q   I   Y   K   A   V   L   T   A   A   Q   Q   H   G   T   K   R   L   G   W    420

1261 CGCAACTTCGTATTCAACATGGGTACAACTAAAAAACCAGCAACGAGTAAACCAGCAAAG 1320
 421 R   N   F   V   F   N   M   G   T   T   K   K   P   A   T   S   K   P   A   K    440

1321 CCGCAAGATTCCATCGGGACTGGTCAAGTTCTCCCAAAACAGCTATCGTCCGACTCGCTG 1380
 441 P   Q   D   S   I   G   T   G   Q   V   L   P   K   Q   L   S   S   D   S   L    460

1381 CCAGTTCGACAGGCTCATGGGGTCAAACCGGATCCCGAATGA 1422
 461 P   V   R   Q   A   H   G   V   K   P   D   P   E   *   473
```

Figure 2D (mutant eat-16)

```
  1 ATGATGCCACCGTTGACCAAGATCGAGGTGCTCGCGAAGCGAGTGATGGAAGGTGCGCAA  60
  1  M  M  P  P  L  T  K  I  E  V  L  A  K  R  V  M  E  G  A  Q   20

61 TTGAAAACGCATAAATACTTCCGGATCGCCGTGCCTCATGCCATCACCGGTCAGCAATTG 120
 21  L  K  T  H  K  Y  F  R  I  A  V  P  H  A  I  T  G  Q  Q  L   40

121 ATAGCTCTCGTTCTTGAGCGAGGTGCTCCTGACGATGAGGCTGAAGCGAGTCATCTGGCA 180
 41  I  A  L  V  L  E  R  G  A  P  D  D  E  A  E  A  S  H  L  A   60

181 AGTTTGTTACTTCACCACGGTTACATGTTTCCAGTTATCGAACATGGCCAACCTTTCAAA 240
 61  S  L  L  L  H  H  G  Y  M  F  P  V  I  E  H  G  Q  P  F  K   80

241 GACGATGGAACGTTATACAGGCTTCAAAGGCCGTATTTTGGCCTTCACAGGCTGAACTG 300
 81  D  D  G  T  L  Y  R  L  Q  R  P  Y  F  W  P  S  Q  A  E  L  100

301 GTTCCGGATGTTGAATATGCCATTTACCTCAACAAGCGATTGCTCCGAAATGAGCAAAAA 360
101  V  P  D  V  E  Y  A  I  Y  L  N  K  R  L  L  R  N  E  Q  K  120

361 CACGGGTTAGAAGAAGATGAAGTTGAGTCATTCAACAGACTTGCCGATGTTCTCGCACAC 420
121  H  G  L  E  E  D  E  V  E  S  F  N  R  L  A  D  V  L  A  H  140

421 ATGTGGGCTTTCATCGTTCAACAGTCTGAGCTTCAATTGAAGCAGCAAAAAAAAAAAAAG 480
141  M  W  A  F  I  V  Q  Q  S  E  L  Q  L  K  Q  Q  K  K  K  K  160

481 AAAGTGGACAAGGTAGTGTTCGATTCAGAAGAACGAGCGTTTTGGAAGATACGAAAACCA 540
161  K  V  D  K  V  V  F  D  S  E  E  R  A  F  W  K  I  R  K  P  180
```

Figure 2D (Con'd)

```
541 AGTCGTGGTGGACCAAATTTCCTAGAGGACCCTTATATGAAAATAGAAAAGAAAATACGA 600
181  S  R  G  G  P  N  F  L  E  D  P  Y  M  K  I  E  K  K  I  R  200

601 CGGCAGAATGCACAAGGTTATAGATGTCTTATGGATCGATTACGATTTGCAATCAAGACA 660
201  R  Q  N  A  Q  G  Y  R  C  L  M  D  R  L  R  F  A  I  K  T  220

661 AAGCCATGGCTAAAAGCATTAAAAGCATCGGATACAATGGTGACGTGGGTTGACCAAAGA 720
221  K  P  W  L  K  A  L  K  A  S  D  T  M  V  T  W  V  D  Q  R  240

721 GCTGAATTCGATCCATTCCTTCACCCTCCACAACCATCCAATCCATGGATCAGTGATGAA 780
241  A  E  F  D  P  F  L  H  P  P  Q  P  S  N  P  W  I  S  D  E  260

781 GCTTCATTTTGGAATCAGCCTACTGACACGTCAAGTGCCGAGATCCCTACCGAGAAACGG 840
261  A  S  F  W  N  Q  P  T  D  T  S  S  A  E  I  P  T  E  K  R  280

841 GTAAAACGATGGGGACTTTCTGTTCAAGAGCTTGTGAAAGATCCTATAGGACGGCAAGTG 900
281  V  K  R  W  G  L  S  V  Q  E  L  V  K  D  P  I  G  R  Q  V  300

901 CTCGAAACATTTTTAGAATCCGAATTTTCGTCGGAAAATATACGGTTCTGGATAGCGATA 960
301  L  E  T  F  L  E  S  E  F  S  S  E  N  I  R  F  W  I  A  I  320

961 CAAGATTTGAAATATGCACCGAATGAGCAGATATACCAGAAAGCTGAAAGAATACGAGAA 1020
321  Q  D  L  K  Y  A  P  N  E  Q  I  Y  Q  K  A  E  R  I  R  E  340

1021 GAATTTTTGGCTCAAGGAGCACCTGCACAAGTAAATGTAGACAATAGAACCCTCGATCAG 1080
341  E  F  L  A  Q  G  A  P  A  Q  V  N  V  D  N  R  T  L  D  Q  360

1081 ACATTGGAGTGTATTTCGAAAGCGAAAGATGCTTCACAAATGAGATTCGCATTCTATCAT 1140
361  T  L  E  C  I  S  K  A  K  D  A  S  Q  M  R  F  A  F  Y  H  380
```

Figure 2D (Con'd)

```
1141 TCTGAAGAGCACGTGTTCACATTGATGGCAAAGGATTCATATCCACGTTTCGTCCGATCC 1200
 381 S   E   E   H   V   F   T   L   M   A   K   D   S   Y   P   R   F   V   R   S    400

1201 CAAATCTACAAAGCAGTATTGACAGCAGCGCAACAGCACGGAACAAAGCGACTCGGGTGG 1260
 401 Q   I   Y   K   A   V   L   T   A   A   Q   Q   H   G   T   K   R   L   G   W    420

1261 CGCAACTTCGTATTCAACATGGGTACAACTAAAAAACCAGCAACGAGTAAACCAGCAAAG 1320
 421 R   N   F   V   F   N   M   G   T   T   K   K   P   A   T   S   K   P   A   K    440

1321 CCGCAAGATTCCATCGGGACTGGTCAAGTTCTCCCAAAACAGCTATCGTCCGACTCGCTG 1380
 441 P   Q   D   S   I   G   T   G   Q   V   L   P   K   Q   L   S   S   D   S   L    460

1381 CCAGTTCGACAGGCTCATGGGGTCAAACCGGATCCCGAATGA 1422
 461 P   V   R   Q   A   H   G   V   K   P   D   P   *            473
```

(I)

(II)

(III)

Figure 7:
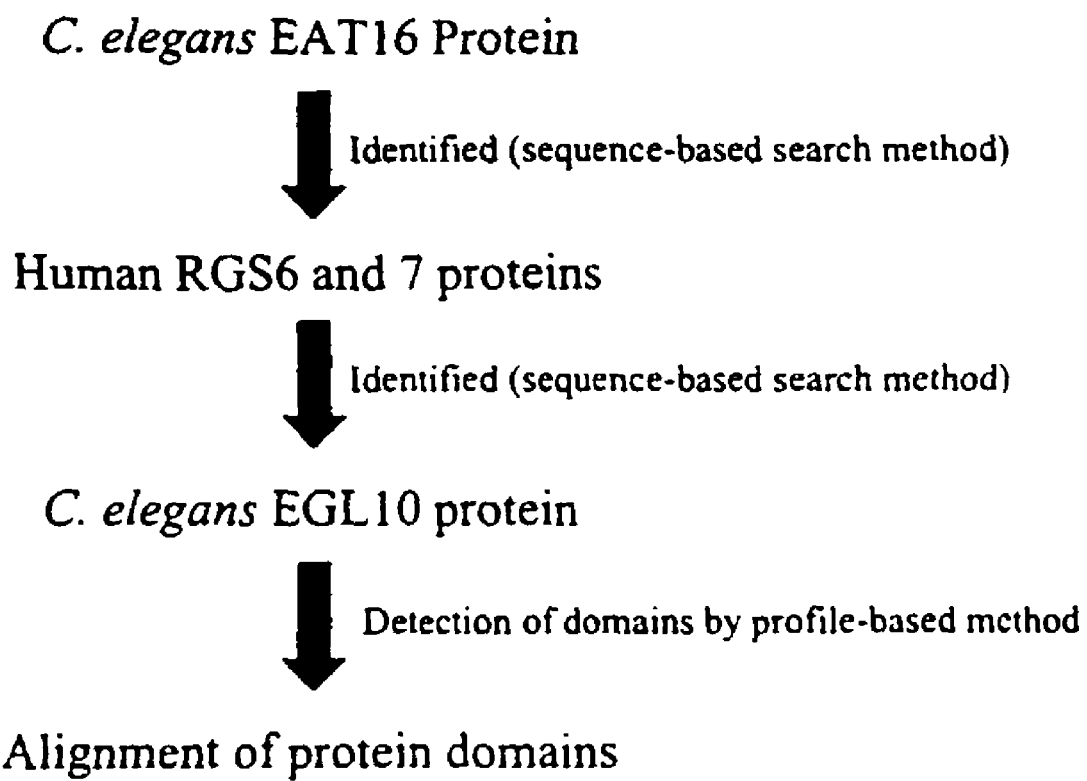

FIG. 7: Bioinformatics Analysis Workflow

Figure 11:
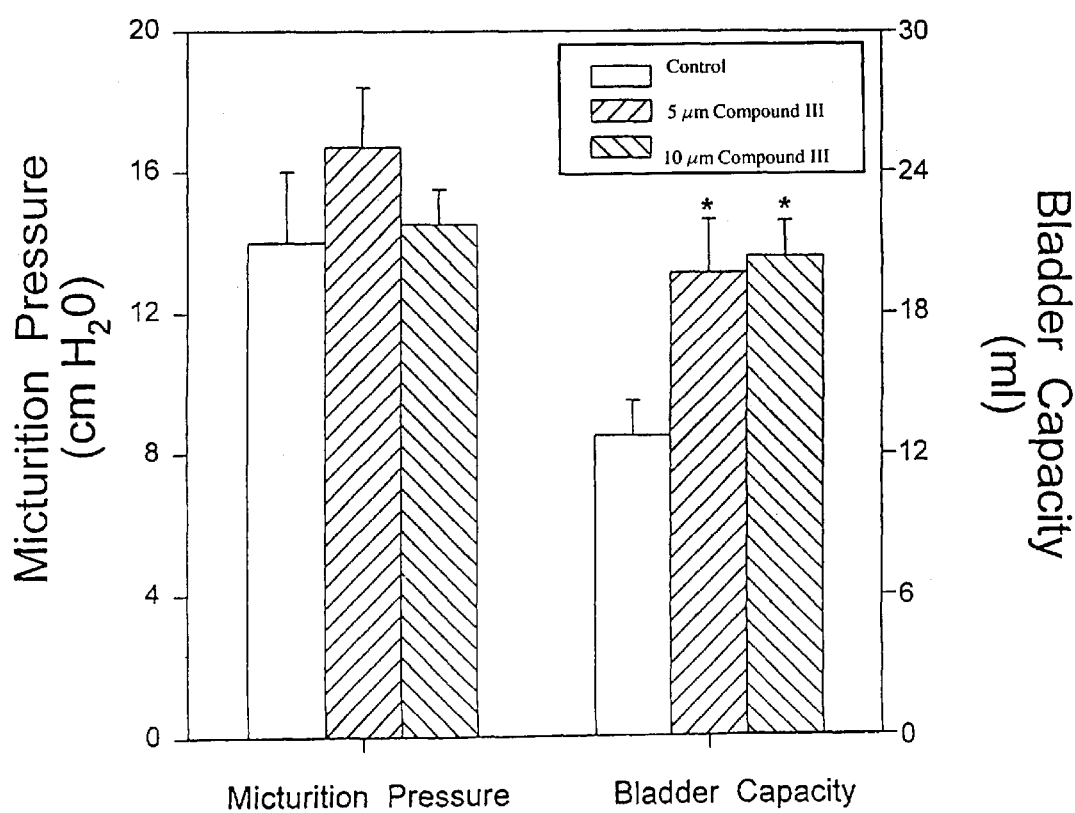

FIG. 11 Effect of Compound III on bladder cystometry

METHODS OF SCREENING FOR AGENTS THAT MODULATE THE INTERACTION OF RGS AND GαQ AND URINARY INCONTINENCE This application is entitled to and claims priority to U.S. Provisional Application Ser. No. 60/352,720, filed Jan. 28, 2002, which is hereby incorporated by reference in its entirety.

1. FIELD OF THE INVENTION

The present invention provides methods for treating and/or preventing conditions in smooth muscle such as urinary incontinence and compounds useful in such methods. In certain embodiments of the invention, the compounds are capable of modulating Gαq and RGS complex activity. In one aspect, the invention provides compounds and methods for identifying compounds that have agonizing effects on RGS and that affect the RGS/Gαq complex. The compounds are capable of altering G-protein coupled receptor protein pathway signals in vitro or in vivo.

2. BACKGROUND OF THE INVENTION

Urinary incontinence is a common condition that is a frequent cause of confinement to nursing homes among the elderly. It afflicts significant numbers among both men and women of all ages. Urinary incontinence is believed to currently affect over 12 million people in the United States alone, and to occur in between 15 and 30% of the population over the age of 60. In addition, studies show some degree of daily incontinence reported among as many as 17% of young, apparently healthy women.

Urinary incontinence is a manifestation of the failure to control the muscles of the bladder or urinary sphincter. Incontinence results when the pressure within the bladder is too great as a result of excessive force exerted by the bladder muscles, or when the sphincter muscles are too weak. Urinary incontinence can be a manifestation of other diseases such as Parkinsonism, multiple sclerosis, lesions of the central nervous system, or bladder infections. Interstitial cysts can result in instability of the bladder detusor muscles and a particularly unpleasant form of urge incontinence.

Current treatments for urinary incontinence rely on the control of G protein coupled receptors (GPCR) of the muscarinic class. These GPCR proteins are intracellular proteins that act as transducers of binding by extracellular ligands to cell surface G protein coupled receptors ("GPCRs"). Zhong and Neubig, 2001, *Perspectives in Pharmacology* 297:837-845, and the references cited therein, provide a review of GPCRs and their functions. Modulation of the signaling pathways downstream of the muscarinic GPCR's is responsible for proper muscle contraction within the bladder, and antagonists of these receptors have been utilized for this purpose, but have problems with specificity and side effects do to a lack of specificity.

The current standard of care is quite unsatisfactory. All of the current drugs now utilized to treat urinary incontinence suffer from polypharmacology and unwanted side effects. Safe and reliable methods and compounds are needed to improve the treatment and/or prevention of conditions involving defects in muscle contraction or the control of muscle contraction with one such example being urinary incontinence.

3. SUMMARY OF THE INVENTION

Accordingly, the present invention provides methods for the treatment of smooth muscle disorders such as urinary incontinence. The invention is based, in part, on the discovery that RGS/Gαq polypeptides complexes are involved in smooth muscle function and that this function can be modulated by agents that increase or decrease the affinity or activity of complex formation of these proteins. Accordingly, the present invention provides compounds that are capable of modulating the interaction of an RGS/Gαq protein complex, methods for identifying such compounds and methods of their use. The proper regulation of RGS/Gαq complexes downstream from GPCR signals is critical for conditions such as urinary incontinence, depression, anxiety, arrhythmia, cognition, psychosis, muscle disorders, skeletal muscle disorders, cardiac muscle disorders, smooth muscle disorders, muscle spasms, skeletal muscle spasms, cardiac muscle spasms, smooth muscle spasms, muscle contraction disorders, and muscle relaxation disorders. As such the compounds of the invention can be used for the treatment of such disorders.

In one aspect, the present invention provides methods for the identification of compounds that can be used to treat and/or prevent disorders such as urinary incontinence. In particular, the present invention provides the use of any RGS polypeptide or any Gαq polypeptide to identify compounds that can bind to and/or modulate the activity of an RGS or a Gαq polypeptide or a complex of the polypeptides. The identification of such compounds can comprise assay methods described herein as well as those known to one of skill in the art. Such compounds can be useful, for example, for the treatment and/or prevention of urinary incontinence, depression, anxiety, arrhythmia, cognition, psychosis, muscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders. The present invention also encompasses the use of such compounds for the treatment of such disorders.

In another aspect, the present invention provides mutant Gαq polypeptides. Typically, a mutant Gαq polypeptide of the invention comprises a mutation of a conserved methionine residue within its switch III region. The mutant Gαq polypeptides of the invention can be used to screen for compounds useful for the treatment of conditions such as urinary incontinence, or to counter-screen compounds for specificity with regards to compounds that increase or decrease the affinity of RGS binding to Gαq with a resultant effect on Gαq signaling and muscle contraction. In another embodiment the conserved methionine residue in the switch III region defines a compound interaction site for compounds that increases the affinity of Gαq for RGS protein. Compounds which interact with this site may antagonize or agonize Gαq activity and be useful for the treatment and/or prevention of urinary incontinence, depression, anxiety, arrhythmia, cognition, psychosis, muscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders. The present invention also encompasses the use of such compounds for the treatment of such disorders.

In another aspect, the present invention provides mutant RGS polypeptides. A mutant RGS polypeptide of the invention comprises a DEP domain and a GGL domain, an RGS domain, and, typically, a mutation of a glutamine residue between the DEP domain and the GGL domain. Preferably, the mutant RGS polypeptide of the invention activates Gαq. Experiments here have shown that mutation of this amino acid to other non-conserved amino acids renders compounds I, II and III unable to affect the Gαq pathway. These experiments show convincingly that this amino acid residue defines a site critical for compound action and therefore is the likely compound binding site. The mutant RGS polypeptides of the invention can be used to screen for compounds useful for the treatment of conditions such as urinary incontinence. In another preferred embodiment residue 158 in eat-16 or the conserved motif in an RGS family member defines a binding site for compounds which affect its affinity for Gαq or other proteins, and compounds which bind such site that agonize RGS activity or antagonize Gαq signals or act as uncompetitive inhibitors of the complex such that Gαq is unable to recycle to the active state. Such compounds can be useful, for example, for the treatment and/or prevention of urinary incontinence, depression, anxiety, arrhythmia, cognition, psychosis, muscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders. The present invention also encompasses the use of such compounds for the treatment of such disorders.

In another aspect, the invention provides computer-readable media embedded with the three-dimensional structural information obtained from the *C. elegans* RGS polypeptide eat-16, or portions or substrates thereof. This aspect of the invention is illustrated by way of working examples demonstrating the determination and analysis of the three-dimensional structure of eat-16. Such three-dimensional structural information typically includes the atomic structure coordinates of the polypeptide, or the atomic structure coordinates of a portion thereof such as, for example, an active or binding site, but may include other structural information, such as vector representations of the atomic structure coordinates, etc. The computer readable media of the invention may further comprise additional information that is useful for representing the three-dimensional structure, including, but not limited to, thermal parameters, chain identifiers, and connectivity information.

In yet another aspect, the invention provides computer-readable media embedded with the three-dimensional structural information obtained from the human RGS polypeptide RGS-7, or portions or substrates thereof. This aspect of the invention is illustrated by way of working examples demonstrating the determination and analysis of the three-dimensional structure of RGS-7. Such three-dimensional structural information typically includes the atomic structure coordinates of the polypeptide, or the atomic structure coordinates of a portion thereof such as, for example, an active or binding site, but may include other structural information, such as vector representations of the atomic structure coordinates, etc. The computer readable media of the invention may further comprise additional information that is useful for representing the three-dimensional structure, including, but not limited to, thermal parameters, chain identifiers, and connectivity information.

The atomic structure coordinates of the invention have a variety of uses. For example, the coordinates are useful for a variety of molecular modeling and computer-based screening applications to, for example, computationally design and identify compounds that bind the eat-16 or RGS-7 polypeptide or a portion or fragment of the eat-16 or RGS-7 polypeptide, such as domains therein or the active site. Such compounds may be used as lead compounds in pharmaceutical efforts to identify compounds that agonize or inhibit eat-16 or RGS-7 as a therapeutic approach toward the treatment of, e.g., urinary incontinence.

The present invention also comprises compounds identified by screening compounds or libraries of compounds against the RGS or Gαq polypeptides or complexes thereof. Any compound identified by the methods of the invention can be assayed to determine its efficacy of binding or their modulation of, for example, Gαq activity or RGS/Gαq affinity.

Compounds which modulate complexes containing RGS and/or Gαq polypeptides have utility in all diseases where hyperactivating or inactivating G-protein coupled receptors would be of therapeutic value, including urinary incontinence, depression, anxiety, arrhythmia, cognition, psychosis, muscle disorders, skeletal muscle disorders, cardiac muscle disorders, smooth muscle disorders, muscle spasms, skeletal muscle spasms, cardiac muscle spasms, smooth muscle spasms, muscle contraction disorders, muscle relaxation disorders.

4. BRIEF DESCRIPTION OF THE FIGURES

FIGS. 1A and 1B provide an amino acid sequence alignment of RGS polypeptides and G polypeptides of the invention (RGS7 (SEQ ID NO.:7); EGL-10 (SEQ ID NO.:8); RGS11 SEQ ID NO.:9); EAT-16 SEQ ID NO.:10); RGS9 (SEQ ID NO.:11); EGL-30 (SEQ ID NO.:12); G(q) (SEQ ID NO.:13); G(i) (SEQ ID NO.:14); G(t) (SEQ ID NO.:15); G(o) (SEQ ID NO.:16); G(x) (SEQ ID NO.:17); G(s) (SEQ ID NO.:18); and G(13) (SEQ ID NO.:19));

FIGS. 2A-2D provide the sequences of exemplary RGS and G alpha q wild-type and mutant polypeptides of the invention (wt egl-30 ((SEQ ID NO.:20); mutant egl-30 (SEQ ID NO.:21); wt eat-16(SEQ ID NO.:22); and mutant eat-16 (SEQ ID NO.:23).

Figure 3B:
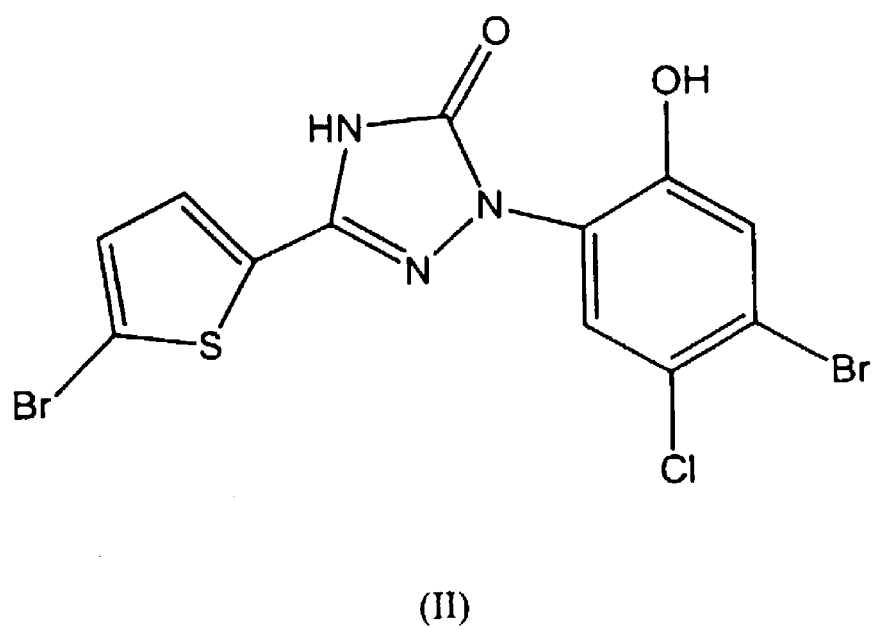
Figure 3C:
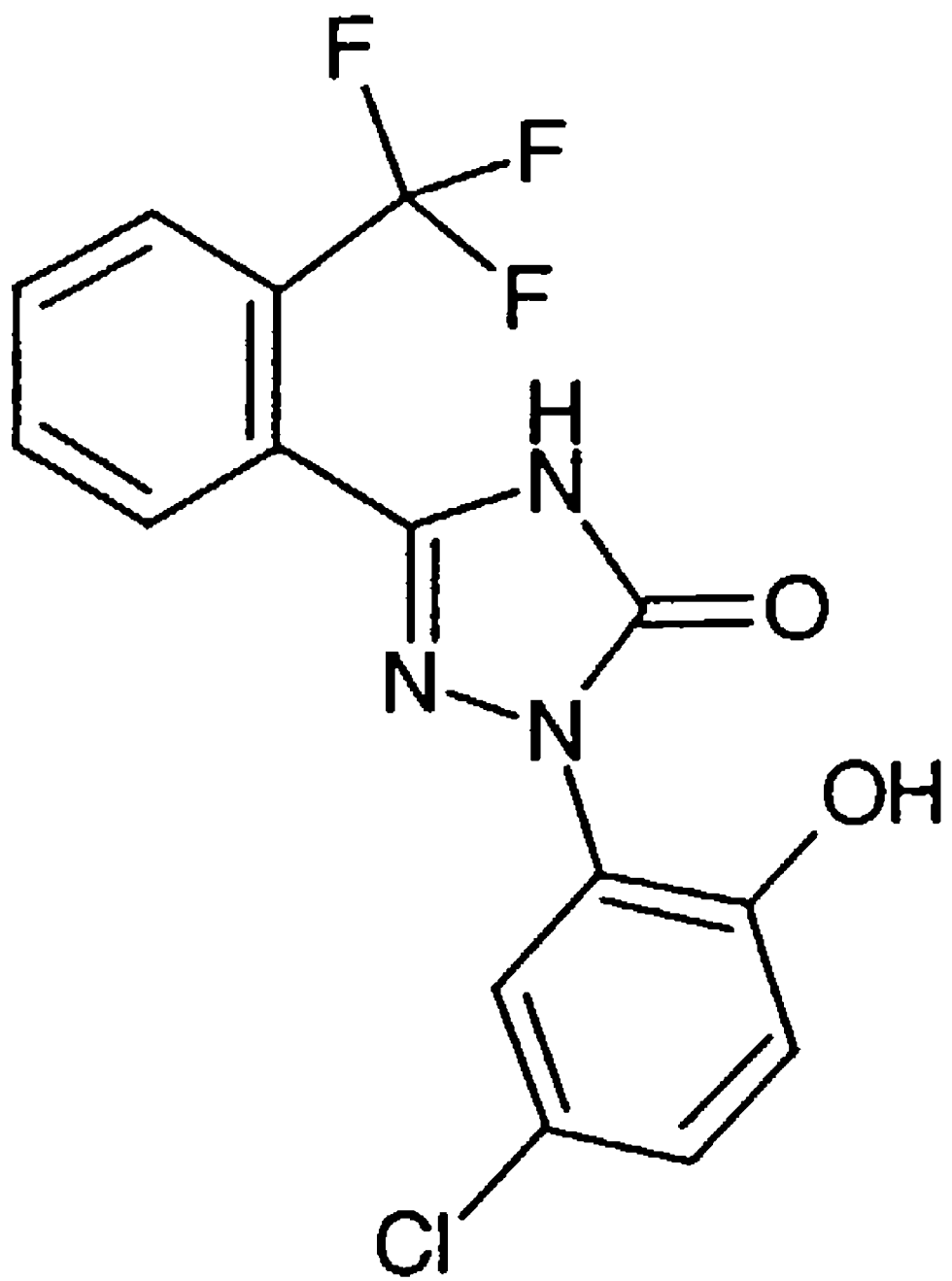
Figure 4:
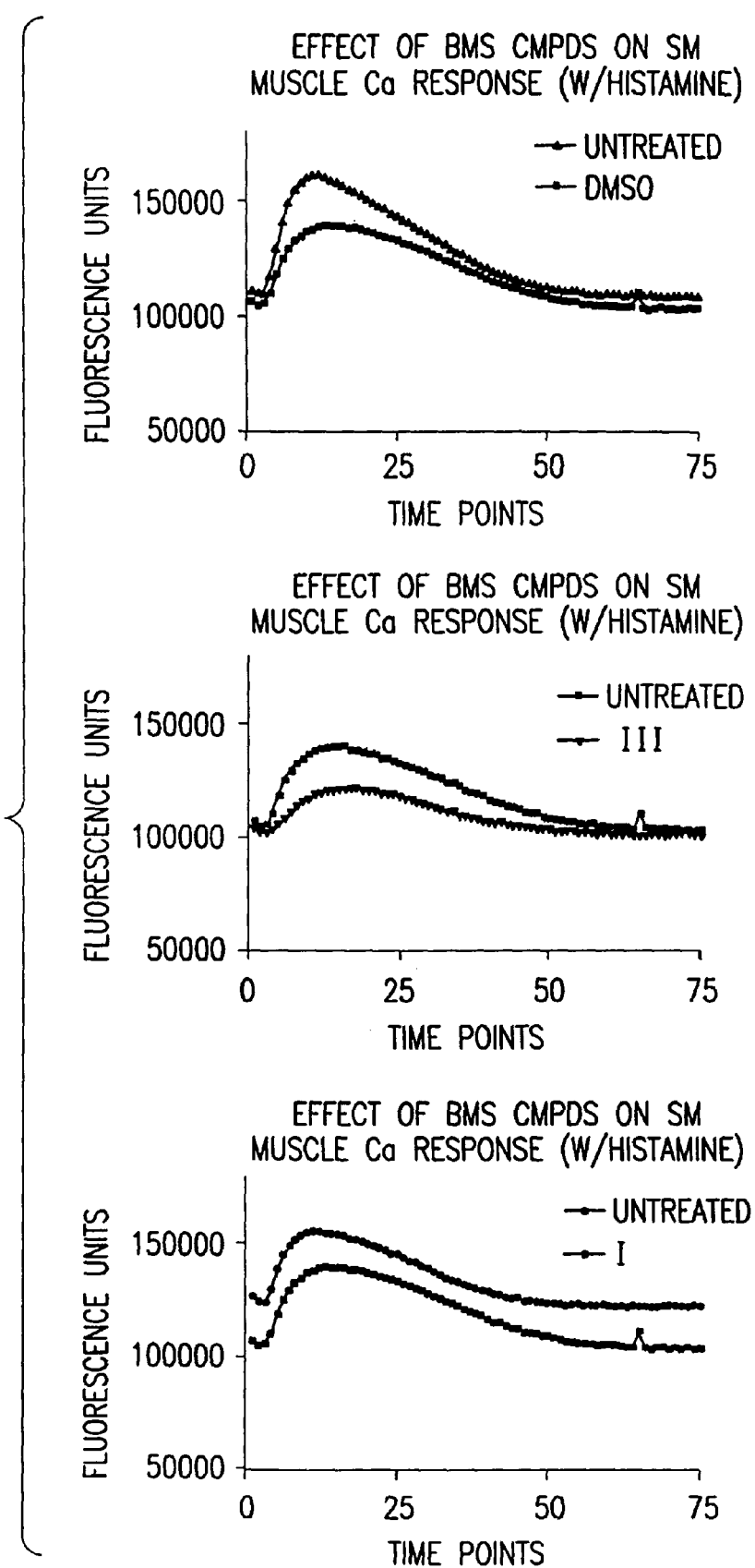
Figure 5:
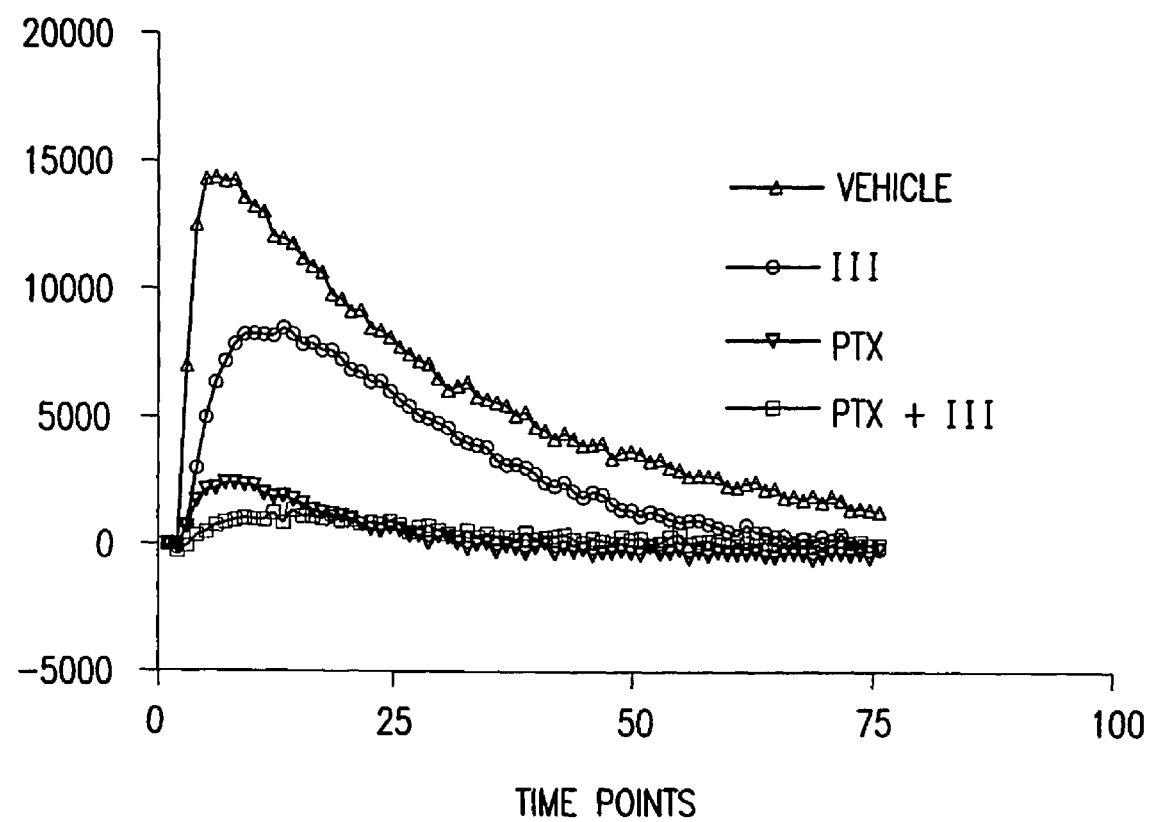
Figure 6:
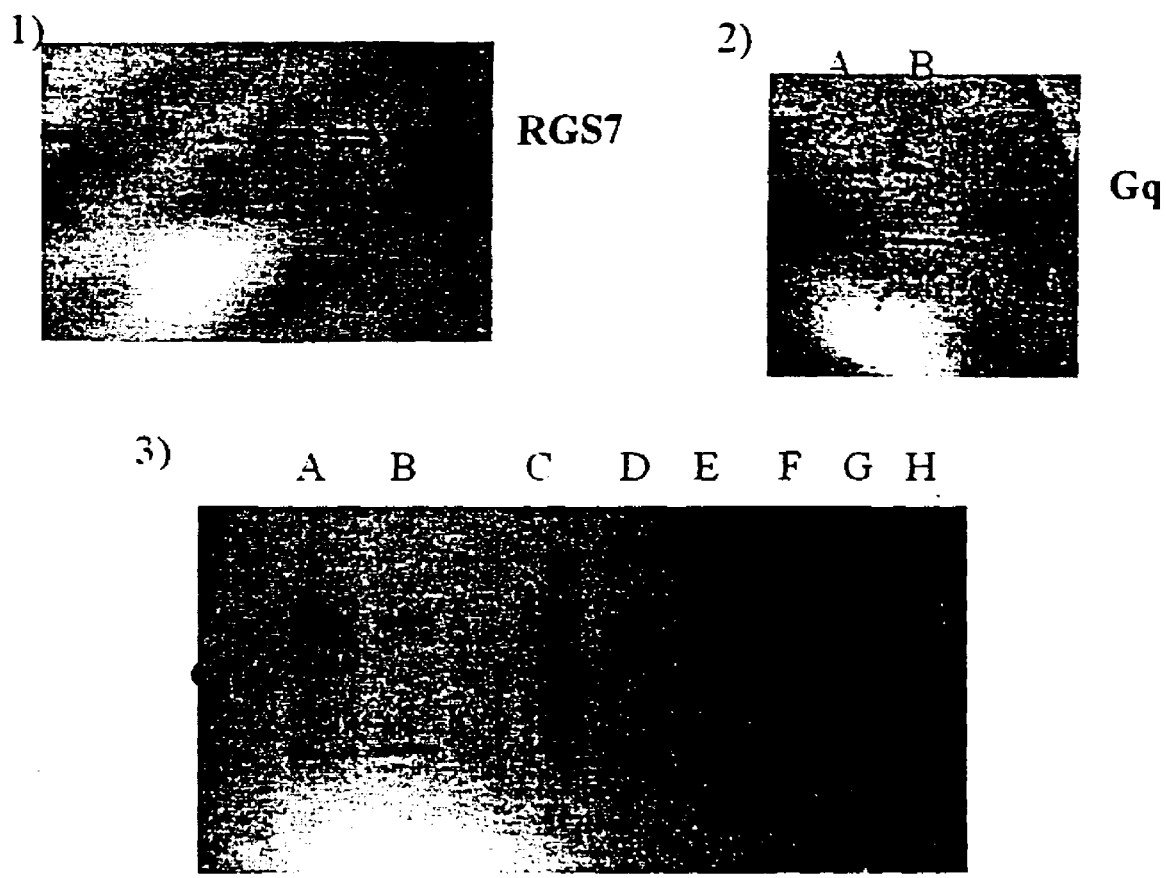
Figure 8:
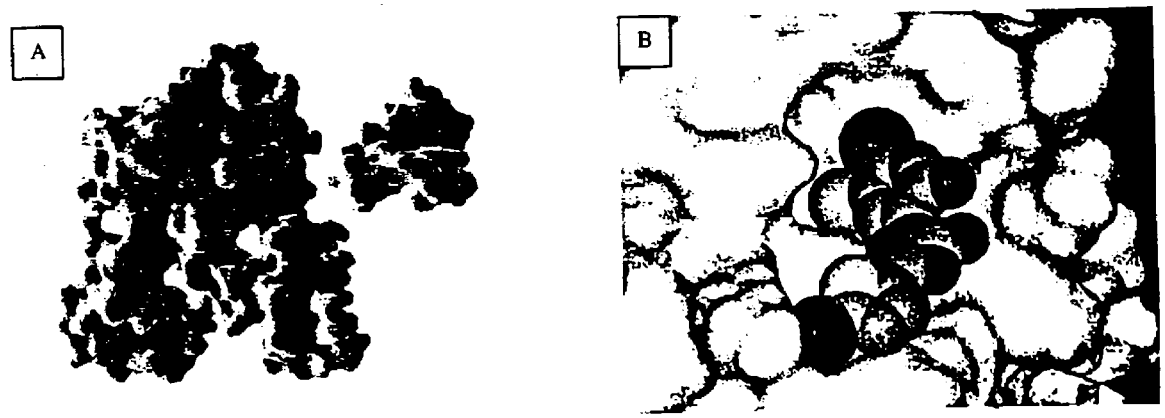

FIG. 3A provides compound I;

FIG. 3B provides compound II;

FIG. 3C provides compound III;

FIG. 4 provides the effects of compounds I and III on smooth muscle cells;

FIG. 5 provides the results of a calcium assay illustrating that compound I specifically inhibits Gαq signalling;

FIG. 6 provides an immunoprecipitation blot indicating that compounds I and II increase the affinity of Gαq and RGS;

FIG. 7 provides a bioinformatics work flow diagram;

FIG. 8A provides a depiction of the PDE binding site in the Gα/RGS/PDE trimer;

FIG. 8B provides a depiction of compound II docked into the binding site in the Gα/RGS/PDE trimer, showing surface complementarity.

Figure 9:
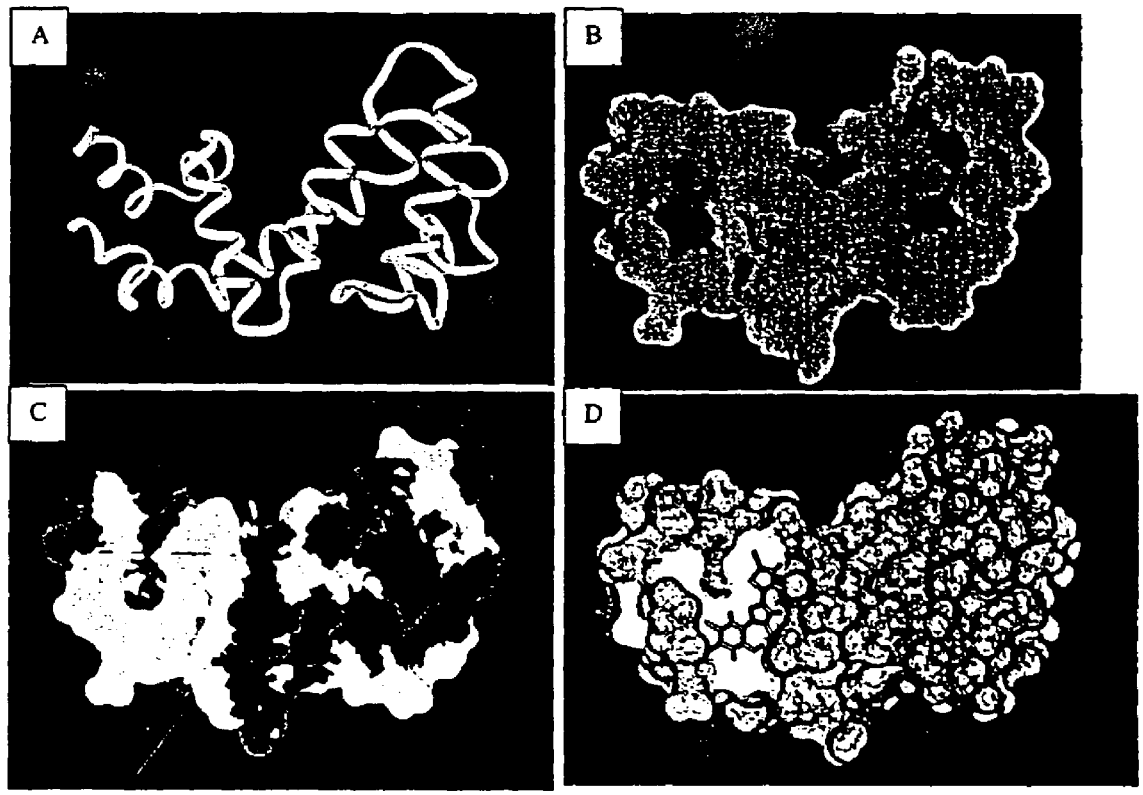
Figure 10:
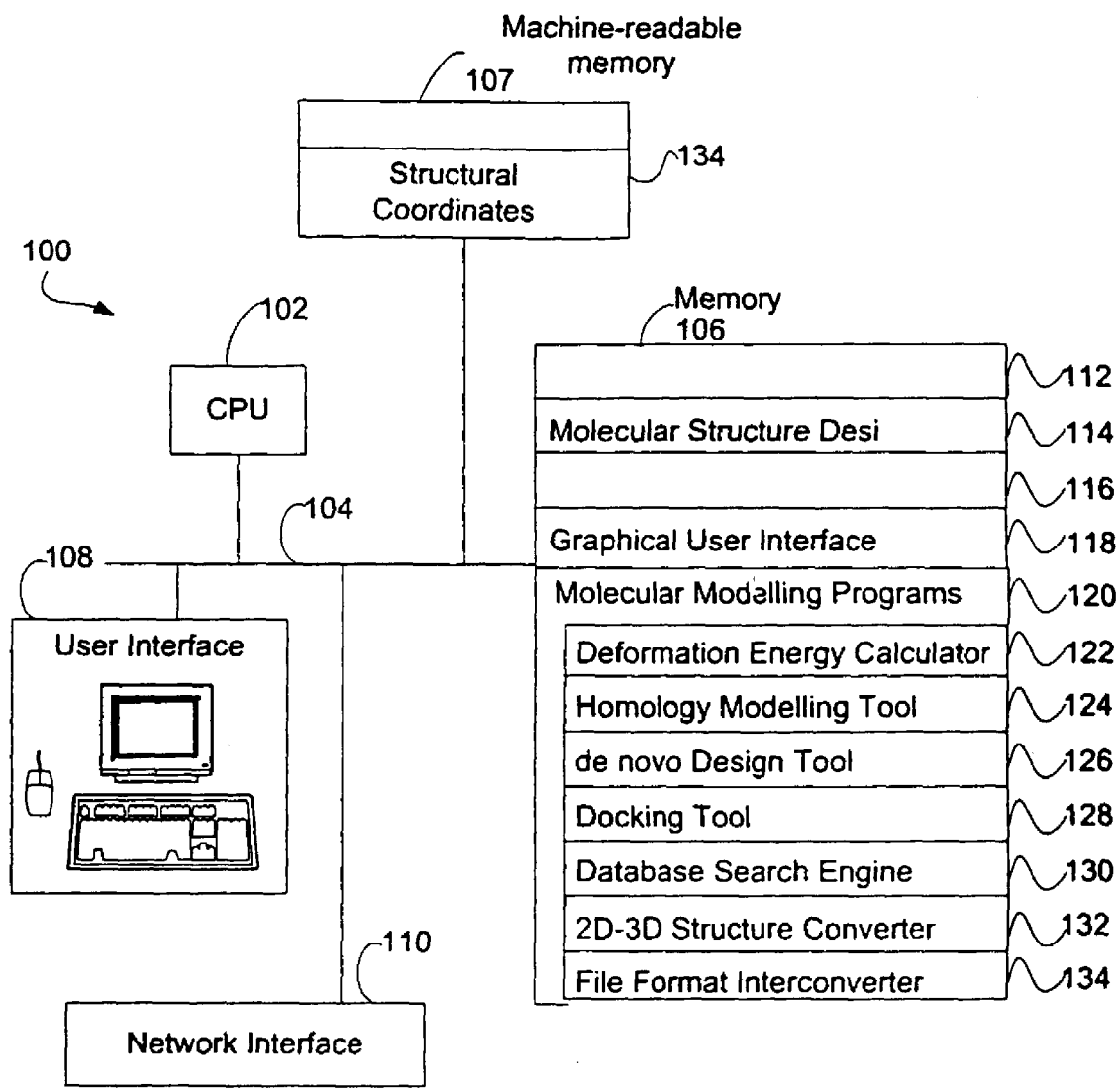

FIG. 9A provides a ribbon diagram of the eat-16 model;

FIG. 9B provides a "molecular elevation" plot view of the eat-16 model;

FIG. 9C provides the surface of the eat-16 model colored according to hydrophobic character;

FIG. 9D provides superposition of compound II, stick figure, onto the hydrophobic pocket, shown in white, showing that they are of similar size; and FIG. 10 provides an illustration of a computer system for use in the present invention.

FIG. 11 provides the effects of compound III on the micturition pressure and bladder capacity of a normal rabbit: each bar represents the mean +/− SEM of between 3 and 5 individual preparations.

Figure 12:
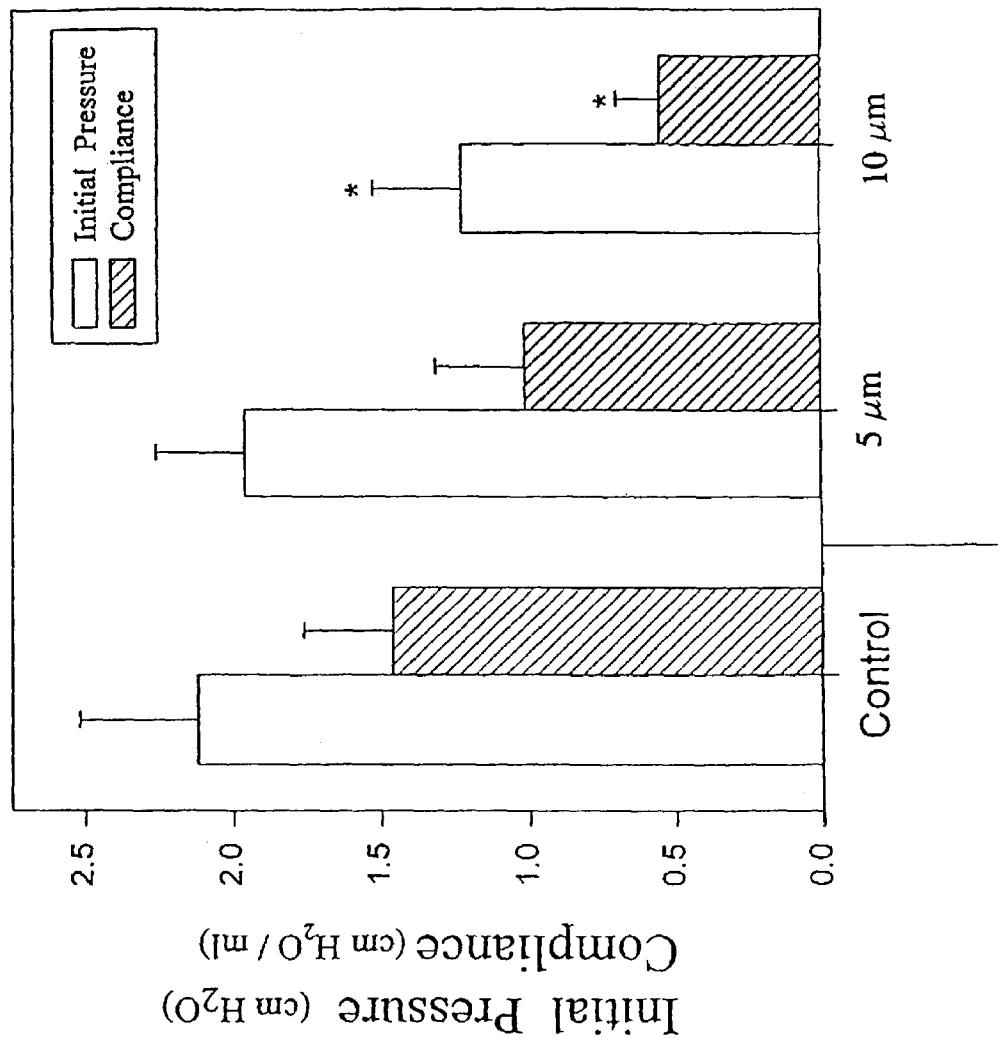

FIG. 12 provides the effects of compound III on initial bladder pressure (at 10% of bladder capacity) and compliance (resistance to stretch between 10% and 20% of capacity). Each bar represents the mean +/− SEM of 4-6 individual preparations.

Figure 13:
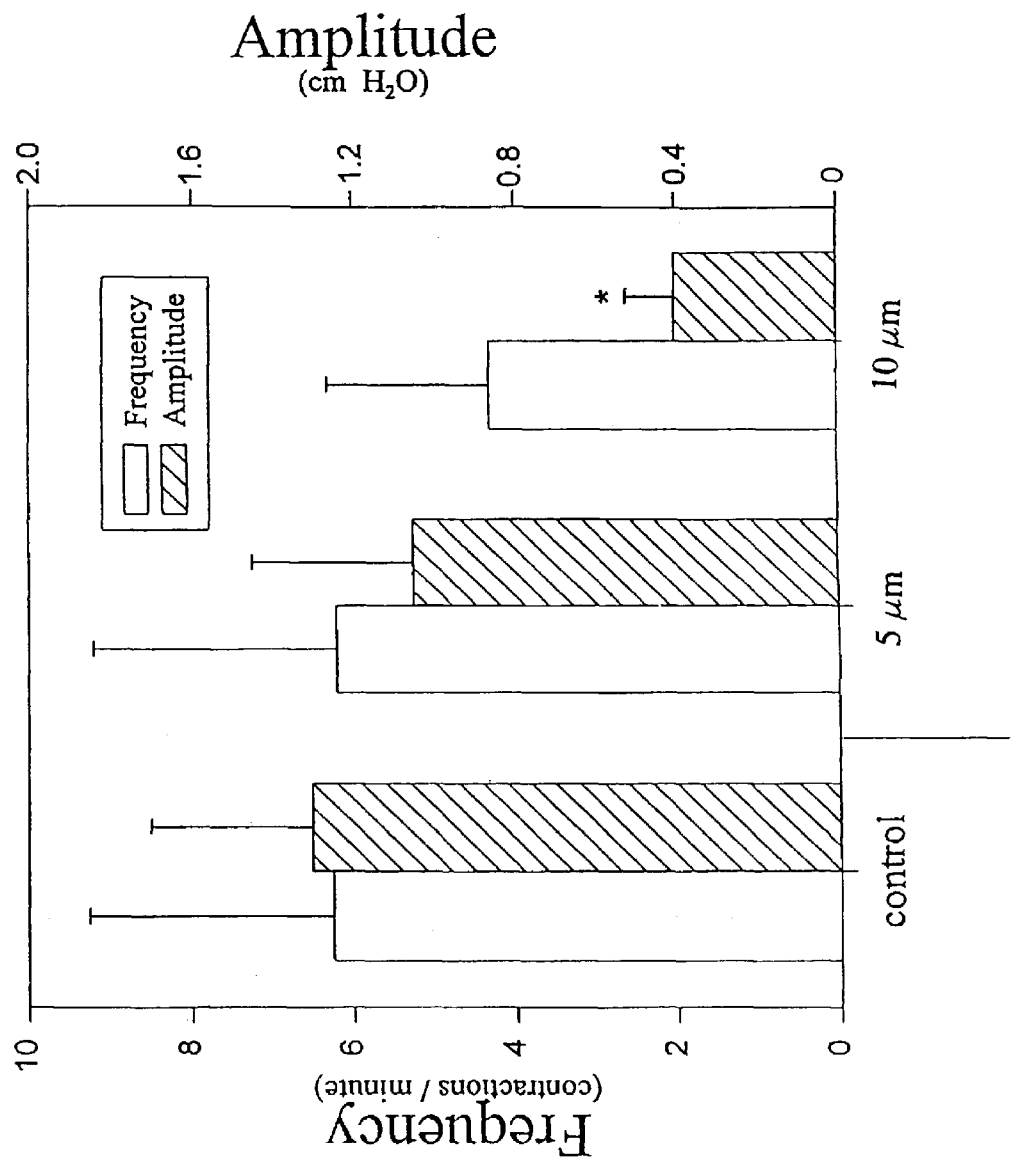

FIG. 13 provides the effects of compound III on the frequency and amplitude of unstable bladder contractions induced by partial outlet obstruction. Each bar represents the mean +/− SEM of 4-6 individual preparations.

5. BRIEF DESCRIPTION OF THE TABLES

Table 1 provides a structure-based sequence alignment of eat-16 and rat RGS-4;

Table 2 provides a sequence alignment of human RGS-7 and rat RGS-4;

Table 3 provides the atomic structure coordinates of wild type eat-16; and

Table 4 provides the atomic structure coordinates of wild type RGS-7.

6. ABBREVIATIONS

The amino acid notations used herein for the twenty genetically encoded L-amino acids are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter amino acid abbreviations designate amino acids in the L-configuration. Amino acids in the D-configuration are preceded with a "D-." For example, Arg designates L-arginine and D-Arg designates D-arginine. Likewise, the capital one-letter abbreviations refer to amino acids in the L-configuration. Lower-case one-letter abbreviations designate amino acids in the D-configuration. For example, "R" designates L-arginine and "r" designates D-arginine.

Unless noted otherwise, when polypeptide sequences are presented as a series of one-letter and/or three-letter abbreviations, the sequences are presented in the N→C direction, in accordance with common practice wherein "N" refers to the amino terminus of a polypeptide, and "C" refers to the carboxy terminus of a polypeptide.

7. DETAILED DESCRIPTION OF THE PREFERRED EMBODIMENTS

The present invention is based, in part, on the inventors' discovery of the importance of Gαq polypeptides and RGS polypeptides in cellular pathways that have been linked to a variety of conditions such as urinary incontinence, depression, anxiety, arrhythmia, cognition, psychosis, muscle disorders, skeletal muscle disorders, cardiac muscle disorders, smooth muscle disorders, muscle spasms, skeletal muscle spasms, cardiac muscle spasms, smooth muscle spasms, muscle contraction disorders, muscle relaxation disorders.

The present invention targets a protein complex of Gαq and RGS, which regulates aspects of signals downstream of GPCR signaling, and therefore allows for better specificity in controlling that signal due to tissue specific expression of RGS proteins. Ligand binding to GPCRs results in the activation of one or more heterotrimeric G-proteins. G-proteins comprise several families including Gi, Gq, Gs and $G_{12}$. Heterotrimeric G-proteins in their resting states are complexes comprised of three subunits, known as Gα, Gβ and Gγ. In mammalian cells there are at least three classes of subunits, comprising 15 Gα, 5 Gβ and 7 Gγ genes. G-proteins have also been identified in invertebrate animals and some of these are capable of functionally substituting for their mammalian counterparts and are therefore equivalent.

The Gα subunits have intrinsic GTPase activity. This structure and associated mechanism are shared with the monomeric GTP-binding proteins of the ras superfamily. In the resting state, the complex contains bound GDP (Gα-GDP .beta..gamma.). Activation sets in motion a release of GDP and the subsequent binding of GTP resulting in the concurrent dissociation of the complex into two signaling complexes: Gα-GTP and .beta..gamma.. Signaling through Gα-GTP is terminated by GTP hydrolysis to GDP, and this reaction is catalyzed by regulator of G-protein signaling ("RGS") proteins. The regulation of Gαq by RGS proteins has been shown to depend on the "RGS" catalytic domain of these proteins and in vitro many RGS domain containing members of the RGS family are interchangeable in this activity. Specifically RGS6 (Genbank Accession No. XM.sub.—027292; SEQ ID NO.:27), RGS7 (Genbank Accession No. XM.sub.—010645), RGS9 (Genbank Accession No. XM.sub.—032141), RGS11 (Genbank Accession No. XM.sub.—027524, Genbank Accession No. XM.sub.—027525), RGS 1 (Genbank Accession No. XM.sub.—001330), RGS2 (Genbank Accession No. XM.sub.—029884; SEQ ID NO.:26), RGS3 (Genbank Accession No. XM.sub.—005324), RGS4 (Genbank Accession No. XM.sub.—034023), RGS5 (Genbank Accession No. XM.sub.—002185), and RGS16 (Genbank Accession No. XM.sub.—046463) have been published previously to effect in vitro Gαq signaling in an essentially equivalent fashion. Upon catalysis, Gα-GDP is free to reassociate with βγ to reform the inactive, heterotrimeric complex.

The present invention provides compounds that modulate Gαq activity, RGS activity and/or activity of the protein complex of RGS and Gαq in vivo and/or in vitro. In particular, the present invention provides methods of using Gαq polypeptides, mutant Gαq polypeptides, RGS polypeptides and mutant RGS polypeptides to identify compounds that can be used to treat or prevent conditions such as urinary incontinence.

7.1 Methods of Identifying Compounds that Modulate the Activity of RGS and Gαq Complexes RGS polypeptides of the invention, such as human RGS- and its conserved human homologs, can be used to identify compounds that selectively bind to and/or modulate the activity of the RGS polypeptide, a domain thereof or complex thereof with Gαq molecules. In addition, any of the mutant RGS polypeptides of the invention discussed below, can be used to identify a compound that selectively binds to and/or modulates the activity of the corresponding wild-type polypeptide, or domain thereof or complex with Gαq. Such compounds include, for example, compound I (FIG. 3A) and compound II (FIG. 3B) which are also described in co-pending U.S. Provisional Application No. 60/336,865, filed Nov. 2, 2001, the content of which is hereby incorporated by reference in its entirety.

As used in the present invention, the term modulation refers to a change in the activity of an active agent such as a polypeptide of the invention. The activity can be increased or decreased as measured by techniques described herein for detecting the activity of the active agent. The change in activity can be detected, for example, when the active agent is contacted with a compound of the invention. A modulator of an active agent refers to a substance, for example a compound of the invention, that is capable of altering the activity of the active agent.

In general, such methods comprise contacting a test compound with a polypeptide of the invention and assaying for the presence of the bound test compound or assaying for modulation of the activity of the polypeptide. The polypeptide can be, for example, expressed within a cell, and immunoprecipitated with an antibody according to standard protocols in the presence or absence of a radioactively or fluorescently labeled compound. The binding of the compound to the immunoprecipitated protein or protein complex can be measured by the degree of radiation or fluorescence that is precipitated with the protein. Controls from cells not transfected and expression the polypeptide or competition studies with non-radioactive compound can be utilized to prove the specificity of binding.

As used herein the term "selectively binds" refers to a compound (e.g., an antibody, a peptide, a lipid or a small organic molecule) that binds to a native polypeptide or to a chimeric polypeptide or a complex of polypeptides preferentially relative to other unrelated polypeptides. A compound selectively binds to a wild-type polypeptide or a mutant polypeptide of the invention if it has at least a 10%, preferably at least a 25%, at least a 50%, at least a 75%, at least a 90%, at least a 95%, or at least a 100% higher affinity and/or avidity for the native polypeptide or mutant polypeptide than an unrelated polypeptide.

The assay for the presence of the bound test compound can be any assay known to those of skill in the art to be useful for assaying binding to the wild-type polypeptide or mutant polypeptide and/or any assay known to those of skill in the art to be useful for assaying activation of the wild-type polypeptide or mutant polypeptide or protein complexes thereof. In particularly convenient embodiments of the invention, the presence of the test compound can be assayed by detecting the activity of a downstream effector of the wild-type polypeptide or mutant polypeptide such as phospholipase C (PLC) activity and/or mobilization of intracellular calcium. Examples of such assays are discussed in detail below. In addition direct binding of a labeled compound to a polypeptide or complex of a polypeptide can be detected by ligand binding assays known to one skilled in the art.

The assay for the presence of the bound test compound can be any assay known to those of skill in the art to be useful for assaying binding to the wild-type polypeptide or mutant polypeptide and/or any assay known to those of skill in the art to be useful for assaying activation of the wild-type polypeptide or mutant polypeptide or protein complexes thereof. In certain embodiments of the invention, the presence of the test compound can be assayed by detecting the activity of a downstream effector of a wild-type polypeptide or mutant polypeptide such as phospholipase C (PLC) activity and/or mobilization of intracellular calcium. Examples of such assays are discussed in detail herein. Optionally, a compound that binds a mutant polypeptide can then be tested against a corresponding wild-type polypeptide from the same species or from another species according to standard techniques.

In addition, direct binding of a labeled compound to a polypeptide or complex of a polypeptide is standard for ligand binding assays known to one skilled in the art. Direct binding of radioactive compounds to proteins or displacement of a radioligand by a subsequent higher affinity compound is often utilized as a method of screening for novel compounds by one skilled in the art.

For example, a Gαq polypeptide and an RGS polypeptide can be produced according to methods known to those of skill in the art, such as those discussed in detail below. The polypeptides can then be contacted with a candidate compound under suitable conditions. The polypeptides can then be assayed for complex formation according to standard techniques such as immunoprecipitation. In order to conduct assays, one or more of the components, such as the candidate compound, the Gαq polypeptide or the RGS polypeptide, can be suitably labeled for use in the assay for complex formation, as will be apparent to those of skill in the art. For instance, the candidate compound can be radiolabeled to facilitate radioassays. Also for instance, either or both polypeptides can be epitope-labeled to facilitate immunoprecipitation assays.

Such methods can be used to identify compounds that interact with and produce agonist or antagonistic activity on RGS/Gαq complexes and subsequent signals downstream of these complexes. Such perturbations of signaling are useful for the treatment and/or prevention of, for example, urinary incontinence, depression, anxiety, arrhythmia, cognition, psychosismuscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders.

Fluorescence resonance energy transfer microscopy (FRET) can also be used to identify compounds that affect the affinity of RGS and G alpha proteins. FRET technology is capable of detecting the affinity of interactions of two proteins. Compounds which inhibit this signal or increase this signal indicating a stronger or weaker affinity of RGS and G alpha q for one another can be found utilizing this technology as a screen. Such techniques are described, for example, in PCT publication WO 9806737 and in Janetopoulous et al., 2001, Science 291:2408-2410, the contents of which are hereby incorporated by reference in their entireties. For example, an RGS polypeptide can be fused to CFP or YFP using methods and materials readily available to those of skill in the art. Other similar fusion proteins can be easily designed by one skilled in the arts of Polymerase chain reaction (PCR) and FRET technologies, and either N-terminal protein fusions or C terminal protein fusions utilizing other conserved RGS proteins could easily be utilized by one skilled in the arts and simply substituted into this screening assay.

In addition, BRET technology which is based on very similar principles could also be utilized; the use of BRET is extensively taught in WO 9966324, the content of which is hereby incorporated by reference in its entirety. In this case PCR of RGS family members, G alpha q or G beta 5 could be utilized to create expression vectors and tools suitable for BRET analysis.

Other assays can be used to detect G-protein activation (see, e.g., "Regulation of G Protein-Coupled Receptor Function and Expression" ed. Benovic, J. L. pp 119-132., 2000, Wiley-Liss, New York). Such assays include receptor-stimulated GTP Binding to Gα subunits. Since activation of GPCR results in GDP-GTP exchange in the Gα subunit, this exchange can be quantified and used as a direct measurement of receptor-G protein interaction. This typically involves the use of radiolabeled guanine nucleotide ($^{35}$S-GTPγS or α$^{32}$P-GTP) incubated with the receptor (either in cell-free membrane preparations or artificial lipid membranes). The amount of $^{35}$S-GTPγS incorporated can be used as a measure of the extent of G protein activation. Another assay for receptor mediated G-protein activation is measurement of the hydrolysis of GTP by Gα. The final outcome of Gα activation is hydrolysis of bound GTP to GDP by intrinsic GTPase activity. Using γ$^{32}$P-GTP, the release of $^{32}$P$_i$ upon GTP-GDP exchange can be used as an indication of G-protein activation.

Such methods can be used to identify compounds that are useful for the treatment and/or prevention of, for example, urinary incontinence, depression, anxiety, arrhythmia, cognition, psychosismuscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders.

Furthermore, compounds that interact with and produce agonist or antagonistic activity on RGS/Gαq complexes and subsequent signals downstream of these complexes can be further tested in in vivo assays to assess their utility in the treatment and/or prevention of, for example, urinary incontinence, depression, anxiety, arrhythmia, cognition, psychosis-muscle disorders, skeletal muscle disorders, cardiac muscle disorders, preferably smooth muscle disorders, muscle spasms, skeletal muscle spasms, cardiac muscle spasms, preferably smooth muscle spasms, muscle contraction disorders and muscle relaxation disorders. The in vivo assays can be any assay known to one of skill in the art to be effective in assessing a test compound's utility in treating such disorders known to one of skill in the art without limitation.

When testing a compound's effect on urinary incontinence, the in vivo assay can be an in situ assay that tests a compound's effect on bladder cystometry. In other embodiments, the in vivo assay can be an in situ assay that tests a compound's effect on bladder contractile response. In certain embodiments, the bladder can be a normal bladder. In other embodiments, the bladder can be a hypertrophied bladder. These assays can be used to identify compounds that decrease initial bladder pressure during filling, increase bladder compliance, and decrease the amplitude of unstable bladder contractions. A decrease in initial bladder pressure during filling, decreased resistance to stretch (increased compliance), and inhibition of the amplitude of unstable bladder contractions, would all be beneficial in the treatment of urinary incontinence, and in the treatment of bladder dysfunction secondary to benign prostatic hyperplasia ("BPH").

7.2 Gαq Polypeptides

In the methods of identifying compounds of the invention, a Gαq polypeptide or a complex of a Gαq with a related RGS polypeptide can be used to identify compounds that are useful for the treatment of conditions such as urinary incontinence. Preferred Gαq polypeptides for use in methods to identify such compounds include human Gαq polypeptides such as those described in GI:12620875 and GI:1181671, the contents of which are hereby incorporated by reference in their entireties.

In certain embodiments of the invention, mutant Gαq polypeptides that display increased Gαq activity in vivo and/or in vitro or which define a binding site for compounds which affect the affinity of complex formation between Gαq and RGS proteins can be used to identify compounds of the invention. According to this aspect of the invention, the mutant Gαq polypeptide comprises a mutation of a conserved methionine residue in its switch III domain. Preferably, the methionine residue is mutated to a hydrophobic residue. More preferably, the methionine residue is mutated to an aliphatic residue. Most preferably, the methionine residue is mutated to isoleucine.

In preferred embodiments, the remainder of the amino acid sequence of the mutant Gαq polypeptide corresponds identically to the amino acid sequence of the wild-type Gαq polypeptide. However, in other embodiments of the invention, the remainder of the polypeptide can comprise additional mutations. The mutations can, for example, be conservative or non-conservative. For example, a mutated residue of the mutant polypeptide can belong to the same amino acid class or sub-class as the corresponding residue of the wild type Gαq polypeptide.

Preferably, the mutant Gαq polypeptide displays increased Gαq activity in vivo and/or in vitro. Gαq activity can be measured readily according to assays known to those of skill in the art. For example, Gαq activity can be measured by assaying the activity of downstream effectors of Gαq such as phospholipase C (PLC) activity or mobilization of intracellular calcium. Calcium mobilization can be observed by contacting cells comprising the mutant Gαq polypeptide with an appropriate calcium-sensitive dye. Changes in fluorescence of the dye indicate changes in intracellular calcium resulting from the activation of a Gαq —coupled GPCR. Such changes can be measured advantageously in whole cells in "real-time" (See, e.g., Berridge et al., Nature Reviews 2000 1:11-21). In another method, a mutant Gαq polypeptide can be expressed in *Xenopus laevis* oocytes followed by measurement of calcium activated chloride currents (see Weber, 1999, *Biochim Biophys Acta* 1421:213-233).

7.3 RGS Polypeptides

In the methods of the identifying compounds of the invention, an RGS polypeptide or a complex of an RGS polypeptide with a related Gαq polypeptide can be used to identify compounds useful for the treatment of conditions such as urinary incontinence. Preferred RGS polypeptides include the human RGS polypeptides RGS6, RGS7, RGS9, RGS11, RGS1, RGS2, RGS3, RGS4, RGS5, and RGS16.

RGS proteins are known to regulate agonist-evoked calcium oscillations in muscle which control proper bladder function. In particular, RGS proteins are thought to catalyze the hydrolysis of GTP by Gα thereby regulating the activity of Gα. Thus, by modulating these RGS proteins, it should be possible to control the strength and timing of bladder muscle contractions and therefore modulate diseases in the area of urinary incontinence, as well as cardiovascular and neuropathology. In the area of urinary incontinence it can reasonably be expected that compounds which act as agonists of bladder specific RGS protein activity will have therapeutic effects on the muscle spasms characteristic of incontinence disease.

The founding member of the regulator of G-protein signals is yeast SST-2, a protein identified in genetic screens for negative regulators of the pheromone response pathway in yeast. Genetic analysis in *Caenorhabditis elegans* (*C. elegans*) uncovered the SST-2 related gene, Egl-10, which was shown to negatively regulate *C. elegans* Gα0 involved in the control of egg-laying. RGS proteins have been found in all eukaryotic species for which searches have been performed, and are generally split into several different families based on protein structure. All of the RGS proteins share a common "RGS" core domain, and all are thought to affect the duration of active Gα by catalyzing GTP hydrolysis.

RGS proteins have been found in all eukaryotic species for which they have been searched, and are generally split into several different families based on protein structure. All of the RGS proteins share a common "RGS" core domain, and all are thought to affect the duration of active Gα by catalyzing GTP hydrolysis. These RGS domains in many cases are interchangeable in their activity. A subfamily of RGS proteins has been identified in which each member possesses a "DEP" (disheveled, Egl-10, pleckstrin) domain, and a "GGL" (G-protein γ subunit-like) domain, in addition to, their core RGS domain. The functions of these other domains is not clear although there is some evidence that they may control the cellular localization and protein-protein interactions of this class of RGS proteins. In *C. elegans* there are two RGS homologues that contain the DEP and GGL domains: egl-10 and eat-16; while in humans there are four that have been identified thus far: RGS 6, 7, 9, and 11. This family of RGS proteins is found predominantly in the nervous system, and the extent of their cellular roles is still being determined.

In one aspect, the present invention provides mutant RGS polypeptides that increase Gαq activity in vivo and/or in vitro. According to this aspect of the invention, the mutant RGS polypeptide comprises an RGS domain, a DEP domain, a GGL domain and a mutation of a glutamine residue between the DEP domain and the GGL domain. Preferably, the glutamine residue is mutated to a hydrophilic residue. More preferably, the methionine residue is mutated to a basic residue. Most preferably, the methionine residue is mutated to lysine. In preferred embodiments, the mutant RGS polypeptide is a mutant eat-16 polypeptide (see FIG. 2D) from *C. elegans* or a mutant human RGS-7.

In preferred embodiments, the remainder of the amino acid sequence of the mutant RGS polypeptide corresponds identically to the amino acid sequence of the wild-type RGS polypeptide. However, in other embodiments of the invention, the remainder of the polypeptide can comprise additional mutations. The mutations can be, for example, conservative or non-conservative. In certain embodiments, a mutated residue of the mutant polypeptide can belong to the same amino acid class or sub-class as the corresponding residue of the wild type RGS polypeptide.

Preferably, the mutant RGS polypeptide of the invention modulates, e.g. increases, Gαq activity in vivo or in vitro. Gαq activity can be measured readily according to assays known to those of skill in the art such as those described above. In certain embodiments, mutant *C. elegans* RGS polypeptides of the invention can be assayed for resistance to the egg-laying defects caused by compound I, II or III as described above.

7.4 Production of Polypeptides

The native and mutated polypeptides described herein may be chemically synthesized in whole or part using techniques, that are well-known in the art (see, e.g., Creighton, *Proteins: Structures and Molecular Principles*, 1983 W. H. Freeman & Co., NY.). Alternatively, methods that are well known to those skilled in the art can be used to construct expression vectors containing the native or mutated polypeptide coding sequence and appropriate transcriptional/translational control signals. These methods include in vitro recombinant DNA techniques, synthetic techniques and in vivo recombination/genetic recombination. See, for example, the techniques described in Maniatis et al., 1989, *Molecular Cloning: A Laboratory Manual*, Cold Spring Harbor Laboratory, NY and Ausubel et al., 1989, *Current Protocols in Molecular Biology*, Greene Publishing Associates and Wiley Interscience, NY.

A variety of host-expression vector systems may be utilized to express the polypeptide coding sequence. These include, but are not limited to, microorganisms such as bacteria transformed with recombinant bacteriophage DNA, plasmid DNA or cosmid DNA expression vectors containing the polypeptide coding sequence; yeast transformed with recombinant yeast expression vectors containing the polypeptide coding sequence; insect cell systems infected with recombinant virus expression vectors (e.g., baculovirus) containing the polypeptide coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the polypeptide coding sequence; or animal cell systems. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

Depending on the host/vector system utilized, any of a number of suitable transcription and translation elements, including constitutive and inducible promoters, may be used in the expression vector. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the tyrosine kinase domain DNA, SV40-, BPV- and EBV-based vectors may be used with an appropriate selectable marker.

The expression vector may be introduced into host cells via any one of a number of techniques including but not limited to transformation, transfection, infection, protoplast fusion, and electroporation. The expression vector-containing cells are clonally propagated and individually analyzed to determine whether they produce eat-16 or egl-30. Identification of polypeptide expressing host cell clones may be done by several means, including but not limited to immunological reactivity with antibodies with specificity for the polypeptide, and the presence of host cell-associated polypeptide activity.

Expression of cDNA encoding the polypeptide may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes.

To determine cDNA sequence(s) that yields optimal amounts of polypeptide and/or levels of polypeptide activity, modified cDNA molecules are constructed. Host cells are transformed with the cDNA molecules and the levels of RNA and/or protein are measured.

Levels of polypeptide in host cells are quantitated by a variety of methods such as immunoaffinity and/or ligand affinity techniques, polypeptide-specific affinity beads or polypeptide-specific antibodies are used to isolate $^{35}$S-methionine labeled or unlabeled polypeptide protein. Labeled or unlabeled polypeptide is analyzed by SDS-PAGE. Unlabeled polypeptide is detected by Western blotting, ELISA or RIA employing polypeptide-specific antibodies.

Following expression of the polypeptide in a recombinant host cell, the polypeptide may be recovered to provide the polypeptide in active form. Several polypeptide purification procedures are available and suitable for use. Recombinant polypeptide may be purified from cell lysates or from conditioned culture media, by various combinations of, or individual application of, fractionation, or chromatography steps that are known in the art.

In addition, recombinant polypeptide can be separated from other cellular proteins by use of an immuno-affinity column made with monoclonal or polyclonal antibodies specific for full length nascent polypeptide or fragments thereof.

Alternatively, the polypeptide may be recovered from a host cell in an unfolded, inactive form, e.g., from inclusion bodies of bacteria. Polypeptides recovered in this form may be solublized using a denaturant, e.g., guanidinium hydrochloride, and then refolded into an active form using methods known to those skilled in the art, such as dialysis.

7.5 Further Manipulations of the RGS or G$\alpha$q Polypeptide Structures and Binding Molecules Once an RGS or G$\alpha$q polypeptide-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity, polarity and charge as the original group. For selection of appropriate groups, any of several chemical models can be used, e.g., isolobal or isosteric analogies. Groups known to be bio-isosteres of one another are particularly preferred. One of skill in the art will understand that substitutions known in the art to alter conformation should be avoided. Such altered chemical compounds may then be analyzed for efficiency of binding to or modulation of the activity of an RGS polypeptide or a G$\alpha$q polypeptide, or a complex thereof, by the methods described in detail above.

7.6 Activity of Binding Molecules

The binding molecules described above can be synthesized according to synthetic techniques well known to those of skill in the art. The binding molecules preferably modulate the activity of the RGS or G$\alpha$q polypeptide and/or a molecule that interacts with the RGS or G$\alpha$q polypeptide. The activity of a binding molecule can be assayed easily by methods well known to those of skill in the art. For instance, an RGS or G$\alpha$q polypeptide or a cell comprising the RGS or G$\alpha$q polypeptide can be contacted with the binding molecule and then assayed for modulation of RGS activity or G$\alpha$q activity. Assays for RGS activity or G$\alpha$q activity are described in detail above.

Preferably, binding molecules may be identified by high throughput screening methods, according to which large libraries of ligands are screened against a particular target. A large library of ligands preferably contains more than 1,000 distinct ligands, more preferably contains more than 10,000 distinct ligands, even more preferably contains more than 100,000 distinct ligands and most preferably contains more than 1,000,000 distinct ligands. High throughput screening techniques typically employ robotically controlled assay systems, and take advantage of the latest improvements in miniaturization and automation. Samples are typically assayed on 96-well plates or microtiter plate arrays, and measurements may be taken in parallel. For an overview of high throughput screening techniques, see, for example, Razvi, E. S., "High-Throughput Screening—Where Are We Today?," *Drug & Market Development Publications*, (June 1999), and Razvi, E. S., "Industry Trends in High-Throughput Screening," *Drug & Market Development Publications*, (August 2000).

7.7 Therapeutic Methods

The present invention also provides methods of treating conditions such as urinary incontinence by administering a therapeutically effective amount of an agent of the invention or a compound identified in the methods described above.

The present invention provides for both prophylactic and therapeutic methods of treating a subject at risk of (or susceptible to) a disorder or having a disorder associated with aberrant G$\alpha$q activity or smooth muscle finction. In particular, the compounds of the invention can be used to treat or prevent urinary incontinence, depression, anxiety, arrythmia, cognition, psychosismuscle disorders, skeletal muscle disorders, cardiac muscle disorders, smooth muscle disorders, muscle spasms, skeletal muscle spasms, cardiac muscle spasms, smooth muscle spasms, muscle contraction disorders, muscle relaxation disorders.

A compound of the invention can be administered in a composition comprising the compound to treat or prevent the disorder.

7.7.1 Compositions

The pharmaceutical compositions of the invention include compositions which comprise compounds of the invention. These compounds are also referred to herein as "active compounds" or "active agents."

The compositions of the invention typically comprise an active agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

7.7.2 Effective Dosages

The agents of the invention, or compositions thereof, will generally be used in an amount effective to achieve the intended purpose. Of course, it is to be understood that the amount used will depend on the particular application.

For example, for use to treat urinary incontinence, a therapeutically effective amount of an agent, or composition thereof, is applied or administered to an animal or human in need thereof. By therapeutically effective amount is meant an amount of agent or composition that inhibits or ameliorates urinary incontinence in the subject. The actual therapeutically effective amount will depend on a particular application. An ordinarily skilled artisan will be able to determine therapeutically effective amounts of particular agents for particular applications without undue experimentation using, for example, the in vitro assays for the particular disease target known to those of skill in the art.

For use to treat or prevent diseases related to the function or abnormal expression of a Gαq polypeptide, the agents of the invention, or compositions thereof, are administered or applied in a therapeutically effective amount. By therapeutically effective amount is meant an amount effective to ameliorate the symptoms of, or ameliorate, treat or prevent diseases related to the function or abnormal expression of the Gαq polypeptide. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating agent concentration range that includes the $I_{50}$ as determined in cell culture (i.e., the concentration of the agent that is lethal to 50% of a cell culture), the MIC, as determined in cell culture (i.e., the minimal inhibitory concentration for growth) or the $I_{100}$ as determined in cell culture (i.e., the concentration of the agent that is lethal to 100% of a cell culture). Such information can be used to more accurately determine useful doses in humans. Initial dosages can also be estimated from in vivo data, e.g., animal models, using techniques that are well known in the art. One having ordinary skill in the art could readily optimize administration to humans based on animal data.

The amount of agent administered will, of course, be dependent on the subject being treated, on the subject's weight, the severity of the affliction, the manner of administration and the judgment of the prescribing physician.

The therapy may be repeated intermittently. The therapy may be provided alone or in combination with other drugs, such as for example other antiviral entities or other pharmaceutically effective entities.

7.7.3 Toxicity

Preferably, a therapeutically effective dose of the agents described herein will provide therapeutic benefit without causing substantial toxicity.

Toxicity of the agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Agents which exhibit high therapeutic indices are preferred. The data obtained from these cell culture assays and animal studies can be used in formulating a dosage range that is not toxic for use in human. The dosage of the agents described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

7.7.4 Therapeutic Methods

In one aspect, the invention provides a method for preventing in a subject, a disease or condition associated with an aberrant expression of a Gαq polypeptide or a molecule that interacts with a Gαq polypeptide, by administering to the subject a composition comprising an agent of the invention.

In another aspect, the present invention provides a method of treating or preventing such a disease or condition by administering to the subject composition comprising a nucleic acid encoding a polypeptide of the invention. Administration of a prophylactic agent can occur prior to the manifestation of symptoms characteristic of the aberrance, such that a disease or disorder is prevented or, alternatively, delayed in its progression.

Another aspect of the invention pertains to methods of modulating expression or activity of a Gαq polypeptide or a molecule that interacts with a Gαq polypeptide. The modulatory method of the invention involves contacting a cell with an agent that modulates one or more of the activities of the Gαq polypeptide or molecule that interacts with the Gαq polypeptide. An agent that modulates activity can be an agent as described herein, such as a compound of the invention. In one embodiment, the agent stimulates one or more of the biological activities of the Gαq polypeptide. Examples of such stimulatory agents include a compound of the invention. In another embodiment, the agent inhibits one or more of the biological activities of the Gαq polypeptide. These modulatory methods can be performed in vitro (e.g., by culturing the cell with the agent) or, alternatively, in vivo (e.g., by administering the agent to a subject).

As such, the present invention provides methods of treating an individual afflicted with a disease or disorder characterized by aberrant expression or activity of a Gαq polypeptide or a molecule that interacts with a Gαq polypeptide. In one embodiment, the method involves administering an agent (e.g., an agent identified by a screening assay described herein), or combination of agents that modulates (e.g., upregulates or downregulates) expression or activity. In another embodiment, the method involves administering a compound of the invention as therapy to compensate for reduced or aberrant expression or activity of the Gαq polypeptide or a molecule that interacts with the Gαq polypeptide.

7.8 Structure of *C. elegans* eat-16

The present invention provides, for the first time, the high-resolution predicted three-dimensional structures and atomic structure coordinates of eat-16. The specific methods used to obtain the structure coordinates are provided in the examples, infra. The atomic structure coordinates of eat-16, are listed in Table 3, infra.

The following abbreviations are used in Table 3:

"Residue" refers to amino acid by number.

"Atom Name" refers to the atom whose coordinates are provided.

"X coord", "Y coord" and "Z coord" provide the Cartesian coordinates of the element.

Structure coordinates for eat-16 according to Table 3 may be modified by mathematical manipulation. Such manipulations include, but are not limited to, fractionalization of the raw structure coordinates, integer additions or subtractions to sets of the raw structure coordinates, inversion of the raw structure coordinates and any combination of the above.

Those having skill in the art will recognize that atomic structure coordinates are not without error. Thus, it is to be understood that any set of structure coordinates obtained for eat-16, that have a root mean square deviation ("r.m.s.d.") of less than or equal to about 2.0 Å when superimposed, using backbone atoms (N, Cα, C and O), on the structure coordinates listed in Table 3 are considered to be identical with the structure coordinates listed in the Table when at least about 50% to 100% of the backbone atoms of eat-16 are included in the superposition.

7.9 Structure of RGS-7

The present invention provides, for the first time, the high-resolution three-dimensional structures and atomic structure coordinates of RGS-7. The specific methods used to obtain the structure coordinates are provided in the examples, infra. The atomic structure coordinates of RGS-7, are listed in Table 4, infra.

The following abbreviations are used in Table 4:

"Residue" refers to amino acid by number.

"Atom Name" refers to the atom whose coordinates are provided.

"X coord", "Y coord" and "Z coord" provide the Cartesian coordinates of the element.

Structure coordinates for RGS-7 according to Table 4 may be modified by mathematical manipulation. Such manipulations include, but are not limited to, fractionalization of the raw structure coordinates, integer additions or subtractions to sets of the raw structure coordinates, inversion of the raw structure coordinates and any combination of the above.

Those having skill in the art will recognize that atomic structure coordinates are not without error. Thus, it is to be understood that any set of structure coordinates obtained for eat-16, that have a root mean square deviation ("r.m.s.d.") of less than or equal to about 2.0 Å when superimposed, using backbone atoms (N, Cα, C and O), on the structure coordinates listed in Table 4 are considered to be identical with the structure coordinates listed in the Table when at least about 50% to 100% of the backbone atoms of eat-16 are included in the superposition.

7.9 Structure Coordinates

7.9.1 Obtaining Structure Coordinates

Structure coordinates of eat-16 and RGS-7 are provided in Table 3 and Table 4, respectively. Alternatively, structure coordinates of eat-16 or RGS-7 can be obtained using principles of homology modeling according to the description of the present invention. For instance, such homology models can be based on structures of related polypeptides known to those of skill in the art such as rat RGS-4 (Tesmer et al., 1997, Cell:251-61; Protein Data Bank structure 1AGR). Rat RGS-4 displays 33% primary sequence homology to eat-16 and 34% primary sequence identity to human RGS-7 (see Tables 1&2).

Programs are available to one of ordinary skill in the art for the purpose of homology modeling, often embedded within a larger molecular modeling package or suite of related programs. For examples of homology modeling tools, see:

1. SEGMOD, part of LOOK (Levitt, 1992, *J. Mol. Biol.* 226: 507-533; Levitt, 1983, *J. Mol. Biol.* 170: 723-764; formerly available from the Molecular Applications Group, Palo Alto, Calif.)
2. MoE: The Structure Prediction tool within the "Molecular Operating Environment," (Chemical Computing Group Inc., 1010 Sherbrooke Street West, Suite 910, Montreal, Quebec, Canada.
3. Modeler (within the Quanta suite of programs, available from Accelrys, a subsidiary of Pharmacopeia, Inc.;
4. COMPOSER (Blundell et al., see e.g., *Protein Eng.*, 1:377-384, 1987; available as part of the *Sybyl* package, from Tripos, Inc., 1699 South Hanley Road, St. Louis, Mo.; see www.tripos.com/software/composer.html)

7.9.2 Representations of Structure Coordinates

The atomic structure coordinates of eat-16 or RGS-7 (either of which are referred to herein as the "RGS polypeptide") can be used in molecular modeling and design, as described more fully below. The present invention encompasses the structure coordinates and other information, e.g., amino acid sequence, connectivity tables, vector-based representations, temperature factors, etc., used to generate the three-dimensional structure of the RGS polypeptide for use in the software programs described herein and other software programs.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to a third atom, and at a specified torsion angle with respect to a fourth atom.

Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, are also useful for representing a three-dimensional molecular structure.

7.9.3 Computational Implementation:

The structural coordinates of the proteins of the present invention are stored in electronic form on computer-readable medium for use with a computer. Additionally, methods of rational drug design and virtual screening that utilize the coordinates of the proteins of the present invention are preferably performed on one or more computers, as depicted in FIG. 10.

According to FIG. 10, a computer system 100 on which the molecular modeling methods of the present invention may be carried out, comprises:

at least one central-processing unit 102 coupled via a bus 104 to working memory 106, a user interface 108, a network interface 110 and a machine-readable memory 107, for processing machine readable data; and a machine-readable memory 107 comprising a data storage material encoded with machine-readable data, wherein the data comprises the structural coordinates 134 of at least one of eat-16 and RGS-7 proteins;

a working memory 106 for storing an operating system 112, optionally one or more molecular structure databases 114, one or more pharmacophores 116 derived from the structural coordinates 134, a graphical user interface 118 and instructions for processing machine-readable data comprising one or more molecular modeling programs 120 such as a deformation energy calculator 122, a homology modeling tool 124, a de novo design tool, 126, a "docking tool" 128, a database search engine 130, a 2D-3D structure converter 132 and a file format interconverter 134.

Computer system 100 may be any of the varieties of laptop or desktop personal computer, or workstation, or a networked or mainframe computer or super-computer, that would be available to one of skill in the art. For example, computer system 100 may be an IBM-compatible personal computer, a Silicon Graphics, Hewlett-Packard, Fujitsu, NEC, Sun or DEC workstation, or may be a Convex supercomputer. Computer system 100 may also support multiple processors, as, for example in a Silicon Graphics Origin system.

Operating system 112 may be any suitable variety that runs on any of computer systems 100. For example, in one embodiment, operating system 112 is selected from the UNIX family of operating systems, for example, Ultrix from DEC, AIX from IBM, or IRIX from Silicon Graphics. It may also be a LINUX operating system. In another embodiment, operating system 112 may be a VAX VMS system. In a preferred embodiment, operating system 112 is a Windows operating system such as Windows 3.1, Windows NT, Windows 95, Windows 98, Windows 2000, or Windows XP. In yet another embodiment, operating system 112 is a Macintosh operating system such as MacOS 7.5.x, MacOS 8.0, MacOS 8.1, MacOS 8.5, MacOS 8.6, MacOS 9.x and MaxOS X.

The graphical user interface (GUI) 118 is preferably used for displaying representations of structural coordinates 134, or variations thereof, in 3-dimensional form on user interface 108. GUI 118 also preferably permits the user to manipulate the display of the structure that corresponds to structural coordinates 134 in a number of ways, including, but not limited to: rotations in any of three orthogonal degrees of freedom; translations; zooming in on specific portions of the structure; coloring of the structure according to a property that varies amongst to different regions of the structure; displaying subsets of the atoms in the structure; coloring the structure by atom type; and displaying tertiary structure such as α-helices and β-sheets as solid objects. Structural coordinates 134 are also optionally copied into memory 106 to facilitate manipulations with one or more of the molecular modeling programs 120.

Network interface 110 may optionally be used to access one or more molecular structure databases stored in the memory of one or more other computers.

7.9.4 Data Storage Media

The invention encompasses machine readable media embedded with the three-dimensional structure of the model described herein, or with portions thereof. As used herein, "machine readable medium" or "computer readable medium" refers to any media that can be read and accessed directly by a computer or scanner. Such media include, but are not limited to: magnetic storage media, such as floppy discs, hard disc storage media and magnetic tape; optical storage media such as optical discs; CD-ROM, CD-R or CD-RW; electronic storage media such as RAM or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with optical character recognition (OCR) technology.

A variety of data storage structures are available to a skilled artisan for creating a computer readable medium having recorded thereon the atomic structure coordinates of the invention or portions thereof and/or X-ray diffraction data. The choice of the data storage structure will generally be based on the means chosen to access the stored information.

In addition, a variety of data processor programs and formats can be used to store the sequence and structure information on a computer readable medium. Such formats include, but are not limited to, Protein Data Bank ("PDB") format (Research Collaboratory for Structural Bioinformatics); Cambridge Crystallographic Data Centre format; Structure-data ("SD") file format (MDL Information Systems, Inc.; Dalby et al., 1992, J. Chem. Inf. Comp. Sci. 32:244-255), and line-notation, e.g., as used in SMILES (Weininger, D., "SMILES, a Chemical Language and Information System. 1. Introduction to Methodology and Encoding Rules," 1988, J. Chem. Inf. Comp. Sci. 28:31-36), and CHUCKLES (Siani, M. A., Weininger, D., Blaney, J., "CHUCKLES: a method for representing and searching peptide and peptoid sequences on both monomer and atomic levels," J. Chem. Inf. Comp. Sci., 1994, 34:588-593).

Methods of converting between various formats read by different computer software will be readily apparent to those of skill in the art and programs for carrying out such conversions are widely available, either as stand-alone programs, e.g., BABEL (v. 1.06, Walters, P. & Stahl, M., ©1992, 1993, 1994) or integrated into other computer packages. All format representations of the polypeptide coordinates described herein, or portions thereof, are contemplated by the present invention. By providing a computer readable medium having stored thereon the atomic coordinates of the invention, one of skill in the art can routinely access the atomic coordinates of the invention, or portions thereof, and related information for use in modeling and design programs, described in detail below.

7.10 Uses of the Atomic Structure Coordinates 7.10.1 Molecular Modeling Methods In General Structure information, typically in the form of the atomic structure coordinates, can be used in a variety of computational or computer-based methods to, for example, design, screen for and/or identify compounds that bind the RGS or Gαq polypeptide or a portion or fragment thereof, or to intelligently design mutants that have altered biological properties.

In one embodiment, the structure coordinates of the present invention are useful for identifying and/or designing compounds that bind the RGS or Gαq polypeptide as an approach towards developing new therapeutic agents.

In another embodiment, the structure is probed with a plurality of molecules to determine their ability to bind to the RGS or Gαq polypeptide at various sites. Such compounds can be used as targets or leads in medicinal chemistry efforts to identify modulators, for example, inhibitors of potential therapeutic importance.

In still another embodiment, compounds that can isomerize to short-lived reaction intermediates in the chemical reaction of an RGS or Gαq polypeptide-binding compound with an RGS or Gαq polypeptide can be developed. Thus, the time-dependent analysis of structural changes in the RGS or Gαq polypeptide during its interaction with other molecules is enabled. The reaction intermediates of an RGS or Gαq polypeptide can also be deduced from the reaction product in co-complex with the RGS or Gαq polypeptide. Such information is useful to design improved analogues of known RGS or Gαq polypeptide modulators, e.g., inhibitors or to design novel classes of modulators based on the reaction intermediates of RGS or Gαq polypeptide-inhibitor co-complexes. This provides a novel route for designing RGS or Gαq polypeptide modulators, e.g., inhibitors, with both high specificity and stability.

In yet another embodiment, the structure can be used to computationally screen small molecule databases for chemical entities or compounds that can bind in whole, or in part, to an RGS or Gαq polypeptide. In this screening, the quality of fit of such entities or compounds to the binding site may be judged either by shape complementarity or by estimated interaction energy. Meng et al., 1992, *J. Comp. Chem.*, 13:505-524.

The computational methods of the present invention may be carried out with commercially available programs or with computer programs that are developed specially for the purpose and implemented on computer system 100. Commercially available programs comprise large integrated molecular modeling packages that contain at least two of the types of molecular modeling programs 120 shown in FIG. 10. Examples of such large integrated packages that are known to those skilled in the art include: Cerius2 (available from Accelrys, a subsidiary of Pharmacopeia, Inc.), Molecular Operating Environment (available from, Chemical Computing Group Inc., 1010 Sherbrooke Street West, Suite 910, Montreal, Quebec, Canada), Sybyl (available from Tripos, Inc., 1699 South Hanley Road, St. Louis, Mo.) and Quanta (available from Accelrys, a subsidiary of Pharmacopeia, Inc). Alternatively, the computational methods of the present invention may be achieved with one or more stand-alone programs that carries out one of the functions performed by molecular modeling programs 120. In particular certain aspects of the display and visualization of molecular structures may be accomplished by specialized tools, for example, GRASP (Nicholls, A.; Sharp, K.; and Honig, B., PROTEINS, Structure, Function and Genetics, 1991, Vol. 11 (No.4), pg. 281ff; available from Department of Biochemistry Rm 221, Columbia University Box 36, 630, W. 168th St., New York.

7.10.2 Computational Screening

In a preferred method, potential binding compounds may be obtained by rapid computational screening. Such a screening comprises testing a large number, which may be hundreds, or may preferably be thousands, or more preferably tens of thousands or even more preferably hundreds of thousands of molecules whose formulae are known. The molecules are obtained from one or more molecular structure databases, available in electronic form, for example, the "Available Chemicals Directory" ("ACD", available from MDL Information Systems, Inc., 14600 Catalina Street, San Leandro, Calif.); the National Cancer Institute database (NCIDB; also available from MDL Information Systems, Inc., 14600 Catalina Street, San Leandro, Calif.); the "MDL Drug Data Report" (MDDR, available from MDL Information Systems, Inc., 14600 Catalina Street, San Leandro, Calif.); the Comprehensive Medicinal Chemistry Database (CMC, available from MDL Information Systems, Inc., 14600 Catalina Street, San Leandro, Calif.); and any proprietary database of compounds with known medicinal properties, as is found in a large or small pharmaceutical company. The molecules in such databases are preferably stored as a connection table with or without a 2D representation comprising coordinates in just 2 dimensions, say x and y, and more preferably stored as at least one set of 3D coordinates corresponding to an experimentally derived or computer-generated molecular conformation. If the molecules are only stored as a connection table or a 2D set of coordinates, then it can be necessary to generate a 3D structure for each molecule before proceeding. Programs for converting 2D molecular structures or molecule connection tables to 3D structures include Converter (available from Accelrys, a subsidiary of Pharmacopeia, Inc.) and CONCORD (A. Rusinko III, J. M. Skell, R. Balducci, C. M. McGarity, and R. S. Pearlman, "CONCORD, A Program for the Rapid Generation of High Quality Approximate 3-Dimensional Molecular PlStructures," 1988 The University of Texas at Austin and Tripos Associates, available from Tripos, Inc., 1699 South Hanley Road, St. Louis, Mo.

As part of a computational screen, it is possible to "dock" 3D structures of molecules from a database into the active site of the protein in question, on a high throughput basis. Such a procedure can normally be subject to a number of user-defined parameters and thresholds according to desired speed of throughput and accuracy of result. Such parameters include the number of different starting positions from which to start a docking simulation and the number of energy calculations to carry out before rejecting or accepting a docked structure. Such parameters and their choices are familiar to one of skill in the art. Structures from the database can be selected for synthesis if their docked energy is below a certain threshold.

Alternatively, it is possible to carry out a "molecular similarity" search if a pharmacophore has been developed from the active site of the protein in question. A pharmacophore defines a set of contact sites on the surface of the active site, accompanied by the distances between them. A similarity search attempts to find molecules in a database that have at least one favorable 3D conformation whose structure overlaps favorably with the pharmacophore. For example, a pharmacophore may comprise a lipophilic pocket at a particular position, a hydrogen-bond acceptor site at another position and a hydrogen bond donor site at yet another specified position accompanied by distance ranges between them. A molecule that could potentially fit into the active site is one that can adopt a conformation in which a H-bond acceptor can reach the H-bond acceptor site on the pharmacophore, a H-bond donor can simultaneously reach the H-bond donor site of the pharmacophore and, for example, a group such as a phenyl ring can orient itself into the lipophilic pocket.

Even where a pharmacophore has not been developed, molecular similarity principles may be employed in a database searching regime. (See, for example, Johnson, M. A.; Maggiora, G. M., Eds. *Concepts and Applications of Molecular Similarity*, New York: John Wiley & Sons (1990)) In one embodiment, it is possible to search for molecules that have certain properties in common, for example, numbers of hydrogen bond donors or numbers of hydrogen bond acceptors, or overall hydrophobicity within a particular range of values. Alternatively, even where a pharmacophore is not known, similar molecules may be selected on the basis of optimizing an overlap criterion with the molecule of interest.

In searching a molecular structure database, a specialized database searching tool that permits searching molecular structures and sub-structures is typically employed. Examples of suitable database searching tools, known to one of skill in the art are: ISIS/Host and ISIS/Base (available from MDL Information Systems, Inc., 14600 Catalina Street, San Leandro, Calif.), Unity (available from Tripos, Inc., 1699 South Hanley Road, St. Louis, Mo.) or Catalyst (available from Accelrys, a subsidiary of Pharmacopeia, Inc.).

A molecular property of particular interest when assessing suitability of drug compounds is its hydrophobicity. An accepted and widespread measure of hydrophobicity is LogP, the $\log_{10}$ of the octanol-water partition coefficient. Measured values of LogP are available for many compounds. Methods and programs for calculating LogP are also available, see for example: CLOGP (Hansch, C., and Leo, A.; available from Tripos, Inc., 1699 South Hanley Road, St. Louis, Mo.); and ACD/LogP DB (Advanced Chemistry Development Inc., 90 Adelaide Street West, Suite 702, Toronto, Ontario Canada)

7.10.2 Rational Design Considerations

The design of compounds that bind to or inhibit an RGS or G$\alpha$q polypeptide according to this invention generally involves consideration of two factors. First, the compound must be capable of physically and structurally associating with an RGS or Gαq polypeptide. This association can be covalent or non-covalent. For example, covalent interactions may be important for designing irreversible or suicide inhibitors of a protein. Non-covalent molecular interactions important in the association of an RGS or Gαq polypeptide with its substrate include hydrogen bonding, ionic interactions and van der Waals and hydrophobic interactions. Second, the compound must be able to assume a conformation that allows it to associate with an RGS or Gαq polypeptide. Although certain portions of the compound will not directly participate in this association with an RGS or Gαq polypeptide, those portions may still influence the overall conformation of the molecule. This, in turn, may have a significant impact on potency. Such conformational requirements include the overall three-dimensional structure and orientation of the chemical group or compound in relation to all or a portion of the binding site, or the spacing between functional groups of a compound comprising several chemical groups that directly interact with an RGS or Gαq polypeptide.

The potential modulatory or binding effect of a chemical compound on an RGS or Gαq polypeptide may be analyzed prior to its actual synthesis and testing by the use of computer modeling techniques. If the theoretical structure of the given compound suggests insufficient interaction and association between it and an RGS or Gαq polypeptide, synthesis and testing of the compound is unnecessary. However, if computer modeling indicates a strong interaction, the molecule may then be synthesized and tested for its ability to bind to an RGS or Gαq polypeptide and inhibit its activity. In this manner, synthesis of ineffective compounds may be avoided. Visualization of molecular properties can be particularly important and may be aided by computer programs such as MOLCAD (Brickmann, J., and coworkers, see, for example, J. Comp.-Aid. Molec. Des., 7:503(1993); available from Tripos, Inc., 1699 South Hanley Road, St. Louis, Mo.).

7.10.3 Constructing Potential Molecules That Bind to RGS or Gαq Polypeptides

A modulatory or other binding compound of an RGS or Gαq polypeptide may be computationally evaluated and designed by means of a series of steps in which chemical groups or fragments are screened and selected for their ability to associate with the individual binding pockets or other areas of an RGS or Gαq polypeptide, for example, hydrophobic patches 1, 2 and/or 3 of an RGS polypeptide, as described hereinbelow. One skilled in the art may use one of several methods to screen chemical groups or fragments for their ability to associate with an RGS or Gαq polypeptide. This process may begin by visual inspection of, for example, the active site on the computer display based on the RGS or Gαq polypeptide coordinates. Selected fragments or chemical groups may then be positioned in a variety of orientations, or docked, within an individual binding pocket of an RGS or Gαq polypeptide as defined supra. Docking may be accomplished using software such as QUANTA (available from Accelrys, a subsidiary of Pharmacopeia, Inc.) and SYBYL, (available from Tripos, Inc., 1699 South Hanley Road, St. Louis, Mo.), followed by energy minimization and molecular dynamics simulations with molecular mechanics forcefields such as MM2 (see, e.g., Rev. Comp. Chem., 3, 81 (1991)), MM3 (Allinger, N. L., Bowen, J. P., and coworkers, University of Georgia; see, J. Comp. Chem., 17:429(1996); available from Tripos, Inc., 1699 South Hanley Road, St. Louis, Mo.), CHARMM and AMBER version 6 (Kollman, P. A., et al., School of Pharmacy, Department of Pharmaceutical Chemistry, University of California at San Francisco, ©2000), and Discover (available from Accelrys, a subsidiary of Pharmacopeia, Inc.).

Specialized computer programs may also assist in the process of selecting fragments or chemical groups. These include:

1. GRID (Goodford, (1985), *J. Med. Chem.*, 28:849-857). GRID is available from Oxford University, Oxford, UK;

2. MCSS (Miranker & Karplus, (1991), Proteins: Structure, Function and Genetics 11:29-34). MCSS is available from Accelrys, a subsidiary of Pharmacopeia, Inc., as part of the Quanta package;

3. AUTODOCK (Goodsell & Olsen, (1990), *Proteins: Structure, Function, and Genetics* 8:195-202). AUTODOCK is available from Scripps Research Institute, La Jolla, Calif.; and 4. DOCK (Kuntz et al., (1982), J. Mol. Biol., 161:269-288). DOCK is available from University of California, San Francisco, Calif.

5. GOLD (Jones, et al., (1995), J. Mol. Biol., 245:43-53). GOLD is available from the Cambridge Crystallographic Data Center, 12 Union Road. Cambridge, U.K.;

6. GLIDE. GLIDE is available from Schrodinger, Inc.

7. ICM (Abagayan, et al.) ICM is available from MolSoft, L.L.C., 3366 North Torrey Pines Court, Suite 300, La Jolla, Calif. 92037.

Once suitable chemical groups or fragments have been selected, they can be assembled into a single compound or inhibitor. Assembly may proceed by visual inspection of the relationship of the fragments to each other in the three-dimensional image displayed on a computer display in relation to the structure coordinates of an RGS or Gαq polypeptide. This would be followed by manual model building using software such as QUANTA or SYBYL.

Useful programs to aid one of skill in the art in connecting the individual chemical groups or fragments include:

1. CAVEAT (Bartlett et al., 1989, "CAVEAT: A Program to Facilitate the Structure-Derived Design of Biologically Active Molecules," *In Molecular Recognition in Chemical and Biological Problems*, Special Pub., Royal Chem. Soc. 78:182-196). CAVEAT is available from the University of California, Berkeley, Calif.;

2. 3D Database systems such as MACCS-3D (MDL Information Systems, San Leandro, Calif.). This area is reviewed in Martin, (1992), *J. Med. Chem.*, 35:2145-2154); and 3. HOOK (available from Accelrys, a subsidiary of Pharmacopeia, Inc., as part of the Quanta package).

Instead of proceeding to build a RGS or Gαq modulator in a step-wise fashion one fragment or chemical group at a time, as described above, RGS or Gαq binding compounds may be designed as a whole or de novo using either an empty active site or optionally including some portion(s) of a known inhibitor(s). These methods include:

1. LUDI (Bohm, (1992), J. Comp. Aid. Molec. Design 6:61-78). LUDI is available from Accelrys, a subsidiary of Pharmacopeia, Inc., as part of the Insight package, see www.accelrys.com/insight/ludi.html;

2. LEGEND (Nishibata & Itai, (1991), *Tetrahedron* 47:8985). LEGEND is available from Molecular Simulations, Burlington, Mass.; and 3. LeapFrog (available from Tripos, Inc., 1699 South Hanley Road, St. Louis, Mo.; www.tripos.com/software/leapfrog.html).

Other molecular modeling techniques may also be employed in accordance with this invention. See, e.g., Cohen et al., (1990), *J. Med. Chem.* 33:883-894. See also, Navia & Murcko, (1992), *Current Opinions in Structural Biology* 2:202-210.

7.10.4 Quantifying Potential Binding Molecules

Once a compound has been designed or selected by the above methods, the efficiency with which that compound may bind to RGS or Gαq polypeptide may be tested and optimized by computational evaluation. For example, a compound that has been designed or selected to function as a RGS or Gαq polypeptide activator (agonist) or inhibitor (antagonist) also preferably occupies a volume not overlapping the volume occupied by the active site residues when the native substrate is bound. An effective RGS or Gαq polypeptide activator or inhibitor must preferably demonstrate a relatively small difference in energy between its bound and free states (i.e., it must have a small deformation energy of binding). Thus, the most efficient RGS or Gαq polypeptide activators or inhibitors should preferably be designed with a deformation energy of binding of not greater than about 10 kcal/mol, preferably, not greater than 7 kcal/mol. RGS or Gαq polypeptide activators or inhibitors may interact with the protein in more than one conformation that is similar in overall binding energy. In those cases, the deformation energy of binding is taken to be the difference between the energy of the free compound and the average energy of the conformations observed when the activator or inhibitor binds to the enzyme.

A compound selected or designed for binding to RGS or Gαq polypeptide may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the activator or inhibitor and the protein when the activator or inhibitor is bound to it preferably make a neutral or favorable contribution to the enthalpy of binding.

Specific computer software is available in the art to evaluate compound deformation energy and electrostatic interaction. Examples of programs designed for such uses fall into approximately three levels of sophistication. The crudest level of approximation, molecular mechanics, is also the cheapest to compute and can most usefully be used to calculate deformation energies. Molecular mechanics programs find application for calculations on small organic molecules as well as polypeptides, nucleic acids, proteins and most other biomolecules. Examples of programs which have implemented molecular mechanics force fields include: AMBER, version 6 (Kollman, P. A., et al., School of Pharmacy, Department of Pharmaceutical Chemistry, University of California at San Francisco, ©2000); CHARMM (see B. R. Brooks, R. E. Bruccoleri, B. D. Olafson, D. J. States, S. Swaminathan, and M. Karplus, "CHARMM: A Program for Macromolecular Energy, Minimization, and Dynamics Calculations," J. Comp. Chem., 4, 187-217, (1983); A. D. MacKerell, Jr., B. Brooks, C. L. Brooks, Ill, L. Nilsson, B. Roux, Y. Won, and M. Karplus, "CHARMM: The Energy Function and Its Parameterization with an Overview of the Program," in The Encyclopedia of Computational Chemistry, 1, 271-277, P. v. R. Schleyer et al., editors, John Wiley & Sons: Chichester, (1998); QUANTA/CHARMm (available from Accelrys, a subsidiary of Pharmacopeia, Inc.); and Insight II/Discover (available from Accelrys, a subsidiary of Pharmacopeia, Inc.).

The next level of sophistication comprises the so-called "semi-empirical" methods, which are relatively inexpensive to compute and are most useful for calculating deformation energies of organic molecules. Examples of program packages that provide semi-empirical capability are MOPAC 2000 (Stewart, J. J. P., et al., available from Schrodinger, Inc., 1500 S.W. First Avenue, Suite 1180, Portland, Oreg.) and AMPAC (Holder, A., et al., available from Tripos, Inc., 1699 South Hanley Road, St. Louis, Mo.;

The highest level of sophistication is achieved by those programs that employ so-called ab initio quantum chemical methods and those from density functional theory, for example: Gaussian 98, Revision A.9, (available from Gaussian, Inc., Carnegie Office Park, Building 6, Suite 230, Carnegie, Pa.); and Q-Chem2.0 ("A high-performance ab initio electronic structure program," J. Kong, et al., J. Comput. Chem., (2000) 21, 1532-1548; available from Four Triangle Lane, Suite 160, Export, Pa). These programs may be installed, for instance, on a computer workstation, as is well-known in the art. Other hardware systems and software packages will be known to those skilled in the art.

7.10.5 Further Manipulations of the RGS or Gαq Polypeptide Structures and Binding Molecules Once an RGS or Gαq polypeptide-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity, polarity and charge as the original group. For selection of appropriate groups, any of several chemical models can be used, e.g., isolobal or isosteric analogies. Groups known to be bio-isosteres of one another are particularly preferred. One of skill in the art will understand that substitutions known in the art to alter conformation should be avoided. Such altered chemical compounds may then be analyzed for efficiency of binding to eat-16 by the same computer methods described in detail above.

The structure coordinates of wild-type eat-16 and its mutants will also facilitate the identification of related proteins or enzymes analogous to eat-16 in function, structure or both, thereby further leading to novel therapeutic modes for treating or preventing eat-16 mediated diseases.

Subsets of the atomic structure coordinates can be used in any of the above methods. Particularly useful subsets of the coordinates include, but are not limited to, coordinates of single domains, coordinates of residues lining an active site, coordinates of residues that participate in important protein-protein contacts at an interface, and Cα coordinates. For example, the coordinates of one domain of a protein that contains the active site may be used to design inhibitors that bind to that site, even though the protein is fully described by a larger set of atomic coordinates. Therefore, a set of atomic coordinates that define the entire polypeptide chain, although useful for many applications, do not necessarily need to be used for the methods described herein.

7.10.6 Activity of Binding Molecules

The binding molecules described above can be synthesized according to synthetic techniques well known to those of skill in the art. The binding molecules preferably modulate the activity of the RGS or Gαq polypeptide and/or a molecule that interacts with the RGS or Gαq polypeptide. The activity of a binding molecule can be assayed easily by methods well known to those of skill in the art. For instance, an RGS or Gαq polypeptide or a cell comprising the RGS or Gαq polypeptide can be contacted with the binding molecule and then assayed for modulation of RGS activity or Gαq activity. Assays for RGS activity or Gαq activity are described in detail above.

Preferably, binding molecules may be identified by high throughput screening methods, according to which large libraries of ligands are screened against a particular target. A large library of ligands preferably contains more than 1,000 distinct ligands, more preferably contains more than 10,000 distinct ligands, even more preferably contains more than 100,000 distinct ligands and most preferably contains more than 1,000,000 distinct ligands. High throughput screening techniques typically employ robotically controlled assay systems, and take advantage of the latest improvements in miniaturization and automation. Samples are typically assayed on 96-well plates or microtiter plate arrays, and measurements may be taken in parallel. For an overview of high throughput screening techniques, see, for example, Razvi, E. S., "High-Throughput Screening—Where Are We Today?," Drug & Market Development Publications, (June 1999), and Razvi, E. S., "Industry Trends in High-Throughput Screening," Drug & Market Development Publications, (August 2000).

8. EXAMPLES

8.1 Example 1

Compounds That Modulate Bladder Contractility

This example demonstrates the identification of Compound I (FIG. 3A), Compound II (FIG. 3B) and Compound III (FIG. 3C) via screening methods of the instant invention. Compounds I, II and III are capable of modulating bladder contractility.

Isolated Rat Bladder Strips

Tissue Preparation

Male rats (Harlan, Sprague Dawley, 250-350 g) were sacrificed by decapitation, the bladder removed and cleaned of connective tissue. Strips of bladder were then cut from the bladder body and each was placed in an organ bath, suspended between a fixed hook and a force transducer, containing oxygenated physiological buffer (composition in mM: NaCl 118.4, KCl 4.7, $KH_2PO_4$ 1.2, $MgSO_4$ 1.3, $CaCl_2$ 1.8, glucose 10.1, $NaHCO_3$ 25, gassed with 95%$O_2$/5%$CO_2$) and maintained at 37° C. Force generated by the bladder strips was recorded and measured using an *AcqKnowledge* data acquisition system (*AcqKnowledge* for MP100WS, Biopac Systems Inc., Goleta, Calif.).

Experimental Design:

The bladder strips were primed by stimulating them with 10 µM carbachol to evoke a contraction. The strips were then washed multiple times with fresh physiological buffer and allowed to fully relax. Following a period of recovery, the strips were again challenged with 10 µM carbachol to produce a contraction; this contractile response served as the control response. The strips were again washed multiple times and allowed to fully relax (45 minutes). Test compound or vehicle was then added to each organ bath. Following a one hour incubation period, the strips were again stimulated with 10 µM carbachol and the contractile response measured.

Data Analysis

The percent inhibition of the carbachol response by the test compounds was calculated by comparing control and post-compound carbachol responses corrected for vehicle effects.

| Results | | |
|---|---|---|
| Compound | Inhibition | N |
| Compound I (10 µM) | ++ | 10 |
| Compound III (3 µM) | + | 6 |
| Compound II (3 µM) | + | 3 |

+ 20-40%
++ 40-60%

8.2 Example 2

Methods for Preparation of Compounds I, II and III

This example provides methods for synthesizing compounds I, II and III.

Compound I may be prepared by the general procedures described by J. L. Romine et al., in U.S. Pat. No. 5,869,509, issued Feb. 9, 1999, and, more specifically, in Example 140 of said U.S. patent. Compound III is identical to Formula XXVIII of J. L. Romine et al., U.S. Pat. No. 6,077,861, issued Jun. 20, 2000, and may be prepared by the general procedures described therein and, more specifically, in Example 141 of said U.S. patent. The contents of U.S. Pat. Nos. 5,869,509 and 6,077,861 are hereby incorporated by reference in their entireties.

Compound II was prepared according to the method depicted in Reaction Scheme 1.

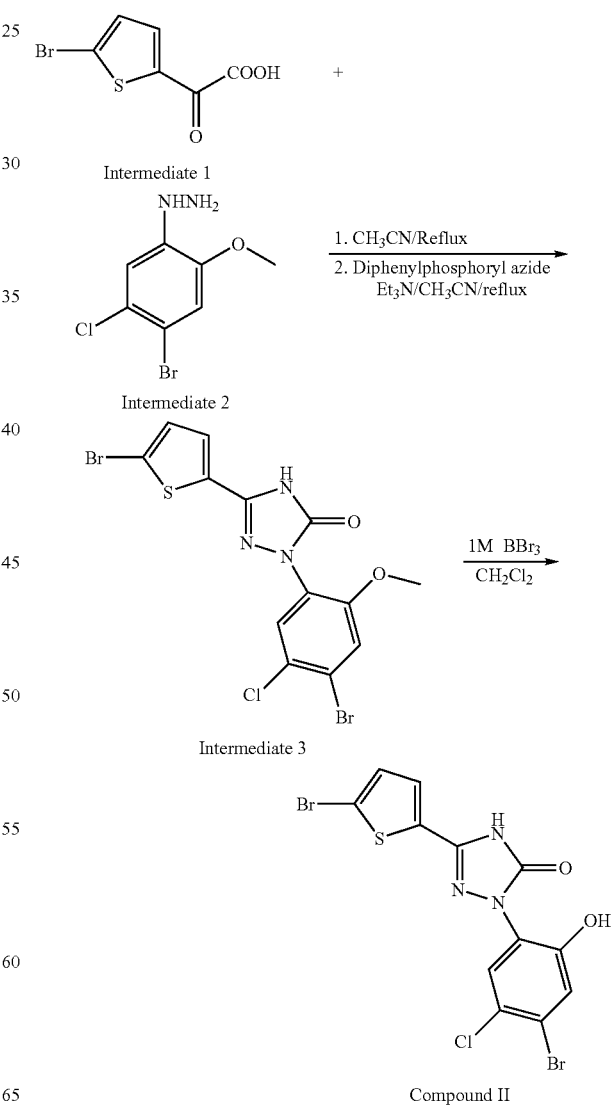

Compound II

Preparation of Intermediate 1

Step A: Preparation of Ethyl 2-(5-bromothien-2-yl)glyoxalate

A solution of $AlCl_3$ (61 g, 455 mmol) in nitromethane (125 mL) was added dropwise to a stirring mixture of ethyloxalyl-chloride (50.8 ml, 455 mmol) and 2-bromothiophene (49.5 g, 304 mmol) at 0-5° C. The reaction was stirred for 1 hour at 0.5° C. following the addition step, then 3 hours at room temperature. The reaction was then poured into 1 L ice water and extracted with diethyl ether (3×250 mL). The combined diethyl ether layers were extracted with saturated aqueous $NaHCO_3$ solution (250 mL), dried over $Na_2SO_4$, and concentrated under vacuum. The residue was Kugelrohr distilled to yield ethyl 2-(5-bromothien-2-yl)glyoxalate as a yellow solid (45.7 g, 57%). MS (MH+): 262.98; $^1H$ NMR (300 MHz, $CDCl_3$) d 7.90 (1H, d, J=4.1 Hz), 7.17 (1H, d, J=4.2 Hz), 4.42 (2H, q, J=7.2 Hz), 1.43 (3H, t, J=7.1 Hz); m.p. 63-66° C.

Step B: Preparation of 2-(5-bromothien-2-yl)glyoxalic Acid, Intermediate 1

Ethyl 2-(5-bromothien-2-yl)glyoxalate (45.6 g, 173 mmol) from Step A was dissolved in a mixture of 100 mL THF, 100 mL methanol, and 300 mL water, then treated with 10 N NaOH (26 ml, 260 mmol) at room temperature for 20 hours. Volatile solvents were removed by rotary evaporation. The residue was dissolved in 2 L water and extracted with diethyl ether (250 mL). The aqueous layer was acidified to pH 1 with 6 N HCl, and extracted with diethyl ether (3×300 mL). The combined diethyl ether extracts were dried over $Na_2SO_4$ and concentrated in vacuo to yield 2-(5-bromothien-2-yl)glyoxalic acid, Intermediate 1 (38.7 g, 95%). The product was then recrystallized from diethyl ether. m.p. 119-120° C.; MS (M−H) 235.1; $^1H$ NMR (300 MHz, $CDCl_3$) d 9.00 (1H, br s), 8.15 (1H, d, J=4.2 Hz), 7.16 (1H, d, J=4.2 Hz); $^{13}C$ NMR (75 MHz, $CDCl_3$) d 173.80, 159.58, 140.14, 137.17, 132.58, 130.48; IR (KBr) 3326, 3124, 1756, 1634, 1415, 1363, 1308, 1253 $cm^{-1}$;

Analytic composition for $C_6H_3O_3SBr$:

| Calculated: | C, 30.66; | H, 1.29; | Br, 33.99. |
|---|---|---|---|
| Found: | C, 30.92; | H, 1.46; | Br, 33.94. |

Preparation of Intermediate 2:

Step A: Preparation of 4-chloro-5-bromo-2-aminoanisole

Bromine (26.4 g) was added to a solution of 4-chloro-o-anisidine (23.55 g) in dichloromethane (400 mL) at room temperature. The resulting mixture was stirred for 10 hours and quenched with NaOH. The organic layer was washed with brine, dried over $MgSO_4$, and concentrated. Purification by flash chromatography over silica gel (elution with 10% ethyl acetate in hexanes) gave 11.8 g (33%) of the desired 4-chloro-5-bromo-2-aminoanisole. $^1H$ NMR (300 MHz, CDC13) d 6.94 (s, 1 H), 6.78 (s, 1 H), 3.83 (s, 3 H).

Step B: Preparation of (4-bromo-5-chloro-2-methoxyphenyl)hydrazine, Intermediate 2

A suspension of 4-chloro-5-bromo-2-aminoanisole (7.68 g) from Step A in 100 mL concentrated HCl was cooled to −10° C. With mechanical stirring, a solution of sodium nitrite (2.25 g) in 10 mL water was added slowly, maintaining the reaction temperature at −10° C. The tip of the addition pipette was kept below the surface of the reaction. The reaction was warmed to 0° C. and stirred for 1 hour. The reaction was then cooled to −35° C., and a solution of $SnCl_2 \cdot 2H_2O$ (15 g) in 17 mL concentrated HCl was added slowly, maintaining the reaction temperature at −35° C. The reaction was warmed to 0° C. and stirred for 1 hour. The solid product was filtered and washed with concentrated HCl and water. The solid was then stirred in a mixture of 200 mL ethyl acetate and 335 mL 3N NaOH for 1 hour. The organic layer was separated, dried over sodium sulfate, and concentrated to dryness under vacuum to yield 5.5 g (73%) of the desired product (4-bromo-5-chloro-2-methoxyphenyl)hydrazine, Intermediate 2, which was used in the next step without purification.

Preparation of Intermediate 3:

(4-Bromo-5-chloro-2-methoxyphenyl)hydrazine (Intermediate 2) (5.0 g) and 2-(5-bromothien-2-yl)glyoxylic acid (4.7 g) were refluxed in acetonitrile (15-25 ml/mmol starting material) for 30-60 minutes. The reaction was cooled to room temperature. Triethylamine (2.22 g) and diphenylphosphorylazide (6.05 g) were added, and the reaction was heated at reflux 3-18 hours. After cooling to room temperature, solids were filtered and washed with acetonitrile and ether to yield (75%) 2-(4-bromo-5-chloro-2-methoxyphenyl)-2,4-dihydro-5-(5-bromothien-2-yl)-3H-1,2,4-triazol-3-one (Intermediate 3).

$^1H$ NMR (300 MHz, DMSO-$d_6$) δ12.60 (s, 1 H), 7.70 (s, 1 H), 7.59 (s, 1 H), 7.40 (d, J=4.0 Hz, 1 H), 7.34 (d, J=4.0 Hz, 1 H), 3.82 (s, 3 H) ppm;

$^{13}C$ NMR (75 MHz, DMSO-$d_6$) 154.3, 152.8, 140.8, 131.4, 130.0, 129.9, 128.2, 125.2, 124.0, 122.7, 117.9, 114.5, 56.8 ppm; IR (KBr, $cm^{-1}$) 3442, 1712; MS(ESI) 464 (M−1)+;

Anal composition for $C_{13}H_9Br_2ClN_3O_2S$

| Calculated: | C, 33.54; | H, 1.73; | N, 9.03. |
|---|---|---|---|
| Found: | C, 33.95; | H, 1.92; | N, 9.04. |

Preparation of 2-(4-bromo-5-chloro-2-hydroxyphenyl)-2,4-dihydro-5-(5-bromothien-2-yl)-3H-1,2,4-triazol-3-one (Compound II)

2-(4-Bromo-5-chloro-2-methoxyphenyl)-2,4-dihydro-5-(5-bromothien-2-yl)-3H-1,2,4-triazol-3-one (Intermediate 3) (1.395 g) was suspended in anhydrous dichloromethane (20-25 mL/mmol of Intermediate 3) under argon and cooled to −78° C. A 1 M solution of $BBr_3$ (9 mL) in anhydrous dichloromethane was added via a dropping funnel over a 45 minute period. After the addition was complete, the reaction was warmed to room temperature and stirred for 5 hours. The reaction was quenched by the addition of 5-10 mL water. Volatile solvent was removed under vacuum and the crude product was filtered and washed with water. The solid was refluxed in a mixture of acetone and ethanol for 15 minutes. After cooling to room temperature, the purified product was filtered and washed with acetone and ethanol. The solid was dried under high vacuum to yield 1.1 g (81%) of the desired product, Compound II.

$^1H$ NMR (300 MHz, DMSO-$d_6$) 12.6 (s, 1 H), 10.5 (s, 1 H), 7.63 (s, 1 H), 7.43 (d, J=4 Hz, 1 H), 7.34 (d, J=4 Hz, 1 H), 7.33 (s, 1 H) ppm;

$^{13}$C NMR (75 MHz, DMSO-d$_6$) 153.1, 152.5, 140.9, 131.4, 130.1, 129.2, 128.2, 124.3, 122.4, 121.7, 121.5, 114.5 ppm; IR (KBr, cm$^{-1}$) 3224 (br), 1776; MS(ESI) 450(M−1)$^+$;

Analytic composition for $C_{12}H_6Br_2ClN_3O_2S$

| Calculated: | C, 31.92; | H, 1.34; | N, 9.31. |
| Found: | C, 32.34; | H, 1.46; | N, 9.24. |

8.3 Example 3

Validation of Activity of Compounds I and II

This example demonstrates the activity of Compounds I, II and III in in vitro bladder function assays.

In Vitro Whole Bladder Model

Isolated Bladder Preparation

The model used for these experiments was a modified version of that previously described by Malkowicz et al., 1986, *J. Urol.* 136: 1324-1329. Briefly, a female rat (Harlan, Sprague Dawley, 250-350 g) was sacrificed by decapitation. The bladder was excised, cleaned of connective tissue and the ureters were tied. The bladder was emptied, catheterized at the urethral opening and mounted in a 50 ml organ bath containing physiological buffer (composition in mM: NaCl 118.4, KCl 4.7, KH$_2$PO$_4$ 1.2, MgSO$_4$ 1.3, CaCl$_2$ 1.8, glucose 10.1, NaHCO$_3$ 25, gassed with 95%O$_2$/5%CO$_2$ and maintained at 37° C.). A three-way valve connected the bladder catheter to an infusion pump and to another three-way valve. The latter valve was connected to a pressure transducer and an "emptying tube". The emptying tube was suspended approximately 10 cm above the pressure transducer and it was graduated to allow a direct reading of the volume of bladder emptying at the end of the infusion. The bladder was held at the same height as the pressure transducer.

Experimental Design

The bladder was infused with physiologfical buffer at a rate of 0.05 ml/min for 30 minutes. The pressure developed in the bladder during the infusion was recorded on-line using an *AcqKnowledge* data acquisition system (*AcqKnowledge* for MP100WS, Biopac Systems Inc., Goleta, Calif.). When the infusion was complete, the second three-way valve was opened allowing the bladder to empty ("spontaneous bladder emptying"). After spontaneous emptying, which produced only a partial emptying, 1 μM carbachol and then 10 μM carbachol was added to the bath to induce complete emptying. The volume of spontaneous emptying and emptying due to 1 μM and 10 μM carbachol were measured. This procedure was repeated multiple times in the same bladder. The second bladder filling served as a pre-drug or pre-vehicle baseline. Bladders were exposed to vehicle or drug for 1 hour prior to the third bladder filling.

Data Analysis

Bladder function was assessed by comparing the pressure developed in the bladders as a function of volume (statistical analysis compared pressure developed from 0.2 to 1.3 ml filling volume in 0.1 ml increments). Additionally, changes in spontaneous and carbachol-induced emptying volumes were also compared. Statistical analysis of the data was performed using a t-test and the significance of difference was determined by two-tailed P value of less than 0.05.

Results

Compound III (100 and 300 nM) significantly reduced the pressure developed within the bladder at any given infusion volume when compared to the pre-drug control filling (i.e. bladder compliance was improved). Vehicle treatment did not produce any significant changes.

8.4 Example 4

Identification of Pathway and Targets via Model Organisms

This example demonstrates that compounds I and II are capable of modulating the interaction of Gαq proteins and RGS proteins.

Methods

Phenotypic and Genetic Analysis

*C. elegans* strains were cultured and maintained according to standard procedures (Brenner, 1974; Hodgkin, 1988). All strains were assayed at 20° C. unless otherwise indicated.

Compound Treatment

Treatment of *C. elegans* with various compounds was conducted as follows:

compound was mixed with killed bacteria slurry (strain OP50, taken through multiple freeze-thaw cycles) to 2× desired final concentration. Adult wildtype (Bristol N2) or mutant hermaphrodites were collected in M9. Worms were mixed 1:1 with compound/bacteria mixture, and plated on peptone-free NGM plates. Plates were allowed to dry, and then placed at 20° C. until assayed.

For egg-laying assays, adults were treated overnight with compound. Approximately thirty animals were loaded onto agar pads made on glass slides and examined under Nomarski optics. Animals were scored as egg-laying defective if they contained>comma stage embryos.

EMS Mutagenesis/Screening

EMS mutagenesis was conducted according to standard procedures (Brenner, 1974). Briefly, Bristol N2 hermaphrodites of L4 stage were treated with 0.25% EMS (Sigma) in M9 for 4 hours at 20° C. Worms were washed 4× in M9, and plated onto seeded NGM plates (Po). Staged collections were taken of the F1 generation, and these were plated onto NGM plates at either 20° C. or 15° C. Staged collections of the F2 generation were plated onto NGM plates and allowed to grow until adulthood. These adults were then collected and treated with compound. After overnight treatment, animals that were not visibly egg-laying defective were isolated and re-tested for resistance to compound.

Mapping/Cloning Resistant Mutants

Mutant hermaphrodites were crossed to males of the polymorphic strain CB4856 (Hawaiian isolate). Recombinant homozygous mutants in the F2 generation were selected by visible phenotype and assayed for SNPs identified both through the Washington University SNP project and at Exelixis. Genotyping of SNP markers was performed using standard methods (Kwok, 2000). For eat-16(ep273) and egl-30(ep271), the genes were identified by sequence analysis of the corresponding genes in the mutant strains. Sequencing was performed according to manufacturer's instructions (Perkin Elmer Applied Biosystems). The eat-16(ep273) missense mutation changes a glutamine at position 158 to a lysine. egl-30(ep271) results in an amino acid substitution of an isoleucine at position 244 for methionine.

References

Brenner, 1974, *Genetics* 77, 71-94.

Hodgkin et al., 1988, *The Nematode Caenorhabditis elegans* (ed. W. B. Wood), Cold Spring Harbor, N.Y. Cold Spring Harbor Laboratory.

Kwok, 2000, *Pharmacogenomics* 1, 95-100.

8.5 Example 5

Identification of *C. elegans* Mutants

This example demonstrates the identification of the biological targets of Compounds I and II in *C. elegans*.

Compound I, causes neuromuscular defects in *C. elegans*, including pharyngeal pumping, body movement, and egg-laying. The *C. elegans* genome was surveyed for mutations that confer resistance to the egg-laying defect caused by compound. Mutations were identified in members of a conserved G-protein signaling pathway. Loss of function mutations in an RGS homolog, eat-16, conferred very strong resistance to compound effect. In addition, an activating mutation in a Gαq homolog, egl-30(ep271), was also identified. In *C. elegans*, RGS/eat-16 had been shown to negatively regulate the activity of Gαq/egl-30.

The mutation identified in Gαq/egl-30(ep271) was unique in its effect on compound response: other activating mutations in Gαq/egl-30 did not confer resistance (See below). The altered residue in egl-30(ep271) is absolutely conserved in all heterotrimeric Gα subunits that are regulated by RGS proteins. It is therefore possible to speculate that this mutation disrupts the ability of the RGS to regulate Gαq, mimicking a loss of RGS function. Experiments in yeast back this contention. Taken together, these results suggest that compound AG4A modulates the activity of the RGS or RGS/Gαq complex, resulting in decreased Gαq signaling.

Identification of the egl-30(M2441) Mutation:

The r4A-1 strain was identified in a screen for resistance to the BMS AG4A compound. The mutation causing resistance in this strain was mapped to a region containing a *C. elegans* Gαq homolog, egl-30. The phenotypes of known activating mutations in egl-30 resembles that observed in the r4A-1 strain. Sequencing of the egl-30 genomic region in the r4A-1 strain identified a G to A change in exon 6 of the coding sequence. This results in a methionine(M) to isoleucine(I) change at position 244 in the amino acid sequence of the protein. This residue is located in the Switch III region of the protein, which is known to be involved in many aspects of Gα function, including GTP hydrolysis, effector binding, and RGS binding. M244 is absolutely conserved in all Gαs that are regulated by RGS proteins. Interestingly, in those Gαs that are not regulated by RGS proteins, the analogous residue is a leucine (L). The conserved nature of this change suggest that this region of the protein may be involved in compound binding.

Identification of the eat-16(E158K) Mutation: Method Above

The r4A-3 strain was identified in an EMS mutagenensis screen for resistance to the BMS AG4A compound. The mutation causing resistance in this strain was mapped to a region containing a *C. elegans* RGS homolog, eat-16. The phenotypes of known loss of function mutations in eat-16 resembles that observed in the r4A-3 strain. Sequencing of the eat-16 genomic region in the r4A-3 strain identified a G to A change in exon 6 of the coding sequence. This results in a glutamine(E) to lysine(K) change at position 158 in the amino acid sequence of the protein. This region of the protein lies is in the N-terminus, separating the DEP domain from the GGL domain. To date, there is no known functional role for this region.

8.6 Example 6

Human Targets of Compounds I and II

This example demonstrates the identification of human homologues of the *C. elegans* polypeptides of Example 5. The human homologues are targets of Compounds I and II.

*C. elegans* EAT16 protein has been hypothesized to play a role in the mechanism of action of UI (Urge Incontinence) Compound I. Bioinformatics analysis was initiated to find the potential human homologue of *C. elegans* EAT16.

EAT16 is a 473 amino acid protein. Protein domain analysis using Hidden Markov Models (HMM) profiles revealed there are two domains in this protein. The domain information is as follows:

DEP (Domain found in Dishevelled, EGL10 and Pleckstrin): Amino acids: 15-96

RGS (Regulator of G-protein Signaling domain): Amino acids: 287-407

The EAT16 sequence was searched against the non-redundant protein database using the gapped BLAST program. The search identified the human RGS7 (Regulator of G-protein signaling) protein as the top hit. The other top hits include RGS6, RGS9 and RGS 11.

The RGS protein superfamily consists of six sub-families. RGS6, 7, 9 and 11 are related to each other and they have been shown to belong in a single subfamily by phylogenetic analysis (B. Zheng, et al. TIBS, 24:411-414, (1999)). The search results are consistent with the phylogenetic analysis. EAT16 is closer to the RGS 6,7,9 and 11 proteins when compared to other members of the RGS protein family. Among the subfamily members, EAT16 is closer to RGS7 when compared to RGS6, 9 and 11.

Comparison of EAT16 Against Various RGS Proteins:

EAT 16 vs. RGS6: Identity=156/439 (35%), Similarity=244/439 (55%)

RGS7: Identity=161/440 (36%), Similarity=255/440 (57%)

RGS9: Identity=139/423 (32%), Similarity=235/423 (54%)

RGS11: Identity=136/417 (32%), Similarity=237/417 (56%)

Domain analysis of RGS6 and RGS7 revealed that they have DEP and RGS domains consistent with EAT16. RGS6 has a G-gamma domain in addition to the above two domains. The profile score for the G-protein gamma subunit is not high. No conclusion can be derived based on this score. Nonetheless, from the absence of this domain and from sequence similarity, it appears as if EAT16 is closer to RGS7 than RGS6.

The next step is to take the human RGS6 and 7 proteins and search against all proteins present in *C. elegans*. This will detect which *C. elegans* proteins are closer to the human RGS6 and 7. Both RGS6 and 7 identified EGL10, another *C. elegans* protein, as the top hit. FIG. 7 illustrates the bioinformatics analysis workflow starting from EAT16.

EGL10 is a 558 amino acid protein. The sequence similarity between the RGS proteins and EGL10 is in two distinct regions.

| Comparison of EGL10 against RGS6 and 7 proteins: | |
| --- | --- |
| EGL10: | Amino acids 19 to 256: 61% identity (76% similarity) with RGS6 |
| | Amino acids 357 to 548: 41% identity (63% similarity) with RGS6 |
| EGL10: | Amino acids 19 to 226: 71% identity (84% similarity) with RGS7 |
| | Amino acids 337 to 546: 41% identity (60% similarity) with RGS7 |

The region between amino acid 225 to amino acid 350 of EGL10 does not match the RGS proteins. To determine how the matching regions correspond to the functional domains of EGL10, an analysis using Hidden Markov Model (HMM) profiles was performed. The results of the analysis are given below:

| EGL10: | Amino acids 37 to 118: DEP domain |
| --- | --- |
| | Amino acids 329 to 395: G-protein gamma subunit |
| | Amino acids 421 to 537: RGS domain |

There is no functional domain present in the sequence region between amino acid 225 to amino acid 330. This region seems to be unique to EGL10. This suggests that EGL10 and EAT16 are both closer to the RGS6 and 7 proteins. However, EGL10 differs from these proteins in having a unique domain that does not correspond to RGS6, RGS7 or EAT 16. Also, this region of EGL10 is not similar to any of the proteins present in the complete protein database. FIG. 1A gives the alignment of various domains in EGL10, EAT16, RGS6 and RGS7 proteins.

Experimental analysis revealed that EGL10 is not involved in the mode of action of Compound I. The difference between EAT16 and EGL10 can be attributed to:
1. Absence of an obvious G-protein gamma subunit domain in EAT16
2. Unique region in EGL10 which does not have homology to any protein in the database.

There are two conclusions:
1. The closest human protein to *C. elegans* EAT16 seems to be RGS7. The second best match, based on sequence similarity, is RGS6. Human RGS6 is highly related to RGS7 (73% identity and 82% similarity) and also aligns closely to EAT16. They also belong to the sub-family of RGS proteins and may have functional commonality with EAT 16.
2. EGL10 has a striking sequence similarity with the N-terminus region of RGS 6 and 7. This fact suggests that EGL10 and EAT16 are closely related to the same human proteins RGS6 and RGS7. But they seem to play a different role in their response to Compound I. This difference can be attributed to the unique region in EGL10 and absence of an obvious G-protein gamma subunit domain in EAT16.

8.7 Example 7

RGS Domain mRNA Expression in Bladder Cells

This example demonstrates that the human RGS polypeptide is expressed in human bladder cells.

Total RNA from a primary smooth muscle cell line was isolated and hybridized to affymetrix gene chips. The results show that following RGS protein are expressed in Bladder and 293 cells. (Qiagen RNeasy midi-prep) for the HEK293 and smooth muscle cells. Confluent t175 cm flask each (approximately 10E7 cells). Qiashredders were utilized for the homogenization step, and RNA was eluted in 250 uL of RNAse-free water. mRNA was labeled and hybridized to Affymetrix chips to analyze gene expression levels. Analysis clearly showed differential specific expression of RGS proteins between HEK 293 human kidney cells and primary mouse bladder cell lines. In Primary bladder cells there was evidence for expression of RGS 1-7,9,10,20. In HEK 293 cells there was evidence for expression of RGS 1,2,7,9,10,16 and 19. The overlapping expressors are RGS 1,2,7,9, and 10.

8.8 Example 8

RGS Expression Across Affymetrix Chips Bladder Cells

This example demonstrates the expression patterns of the human RGS polypeptide.

Array Hybridization and Data Analysis

The cRNA preparation and array hybridization was performed according to the Affymetrix protocol (Affymetrix, CA). Briefly, cRNA was prepared from 10 mg of total RNA. The RNA was denatured at 70 C with T7-tagged oligo-dT primers and then reverse transcribed with Superscript II (GIBCO BRL) at 42 C for 1 hr. Second-strand cDNA was synthesized by adding DNA pol I, *E. coli* DNA ligase and RNase H, and incubation was carried out for 2 hrs at 16° C. After extracted once with phenol/chloroform, the synthesized cDNA was used for in vitro transcription with a BioArray High Yield RNA Transcript Labeling Kit (Enzo). Labeled cRNA was purified with RNeasy columns (Qiagen) and then fragmented (10 mg/per chip) before hybridization.

Human GenomeU95A arrays (HG-U95A, Affymetrix), containing ~12,000 full-length genes, were used for hybridization. The oligo array cartridges were prehybridized at 45 C for 10 min. The cRNA samples were added to cartridges and hybridization was performed for 16 hrs at 45° C. with 60 rpm rotation. After hybridization, the chips were washed and stained in a fluidics station using the antibody amplification protocol from Affymetrix. The chips were then scanned using a Hewlett-Packard GeneArray scanner. The data was analyzed using GeneChip software (Affymetrix). An intensity value and presence/absence (P/A) call was derived from hybridization signal for each gene to represent its expression level.

| RGS | Intensity | Presence/Absence |
| --- | --- | --- |
| Bladder Cell Line | | |
| 1 | 9 | P |
| 2 | 53 | P |
| 3 | 79 | P |
| 4 | 166 | P |
| 5 | 8 | P |
| 6 | 18 | P |
| 7 | 50 | P |
| 9 | 250 | A |
| 10 | 250 | P |
| 11 | 47 | A |
| 12 | 16 | A |
| 14 | 84 | A |
| 16 | 46 | A |
| 19 | 19 | A |
| 20 | 32 | P |

-continued

| RGS | Intensity | Presence/Absence |
|---|---|---|
| HEK 293 | | |
| 1 | 9 | P |
| 2 | 14 | P |
| 3 | 10 | A |
| 4 | 8 | A |
| 5 | 18 | A |
| 6 | 28 | A |
| 7 | 28 | P |
| 9 | 387 | A |
| 10 | 127 | P |
| 12 | 30 | A |
| 14 | 97 | A |
| 16 | 59 | P |
| 19 | 29 | P |
| 20 | 2 | A |

Common RGS Proteins in Bladder and HEK: 1,2,7,10

8.9 Example 9

Compounds I and II Selectively Modulate the Gαq Signaling Pathway

This example demonstrates that the effects of Compounds I and II on Hek293 Cells and bladder smooth muscle cells stimulated by carbochol or histamine are consistent with and RGS/Gq mechanism.

Procedure for [Ca2+]i Measurements
1. HEK 293 or Clonetics primary human bladder smooth muscle cells were plated at a concentration of 7e3 cells/well in Poly-L lysine coated 96 well plates, white with clear bottoms (Costar).
2. The plates are allowed to attach overnight at 37° C. 5%CO2. The cells were rinsed 2× with Krebs-HEPES buffer and then loaded with 4 uM Fluo4 (Molecular Probes) for 60 minutes in the same buffer containing 1% (wt/vol) Pluronic F-127 and 0.25 mM sulfinpyrazone.
3. After loading the cells were rinsed 3× with Krebs-HEPES buffer containing 0.5% (wt/vol) BSA (Sigma Chemical)
4. Buffer alone or buffer containing test compounds, was injected sequentially into separate wells and the fluorescence intensity monitored in a Victor2 96 well plate fluorometer (PE-Wallac). Measurements were taken at 1-s intervals using an excitation wavelength of 485 nm and emissions filter of 535 nm.
5. Five baseline measurements were taken at 1-s intervals prior to each injection (see FIGS. 4A and 4B).

8.10 Example 10

Compound I Targets Gαq and RGS Polypeptides

This example demonstrates that Compound I specifically targets Gαq signaling.

Calcium assays were run by standard protocols as described above and in Zhu et al., 1998, *J. Biol Chem* 273: 133-142. It is known that calcium signals in response to carbachol have both a Gq and a Go/Gi signaling component. Pertussis toxin is a known inhibitor of Go/Gi signaling in cells. We asked the question if Compound I was inhibiting Gq or Go/Gi signals in Hek 293 kidney cells. We already were able to show that carbachol induced calcium influxes were blocked by Compound I, as well as Compounds II and III, the question was if this was a Gq specific effect. Go/Gi is known to block the Go/I but not Gq signals. If the compound blocked Go/Gi then we would expect the combination of pertussis toxin and Compound I would not be cumulative as they would both be inhibiting the same signal. If however Compound I were inhibiting Gq signal specifically, then we would expect the combination of pertussis toxin (hitting Go/Gi) and Gq. Our results (see FIG. 5A) show that the effect of Compound I as exemplified in this figure clearly shows the effects of Compound I and Pertussis toxin are cumulative, there by showing that the Compound I is specifically inhibiting Gq signaling and not Go/Gi.

8.11 Example 11

Compounds I, II and III Modulate the Interaction of Gαq Polypeptide and RGS Polypeptide This example demonstrates that compounds I, II and III modulate the affinity of a Gαq polypeptide and an RGS polypeptide for one another.

Compounds I and III were discovered in assays of smooth muscle contraction. Specifically these compounds are capable of relaxing strips of bladder smooth muscle that have been induced to contract with the muscarinic agonist carbochol. The compounds were synthesized and retested for activity. The molecular targets of these compounds were not know but have been discovered utilizing a combination of model systems genetics and biochemistry.

*C. elegans* animals were treated with Compounds I and III and their effects were observed on the pumping of the animals pharynx, the contraction of the egg laying muscles and on the ability of the mobility muscles to function properly. The ability of these compounds to effect muscle contraction in human tissue strips is consistent with the effects on muscle seen in *C. elegans*. A mutagenesis and selection process was carried out to find *C. elegans* animals that were resistant to the muscle effects of the compounds and via this process genes involved in the compounds action were identified. In particular the Eat-16(RGS) and Egl-30 (Galpha q) proteins were implicated in the action of these compounds by virtue of specific amino-acid changes rendering the compound unable to effect its action on *C. elegans* muscle. Human orthologs for Eat-16 and Egl-30 were identified as RGS 6,7,9, and 11 (other RGS family members of which there are 23 are known to play similar roles and in may cases have interchangeable activities), and G alpha q respectively. Based on the information from the *C. elegans* experiments these human proteins are hypothesized to play a role in the function of Compounds I and III.

Compounds I and III were then tested in a human tissue culture cell line Human Kidney cell line Hek 293 for their ability to effect the function of human RGS and Gq signaling proteins via their role in Ca++ signaling. Compounds I and III were clearly able to effect the function of Gq and RGS in these assays, thereby validating their role in the action of Compounds I and III. The mammalian assays and *C. elegans* assays suggested that Compounds I and III were able to agonize the ability of RSG proteins to inactivate the signaling of G alpha q. This agonistic activity could be explain in several ways and these were tested. In particular we have shown biochemically that Compounds I and III increase the affinity of RGS7 with Gq in immunoprecipitation assays. This explains the biological activity of Compounds I and III, in that they increase the affinity of RGS-7 and Gq thereby increasing the ability of RGS-7 to inactivate Gq thereby agonizing G protein signals. In addition we have modeled the ability of Compounds I and III to bind RGS proteins or the combination of RGS-7 and Gq and have found likely binding pockets for these compounds.

GDP ALF(4)- is known to mimic the putative pentavalent transition state of Gq between active GTP bound and inactive GDP bound. GDP ALF4- also is known to increase the affinity of RGS proteins for Gq such that this interaction can be visualized by immunopreciptation assay. Here we are able to show that Compound III increase the affinity of RGS7 for Gq in a similar fashion to GDP Alf(4)-. This provides direct biochemical evidence that Compound III increase the affinity of RGS7 (and family members) to Gq and is completely consistent with its RGS7 agonist activity. Furthermore this ability proves a functional screening assay for additional compounds that act as agonists/antagonist or RGS related proteins and their binding to their respective G proteins.

Hek 293 cells were transfected with CMV-G alpha qHA, CMV-mycRGS-7 and CMV-Gbeta5. 48 hours later the cells were harvested and lysed. Antibody to the myc epitope was utilized to immunoprecipitate RGS-7 in the presence or absence of ALF4-. The precipitated proteins were split into two fractions and loaded onto gels and western blotted on to nitrocellulose. In FIG. 6, the left blot (1) was probed with anti-myc antibody to detect RGS-7. RGS-7 was immunoprecipitated by the anti-myc antibody in the presence and absence of ALF4-. The right blot shows the second fraction which was probed against the Hemagglutanin (HA) tag that was fused to G alpha q. A G alpha q protein band was detected to have associated with RGS-7 and precipitated in the presence of ALF4- (lanes A) but not in the absence of ALF4- (lane B). In the second experiment, RGS-7 was immuno-precipitated again with the Myc epitope to which it was fused and the presence of G alpha q was detected in the presence or absence of ALF4- or different concentrations of Compound III. As shown in 3) Lane (F) G alpha q was detected in the presence of ALF4- but also was present in the presence of Compound III (Lane F) this was true for multiple concentrations of Compound III (Lane H) and shows biochemically that Compound III and related compounds affect directly the affinity of RGS-7 and Gq. This increase in RGS-7 affinity would be predicted to be the same for other RGS7 family members such as RGS 6,9 and 11, as they have been shown previously to have similar affinities and effects on G alpha q. In addition this assay provides a method for screening for compounds that affect the interaction of RGS proteins and G alpha q.

In FIG. 5B, Compounds I, II and III affect the affinity of Gq and RGS proteins for one another. FIG. 5B is an immunoprecipitation blot of myc tagged RGS which has been probed with an anti hemagglutinin antibody to detect a hemagglutinin tagged Gαq. The negative control lane "Ctrl" shows (lane 10 from the left) that very little Gq is immunoprecipitated I the absence of Alf4-. Alf4- mimics the transition state of Gq and increases its affinity with RGS such that it can be detected "Alf4-" lane 10 from the left. Compound I, and Compound II alone, lane 4 and 6 from the left respectively, clearly increase the affinity of Gq for RGS enough to be visualized as compared to the Ctrl lane alone. The ability of Compounds I, II and III to increase the affinity of Gq and RGS is a novel mechanism by which one can Gαq activity and such compounds and screens for additional compounds with such activity are useful wherever one desires to antagonize g protein signaling that involves Gαq and RGS proteins.

Protocol for co-IP of Gq with RGS7 Protein
Add 1 ug mouse IgG, 20 ul A/G agarose beads to lysate
Rotate at 4° C. for 30 mins
Spin
Split the lysate into two tubes, add volume to 1 ml
Add 4 ul of AlF4 mix to one of the tube
Let sit on ice for 1 hour
Add 4 ug Ab to supernate
Rotate at 4° C. at least 1 hr
Add 40 ul A/G plus agarose beads
Rotate at 4° C. at lease 1 hr
Spin, aspirate supe
Wash three times
Spin, aspirate super
Boil
Load on gel Buffer Condition:
20 mM Tris pH 7.4
1 mM EDTA
1 mM DTT
100 mM NaCl
5 mM MgCl2
0.7%
riton X-100
1 mM PMSF
leupeptin
aprotinin
50 uM AlCl3
10 mM MgCl2
5 mM NaF 8.12 Example 12

Determination of the Structure of eat-16

A model of the C-terminal domain of *C. elegans* protein eat-16 was developed based on sequence alignment with the homologous (33% identity with substantial additional conservation) protein rat RGS-4 (Genbank accession no. gi| 8394182) whose structure in complex with a G-protein is available in the Protein Data Bank structure as 1AGR (Tesmer et al., (1997), *Cell,* 89:251-61). Sequence alignments are shown in Table 1.

TABLE 1

Sequence Alignment of *C. elegans* eat-16 onto 1AGR chain E (Rat RGS4)

Rat RGS4 VSQEEVKKWA ESLENLINHE CGLAAFKAFL KSEYSEENID FWISCEEYKK
(SEQ ID NO.: 1)

eat-16 .TEKRVKRWG LSVQELVKDP IGRQVLETFL ESEFSSENIR FWIAIQDLK.
(SEQ ID NO.: 2)

TABLE 1-continued

Sequence Alignment of C. elegans eat-16 onto 1AGR chain E (Rat RGS4)

```
Rat RGS4  IKSPSKLSPK AKKIYNEFIS VQATKEVNLD SCTREET...  .SRNMLEPTI
(SEQ ID
NO.: 1)

eat-16    YAPNEQIYQK AERIREEFLA QGAPAQVNVD NRTLDQTLEC ISKAKDASQM
(SEQ ID
NO.: 2)

Rat RGS4  T.CFDEAQKK IFNLMEKDSY RRFLKSRFYL DLT
(SEQ ID
NO.: 1)

eat 16    RFAFYHSEEH VFTLMAKDSY PRFVRSQIYK AVL
(SEQ ID
NO.: 2)
```

The program LOOK was used for alignments and the model building module within LOOK, SEGMOD, was used to build the homology models (Levitt, (1992), *J. Mol. Biol.* 226: 507-533; Levitt, (1983), *J. Mol. Biol.* 170: 723-764).

Table 3, infra, provides the atomic structure coordinates of eat-16 built in this way.

Modeling Compounds in the eat-16 Active Site:

The surface of the resulting model of eat-16 was analyzed for pockets or depressions of a size that could accommodate the active compounds I and II, shown hereinbelow. (Surfaces were rendered and displayed using program GRASP (Nicholls, A.; Sharp, K.; and Honig, B., *PROTEINS, Structure, Function and Genetics*, (1991), Vol. 11 (No.4), pg. 281ff). A "molecular elevation" surface rendering was used to highlight pockets (FIG. 9B). The "molecular elevation" plot view of the eat-16 model accentuates pockets, which appear darker than the surrounding protein. A distinct, relatively large pocket can be seen on the middle left of the protein. As discussed hereinbelow, the region around the pocket is decidedly hydrophobic. FIG. 9A shows a ribbon diagram of the eat-16 model. The N-terminus is the upper terminus and the C terminus is the lower terminus. The pocket occurs on the C terminal face and is composed of residues from helices 1, 2, and 7.

Because both of the compounds I and II that were known to bind are substantially hydrophobic, the surface was further analyzed for hydrophobic characteristics, again using the program GRASP (Nicholls, 1991).

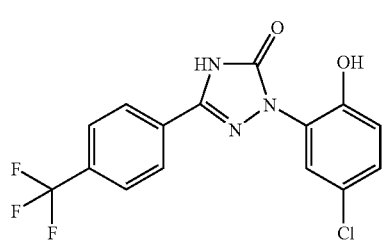

(I)

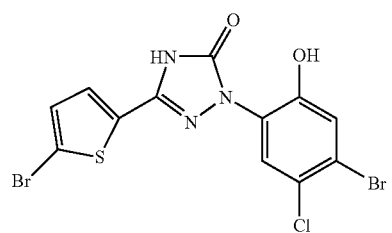

(II)

Two to three hydrophobic patches (identified as hydrophobic patches 1-3) of a size that could accommodate the two molecules (FIGS. 9C and 9D) were identified. In FIG. 9C, the surface of the eat-16 model has been shaded according to the hydrophobic character of the underlying amino acids: lighter denotes hydrophobic; darker, hydrophilic. The region around the pocket is decidedly hydrophobic. A tyrosine residue lies at the bottom of the pocket. FIG. 9D depicts a superposition of structure II, as a stick figure, onto the hydrophobic pocket, shown in white, showing that the molecule and the pocket are of similar size. The pocket and structure I are also of similar size.

One of the hydrophobic patches (hydrophobic patch 1) was coincident with a pocket of substantial size, as discussed above. Starting the numbering at the RGS domain of the eat-16 protein with sequence TEKRVKRWGLSVQ (SEQ ID NO:24), (TEKR being numbered 1, 2, 3, 4, respectively) this patch was comprised of residues including: Arg 4, Val 5, Lys 6, Arc 7, Trp 8, Leu 15, Ile 20, Gly 21, Val 24, Phe 121, Val 122, Ile 126, Tyr 127, Ala 129, Val 130. The corresponding residues in the human protein are (numbering in a similar way from sequence SQQRVKRWGRGMD (SEQ ID NO.:25)): Arg 4, Val 5, Lys 6, Arg 7, Trp 8, Ala 15, Val 20, Gly 21, Gln 24, Phe 116, Val 117, Ile 121, Tyr 122, Ala 124, Val 125.

Another hydrophobic patch (hydrophobic patch 2) was located on the reverse side of the eat-16 molecule. This patch is not associated with a well-defined "pocket" however, but it is of a size comparable to that of active molecules. Also, it is in a region of the RGS proteins that demonstrates conformational flexibility between the free and G-protein-bound forms and consequently is potentially a sensitive site for regulating the conformational change and hence activity. For the *C. elegans* eat-16 protein model, this patch was composed of residues (numbering in the same way as above): Leu 10, Ser 11, Val 12, Val 24, Val 122, Tyr 127, Ala 129, Val 130.

Additionally, another small pocket with hydrophobic characteristics (hydrophobic patch 3) was found in the other domain of the protein. It is composed of residues: Phe 102 (at the center of the pocket), and (surrounding the pocket) Lys 48, Leu 47, Arg 99, Tyr 103, His 104.

In general terms, active molecules are expected to be hydrophobic in character or to contain two or more substantially hydrophobic groups, wherein two hydrophobic portions of the molecules separated from one another by a group containing a hydrogen bonding moiety.

This information permits molecules that are potentially inhibitory of eat-16 to be identified in databases and through screening.

Applications to Docking and Structure Prediction from the Distorted Native Conformation: RGS Mechanism of Action eat16 and Human RGS7

None of the three binding sites is in the region found to be in direct contact with the G-I-alpha-1 protein in its complex with RGS4. It is known (from X-ray crystallographic and NMR structural determination studies) that RGS4 undergoes a substantial conformational change on binding to the G-protein (Moy, F. J.; Chanda, P. K.; Cockett, M. I.; Edris, W.; Jones, P. G.; Mason, K.; Semus, S.; Powers, R., *Biochemistry,* 39(24):7063-73, (2000)). "NMR Structure of Free RGS4 Reveals an Induced Conformational Change upon Binding Gα" *Biochemistry,* 39(24): 7063-7073 (2000); Tesmer, J. J., Berman, D. M., Gilman, A. G., Sprang, S. R., "Structure of RGS4 Bound to ALF4(-)-Activated G(I Alpha1): Stabilization of the Transition State for GTP Hydrolysis," *Cell* (Cambridge, Mass.) 89:251, (1997).

This results in a repacking of the N and C terminal regions of RGS4 which induces the formation of the binding pocket on RGS4 by which RGS4 binds to the G-protein. This binding pocket and the interactions that it can make with the G-protein are not fully realized in the free protein. The latter conformation could be considered to be an "active" conformation. The two principal binding pockets that we disclose on our RGS7 model are found in the corresponding N and C terminal regions of the model. It is proposed that compounds could activate the RGS proteins, and hence the GTP hydrolytic activity of the G-proteins, by stabilizing the active conformation in solution. It is expected that in solution, the predominant conformation of the RGS proteins would be the inactive form with a small probability that the active form would be transiently assumed. The compounds in question could bind to the pockets during those low probability events and could stabilize the active form and so effectively increase the concentration of the active conformer. This would effectively increase the probability of agonism of the GTPase activity of the G-protein.

Alternatively, the compounds could act directly on the RGS-G-protein complex after it is formed. By binding to the pockets, they could "lock" RGS into the already-assumed active conformation. Possibly this binding and locking could not only increase the percentage of RGS assuming an active conformation at any given time, but also—and possibly preferentially—increase the time that the two proteins stay in contact by preventing a separation of the proteins once a complex between them has been formed.

Additionally, the possibility that the compounds in question could exert a similar effect by binding at the some interfacial region between the RGS and G-protein or in a pocket formed when the two proteins complex should not be excluded.

Another possible mechanism of action involves potentiation of the GTPase activity through direct interaction with the G-alpha protein. It has been shown that the G-alpha effector cyclic GMP phosphodiesterase as well as the unrelated adenylyl cyclase proteins induce changes in the G-alpha conformation that potentiates its interaction with the RGS proteins (Slep, K. C., Kercher, M. A., He, W., Cowan, C. W., Wensel, T. G., Sigler, P. B., "Structural Determinants for Regulation of Phosphodiesterase by a G-Protein at 2.0 Å," *Nature,* 409: 1071, (2001); Tesmer, J. J. G., Dessauer, C. A., Sunahara, R. K., Murray, L. D., Johnson, R. A., Gilman, A. G., Sprang, S. R., "Molecular Basis for P-Site Inhibition of Adenylyl Cyclase," *Biochemistry,* 39:14464 (2000)). This potentiation increases RGS binding and consequently GTPase activity. The compounds discussed could induce or stabilize the same or a similar conformational change in the G-alpha protein that would similarly potentiate and stabilize RGS binding to the G-protein.

8.13 Example 13

Determination of the Structure of RGS-7

Following the same protocol as for Example 13, a model of the C-terminal domain of human RGS-7 was developed based on sequence alignment with the homologous (34% identity with substantial additional conservation) protein rat RGS-4 whose structure in complex with a G-protein is available in the Protein Data Bank structure as 1AGR (Tesmer et al., (1997), *Cell,* 89: 251-61). The program LOOK was used for alignments and the model building module within LOOK, SEGMOD, was used to build the homology models (Levitt, (1992), *J. Mol. Biol.,* 226: 507-533; Levitt, (1983), J. Mol. Biol., 170: 723-764). Sequence alignments are shown in Table 2.

TABLE 2

Sequence Alignment of RGS-7 onto 1AGR chain E (Rat RGS4)

| | | |
|---|---|---|
| Rat RGS4 (SEQ ID NO.: 1) | ....V.SQEE VKKWAESLEN LINHECGLAA FKAFLKSEYS EENIDFWISC | |
| Human RGS-7 (SEQ ID NO.: 4) | GLVP.RGSHR VKRWGFGMDE ALKDPVGREQ FLKFLESEFS SENLRFWLAV | |
| Rat RGS4 (SEQ ID NO.: 1) | EEYKKIKSPS KLSPKAKKIY NEFISVQATK EVNLDSCTRE ETSRNMLEPT | |

TABLE 2-continued

Sequence Alignment of RGS-7 onto 1AGR chain E (Rat RGS4)

```
Human RGS-7  EDLKK.RPIK EVPSRVQEIW QEFLAPGAPS AINLDSKSYD KTTQNVKEPG
(SEQ ID
NO.: 4)

Rat RGS4     ITCFDEAQKK IFNLMEKDSY RRFLKSRFYL DLT
(SEQ ID
NO.: 1)

Human RGS-7  RYTFEDAQEH IYKLMKSDSY PRFIRSSAYQ EL.
(SEQ ID
NO.: 4)
```

Table 4 provides the atomic structure coordinates of RGS-7.

Structures coordinates for RGS-7 according to Table 4 may be modified by mathematical manipulation. Such manipulations include, but are not limited to, fractionalization of the raw structure coordinates, integer additions or subtractions to sets of the raw structure coordinates, inversion of the raw structure coordinates and any combination of the above.

8.14 Example 14

RGS Modeling and Analysis: Gα/RGS/PDE Trimeric Complex: Binding Sites for UI Compounds on the Gα Protein at the PDE Binding Site.

The compounds I and II behave much like the effector, PDE, as well as adenylate cyclase. Both of these effectors bind at the same location of the G-protein chimera. The crystal structure of the heterotrimeric complex of the RGS domain of RGS-9, the γ-subunit of phosphodiesterase and the Gt/I1 chimera α subunit [(rgs9)-(PDE γ)--(gt/i1α)-(GDP)-(α4-)-($Mg^{2+}$)] chimera of guanine nucleotide-binding protein G(t) α-1 subunit and guanine nucleotide-binding protein G(I), α-1 subunit (PDB entry 1FQJ; K. C. Slep, M. A. Kercher, W. He, C. W. Cowan, T. G. Wensel, P. B. Sigler, "Structural Determinants for Regulation of Phosphodiesterase by a G-protein at 2.0 A," *Nature*, (2001) Vol. 409, page 1071) were examined for possible binding sites. The effector molecule, PDE, was removed from its complex with the G-protein. This resulted in a well-defined pocket. Such pockets are not necessarily typical of protein-protein interactions. This pocket had a hydrophobic face and so could be complementary to the hydrophobic ligands. It was composed of residues: Leu 201, Val 202, Ala 204, Glu 205, Glu 207, Glu 208, Arg 211, Phe 236, Asp 241, Glu 244, Glu 245, Lys 248, Lys 249, Ile 254.

The program ICM (the underlying methods of which are described in: Abagyan, R. A., and Totrov, M. M., "Biased probability Monte Carlo conformational searches and electrostatic calculations for peptides and proteins." *J. Mol. Biol.* 235: 983-1002, (1994); and Abagyan, R. A., Totrov, M. M., and Kuznetsov, D. N., "ICM—a new method for protein modeling and design," *J. Comp. Chem.*, 15: 488-506 (1994)) was used to investigate possible binding interactions of one of the molecules, II, with the pocket. It found favorable binding orientations of the molecule within the pocket, showing the characteristic surface complementarity seen in protein/ligand complexes and favorable hydrogen-bonding interactions. The ICM scoring function for protein/ligand interactions was comparable with that calculated for known protein/ligand complexes. See FIGS. 8 and 9.

8.15 Example 15

Effects of Compound III on Rabbit Bladder Cystometry and the Contractile Response to Acetylcholine Using an in situ Preparation: Normal Rabbit Bladder The effects of compound III on bladder compliance were tested as follows. Each rabbit was sedated with Ketamine xylazine. A femoral artery catheter was placed for monitoring blood pressure and heart rate, a urethral catheter was placed for performing cystometry and monitoring bladder pressure, and a second catheter was fed through the other femoral artery, through the descending aorta and to the level of the bladder base to allow drugs to be administered directly to the bladder.

Saline was infused into the bladder at a rate of 1.5 ml/min until a micturition contraction was recorded; bladder pressure was monitored continually. The bladder was emptied and 15 ml of saline placed in the bladder. Acetylcholine ($3 \times 10^{-5}$·M Ach) was administered and the pressure response measured and recorded. After 30 minutes, compound III (5 μM/kg) was given i.v. and the rabbit allowed to rest for 30 minutes. At the end of this period a second cystometry and Ach stimulation were performed. At this time, 10 μM/kg was given and after another 30 minute equilibration period, a third set of studies performed.

Compound III was dissolved in a vehicle of DMSO and propylene glycol. Preliminary studies demonstrated that vehicle alone had no effect on the cystometry or response to Ach. Additionally, there were no significant differences among three sets of studies on each control animal.

There was a progressive decrease in the initial intravesical pressure mediated by compound III but no change in the final pressure at the time of micturition. In addition, compound III significantly increased the volume at the time of the first micturition contraction (bladder capacity; FIG. 11). Compound III did not affect micturition pressure or the pressure response to Ach.

These results indicate that compound III increases bladder compliance thus allowing for a greater bladder capacity at micturition. Clinically, this would be beneficial for the treatment of several conditions characterized by low compliance and early micturition contractions (urgency, frequency, nocturia). Compound III had no negative effects on either the micturition pressure or the response to Ach.

8.16 Example 16

Effects of Compound III on Rabbit Bladder Cystometry and the Contractile Response to Acetylcholine Using an in situ Preparation: Hypertrophied Rabbit Bladder In order to assess the effects of compound III on hypertrophied bladders, model hypertrophied bladders were constructed in rabbits by obstructing the proximal urethra bladder neck. Each rabbit was anesthetized with an intramuscular injection of 3.0 ml of a ketamine/xylazine mixture (25 mg/ml ketamine, 8 mg/ml xylazine), surgical anesthesia was maintained with intravenous infusion of nembutal (25 mg/ml). The animal was shaved, painted with povidone-iodine solution and draped in a sterile fashion. The urethra was catheterized using an 8Fr. feeding-tube. Through a midline incision, the bladder was exposed. The bladder neck was cleared of surrounding connective and fatty tissues. A 3-0 silk ligature was passed around the proximal urethra bladder neck area and tied loosely, such that a small hemostat could be placed through the ligature, along side the urethra, without tension. The abdominal wound was closed in two layers with 2-0 vicryl, using a running stitch on the inner layer and interrupted, vertical mattress stitches on the skin. Each rabbit was recovered under observation.

At 4 weeks following obstruction, the effect of compound III on bladder compliance, unstable bladder contractions, and response to acetylcholine (Ach) was determined using the in situ model (see Section 8.15, above). Bladder capacity of the obstructed bladders were very variable.

8.17 Example 17

Effects of Compound III on Hyperreflexia in Normal Rabbits

The effects of compound III on hyperreflexia in normal rabbits were tested as follows. Each rabbit was anesthetized with ketamine/xylazine as described above. A catheter was placed into the bladder for both filling the bladder and monitoring bladder pressure. Under anesthesia, penile ligature was placed around the base of the penis. 30 minutes later, the bladder was emptied, and filled in 5 ml steps at 15 minute intervals until hyperreflexia was initiated (usually at approximately 30 mls). After 15 minutes of stable contractions, BMS-1 was administered as given above, and the effect on the frequency and amplitude of hyperreflexia was determined.

Partial outlet induces unstable bladder contractions which are mediated primarily by myogenic mechanisms (contractions initiated within the bladder smooth muscle matrix, and they are not dependent upon spinal or supraspinal reflexes). However, the hyperreflexia induced by penile ligation is strictly neurogenic in origin, resulting from the stimulation of spinal reflex mechanisms. This is the key difference between unstable bladder contractions and hyperreflexia.

The administration of 5 or 10 µM/kg compound III had no effects on either blood pressure or heart rate. Partial outlet obstruction induced a significant increase in bladder weight. The cystometric studies demonstrated that compound III produced significant decrease in the initial pressure of the bladder during filling, and an increase in compliance. (decreased resistance to stretch) of the bladder during the initial stages of bladder filling (FIG. 12). Similar to what was observed in the normal bladders (see above), compound III had no effect on the sensitivity of the bladder to Ach stimulation, and had no significant effect on the maximal response to Ach. Partial outlet obstruction induced unstable bladder contractions in approximately 50% of rabbits. Compound III administration significantly reduced the amplitude of the unstable contractions without significantly affecting the frequency of contractions (FIG. 13).

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims. All references cited herein are hereby incorporated by reference in their entireties.

TABLE 3

REMARK 4 C. elegans Eat-16 protein modeled on Rat RGS-4 (E. chain from PDB
REMARK 4 entry 1AGR. See: Tesmer J. J., D. M. Berman, A. G. Gilman, S. R. Sprang
REMARK 4 Structure of RGS4 Bound to ALF4(−)-Activated G(I Alpha1):
REMARK 4 Stabilization of the Transition State for GTP Hydrolysis,
REMARK 4 Cell(Cambridge, Mass.) V. 89 251 1997)
REMARK 4
REMARK 4 WRGS COMPLIES WITH FORMAT V. 2.0, 22-NOV-2000

| ATOM | 1  | N   | THR | E | 1 | 6.560 | 26.957 | 66.192 | 1.00 | 0.03 | N |
| ---- | -- | --- | --- | - | - | ----- | ------ | ------ | ---- | ---- | - |
| ATOM | 2  | CA  | THR | E | 1 | 5.444 | 26.073 | 66.568 | 1.00 | 0.02 | C |
| ATOM | 3  | CB  | THR | E | 1 | 4.108 | 26.670 | 66.137 | 1.00 | 0.10 | C |
| ATOM | 4  | OG1 | THR | E | 1 | 4.071 | 26.710 | 64.717 | 1.00 | 0.10 | O |
| ATOM | 5  | CG2 | THR | E | 1 | 3.924 | 28.088 | 66.666 | 1.00 | 0.22 | C |
| ATOM | 6  | C   | THR | E | 1 | 5.610 | 24.713 | 65.910 | 1.00 | 0.03 | C |
| ATOM | 7  | O   | THR | E | 1 | 6.279 | 24.596 | 64.877 | 1.00 | 0.03 | O |
| ATOM | 8  | N   | GLU | E | 2 | 4.807 | 23.761 | 66.355 | 1.00 | 0.03 | N |
| ATOM | 9  | CA  | GLU | E | 2 | 4.886 | 22.401 | 65.807 | 1.00 | 0.04 | C |
| ATOM | 10 | CB  | GLU | E | 2 | 4.138 | 21.457 | 66.738 | 1.00 | 0.18 | C |
| ATOM | 11 | CG  | GLU | E | 2 | 4.287 | 20.001 | 66.307 | 1.00 | 0.64 | C |
| ATOM | 12 | CD  | GLU | E | 2 | 3.468 | 19.115 | 67.238 | 1.00 | 1.13 | C |
| ATOM | 13 | OE1 | GLU | E | 2 | 3.055 | 19.627 | 68.269 | 1.00 | 1.52 | O |
| ATOM | 14 | OE2 | GLU | E | 2 | 3.182 | 17.988 | 66.859 | 1.00 | 1.49 | O |
| ATOM | 15 | C   | GLU | E | 2 | 4.285 | 22.320 | 64.405 | 1.00 | 0.02 | C |
| ATOM | 16 | O   | GLU | E | 2 | 4.823 | 21.591 | 63.564 | 1.00 | 0.02 | O |
| ATOM | 17 | N   | LYS | E | 3 | 3.430 | 23.276 | 64.074 | 1.00 | 0.04 | N |

TABLE 3-continued

| ATOM | 18 | CA | LYS | E | 3 | 2.861 | 23.346 | 62.728 | 1.00 | 0.03 | C |
|---|---|---|---|---|---|---|---|---|---|---|---|
| ATOM | 19 | CB | LYS | E | 3 | 1.663 | 24.280 | 62.773 | 1.00 | 0.30 | C |
| ATOM | 20 | CG | LYS | E | 3 | 0.689 | 23.894 | 63.882 | 1.00 | 1.06 | C |
| ATOM | 21 | CD | LYS | E | 3 | −0.474 | 24.879 | 64.051 | 1.00 | 1.20 | C |
| ATOM | 22 | CE | LYS | E | 3 | −0.103 | 26.179 | 64.777 | 1.00 | 1.19 | C |
| ATOM | 23 | NZ | LYS | E | 3 | 0.595 | 27.162 | 63.927 | 1.00 | 1.80 | N |
| ATOM | 24 | C | LYS | E | 3 | 3.874 | 23.914 | 61.737 | 1.00 | 0.02 | C |
| ATOM | 25 | O | LYS | E | 3 | 3.933 | 23.447 | 60.596 | 1.00 | 0.01 | O |
| ATOM | 26 | N | ARG | E | 4 | 4.840 | 24.654 | 62.257 | 1.00 | 0.02 | N |
| ATOM | 27 | CA | ARG | E | 4 | 5.876 | 25.261 | 61.425 | 1.00 | 0.04 | C |
| ATOM | 28 | CB | ARG | E | 4 | 6.431 | 26.460 | 62.190 | 1.00 | 0.20 | C |
| ATOM | 29 | CG | ARG | E | 4 | 7.525 | 27.195 | 61.428 | 1.00 | 0.81 | C |
| ATOM | 30 | CD | ARG | E | 4 | 7.013 | 27.807 | 60.130 | 1.00 | 1.64 | C |
| ATOM | 31 | NE | ARG | E | 4 | 6.013 | 28.849 | 60.400 | 1.00 | 2.18 | N |
| ATOM | 32 | CZ | ARG | E | 4 | 6.100 | 30.094 | 59.928 | 1.00 | 3.04 | C |
| ATOM | 33 | NH1 | ARG | E | 4 | 5.113 | 30.962 | 60.157 | 1.00 | 3.95 | N |
| ATOM | 34 | NH2 | ARG | E | 4 | 7.146 | 30.453 | 59.181 | 1.00 | 3.35 | N |
| ATOM | 35 | C | ARG | E | 4 | 6.968 | 24.236 | 61.154 | 1.00 | 0.01 | C |
| ATOM | 36 | O | ARG | E | 4 | 7.434 | 24.125 | 60.015 | 1.00 | 0.02 | O |
| ATOM | 37 | N | VAL | E | 5 | 7.088 | 23.294 | 62.078 | 1.00 | 0.03 | N |
| ATOM | 38 | CA | VAL | E | 5 | 8.008 | 22.170 | 61.905 | 1.00 | 0.00 | C |
| ATOM | 39 | CB | VAL | E | 5 | 8.192 | 21.486 | 63.256 | 1.00 | 0.02 | C |
| ATOM | 40 | CG1 | VAL | E | 5 | 9.120 | 20.281 | 63.150 | 1.00 | 0.00 | C |
| ATOM | 41 | CG2 | VAL | E | 5 | 8.715 | 22.469 | 64.297 | 1.00 | 0.01 | C |
| ATOM | 42 | C | VAL | E | 5 | 7.442 | 21.182 | 60.891 | 1.00 | 0.02 | C |
| ATOM | 43 | O | VAL | E | 5 | 8.151 | 20.811 | 59.946 | 1.00 | 0.02 | O |
| ATOM | 44 | N | LYS | E | 6 | 6.126 | 21.030 | 60.901 | 1.00 | 0.01 | N |
| ATOM | 45 | CA | LYS | E | 6 | 5.455 | 20.187 | 59.905 | 1.00 | 0.02 | C |
| ATOM | 46 | CB | LYS | E | 6 | 3.994 | 20.027 | 60.305 | 1.00 | 0.02 | C |
| ATOM | 47 | CG | LYS | E | 6 | 3.845 | 19.343 | 61.657 | 1.00 | 0.01 | C |
| ATOM | 48 | CD | LYS | E | 6 | 2.391 | 19.354 | 62.106 | 1.00 | 0.01 | C |
| ATOM | 49 | CE | LYS | E | 6 | 2.230 | 18.733 | 63.486 | 1.00 | 0.00 | C |
| ATOM | 50 | NZ | LYS | E | 6 | 0.831 | 18.811 | 63.937 | 1.00 | 0.03 | N |
| ATOM | 51 | C | LYS | E | 6 | 5.505 | 20.818 | 58.517 | 1.00 | 0.03 | C |
| ATOM | 52 | O | LYS | E | 6 | 5.808 | 20.117 | 57.544 | 1.00 | 0.02 | O |
| ATOM | 53 | N | ARG | E | 7 | 5.480 | 22.141 | 58.465 | 1.00 | 0.02 | N |
| ATOM | 54 | CA | ARG | E | 7 | 5.603 | 22.846 | 57.188 | 1.00 | 0.03 | C |
| ATOM | 55 | CB | ARG | E | 7 | 5.063 | 24.260 | 57.351 | 1.00 | 0.17 | C |
| ATOM | 56 | CG | ARG | E | 7 | 3.549 | 24.259 | 57.503 | 1.00 | 0.96 | C |
| ATOM | 57 | CD | ARG | E | 7 | 2.993 | 25.674 | 57.605 | 1.00 | 1.31 | C |
| ATOM | 58 | NE | ARG | E | 7 | 3.399 | 26.347 | 58.849 | 1.00 | 2.47 | N |
| ATOM | 59 | CZ | ARG | E | 7 | 2.505 | 26.763 | 59.750 | 1.00 | 3.62 | C |
| ATOM | 60 | NH1 | ARG | E | 7 | 2.893 | 27.490 | 60.799 | 1.00 | 4.65 | N |
| ATOM | 61 | NH2 | ARG | E | 7 | 1.205 | 26.545 | 59.544 | 1.00 | 4.04 | N |
| ATOM | 62 | C | ARG | E | 7 | 7.033 | 22.901 | 56.651 | 1.00 | 0.02 | C |
| ATOM | 63 | O | ARG | E | 7 | 7.194 | 23.058 | 55.438 | 1.00 | 0.02 | O |
| ATOM | 64 | N | TRP | E | 8 | 8.026 | 22.588 | 57.467 | 1.00 | 0.03 | N |
| ATOM | 65 | CA | TRP | E | 8 | 9.399 | 22.476 | 56.962 | 1.00 | 0.03 | C |
| ATOM | 66 | CB | TRP | E | 8 | 10.378 | 22.572 | 58.124 | 1.00 | 0.01 | C |
| ATOM | 67 | CG | TRP | E | 8 | 10.392 | 23.883 | 58.871 | 1.00 | 0.02 | C |
| ATOM | 68 | CD1 | TRP | E | 8 | 9.965 | 25.108 | 58.415 | 1.00 | 0.01 | C |
| ATOM | 69 | NE1 | TRP | E | 8 | 10.137 | 26.017 | 59.405 | 1.00 | 0.03 | N |
| ATOM | 70 | CE2 | TRP | E | 8 | 10.676 | 25.450 | 60.500 | 1.00 | 0.02 | C |
| ATOM | 71 | CZ2 | TRP | E | 8 | 11.016 | 25.948 | 61.749 | 1.00 | 0.02 | C |
| ATOM | 72 | CH2 | TRP | E | 8 | 11.574 | 25.101 | 62.702 | 1.00 | 0.01 | C |
| ATOM | 73 | CZ3 | TRP | E | 8 | 11.785 | 23.758 | 62.408 | 1.00 | 0.03 | C |
| ATOM | 74 | CE3 | TRP | E | 8 | 11.437 | 23.248 | 61.164 | 1.00 | 0.03 | C |
| ATOM | 75 | CD2 | TRP | E | 8 | 10.877 | 24.090 | 60.216 | 1.00 | 0.01 | C |
| ATOM | 76 | C | TRP | E | 8 | 9.608 | 21.113 | 56.323 | 1.00 | 0.02 | C |
| ATOM | 77 | O | TRP | E | 8 | 10.237 | 20.996 | 55.263 | 1.00 | 0.02 | O |
| ATOM | 78 | N | GLY | E | 9 | 8.904 | 20.134 | 56.867 | 1.00 | 0.00 | N |
| ATOM | 79 | CA | GLY | E | 9 | 8.974 | 18.760 | 56.364 | 1.00 | 0.00 | C |
| ATOM | 80 | C | GLY | E | 9 | 8.101 | 18.563 | 55.131 | 1.00 | 0.02 | C |
| ATOM | 81 | O | GLY | E | 9 | 8.337 | 17.643 | 54.339 | 1.00 | 0.02 | O |
| ATOM | 82 | N | LEU | E | 10 | 7.077 | 19.388 | 55.001 | 1.00 | 0.01 | N |
| ATOM | 83 | CA | LEU | E | 10 | 6.248 | 19.362 | 53.796 | 1.00 | 0.02 | C |
| ATOM | 84 | CB | LEU | E | 10 | 4.856 | 19.846 | 54.187 | 1.00 | 0.13 | C |
| ATOM | 85 | CG | LEU | E | 10 | 3.866 | 19.747 | 53.032 | 1.00 | 0.65 | C |
| ATOM | 86 | CD1 | LEU | E | 10 | 3.722 | 18.302 | 52.564 | 1.00 | 0.72 | C |
| ATOM | 87 | CD2 | LEU | E | 10 | 2.510 | 20.315 | 53.436 | 1.00 | 1.20 | C |
| ATOM | 88 | C | LEU | E | 10 | 6.821 | 20.275 | 52.708 | 1.00 | 0.01 | C |
| ATOM | 89 | O | LEU | E | 10 | 6.758 | 19.945 | 51.518 | 1.00 | 0.01 | O |
| ATOM | 90 | N | SER | E | 11 | 7.457 | 21.358 | 53.120 | 1.00 | 0.02 | N |
| ATOM | 91 | CA | SER | E | 11 | 8.028 | 22.300 | 52.161 | 1.00 | 0.01 | C |
| ATOM | 92 | CB | SER | E | 11 | 7.144 | 23.539 | 52.128 | 1.00 | 0.02 | C |
| ATOM | 93 | OG | SER | E | 11 | 7.853 | 24.556 | 51.434 | 1.00 | 0.02 | O |
| ATOM | 94 | C | SER | E | 11 | 9.447 | 22.714 | 52.519 | 1.00 | 0.00 | C |
| ATOM | 95 | O | SER | E | 11 | 9.660 | 23.475 | 53.469 | 1.00 | 0.03 | O |
| ATOM | 96 | N | VAL | E | 12 | 10.341 | 22.475 | 51.572 | 1.00 | 0.00 | N |

TABLE 3-continued

| | | | | | | | | | | |
|---|---|---|---|---|---|---|---|---|---|---|
| ATOM | 97 | CA | VAL | E | 12 | 11.743 | 22.880 | 51.724 | 1.00 | 0.01 C |
| ATOM | 98 | CB | VAL | E | 12 | 12.585 | 22.110 | 50.706 | 1.00 | 1.16 C |
| ATOM | 99 | CG1 | VAL | E | 12 | 11.993 | 22.174 | 49.301 | 1.00 | 0.74 C |
| ATOM | 100 | CG2 | VAL | E | 12 | 14.044 | 22.557 | 50.711 | 1.00 | 1.93 C |
| ATOM | 101 | C | VAL | E | 12 | 11.923 | 24.388 | 51.537 | 1.00 | 0.02 C |
| ATOM | 102 | O | VAL | E | 12 | 12.794 | 24.987 | 52.179 | 1.00 | 0.02 O |
| ATOM | 103 | N | GLN | E | 13 | 10.958 | 25.024 | 50.894 | 1.00 | 0.02 N |
| ATOM | 104 | CA | GLN | E | 13 | 10.994 | 26.476 | 50.786 | 1.00 | 0.02 C |
| ATOM | 105 | CB | GLN | E | 13 | 10.105 | 26.913 | 49.633 | 1.00 | 0.14 C |
| ATOM | 106 | CG | GLN | E | 13 | 10.336 | 28.382 | 49.309 | 1.00 | 1.08 C |
| ATOM | 107 | CD | GLN | E | 13 | 9.438 | 28.805 | 48.155 | 1.00 | 1.65 C |
| ATOM | 108 | OE1 | GLN | E | 13 | 8.718 | 27.981 | 47.580 | 1.00 | 2.23 O |
| ATOM | 109 | NE2 | GLN | E | 13 | 9.488 | 30.087 | 47.840 | 1.00 | 2.39 N |
| ATOM | 110 | C | GLN | E | 13 | 10.524 | 27.108 | 52.094 | 1.00 | 0.03 C |
| ATOM | 111 | O | GLN | E | 13 | 11.194 | 28.020 | 52.588 | 1.00 | 0.02 O |
| ATOM | 112 | N | GLU | E | 14 | 9.564 | 26.486 | 52.766 | 1.00 | 0.01 N |
| ATOM | 113 | CA | GLU | E | 14 | 9.155 | 26.956 | 54.102 | 1.00 | 0.00 C |
| ATOM | 114 | CB | GLU | E | 14 | 7.951 | 26.130 | 54.535 | 1.00 | 0.24 C |
| ATOM | 115 | CG | GLU | E | 14 | 7.398 | 26.548 | 55.893 | 1.00 | 1.07 C |
| ATOM | 116 | CD | GLU | E | 14 | 6.502 | 27.773 | 55.760 | 1.00 | 1.75 C |
| ATOM | 117 | OE1 | GLU | E | 14 | 6.127 | 28.305 | 56.795 | 1.00 | 2.82 O |
| ATOM | 118 | OE2 | GLU | E | 14 | 6.041 | 28.014 | 54.653 | 1.00 | 1.72 O |
| ATOM | 119 | C | GLU | E | 14 | 10.264 | 26.741 | 55.128 | 1.00 | 0.02 C |
| ATOM | 120 | O | GLU | E | 14 | 10.536 | 27.628 | 55.953 | 1.00 | 0.02 O |
| ATOM | 121 | N | LEU | E | 15 | 10.984 | 25.646 | 54.942 | 1.00 | 0.03 N |
| ATOM | 122 | CA | LEU | E | 15 | 12.159 | 25.316 | 55.736 | 1.00 | 0.01 C |
| ATOM | 123 | CB | LEU | E | 15 | 12.690 | 24.003 | 55.167 | 1.00 | 0.02 C |
| ATOM | 124 | CG | LEU | E | 15 | 13.951 | 23.484 | 55.838 | 1.00 | 0.02 C |
| ATOM | 125 | CD1 | LEU | E | 15 | 13.709 | 23.193 | 57.309 | 1.00 | 0.03 C |
| ATOM | 126 | CD2 | LEU | E | 15 | 14.431 | 22.225 | 55.129 | 1.00 | 0.02 C |
| ATOM | 127 | C | LEU | E | 15 | 13.192 | 26.436 | 55.644 | 1.00 | 0.02 C |
| ATOM | 128 | O | LEU | E | 15 | 13.333 | 27.171 | 56.631 | 1.00 | 0.01 O |
| ATOM | 129 | N | VAL | E | 16 | 13.599 | 26.782 | 54.431 | 1.00 | 0.01 N |
| ATOM | 130 | CA | VAL | E | 16 | 14.666 | 27.780 | 54.252 | 1.00 | 0.02 C |
| ATOM | 131 | CB | VAL | E | 16 | 15.350 | 27.541 | 52.911 | 1.00 | 0.50 C |
| ATOM | 132 | CG1 | VAL | E | 16 | 15.970 | 26.152 | 52.867 | 1.00 | 1.11 C |
| ATOM | 133 | CG2 | VAL | E | 16 | 14.401 | 27.740 | 51.736 | 1.00 | 0.96 C |
| ATOM | 134 | C | VAL | E | 16 | 14.233 | 29.250 | 54.344 | 1.00 | 0.02 C |
| ATOM | 135 | O | VAL | E | 16 | 15.108 | 30.120 | 54.424 | 1.00 | 0.02 O |
| ATOM | 136 | N | LYS | E | 17 | 12.941 | 29.542 | 54.381 | 1.00 | 0.02 N |
| ATOM | 137 | CA | LYS | E | 17 | 12.521 | 30.933 | 54.592 | 1.00 | 0.03 C |
| ATOM | 138 | CB | LYS | E | 17 | 11.174 | 31.187 | 53.926 | 1.00 | 0.24 C |
| ATOM | 139 | CG | LYS | E | 17 | 11.244 | 31.121 | 52.403 | 1.00 | 0.57 C |
| ATOM | 140 | CD | LYS | E | 17 | 9.925 | 31.494 | 51.711 | 1.00 | 1.24 C |
| ATOM | 141 | CE | LYS | E | 17 | 8.809 | 30.449 | 51.826 | 1.00 | 1.82 C |
| ATOM | 142 | NZ | LYS | E | 17 | 8.078 | 30.487 | 53.104 | 1.00 | 2.56 N |
| ATOM | 143 | C | LYS | E | 17 | 12.391 | 31.234 | 56.077 | 1.00 | 0.02 C |
| ATOM | 144 | O | LYS | E | 17 | 12.502 | 32.391 | 56.499 | 1.00 | 0.02 O |
| ATOM | 145 | N | ASP | E | 18 | 12.186 | 30.195 | 56.865 | 1.00 | 0.01 N |
| ATOM | 146 | CA | ASP | E | 18 | 12.153 | 30.366 | 58.314 | 1.00 | 0.00 C |
| ATOM | 147 | CB | ASP | E | 18 | 11.276 | 29.251 | 58.876 | 1.00 | 0.63 C |
| ATOM | 148 | CG | ASP | E | 18 | 11.136 | 29.340 | 60.392 | 1.00 | 1.37 C |
| ATOM | 149 | OD1 | ASP | E | 18 | 10.054 | 29.669 | 60.852 | 1.00 | 2.14 O |
| ATOM | 150 | OD2 | ASP | E | 18 | 12.087 | 28.957 | 61.065 | 1.00 | 1.84 O |
| ATOM | 151 | C | ASP | E | 18 | 13.578 | 30.276 | 58.846 | 1.00 | 0.01 C |
| ATOM | 152 | O | ASP | E | 18 | 14.262 | 29.283 | 58.587 | 1.00 | 0.03 O |
| ATOM | 153 | N | PRO | E | 19 | 13.972 | 31.218 | 59.691 | 1.00 | 0.02 N |
| ATOM | 154 | CA | PRO | E | 19 | 15.375 | 31.311 | 60.121 | 1.00 | 0.02 C |
| ATOM | 155 | CB | PRO | E | 19 | 15.460 | 32.601 | 60.877 | 1.00 | 0.30 C |
| ATOM | 156 | CG | PRO | E | 19 | 14.080 | 33.230 | 60.967 | 1.00 | 0.17 C |
| ATOM | 157 | CD | PRO | E | 19 | 13.149 | 32.321 | 60.187 | 1.00 | 0.15 C |
| ATOM | 158 | C | PRO | E | 19 | 15.859 | 30.147 | 60.999 | 1.00 | 0.01 C |
| ATOM | 159 | O | PRO | E | 19 | 17.040 | 29.783 | 60.936 | 1.00 | 0.02 O |
| ATOM | 160 | N | ILE | E | 20 | 14.948 | 29.458 | 61.667 | 1.00 | 0.02 N |
| ATOM | 161 | CA | ILE | E | 20 | 15.339 | 28.290 | 62.455 | 1.00 | 0.02 C |
| ATOM | 162 | CB | ILE | E | 20 | 14.341 | 28.108 | 63.594 | 1.00 | 0.22 C |
| ATOM | 163 | CG2 | ILE | E | 20 | 14.664 | 26.851 | 64.394 | 1.00 | 0.17 C |
| ATOM | 164 | CG1 | ILE | E | 20 | 14.329 | 29.328 | 64.509 | 1.00 | 0.46 C |
| ATOM | 165 | CD1 | ILE | E | 20 | 15.673 | 29.522 | 65.204 | 1.00 | 1.43 C |
| ATOM | 166 | C | ILE | E | 20 | 15.353 | 27.049 | 61.570 | 1.00 | 0.02 C |
| ATOM | 167 | O | ILE | E | 20 | 16.357 | 26.331 | 61.553 | 1.00 | 0.02 O |
| ATOM | 168 | N | GLY | E | 21 | 14.414 | 27.000 | 60.639 | 1.00 | 0.03 N |
| ATOM | 169 | CA | GLY | E | 21 | 14.313 | 25.887 | 59.686 | 1.00 | 0.01 C |
| ATOM | 170 | C | GLY | E | 21 | 15.530 | 25.819 | 58.770 | 1.00 | 0.02 C |
| ATOM | 171 | O | GLY | E | 21 | 16.228 | 24.797 | 58.732 | 1.00 | 0.03 O |
| ATOM | 172 | N | ARG | E | 22 | 15.888 | 26.965 | 58.218 | 1.00 | 0.02 N |
| ATOM | 173 | CA | ARG | E | 22 | 17.055 | 27.092 | 57.344 | 1.00 | 0.01 C |
| ATOM | 174 | CB | ARG | E | 22 | 17.052 | 28.529 | 56.845 | 1.00 | 0.12 C |
| ATOM | 175 | CG | ARG | E | 22 | 18.322 | 28.877 | 56.084 | 1.00 | 0.50 C |

TABLE 3-continued

| ATOM | 176 | CD | ARG | E | 22 | 18.437 | 30.389 | 55.930 | 1.00 | 0.54 | C |
| --- | --- | --- | --- | --- | --- | --- | --- | --- | --- | --- | --- |
| ATOM | 177 | NE | ARG | E | 22 | 18.244 | 31.061 | 57.230 | 1.00 | 1.34 | N |
| ATOM | 178 | CZ | ARG | E | 22 | 19.208 | 31.289 | 58.129 | 1.00 | 2.11 | C |
| ATOM | 179 | NH1 | ARG | E | 22 | 18.926 | 31.948 | 59.254 | 1.00 | 2.95 | N |
| ATOM | 180 | NH2 | ARG | E | 22 | 20.461 | 30.892 | 57.894 | 1.00 | 2.30 | N |
| ATOM | 181 | C | ARG | E | 22 | 18.372 | 26.842 | 58.076 | 1.00 | 0.03 | C |
| ATOM | 182 | O | ARG | E | 22 | 19.231 | 26.128 | 57.547 | 1.00 | 0.03 | O |
| ATOM | 183 | N | GLN | E | 23 | 18.403 | 27.160 | 59.359 | 1.00 | 0.02 | N |
| ATOM | 184 | CA | GLN | E | 23 | 19.610 | 26.977 | 60.165 | 1.00 | 0.02 | C |
| ATOM | 185 | CB | GLN | E | 23 | 19.418 | 27.867 | 61.382 | 1.00 | 0.17 | C |
| ATOM | 186 | CG | GLN | E | 23 | 20.578 | 27.863 | 62.361 | 1.00 | 1.00 | C |
| ATOM | 187 | CD | GLN | E | 23 | 20.246 | 28.877 | 63.448 | 1.00 | 1.48 | C |
| ATOM | 188 | OE1 | GLN | E | 23 | 20.905 | 28.945 | 64.492 | 1.00 | 1.82 | O |
| ATOM | 189 | NE2 | GLN | E | 23 | 19.207 | 29.655 | 63.188 | 1.00 | 2.18 | N |
| ATOM | 190 | C | GLN | E | 23 | 19.800 | 25.519 | 60.590 | 1.00 | 0.03 | C |
| ATOM | 191 | O | GLN | E | 23 | 20.921 | 25.000 | 60.518 | 1.00 | 0.03 | O |
| ATOM | 192 | N | VAL | E | 24 | 18.696 | 24.807 | 60.744 | 1.00 | 0.02 | N |
| ATOM | 193 | CA | VAL | E | 24 | 18.753 | 23.384 | 61.086 | 1.00 | 0.01 | C |
| ATOM | 194 | CB | VAL | E | 24 | 17.429 | 23.013 | 61.750 | 1.00 | 0.31 | C |
| ATOM | 195 | CG1 | VAL | E | 24 | 17.305 | 21.517 | 61.990 | 1.00 | 0.74 | C |
| ATOM | 196 | CG2 | VAL | E | 24 | 17.254 | 23.767 | 63.063 | 1.00 | 0.32 | C |
| ATOM | 197 | C | VAL | E | 24 | 19.013 | 22.528 | 59.844 | 1.00 | 0.02 | C |
| ATOM | 198 | O | VAL | E | 24 | 19.812 | 21.583 | 59.910 | 1.00 | 0.02 | O |
| ATOM | 199 | N | LEU | E | 25 | 18.607 | 23.038 | 58.690 | 1.00 | 0.02 | N |
| ATOM | 200 | CA | LEU | E | 25 | 18.945 | 22.377 | 57.426 | 1.00 | 0.02 | C |
| ATOM | 201 | CB | LEU | E | 25 | 18.065 | 22.933 | 56.312 | 1.00 | 0.10 | C |
| ATOM | 202 | CG | LEU | E | 25 | 18.434 | 22.313 | 54.966 | 1.00 | 0.17 | C |
| ATOM | 203 | CD1 | LEU | E | 25 | 18.163 | 20.812 | 54.953 | 1.00 | 0.27 | C |
| ATOM | 204 | CD2 | LEU | E | 25 | 17.704 | 22.997 | 53.818 | 1.00 | 0.25 | C |
| ATOM | 205 | C | LEU | E | 25 | 20.404 | 22.636 | 57.070 | 1.00 | 0.02 | C |
| ATOM | 206 | O | LEU | E | 25 | 21.113 | 21.703 | 56.675 | 1.00 | 0.03 | O |
| ATOM | 207 | N | GLU | E | 26 | 20.902 | 23.786 | 57.494 | 1.00 | 0.02 | N |
| ATOM | 208 | CA | GLU | E | 26 | 22.306 | 24.130 | 57.290 | 1.00 | 0.02 | C |
| ATOM | 209 | CB | GLU | E | 26 | 22.468 | 25.618 | 57.581 | 1.00 | 0.32 | C |
| ATOM | 210 | CG | GLU | E | 26 | 23.906 | 26.084 | 57.398 | 1.00 | 1.01 | C |
| ATOM | 211 | CD | GLU | E | 26 | 24.015 | 27.567 | 57.724 | 1.00 | 0.99 | C |
| ATOM | 212 | OE1 | GLU | E | 26 | 23.122 | 28.065 | 58.398 | 1.00 | 1.00 | O |
| ATOM | 213 | OE2 | GLU | E | 26 | 24.918 | 28.199 | 57.193 | 1.00 | 1.50 | O |
| ATOM | 214 | C | GLU | E | 26 | 23.217 | 23.327 | 58.210 | 1.00 | 0.04 | C |
| ATOM | 215 | O | GLU | E | 26 | 24.298 | 22.927 | 57.770 | 1.00 | 0.02 | O |
| ATOM | 216 | N | THR | E | 27 | 22.693 | 22.868 | 59.336 | 1.00 | 0.04 | N |
| ATOM | 217 | CA | THR | E | 27 | 23.478 | 22.025 | 60.240 | 1.00 | 0.02 | C |
| ATOM | 218 | CB | THR | E | 27 | 22.875 | 22.144 | 61.633 | 1.00 | 0.14 | C |
| ATOM | 219 | OG1 | THR | E | 27 | 22.944 | 23.514 | 62.006 | 1.00 | 0.18 | O |
| ATOM | 220 | CG2 | THR | E | 27 | 23.656 | 21.332 | 62.660 | 1.00 | 0.21 | C |
| ATOM | 221 | C | THR | E | 27 | 23.492 | 20.567 | 59.782 | 1.00 | 0.01 | C |
| ATOM | 222 | O | THR | E | 27 | 24.547 | 19.920 | 59.833 | 1.00 | 0.03 | O |
| ATOM | 223 | N | PHE | E | 28 | 22.449 | 20.172 | 59.070 | 1.00 | 0.02 | N |
| ATOM | 224 | CA | PHE | E | 28 | 22.420 | 18.835 | 58.471 | 1.00 | 0.01 | C |
| ATOM | 225 | CB | PHE | E | 28 | 20.979 | 18.514 | 58.098 | 1.00 | 0.02 | C |
| ATOM | 226 | CG | PHE | E | 28 | 20.797 | 17.180 | 57.383 | 1.00 | 0.03 | C |
| ATOM | 227 | CD1 | PHE | E | 28 | 20.912 | 15.991 | 58.092 | 1.00 | 0.02 | C |
| ATOM | 228 | CE1 | PHE | E | 28 | 20.749 | 14.776 | 57.440 | 1.00 | 0.04 | C |
| ATOM | 229 | CZ | PHE | E | 28 | 20.469 | 14.751 | 56.081 | 1.00 | 0.02 | C |
| ATOM | 230 | CE2 | PHE | E | 28 | 20.353 | 15.939 | 55.372 | 1.00 | 0.02 | C |
| ATOM | 231 | CD2 | PHE | E | 28 | 20.519 | 17.154 | 56.023 | 1.00 | 0.02 | C |
| ATOM | 232 | C | PHE | E | 28 | 23.304 | 18.783 | 57.226 | 1.00 | 0.03 | C |
| ATOM | 233 | O | PHE | E | 28 | 24.035 | 17.805 | 57.018 | 1.00 | 0.01 | O |
| ATOM | 234 | N | LEU | E | 29 | 23.420 | 19.916 | 56.557 | 1.00 | 0.02 | N |
| ATOM | 235 | CA | LEU | E | 29 | 24.334 | 20.017 | 55.426 | 1.00 | 0.02 | C |
| ATOM | 236 | CB | LEU | E | 29 | 23.877 | 21.182 | 54.555 | 1.00 | 0.03 | C |
| ATOM | 237 | CG | LEU | E | 29 | 22.520 | 20.905 | 53.914 | 1.00 | 0.02 | C |
| ATOM | 238 | CD1 | LEU | E | 29 | 21.938 | 22.149 | 53.262 | 1.00 | 0.02 | C |
| ATOM | 239 | CD2 | LEU | E | 29 | 22.606 | 19.780 | 52.896 | 1.00 | 0.02 | C |
| ATOM | 240 | C | LEU | E | 29 | 25.777 | 20.215 | 55.895 | 1.00 | 0.03 | C |
| ATOM | 241 | O | LEU | E | 29 | 26.701 | 19.723 | 55.235 | 1.00 | 0.03 | O |
| ATOM | 242 | N | GLU | E | 30 | 25.961 | 20.697 | 57.113 | 1.00 | 0.02 | N |
| ATOM | 243 | CA | GLU | E | 30 | 27.306 | 20.810 | 57.696 | 1.00 | 0.03 | C |
| ATOM | 244 | CB | GLU | E | 30 | 27.236 | 21.650 | 58.968 | 1.00 | 0.21 | C |
| ATOM | 245 | CG | GLU | E | 30 | 27.142 | 23.140 | 58.668 | 1.00 | 0.56 | C |
| ATOM | 246 | CD | GLU | E | 30 | 26.505 | 23.876 | 59.842 | 1.00 | 1.50 | C |
| ATOM | 247 | OE1 | GLU | E | 30 | 26.538 | 23.334 | 60.938 | 1.00 | 2.43 | O |
| ATOM | 248 | OE2 | GLU | E | 30 | 25.819 | 24.859 | 59.583 | 1.00 | 2.00 | O |
| ATOM | 249 | C | GLU | E | 30 | 27.863 | 19.440 | 58.042 | 1.00 | 0.03 | C |
| ATOM | 250 | O | GLU | E | 30 | 28.972 | 19.115 | 57.600 | 1.00 | 0.03 | O |
| ATOM | 251 | N | SER | E | 31 | 26.989 | 18.565 | 58.516 | 1.00 | 0.02 | N |
| ATOM | 252 | CA | SER | E | 31 | 27.402 | 17.196 | 58.848 | 1.00 | 0.01 | C |
| ATOM | 253 | CB | SER | E | 31 | 26.420 | 16.610 | 59.858 | 1.00 | 0.02 | C |
| ATOM | 254 | OG | SER | E | 31 | 25.148 | 16.503 | 59.236 | 1.00 | 0.01 | O |

TABLE 3-continued

| | | | | | | | | | | |
|---|---|---|---|---|---|---|---|---|---|---|
| ATOM | 255 | C | SER | E | 31 | 27.485 | 16.282 | 57.621 | 1.00 | 0.02 C |
| ATOM | 256 | O | SER | E | 31 | 27.931 | 15.136 | 57.739 | 1.00 | 0.02 O |
| ATOM | 257 | N | GLU | E | 32 | 27.061 | 16.773 | 56.467 | 1.00 | 0.02 N |
| ATOM | 258 | CA | GLU | E | 32 | 27.256 | 16.041 | 55.213 | 1.00 | 0.02 C |
| ATOM | 259 | CB | GLU | E | 32 | 25.992 | 16.151 | 54.379 | 1.00 | 0.02 C |
| ATOM | 260 | CG | GLU | E | 32 | 24.802 | 15.458 | 55.014 | 1.00 | 0.01 C |
| ATOM | 261 | CD | GLU | E | 32 | 23.586 | 15.747 | 54.148 | 1.00 | 0.01 C |
| ATOM | 262 | OE1 | GLU | E | 32 | 23.428 | 16.898 | 53.761 | 1.00 | 0.00 O |
| ATOM | 263 | OE2 | GLU | E | 32 | 22.845 | 14.818 | 53.870 | 1.00 | 0.02 O |
| ATOM | 264 | C | GLU | E | 32 | 28.397 | 16.611 | 54.374 | 1.00 | 0.02 C |
| ATOM | 265 | O | GLU | E | 32 | 28.695 | 16.056 | 53.309 | 1.00 | 0.03 O |
| ATOM | 266 | N | PHE | E | 33 | 28.995 | 17.703 | 54.836 | 1.00 | 0.03 N |
| ATOM | 267 | CA | PHE | E | 33 | 29.990 | 18.467 | 54.059 | 1.00 | 0.03 C |
| ATOM | 268 | CB | PHE | E | 33 | 31.239 | 17.624 | 53.811 | 1.00 | 0.97 C |
| ATOM | 269 | CG | PHE | E | 33 | 31.964 | 17.198 | 55.083 | 1.00 | 1.76 C |
| ATOM | 270 | CD1 | PHE | E | 33 | 32.616 | 18.148 | 55.860 | 1.00 | 2.00 C |
| ATOM | 271 | CE1 | PHE | E | 33 | 33.274 | 17.764 | 57.020 | 1.00 | 3.14 C |
| ATOM | 272 | CZ | PHE | E | 33 | 33.281 | 16.431 | 57.406 | 1.00 | 3.86 C |
| ATOM | 273 | CE2 | PHE | E | 33 | 32.630 | 15.480 | 56.631 | 1.00 | 3.76 C |
| ATOM | 274 | CD2 | PHE | E | 33 | 31.972 | 15.863 | 55.470 | 1.00 | 2.85 C |
| ATOM | 275 | C | PHE | E | 33 | 29.383 | 18.946 | 52.740 | 1.00 | 0.02 C |
| ATOM | 276 | O | PHE | E | 33 | 29.960 | 18.798 | 51.658 | 1.00 | 0.01 O |
| ATOM | 277 | N | SER | E | 34 | 28.215 | 19.549 | 52.876 | 1.00 | 0.02 N |
| ATOM | 278 | CA | SER | E | 34 | 27.426 | 20.045 | 51.751 | 1.00 | 0.01 C |
| ATOM | 279 | CB | SER | E | 34 | 26.397 | 18.984 | 51.387 | 1.00 | 0.02 C |
| ATOM | 280 | OG | SER | E | 34 | 25.605 | 18.758 | 52.544 | 1.00 | 0.02 O |
| ATOM | 281 | C | SER | E | 34 | 26.710 | 21.326 | 52.159 | 1.00 | 0.03 C |
| ATOM | 282 | O | SER | E | 34 | 25.733 | 21.748 | 51.524 | 1.00 | 0.00 O |
| ATOM | 283 | N | SER | E | 35 | 27.274 | 22.000 | 53.151 | 1.00 | 0.02 N |
| ATOM | 284 | CA | SER | E | 35 | 26.649 | 23.209 | 53.705 | 1.00 | 0.03 C |
| ATOM | 285 | CB | SER | E | 35 | 27.169 | 23.443 | 55.113 | 1.00 | 1.70 C |
| ATOM | 286 | OG | SER | E | 35 | 26.361 | 24.453 | 55.708 | 1.00 | 2.24 O |
| ATOM | 287 | C | SER | E | 35 | 26.938 | 24.439 | 52.862 | 1.00 | 0.02 C |
| ATOM | 288 | O | SER | E | 35 | 26.203 | 25.431 | 52.939 | 1.00 | 0.02 O |
| ATOM | 289 | N | GLU | E | 36 | 27.811 | 24.266 | 51.884 | 1.00 | 0.02 N |
| ATOM | 290 | CA | GLU | E | 36 | 28.118 | 25.330 | 50.932 | 1.00 | 0.02 C |
| ATOM | 291 | CB | GLU | E | 36 | 29.395 | 24.991 | 50.144 | 1.00 | 0.02 C |
| ATOM | 292 | CG | GLU | E | 36 | 29.263 | 23.954 | 49.015 | 1.00 | 0.02 C |
| ATOM | 293 | CD | GLU | E | 36 | 29.246 | 22.509 | 49.512 | 1.00 | 0.02 C |
| ATOM | 294 | OE1 | GLU | E | 36 | 29.607 | 22.335 | 50.672 | 1.00 | 0.02 O |
| ATOM | 295 | OE2 | GLU | E | 36 | 28.523 | 21.728 | 48.912 | 1.00 | 0.03 O |
| ATOM | 296 | C | GLU | E | 36 | 26.955 | 25.587 | 49.972 | 1.00 | 0.01 C |
| ATOM | 297 | O | GLU | E | 36 | 26.765 | 26.747 | 49.600 | 1.00 | 0.02 O |
| ATOM | 298 | N | ASN | E | 37 | 26.028 | 24.646 | 49.848 | 1.00 | 0.01 N |
| ATOM | 299 | CA | ASN | E | 37 | 24.880 | 24.862 | 48.972 | 1.00 | 0.02 C |
| ATOM | 300 | CB | ASN | E | 37 | 24.277 | 23.505 | 48.619 | 1.00 | 0.02 C |
| ATOM | 301 | CG | ASN | E | 37 | 25.309 | 22.604 | 47.940 | 1.00 | 0.02 C |
| ATOM | 302 | OD1 | ASN | E | 37 | 26.009 | 23.009 | 47.000 | 1.00 | 0.02 O |
| ATOM | 303 | ND2 | ASN | E | 37 | 25.415 | 21.391 | 48.454 | 1.00 | 0.02 N |
| ATOM | 304 | C | ASN | E | 37 | 23.825 | 25.740 | 49.649 | 1.00 | 0.03 C |
| ATOM | 305 | O | ASN | E | 37 | 23.328 | 26.683 | 49.018 | 1.00 | 0.00 O |
| ATOM | 306 | N | ILE | E | 38 | 23.709 | 25.636 | 50.965 | 1.00 | 0.02 N |
| ATOM | 307 | CA | ILE | E | 38 | 22.724 | 26.471 | 51.664 | 1.00 | 0.02 C |
| ATOM | 308 | CB | ILE | E | 38 | 22.171 | 25.734 | 52.887 | 1.00 | 0.01 C |
| ATOM | 309 | CG2 | ILE | E | 38 | 23.272 | 25.333 | 53.859 | 1.00 | 0.02 C |
| ATOM | 310 | CG1 | ILE | E | 38 | 21.109 | 26.557 | 53.612 | 1.00 | 0.02 C |
| ATOM | 311 | CD1 | ILE | E | 38 | 19.898 | 26.823 | 52.724 | 1.00 | 0.00 C |
| ATOM | 312 | C | ILE | E | 38 | 23.338 | 27.816 | 52.046 | 1.00 | 0.02 C |
| ATOM | 313 | O | ILE | E | 38 | 22.642 | 28.835 | 51.979 | 1.00 | 0.02 O |
| ATOM | 314 | N | ARG | E | 39 | 24.660 | 27.858 | 52.098 | 1.00 | 0.01 N |
| ATOM | 315 | CA | ARG | E | 39 | 25.359 | 29.112 | 52.364 | 1.00 | 0.03 C |
| ATOM | 316 | CB | ARG | E | 39 | 26.772 | 28.758 | 52.798 | 1.00 | 0.23 C |
| ATOM | 317 | CG | ARG | E | 39 | 27.526 | 29.957 | 53.353 | 1.00 | 0.42 C |
| ATOM | 318 | CD | ARG | E | 39 | 28.953 | 29.560 | 53.709 | 1.00 | 0.91 C |
| ATOM | 319 | NE | ARG | E | 39 | 28.959 | 28.374 | 54.581 | 1.00 | 1.27 N |
| ATOM | 320 | CZ | ARG | E | 39 | 29.656 | 27.270 | 54.304 | 1.00 | 1.63 C |
| ATOM | 321 | NH1 | ARG | E | 39 | 30.395 | 27.209 | 53.195 | 1.00 | 2.16 N |
| ATOM | 322 | NH2 | ARG | E | 39 | 29.611 | 26.226 | 55.134 | 1.00 | 1.77 N |
| ATOM | 323 | C | ARG | E | 39 | 25.395 | 29.951 | 51.093 | 1.00 | 0.02 C |
| ATOM | 324 | O | ARG | E | 39 | 25.187 | 31.170 | 51.144 | 1.00 | 0.03 O |
| ATOM | 325 | N | PHE | E | 40 | 25.369 | 29.260 | 49.966 | 1.00 | 0.02 N |
| ATOM | 326 | CA | PHE | E | 40 | 25.250 | 29.911 | 48.666 | 1.00 | 0.02 C |
| ATOM | 327 | CB | PHE | E | 40 | 25.608 | 28.881 | 47.605 | 1.00 | 0.03 C |
| ATOM | 328 | CG | PHE | E | 40 | 25.280 | 29.289 | 46.176 | 1.00 | 0.02 C |
| ATOM | 329 | CD1 | PHE | E | 40 | 26.094 | 30.188 | 45.502 | 1.00 | 0.02 C |
| ATOM | 330 | CE1 | PHE | E | 40 | 25.786 | 30.556 | 44.200 | 1.00 | 0.02 C |
| ATOM | 331 | CZ | PHE | E | 40 | 24.666 | 30.026 | 43.574 | 1.00 | 0.01 C |
| ATOM | 332 | CE2 | PHE | E | 40 | 23.853 | 29.128 | 44.249 | 1.00 | 0.02 C |
| ATOM | 333 | CD2 | PHE | E | 40 | 24.160 | 28.759 | 45.550 | 1.00 | 0.02 C |

TABLE 3-continued

| ATOM | 334 | C | PHE | E | 40 | 23.836 | 30.419 | 48.426 | 1.00 | 0.02 | C |
|---|---|---|---|---|---|---|---|---|---|---|---|
| ATOM | 335 | O | PHE | E | 40 | 23.688 | 31.550 | 47.956 | 1.00 | 0.01 | O |
| ATOM | 336 | N | TRP | E | 41 | 22.840 | 29.733 | 48.964 | 1.00 | 0.01 | N |
| ATOM | 337 | CA | TRP | E | 41 | 21.461 | 30.210 | 48.828 | 1.00 | 0.03 | C |
| ATOM | 338 | CB | TRP | E | 41 | 20.509 | 29.111 | 49.291 | 1.00 | 0.02 | C |
| ATOM | 339 | CG | TRP | E | 41 | 19.046 | 29.477 | 49.133 | 1.00 | 0.01 | C |
| ATOM | 340 | CD1 | TRP | E | 41 | 18.278 | 29.305 | 48.004 | 1.00 | 0.02 | C |
| ATOM | 341 | NE1 | TRP | E | 41 | 17.034 | 29.785 | 48.253 | 1.00 | 0.03 | N |
| ATOM | 342 | CE2 | TRP | E | 41 | 16.938 | 30.264 | 49.507 | 1.00 | 0.02 | C |
| ATOM | 343 | CZ2 | TRP | E | 41 | 15.907 | 30.875 | 50.205 | 1.00 | 0.02 | C |
| ATOM | 344 | CH2 | TRP | E | 41 | 16.109 | 31.278 | 51.521 | 1.00 | 0.02 | C |
| ATOM | 345 | CZ3 | TRP | E | 41 | 17.339 | 31.074 | 52.138 | 1.00 | 0.02 | C |
| ATOM | 346 | CE3 | TRP | E | 41 | 18.379 | 30.470 | 51.443 | 1.00 | 0.01 | C |
| ATOM | 347 | CD2 | TRP | E | 41 | 18.185 | 30.072 | 50.129 | 1.00 | 0.03 | C |
| ATOM | 348 | C | TRP | E | 41 | 21.240 | 31.472 | 49.660 | 1.00 | 0.02 | C |
| ATOM | 349 | O | TRP | E | 41 | 20.731 | 32.468 | 49.127 | 1.00 | 0.02 | O |
| ATOM | 350 | N | ILE | E | 42 | 21.882 | 31.528 | 50.817 | 1.00 | 0.02 | N |
| ATOM | 351 | CA | ILE | E | 42 | 21.806 | 32.720 | 51.668 | 1.00 | 0.03 | C |
| ATOM | 352 | CB | ILE | E | 42 | 22.416 | 32.370 | 53.019 | 1.00 | 0.03 | C |
| ATOM | 353 | CG2 | ILE | E | 42 | 22.415 | 33.584 | 53.943 | 1.00 | 0.02 | C |
| ATOM | 354 | CG1 | ILE | E | 42 | 21.670 | 31.214 | 53.670 | 1.00 | 0.03 | C |
| ATOM | 355 | CD1 | ILE | E | 42 | 22.412 | 30.706 | 54.900 | 1.00 | 0.01 | C |
| ATOM | 356 | C | ILE | E | 42 | 22.579 | 33.887 | 51.055 | 1.00 | 0.03 | C |
| ATOM | 357 | O | ILE | E | 42 | 22.043 | 35.001 | 50.979 | 1.00 | 0.02 | O |
| ATOM | 358 | N | ALA | E | 43 | 23.665 | 33.574 | 50.367 | 1.00 | 0.01 | N |
| ATOM | 359 | CA | ALA | E | 43 | 24.456 | 34.609 | 49.700 | 1.00 | 0.02 | C |
| ATOM | 360 | CB | ALA | E | 43 | 25.820 | 34.028 | 49.349 | 1.00 | 0.05 | C |
| ATOM | 361 | C | ALA | E | 43 | 23.786 | 35.144 | 48.436 | 1.00 | 0.02 | C |
| ATOM | 362 | O | ALA | E | 43 | 23.872 | 36.352 | 48.194 | 1.00 | 0.01 | O |
| ATOM | 363 | N | ILE | E | 44 | 22.922 | 34.358 | 47.811 | 1.00 | 0.02 | N |
| ATOM | 364 | CA | ILE | E | 44 | 22.199 | 34.858 | 46.635 | 1.00 | 0.03 | C |
| ATOM | 365 | CB | ILE | E | 44 | 21.756 | 33.708 | 45.737 | 1.00 | 0.39 | C |
| ATOM | 366 | CG2 | ILE | E | 44 | 21.088 | 34.254 | 44.481 | 1.00 | 0.92 | C |
| ATOM | 367 | CG1 | ILE | E | 44 | 22.931 | 32.824 | 45.349 | 1.00 | 0.66 | C |
| ATOM | 368 | CD1 | ILE | E | 44 | 24.047 | 33.626 | 44.694 | 1.00 | 1.09 | C |
| ATOM | 369 | C | ILE | E | 44 | 20.980 | 35.654 | 47.074 | 1.00 | 0.02 | C |
| ATOM | 370 | O | ILE | E | 44 | 20.687 | 36.704 | 46.487 | 1.00 | 0.02 | O |
| ATOM | 371 | N | GLN | E | 45 | 20.505 | 35.348 | 48.269 | 1.00 | 0.03 | N |
| ATOM | 372 | CA | GLN | E | 45 | 19.447 | 36.151 | 48.880 | 1.00 | 0.02 | C |
| ATOM | 373 | CB | GLN | E | 45 | 18.902 | 35.380 | 50.078 | 1.00 | 0.15 | C |
| ATOM | 374 | CG | GLN | E | 45 | 17.783 | 36.137 | 50.788 | 1.00 | 0.97 | C |
| ATOM | 375 | CD | GLN | E | 45 | 16.551 | 36.242 | 49.894 | 1.00 | 1.26 | C |
| ATOM | 376 | OE1 | GLN | E | 45 | 15.850 | 35.247 | 49.676 | 1.00 | 1.64 | O |
| ATOM | 377 | NE2 | GLN | E | 45 | 16.324 | 37.429 | 49.358 | 1.00 | 1.96 | N |
| ATOM | 378 | C | GLN | E | 45 | 19.990 | 37.506 | 49.343 | 1.00 | 0.02 | C |
| ATOM | 379 | O | GLN | E | 45 | 19.317 | 38.531 | 49.172 | 1.00 | 0.02 | O |
| ATOM | 380 | N | ASP | E | 46 | 21.274 | 37.531 | 49.676 | 1.00 | 0.03 | N |
| ATOM | 381 | CA | ASP | E | 46 | 21.975 | 38.768 | 50.048 | 1.00 | 0.02 | C |
| ATOM | 382 | CB | ASP | E | 46 | 23.133 | 38.407 | 50.977 | 1.00 | 0.08 | C |
| ATOM | 383 | CG | ASP | E | 46 | 22.660 | 37.666 | 52.226 | 1.00 | 0.16 | C |
| ATOM | 384 | OD1 | ASP | E | 46 | 21.586 | 37.992 | 52.713 | 1.00 | 0.15 | O |
| ATOM | 385 | OD2 | ASP | E | 46 | 23.445 | 36.880 | 52.743 | 1.00 | 0.31 | O |
| ATOM | 386 | C | ASP | E | 46 | 22.543 | 39.511 | 48.831 | 1.00 | 0.03 | C |
| ATOM | 387 | O | ASP | E | 46 | 23.039 | 40.636 | 48.969 | 1.00 | 0.02 | O |
| ATOM | 388 | N | LEU | E | 47 | 22.399 | 38.922 | 47.653 | 1.00 | 0.03 | N |
| ATOM | 389 | CA | LEU | E | 47 | 22.897 | 39.512 | 46.407 | 1.00 | 0.03 | C |
| ATOM | 390 | CB | LEU | E | 47 | 23.281 | 38.341 | 45.496 | 1.00 | 3.01 | C |
| ATOM | 391 | CG | LEU | E | 47 | 23.938 | 38.707 | 44.167 | 1.00 | 4.01 | C |
| ATOM | 392 | CD1 | LEU | E | 47 | 22.944 | 38.979 | 43.043 | 1.00 | 5.12 | C |
| ATOM | 393 | CD2 | LEU | E | 47 | 24.986 | 39.803 | 44.300 | 1.00 | 4.53 | C |
| ATOM | 394 | C | LEU | E | 47 | 21.828 | 40.406 | 45.781 | 1.00 | 0.02 | C |
| ATOM | 395 | O | LEU | E | 47 | 22.153 | 41.297 | 44.984 | 1.00 | 0.02 | O |
| ATOM | 396 | N | LYS | E | 48 | 20.614 | 40.322 | 46.307 | 1.00 | 0.03 | N |
| ATOM | 397 | CA | LYS | E | 48 | 19.497 | 41.155 | 45.838 | 1.00 | 0.01 | C |
| ATOM | 398 | CB | LYS | E | 48 | 18.220 | 40.366 | 46.090 | 1.00 | 0.02 | C |
| ATOM | 399 | CG | LYS | E | 48 | 18.389 | 38.937 | 45.588 | 1.00 | 0.03 | C |
| ATOM | 400 | CD | LYS | E | 48 | 17.142 | 38.095 | 45.817 | 1.00 | 0.01 | C |
| ATOM | 401 | CE | LYS | E | 48 | 17.394 | 36.643 | 45.428 | 1.00 | 0.02 | C |
| ATOM | 402 | NZ | LYS | E | 48 | 17.862 | 36.546 | 44.036 | 1.00 | 0.02 | N |
| ATOM | 403 | C | LYS | E | 48 | 19.445 | 42.499 | 46.578 | 1.00 | 0.02 | C |
| ATOM | 404 | O | LYS | E | 48 | 18.413 | 42.883 | 47.139 | 1.00 | 0.02 | O |
| ATOM | 405 | N | TYR | E | 49 | 20.559 | 43.210 | 46.526 | 1.00 | 0.03 | N |
| ATOM | 406 | CA | TYR | E | 49 | 20.752 | 44.462 | 47.255 | 1.00 | 0.03 | C |
| ATOM | 407 | CB | TYR | E | 49 | 22.227 | 44.490 | 47.653 | 1.00 | 1.91 | C |
| ATOM | 408 | CG | TYR | E | 49 | 22.580 | 45.320 | 48.883 | 1.00 | 2.68 | C |
| ATOM | 409 | CD1 | TYR | E | 49 | 21.651 | 45.493 | 49.903 | 1.00 | 3.02 | C |
| ATOM | 410 | CE1 | TYR | E | 49 | 21.981 | 46.250 | 51.020 | 1.00 | 4.05 | C |
| ATOM | 411 | CZ | TYR | E | 49 | 23.242 | 46.825 | 51.114 | 1.00 | 4.78 | C |
| ATOM | 412 | OH | TYR | E | 49 | 23.566 | 47.588 | 52.214 | 1.00 | 5.92 | O |

TABLE 3-continued

| | | | | | | | | | | |
|---|---|---|---|---|---|---|---|---|---|---|
| ATOM | 413 | CE2 | TYR | E | 49 | 24.173 | 46.641 | 50.102 | 1.00 | 4.52 C |
| ATOM | 414 | CD2 | TYR | E | 49 | 23.843 | 45.886 | 48.987 | 1.00 | 3.43 C |
| ATOM | 415 | C | TYR | E | 49 | 20.388 | 45.657 | 46.367 | 1.00 | 0.03 C |
| ATOM | 416 | O | TYR | E | 49 | 20.096 | 45.497 | 45.177 | 1.00 | 0.02 O |
| ATOM | 417 | N | ALA | E | 50 | 20.283 | 46.822 | 46.980 | 1.00 | 0.02 N |
| ATOM | 418 | CA | ALA | E | 50 | 19.981 | 48.048 | 46.228 | 1.00 | 0.02 C |
| ATOM | 419 | CB | ALA | E | 50 | 19.160 | 49.000 | 47.099 | 1.00 | 0.58 C |
| ATOM | 420 | C | ALA | E | 50 | 21.206 | 48.750 | 45.604 | 1.00 | 0.03 C |
| ATOM | 421 | O | ALA | E | 50 | 21.187 | 48.908 | 44.377 | 1.00 | 0.03 O |
| ATOM | 422 | N | PRO | E | 51 | 22.223 | 49.178 | 46.357 | 1.00 | 0.02 N |
| ATOM | 423 | CA | PRO | E | 51 | 23.363 | 49.850 | 45.714 | 1.00 | 0.03 C |
| ATOM | 424 | CB | PRO | E | 51 | 24.258 | 50.311 | 46.822 | 1.00 | 1.18 C |
| ATOM | 425 | CG | PRO | E | 51 | 23.686 | 49.851 | 48.150 | 1.00 | 1.48 C |
| ATOM | 426 | CD | PRO | E | 51 | 22.395 | 49.122 | 47.820 | 1.00 | 1.19 C |
| ATOM | 427 | C | PRO | E | 51 | 24.109 | 48.916 | 44.771 | 1.00 | 0.03 C |
| ATOM | 428 | O | PRO | E | 51 | 24.719 | 47.927 | 45.202 | 1.00 | 0.03 O |
| ATOM | 429 | N | ASN | E | 52 | 24.278 | 49.388 | 43.548 | 1.00 | 0.01 N |
| ATOM | 430 | CA | ASN | E | 52 | 24.831 | 48.559 | 42.466 | 1.00 | 0.02 C |
| ATOM | 431 | CB | ASN | E | 52 | 24.460 | 49.206 | 41.136 | 1.00 | 0.19 C |
| ATOM | 432 | CG | ASN | E | 52 | 22.972 | 49.553 | 41.103 | 1.00 | 0.21 C |
| ATOM | 433 | OD1 | ASN | E | 52 | 22.610 | 50.735 | 41.079 | 1.00 | 0.31 O |
| ATOM | 434 | ND2 | ASN | E | 52 | 22.136 | 48.529 | 41.099 | 1.00 | 0.27 N |
| ATOM | 435 | C | ASN | E | 52 | 26.348 | 48.431 | 42.556 | 1.00 | 0.02 C |
| ATOM | 436 | O | ASN | E | 52 | 26.910 | 47.401 | 42.162 | 1.00 | 0.02 O |
| ATOM | 437 | N | GLU | E | 53 | 26.937 | 49.309 | 43.351 | 1.00 | 0.03 N |
| ATOM | 438 | CA | GLU | E | 53 | 28.378 | 49.278 | 43.601 | 1.00 | 0.03 C |
| ATOM | 439 | CB | GLU | E | 53 | 28.815 | 50.593 | 44.254 | 1.00 | 0.22 C |
| ATOM | 440 | CG | GLU | E | 53 | 28.401 | 51.840 | 43.471 | 1.00 | 0.87 C |
| ATOM | 441 | CD | GLU | E | 53 | 27.233 | 52.551 | 44.161 | 1.00 | 0.97 C |
| ATOM | 442 | OE1 | GLU | E | 53 | 26.138 | 51.999 | 44.110 | 1.00 | 1.90 O |
| ATOM | 443 | OE2 | GLU | E | 53 | 27.485 | 53.518 | 44.863 | 1.00 | 0.66 O |
| ATOM | 444 | C | GLU | E | 53 | 28.710 | 48.135 | 44.556 | 1.00 | 0.02 C |
| ATOM | 445 | O | GLU | E | 53 | 29.753 | 47.485 | 44.413 | 1.00 | 0.02 O |
| ATOM | 446 | N | GLN | E | 54 | 27.757 | 47.785 | 45.404 | 1.00 | 0.02 N |
| ATOM | 447 | CA | GLN | E | 54 | 27.966 | 46.673 | 46.318 | 1.00 | 0.02 C |
| ATOM | 448 | CB | GLN | E | 54 | 27.271 | 46.961 | 47.638 | 1.00 | 0.43 C |
| ATOM | 449 | CG | GLN | E | 54 | 27.861 | 48.197 | 48.301 | 1.00 | 1.21 C |
| ATOM | 450 | CD | GLN | E | 54 | 27.266 | 48.346 | 49.696 | 1.00 | 2.05 C |
| ATOM | 451 | OE1 | GLN | E | 54 | 26.470 | 49.255 | 49.963 | 1.00 | 2.88 O |
| ATOM | 452 | NE2 | GLN | E | 54 | 27.660 | 47.434 | 50.568 | 1.00 | 2.60 N |
| ATOM | 453 | C | GLN | E | 54 | 27.445 | 45.381 | 45.714 | 1.00 | 0.02 C |
| ATOM | 454 | O | GLN | E | 54 | 28.010 | 44.324 | 46.003 | 1.00 | 0.02 O |
| ATOM | 455 | N | ILE | E | 55 | 26.590 | 45.488 | 44.710 | 1.00 | 0.03 N |
| ATOM | 456 | CA | ILE | E | 55 | 26.129 | 44.292 | 43.998 | 1.00 | 0.02 C |
| ATOM | 457 | CB | ILE | E | 55 | 24.909 | 44.640 | 43.153 | 1.00 | 0.37 C |
| ATOM | 458 | CG2 | ILE | E | 55 | 24.485 | 43.455 | 42.291 | 1.00 | 0.53 C |
| ATOM | 459 | CG1 | ILE | E | 55 | 23.747 | 45.093 | 44.024 | 1.00 | 0.44 C |
| ATOM | 460 | CD1 | ILE | E | 55 | 22.538 | 45.435 | 43.163 | 1.00 | 1.13 C |
| ATOM | 461 | C | ILE | E | 55 | 27.225 | 43.737 | 43.093 | 1.00 | 0.02 C |
| ATOM | 462 | O | ILE | E | 55 | 27.435 | 42.517 | 43.089 | 1.00 | 0.02 O |
| ATOM | 463 | N | TYR | E | 56 | 28.066 | 44.611 | 42.560 | 1.00 | 0.03 N |
| ATOM | 464 | CA | TYR | E | 56 | 29.199 | 44.144 | 41.757 | 1.00 | 0.03 C |
| ATOM | 465 | CB | TYR | E | 56 | 29.859 | 45.340 | 41.076 | 1.00 | 0.28 C |
| ATOM | 466 | CG | TYR | E | 56 | 31.114 | 44.982 | 40.278 | 1.00 | 0.83 C |
| ATOM | 467 | CD1 | TYR | E | 56 | 32.268 | 45.744 | 40.417 | 1.00 | 1.24 C |
| ATOM | 468 | CE1 | TYR | E | 56 | 33.412 | 45.408 | 39.703 | 1.00 | 1.92 C |
| ATOM | 469 | CZ | TYR | E | 56 | 33.399 | 44.310 | 38.853 | 1.00 | 2.21 C |
| ATOM | 470 | OH | TYR | E | 56 | 34.572 | 43.876 | 38.280 | 1.00 | 2.88 O |
| ATOM | 471 | CE2 | TYR | E | 56 | 32.244 | 43.556 | 38.700 | 1.00 | 1.96 C |
| ATOM | 472 | CD2 | TYR | E | 56 | 31.103 | 43.894 | 39.414 | 1.00 | 1.29 C |
| ATOM | 473 | C | TYR | E | 56 | 30.228 | 43.425 | 42.623 | 1.00 | 0.02 C |
| ATOM | 474 | O | TYR | E | 56 | 30.562 | 42.269 | 42.330 | 1.00 | 0.01 O |
| ATOM | 475 | N | GLN | E | 57 | 30.482 | 43.964 | 43.805 | 1.00 | 0.03 N |
| ATOM | 476 | CA | GLN | E | 57 | 31.484 | 43.359 | 44.687 | 1.00 | 0.01 C |
| ATOM | 477 | CB | GLN | E | 57 | 31.898 | 44.387 | 45.727 | 1.00 | 0.12 C |
| ATOM | 478 | CG | GLN | E | 57 | 32.582 | 45.573 | 45.059 | 1.00 | 0.66 C |
| ATOM | 479 | CD | GLN | E | 57 | 32.925 | 46.630 | 46.100 | 1.00 | 1.12 C |
| ATOM | 480 | OE1 | GLN | E | 57 | 33.903 | 46.506 | 46.846 | 1.00 | 1.47 O |
| ATOM | 481 | NE2 | GLN | E | 57 | 32.098 | 47.658 | 46.147 | 1.00 | 1.44 N |
| ATOM | 482 | C | GLN | E | 57 | 30.963 | 42.106 | 45.375 | 1.00 | 0.03 C |
| ATOM | 483 | O | GLN | E | 57 | 31.686 | 41.102 | 45.413 | 1.00 | 0.02 O |
| ATOM | 484 | N | LYS | E | 58 | 29.663 | 42.061 | 45.613 | 1.00 | 0.02 N |
| ATOM | 485 | CA | LYS | E | 58 | 29.040 | 40.898 | 46.243 | 1.00 | 0.02 C |
| ATOM | 486 | CB | LYS | E | 58 | 27.633 | 41.298 | 46.672 | 1.00 | 0.02 C |
| ATOM | 487 | CG | LYS | E | 58 | 26.971 | 40.270 | 47.581 | 1.00 | 0.02 C |
| ATOM | 488 | CD | LYS | E | 58 | 27.746 | 40.113 | 48.884 | 1.00 | 0.03 C |
| ATOM | 489 | CE | LYS | E | 58 | 26.967 | 39.293 | 49.905 | 1.00 | 0.01 C |
| ATOM | 490 | NZ | LYS | E | 58 | 26.648 | 37.957 | 49.385 | 1.00 | 0.02 N |
| ATOM | 491 | C | LYS | E | 58 | 28.966 | 39.743 | 45.257 | 1.00 | 0.03 C |

TABLE 3-continued

| ATOM | 492 | O | LYS | E | 58 | 29.351 | 38.625 | 45.616 | 1.00 | 0.03 | O |
|---|---|---|---|---|---|---|---|---|---|---|---|
| ATOM | 493 | N | ALA | E | 59 | 28.804 | 40.071 | 43.986 | 1.00 | 0.03 | N |
| ATOM | 494 | CA | ALA | E | 59 | 28.785 | 39.048 | 42.942 | 1.00 | 0.02 | C |
| ATOM | 495 | CB | ALA | E | 59 | 28.272 | 39.689 | 41.659 | 1.00 | 0.02 | C |
| ATOM | 496 | C | ALA | E | 59 | 30.175 | 38.471 | 42.711 | 1.00 | 0.03 | C |
| ATOM | 497 | O | ALA | E | 59 | 30.326 | 37.241 | 42.675 | 1.00 | 0.03 | O |
| ATOM | 498 | N | GLU | E | 60 | 31.184 | 39.316 | 42.855 | 1.00 | 0.02 | N |
| ATOM | 499 | CA | GLU | E | 60 | 32.569 | 38.860 | 42.736 | 1.00 | 0.02 | C |
| ATOM | 500 | CB | GLU | E | 60 | 33.492 | 40.073 | 42.733 | 1.00 | 0.15 | C |
| ATOM | 501 | CG | GLU | E | 60 | 33.225 | 40.966 | 41.529 | 1.00 | 0.77 | C |
| ATOM | 502 | CD | GLU | E | 60 | 34.035 | 42.255 | 41.627 | 1.00 | 1.48 | C |
| ATOM | 503 | OE1 | GLU | E | 60 | 33.563 | 43.173 | 42.287 | 1.00 | 2.34 | O |
| ATOM | 504 | OE2 | GLU | E | 60 | 35.036 | 42.351 | 40.931 | 1.00 | 1.92 | O |
| ATOM | 505 | C | GLU | E | 60 | 32.941 | 37.950 | 43.900 | 1.00 | 0.02 | C |
| ATOM | 506 | O | GLU | E | 60 | 33.356 | 36.811 | 43.651 | 1.00 | 0.03 | O |
| ATOM | 507 | N | ARG | E | 61 | 32.517 | 38.312 | 45.100 | 1.00 | 0.02 | N |
| ATOM | 508 | CA | ARG | E | 61 | 32.840 | 37.510 | 46.283 | 1.00 | 0.02 | C |
| ATOM | 509 | CB | ARG | E | 61 | 32.539 | 38.346 | 47.520 | 1.00 | 0.15 | C |
| ATOM | 510 | CG | ARG | E | 61 | 33.556 | 39.473 | 47.662 | 1.00 | 0.49 | C |
| ATOM | 511 | CD | ARG | E | 61 | 33.247 | 40.385 | 48.845 | 1.00 | 0.42 | C |
| ATOM | 512 | NE | ARG | E | 61 | 32.076 | 41.235 | 48.578 | 1.00 | 0.40 | N |
| ATOM | 513 | CZ | ARG | E | 61 | 31.287 | 41.726 | 49.535 | 1.00 | 0.52 | C |
| ATOM | 514 | NH1 | ARG | E | 61 | 30.388 | 42.666 | 49.237 | 1.00 | 0.91 | N |
| ATOM | 515 | NH2 | ARG | E | 61 | 31.515 | 41.406 | 50.811 | 1.00 | 1.11 | N |
| ATOM | 516 | C | ARG | E | 61 | 32.077 | 36.189 | 46.342 | 1.00 | 0.03 | C |
| ATOM | 517 | O | ARG | E | 61 | 32.692 | 35.162 | 46.662 | 1.00 | 0.02 | O |
| ATOM | 518 | N | ILE | E | 62 | 30.878 | 36.150 | 45.783 | 1.00 | 0.03 | N |
| ATOM | 519 | CA | ILE | E | 62 | 30.134 | 34.887 | 45.748 | 1.00 | 0.02 | C |
| ATOM | 520 | CB | ILE | E | 62 | 28.667 | 35.157 | 45.429 | 1.00 | 0.02 | C |
| ATOM | 521 | CG2 | ILE | E | 62 | 27.889 | 33.850 | 45.342 | 1.00 | 0.02 | C |
| ATOM | 522 | CG1 | ILE | E | 62 | 28.023 | 36.053 | 46.474 | 1.00 | 0.03 | C |
| ATOM | 523 | CD1 | ILE | E | 62 | 26.587 | 36.385 | 46.085 | 1.00 | 0.03 | C |
| ATOM | 524 | C | ILE | E | 62 | 30.721 | 33.941 | 44.702 | 1.00 | 0.01 | C |
| ATOM | 525 | O | ILE | E | 62 | 30.989 | 32.777 | 45.034 | 1.00 | 0.02 | O |
| ATOM | 526 | N | ARG | E | 63 | 31.188 | 34.487 | 43.588 | 1.00 | 0.02 | N |
| ATOM | 527 | CA | ARG | E | 63 | 31.811 | 33.640 | 42.566 | 1.00 | 0.02 | C |
| ATOM | 528 | CB | ARG | E | 63 | 31.922 | 34.401 | 41.252 | 1.00 | 0.13 | C |
| ATOM | 529 | CG | ARG | E | 63 | 30.546 | 34.607 | 40.639 | 1.00 | 1.18 | C |
| ATOM | 530 | CD | ARG | E | 63 | 30.626 | 35.286 | 39.278 | 1.00 | 1.07 | C |
| ATOM | 531 | NE | ARG | E | 63 | 31.281 | 36.598 | 39.379 | 1.00 | 1.43 | N |
| ATOM | 532 | CZ | ARG | E | 63 | 30.660 | 37.749 | 39.114 | 1.00 | 2.56 | C |
| ATOM | 533 | NH1 | ARG | E | 63 | 31.355 | 38.888 | 39.080 | 1.00 | 2.76 | N |
| ATOM | 534 | NH2 | ARG | E | 63 | 29.370 | 37.744 | 38.774 | 1.00 | 3.57 | N |
| ATOM | 535 | C | ARG | E | 63 | 33.186 | 33.150 | 42.993 | 1.00 | 0.03 | C |
| ATOM | 536 | O | ARG | E | 63 | 33.435 | 31.944 | 42.901 | 1.00 | 0.02 | O |
| ATOM | 537 | N | GLU | E | 64 | 33.883 | 33.956 | 43.773 | 1.00 | 0.02 | N |
| ATOM | 538 | CA | GLU | E | 64 | 35.204 | 33.561 | 44.268 | 1.00 | 0.03 | C |
| ATOM | 539 | CB | GLU | E | 64 | 35.948 | 34.823 | 44.688 | 1.00 | 0.27 | C |
| ATOM | 540 | CG | GLU | E | 64 | 36.224 | 35.732 | 43.495 | 1.00 | 0.87 | C |
| ATOM | 541 | CD | GLU | E | 64 | 36.803 | 37.062 | 43.969 | 1.00 | 1.38 | C |
| ATOM | 542 | OE1 | GLU | E | 64 | 38.020 | 37.177 | 43.990 | 1.00 | 2.45 | O |
| ATOM | 543 | OE2 | GLU | E | 64 | 36.019 | 37.962 | 44.244 | 1.00 | 1.02 | O |
| ATOM | 544 | C | GLU | E | 64 | 35.137 | 32.597 | 45.454 | 1.00 | 0.03 | C |
| ATOM | 545 | O | GLU | E | 64 | 36.136 | 31.933 | 45.752 | 1.00 | 0.02 | O |
| ATOM | 546 | N | GLU | E | 65 | 33.969 | 32.436 | 46.051 | 1.00 | 0.02 | N |
| ATOM | 547 | CA | GLU | E | 65 | 33.852 | 31.506 | 47.167 | 1.00 | 0.03 | C |
| ATOM | 548 | CB | GLU | E | 65 | 33.084 | 32.211 | 48.277 | 1.00 | 0.03 | C |
| ATOM | 549 | CG | GLU | E | 65 | 32.988 | 31.364 | 49.540 | 1.00 | 0.03 | C |
| ATOM | 550 | CD | GLU | E | 65 | 32.241 | 32.150 | 50.611 | 1.00 | 0.03 | C |
| ATOM | 551 | OE1 | GLU | E | 65 | 31.520 | 33.065 | 50.238 | 1.00 | 0.02 | O |
| ATOM | 552 | OE2 | GLU | E | 65 | 32.426 | 31.846 | 51.781 | 1.00 | 0.01 | O |
| ATOM | 553 | C | GLU | E | 65 | 33.146 | 30.211 | 46.776 | 1.00 | 0.03 | C |
| ATOM | 554 | O | GLU | E | 65 | 33.623 | 29.131 | 47.148 | 1.00 | 0.02 | O |
| ATOM | 555 | N | PHE | E | 66 | 32.103 | 30.303 | 45.966 | 1.00 | 0.02 | N |
| ATOM | 556 | CA | PHE | E | 66 | 31.296 | 29.115 | 45.660 | 1.00 | 0.02 | C |
| ATOM | 557 | CB | PHE | E | 66 | 29.841 | 29.381 | 46.050 | 1.00 | 0.03 | C |
| ATOM | 558 | CG | PHE | E | 66 | 29.546 | 29.844 | 47.474 | 1.00 | 0.02 | C |
| ATOM | 559 | CD1 | PHE | E | 66 | 29.575 | 28.937 | 48.524 | 1.00 | 0.01 | C |
| ATOM | 560 | CE1 | PHE | E | 66 | 29.293 | 29.360 | 49.815 | 1.00 | 0.02 | C |
| ATOM | 561 | CZ | PHE | E | 66 | 28.969 | 30.689 | 50.055 | 1.00 | 0.02 | C |
| ATOM | 562 | CE2 | PHE | E | 66 | 28.923 | 31.593 | 49.002 | 1.00 | 0.03 | C |
| ATOM | 563 | CD2 | PHE | E | 66 | 29.208 | 31.170 | 47.712 | 1.00 | 0.02 | C |
| ATOM | 564 | C | PHE | E | 66 | 31.247 | 28.720 | 44.184 | 1.00 | 0.01 | C |
| ATOM | 565 | O | PHE | E | 66 | 30.674 | 27.665 | 43.881 | 1.00 | 0.01 | O |
| ATOM | 566 | N | LEU | E | 67 | 31.726 | 29.550 | 43.273 | 1.00 | 0.01 | N |
| ATOM | 567 | CA | LEU | E | 67 | 31.390 | 29.299 | 41.859 | 1.00 | 0.02 | C |
| ATOM | 568 | CB | LEU | E | 67 | 30.551 | 30.449 | 41.307 | 1.00 | 0.84 | C |
| ATOM | 569 | CG | LEU | E | 67 | 29.097 | 30.485 | 41.788 | 1.00 | 0.56 | C |
| ATOM | 570 | CD1 | LEU | E | 67 | 28.490 | 29.089 | 41.897 | 1.00 | 0.99 | C |

TABLE 3-continued

| | | | | | | | | | | |
|---|---|---|---|---|---|---|---|---|---|---|
| ATOM | 571 | CD2 | LEU | E | 67 | 28.900 | 31.268 | 43.076 | 1.00 | 0.46 C |
| ATOM | 572 | C | LEU | E | 67 | 32.579 | 29.103 | 40.922 | 1.00 | 0.03 C |
| ATOM | 573 | O | LEU | E | 67 | 32.430 | 28.457 | 39.874 | 1.00 | 0.03 O |
| ATOM | 574 | N | ALA | E | 68 | 33.710 | 29.700 | 41.253 | 1.00 | 0.02 N |
| ATOM | 575 | CA | ALA | E | 68 | 34.923 | 29.561 | 40.443 | 1.00 | 0.02 C |
| ATOM | 576 | CB | ALA | E | 68 | 35.999 | 30.481 | 41.007 | 1.00 | 0.82 C |
| ATOM | 577 | C | ALA | E | 68 | 35.401 | 28.121 | 40.484 | 1.00 | 0.02 C |
| ATOM | 578 | O | ALA | E | 68 | 35.068 | 27.393 | 41.423 | 1.00 | 0.02 O |
| ATOM | 579 | N | GLN | E | 69 | 36.128 | 27.705 | 39.463 | 1.00 | 0.02 N |
| ATOM | 580 | CA | GLN | E | 69 | 36.611 | 26.320 | 39.414 | 1.00 | 0.02 C |
| ATOM | 581 | CB | GLN | E | 69 | 37.028 | 26.009 | 37.980 | 1.00 | 0.34 C |
| ATOM | 582 | CG | GLN | E | 69 | 36.847 | 24.533 | 37.632 | 1.00 | 1.25 C |
| ATOM | 583 | CD | GLN | E | 69 | 35.403 | 24.262 | 37.209 | 1.00 | 1.97 C |
| ATOM | 584 | OE1 | GLN | E | 69 | 34.445 | 24.615 | 37.912 | 1.00 | 2.61 O |
| ATOM | 585 | NE2 | GLN | E | 69 | 35.269 | 23.690 | 36.025 | 1.00 | 2.11 N |
| ATOM | 586 | C | GLN | E | 69 | 37.808 | 26.157 | 40.350 | 1.00 | 0.02 C |
| ATOM | 587 | O | GLN | E | 69 | 38.944 | 26.482 | 39.983 | 1.00 | 0.02 O |
| ATOM | 588 | N | GLY | E | 70 | 37.539 | 25.645 | 41.541 | 1.00 | 0.02 N |
| ATOM | 589 | CA | GLY | E | 70 | 38.558 | 25.554 | 42.586 | 1.00 | 0.03 C |
| ATOM | 590 | C | GLY | E | 70 | 38.224 | 26.507 | 43.734 | 1.00 | 0.02 C |
| ATOM | 591 | O | GLY | E | 70 | 39.109 | 26.918 | 44.496 | 1.00 | 0.02 O |
| ATOM | 592 | N | ALA | E | 71 | 36.958 | 26.881 | 43.823 | 1.00 | 0.03 N |
| ATOM | 593 | CA | ALA | E | 71 | 36.509 | 27.788 | 44.886 | 1.00 | 0.02 C |
| ATOM | 594 | CB | ALA | E | 71 | 35.150 | 28.347 | 44.487 | 1.00 | 0.02 C |
| ATOM | 595 | C | ALA | E | 71 | 36.414 | 27.042 | 46.217 | 1.00 | 0.03 C |
| ATOM | 596 | O | ALA | E | 71 | 36.007 | 25.873 | 46.241 | 1.00 | 0.03 O |
| ATOM | 597 | N | PRO | E | 72 | 36.708 | 27.731 | 47.313 | 1.00 | 0.02 N |
| ATOM | 598 | CA | PRO | E | 72 | 36.912 | 27.058 | 48.610 | 1.00 | 0.03 C |
| ATOM | 599 | CB | PRO | E | 72 | 37.475 | 28.114 | 49.512 | 1.00 | 0.12 C |
| ATOM | 600 | CG | PRO | E | 72 | 37.518 | 29.444 | 48.776 | 1.00 | 0.08 C |
| ATOM | 601 | CD | PRO | E | 72 | 37.050 | 29.156 | 47.360 | 1.00 | 0.07 C |
| ATOM | 602 | C | PRO | E | 72 | 35.640 | 26.465 | 49.228 | 1.00 | 0.03 C |
| ATOM | 603 | O | PRO | E | 72 | 35.722 | 25.573 | 50.079 | 1.00 | 0.02 O |
| ATOM | 604 | N | ALA | E | 73 | 34.487 | 26.917 | 48.769 | 1.00 | 0.02 N |
| ATOM | 605 | CA | ALA | E | 73 | 33.213 | 26.336 | 49.170 | 1.00 | 0.02 C |
| ATOM | 606 | CB | ALA | E | 73 | 32.525 | 27.286 | 50.141 | 1.00 | 0.30 C |
| ATOM | 607 | C | ALA | E | 73 | 32.352 | 26.147 | 47.928 | 1.00 | 0.02 C |
| ATOM | 608 | O | ALA | E | 73 | 31.152 | 26.439 | 47.957 | 1.00 | 0.01 O |
| ATOM | 609 | N | GLN | E | 74 | 32.967 | 25.678 | 46.853 | 1.00 | 0.03 N |
| ATOM | 610 | CA | GLN | E | 74 | 32.266 | 25.531 | 45.573 | 1.00 | 0.02 C |
| ATOM | 611 | CB | GLN | E | 74 | 33.261 | 25.028 | 44.527 | 1.00 | 0.55 C |
| ATOM | 612 | CG | GLN | E | 74 | 32.664 | 25.036 | 43.122 | 1.00 | 0.46 C |
| ATOM | 613 | CD | GLN | E | 74 | 33.724 | 24.744 | 42.065 | 1.00 | 0.54 C |
| ATOM | 614 | OE1 | GLN | E | 74 | 34.929 | 24.705 | 42.359 | 1.00 | 1.12 O |
| ATOM | 615 | NE2 | GLN | E | 74 | 33.259 | 24.627 | 40.833 | 1.00 | 1.25 N |
| ATOM | 616 | C | GLN | E | 74 | 31.064 | 24.591 | 45.682 | 1.00 | 0.02 C |
| ATOM | 617 | O | GLN | E | 74 | 31.129 | 23.517 | 46.293 | 1.00 | 0.02 O |
| ATOM | 618 | N | VAL | E | 75 | 29.940 | 25.082 | 45.189 | 1.00 | 0.01 N |
| ATOM | 619 | CA | VAL | E | 75 | 28.698 | 24.307 | 45.172 | 1.00 | 0.01 C |
| ATOM | 620 | CB | VAL | E | 75 | 27.524 | 25.277 | 45.121 | 1.00 | 0.02 C |
| ATOM | 621 | CG1 | VAL | E | 75 | 27.512 | 26.140 | 46.373 | 1.00 | 0.02 C |
| ATOM | 622 | CG2 | VAL | E | 75 | 27.572 | 26.154 | 43.878 | 1.00 | 0.03 C |
| ATOM | 623 | C | VAL | E | 75 | 28.673 | 23.354 | 43.982 | 1.00 | 0.01 C |
| ATOM | 624 | O | VAL | E | 75 | 29.497 | 23.465 | 43.064 | 1.00 | 0.02 O |
| ATOM | 625 | N | ASN | E | 76 | 27.790 | 22.372 | 44.042 | 1.00 | 0.01 N |
| ATOM | 626 | CA | ASN | E | 76 | 27.689 | 21.413 | 42.931 | 1.00 | 0.02 C |
| ATOM | 627 | CB | ASN | E | 76 | 27.169 | 20.079 | 43.457 | 1.00 | 0.02 C |
| ATOM | 628 | CG | ASN | E | 76 | 27.241 | 19.008 | 42.369 | 1.00 | 0.02 C |
| ATOM | 629 | OD1 | ASN | E | 76 | 28.042 | 19.103 | 41.434 | 1.00 | 0.02 O |
| ATOM | 630 | ND2 | ASN | E | 76 | 26.422 | 17.982 | 42.524 | 1.00 | 0.01 N |
| ATOM | 631 | C | ASN | E | 76 | 26.781 | 21.960 | 41.832 | 1.00 | 0.02 C |
| ATOM | 632 | O | ASN | E | 76 | 25.552 | 21.980 | 41.960 | 1.00 | 0.01 O |
| ATOM | 633 | N | VAL | E | 77 | 27.415 | 22.427 | 40.770 | 1.00 | 0.02 N |
| ATOM | 634 | CA | VAL | E | 77 | 26.702 | 23.048 | 39.646 | 1.00 | 0.02 C |
| ATOM | 635 | CB | VAL | E | 77 | 26.855 | 24.561 | 39.760 | 1.00 | 2.69 C |
| ATOM | 636 | CG1 | VAL | E | 77 | 25.709 | 25.202 | 40.535 | 1.00 | 3.69 C |
| ATOM | 637 | CG2 | VAL | E | 77 | 28.199 | 24.920 | 40.381 | 1.00 | 3.06 C |
| ATOM | 638 | C | VAL | E | 77 | 27.210 | 22.559 | 38.288 | 1.00 | 0.02 C |
| ATOM | 639 | O | VAL | E | 77 | 28.392 | 22.249 | 38.112 | 1.00 | 0.02 O |
| ATOM | 640 | N | ASP | E | 78 | 26.297 | 22.505 | 37.331 | 1.00 | 0.02 N |
| ATOM | 641 | CA | ASP | E | 78 | 26.632 | 22.057 | 35.967 | 1.00 | 0.02 C |
| ATOM | 642 | CB | ASP | E | 78 | 25.343 | 21.728 | 35.206 | 1.00 | 0.01 C |
| ATOM | 643 | CG | ASP | E | 78 | 24.532 | 22.986 | 34.894 | 1.00 | 0.01 C |
| ATOM | 644 | OD1 | ASP | E | 78 | 23.762 | 23.408 | 35.743 | 1.00 | 0.02 O |
| ATOM | 645 | OD2 | ASP | E | 78 | 24.819 | 23.587 | 33.866 | 1.00 | 0.01 O |
| ATOM | 646 | C | ASP | E | 78 | 27.451 | 23.117 | 35.222 | 1.00 | 0.02 C |
| ATOM | 647 | O | ASP | E | 78 | 27.212 | 24.323 | 35.374 | 1.00 | 0.02 O |
| ATOM | 648 | N | ASN | E | 79 | 28.293 | 22.668 | 34.303 | 1.00 | 0.02 N |
| ATOM | 649 | CA | ASN | E | 79 | 29.229 | 23.582 | 33.622 | 1.00 | 0.01 C |

TABLE 3-continued

| | | | | | | | | | | |
|---|---|---|---|---|---|---|---|---|---|---|
| ATOM | 650 | CB | ASN | E | 79 | 30.362 | 22.776 | 33.000 | 1.00 | 0.19 C |
| ATOM | 651 | CG | ASN | E | 79 | 31.170 | 22.100 | 34.100 | 1.00 | 0.21 C |
| ATOM | 652 | OD1 | ASN | E | 79 | 31.104 | 20.877 | 34.269 | 1.00 | 0.31 O |
| ATOM | 653 | ND2 | ASN | E | 79 | 31.900 | 22.909 | 34.848 | 1.00 | 0.27 N |
| ATOM | 654 | C | ASN | E | 79 | 28.618 | 24.480 | 32.546 | 1.00 | 0.02 C |
| ATOM | 655 | O | ASN | E | 79 | 29.200 | 25.533 | 32.267 | 1.00 | 0.02 O |
| ATOM | 656 | N | ARG | E | 80 | 27.388 | 24.226 | 32.130 | 1.00 | 0.02 N |
| ATOM | 657 | CA | ARG | E | 80 | 26.739 | 25.140 | 31.184 | 1.00 | 0.02 C |
| ATOM | 658 | CB | ARG | E | 80 | 25.464 | 24.487 | 30.672 | 1.00 | 0.22 C |
| ATOM | 659 | CG | ARG | E | 80 | 24.692 | 25.417 | 29.741 | 1.00 | 1.30 C |
| ATOM | 660 | CD | ARG | E | 80 | 23.300 | 24.865 | 29.465 | 1.00 | 1.26 C |
| ATOM | 661 | NE | ARG | E | 80 | 22.551 | 24.723 | 30.726 | 1.00 | 1.42 N |
| ATOM | 662 | CZ | ARG | E | 80 | 21.985 | 23.580 | 31.119 | 1.00 | 2.19 C |
| ATOM | 663 | NH1 | ARG | E | 80 | 22.068 | 22.493 | 30.348 | 1.00 | 2.85 N |
| ATOM | 664 | NH2 | ARG | E | 80 | 21.332 | 23.524 | 32.282 | 1.00 | 2.79 N |
| ATOM | 665 | C | ARG | E | 80 | 26.382 | 26.437 | 31.901 | 1.00 | 0.02 C |
| ATOM | 666 | O | ARG | E | 80 | 26.874 | 27.510 | 31.522 | 1.00 | 0.01 O |
| ATOM | 667 | N | THR | E | 81 | 25.868 | 26.266 | 33.109 | 1.00 | 0.02 N |
| ATOM | 668 | CA | THR | E | 81 | 25.501 | 27.402 | 33.949 | 1.00 | 0.02 C |
| ATOM | 669 | CB | THR | E | 81 | 24.600 | 26.891 | 35.069 | 1.00 | 0.02 C |
| ATOM | 670 | OG1 | THR | E | 81 | 23.516 | 26.178 | 34.489 | 1.00 | 0.02 O |
| ATOM | 671 | CG2 | THR | E | 81 | 24.029 | 28.029 | 35.905 | 1.00 | 0.02 C |
| ATOM | 672 | C | THR | E | 81 | 26.754 | 28.024 | 34.551 | 1.00 | 0.02 C |
| ATOM | 673 | O | THR | E | 81 | 26.899 | 29.251 | 34.537 | 1.00 | 0.03 O |
| ATOM | 674 | N | LEU | E | 82 | 27.754 | 27.196 | 34.796 | 1.00 | 0.02 N |
| ATOM | 675 | CA | LEU | E | 82 | 29.022 | 27.697 | 35.326 | 1.00 | 0.01 C |
| ATOM | 676 | CB | LEU | E | 82 | 29.886 | 26.507 | 35.707 | 1.00 | 0.19 C |
| ATOM | 677 | CG | LEU | E | 82 | 29.546 | 25.977 | 37.089 | 1.00 | 1.08 C |
| ATOM | 678 | CD1 | LEU | E | 82 | 30.396 | 24.760 | 37.426 | 1.00 | 1.07 C |
| ATOM | 679 | CD2 | LEU | E | 82 | 29.759 | 27.064 | 38.132 | 1.00 | 1.73 C |
| ATOM | 680 | C | LEU | E | 82 | 29.794 | 28.564 | 34.338 | 1.00 | 0.02 C |
| ATOM | 681 | O | LEU | E | 82 | 30.224 | 29.656 | 34.718 | 1.00 | 0.02 O |
| ATOM | 682 | N | ASP | E | 83 | 29.797 | 28.205 | 33.068 | 1.00 | 0.02 N |
| ATOM | 683 | CA | ASP | E | 83 | 30.582 | 28.963 | 32.092 | 1.00 | 0.02 C |
| ATOM | 684 | CB | ASP | E | 83 | 30.977 | 28.018 | 30.957 | 1.00 | 1.00 C |
| ATOM | 685 | CG | ASP | E | 83 | 31.816 | 26.848 | 31.479 | 1.00 | 1.95 C |
| ATOM | 686 | OD1 | ASP | E | 83 | 32.507 | 27.038 | 32.473 | 1.00 | 2.53 O |
| ATOM | 687 | OD2 | ASP | E | 83 | 31.785 | 25.795 | 30.854 | 1.00 | 2.36 O |
| ATOM | 688 | C | ASP | E | 83 | 29.816 | 30.157 | 31.522 | 1.00 | 0.02 C |
| ATOM | 689 | O | ASP | E | 83 | 30.437 | 31.082 | 30.984 | 1.00 | 0.02 O |
| ATOM | 690 | N | GLN | E | 84 | 28.509 | 30.184 | 31.723 | 1.00 | 0.02 N |
| ATOM | 691 | CA | GLN | E | 84 | 27.694 | 31.297 | 31.235 | 1.00 | 0.03 C |
| ATOM | 692 | CB | GLN | E | 84 | 26.378 | 30.695 | 30.760 | 1.00 | 0.79 C |
| ATOM | 693 | CG | GLN | E | 84 | 25.353 | 31.759 | 30.392 | 1.00 | 1.50 C |
| ATOM | 694 | CD | GLN | E | 84 | 23.996 | 31.093 | 30.212 | 1.00 | 1.49 C |
| ATOM | 695 | OE1 | GLN | E | 84 | 23.142 | 31.142 | 31.107 | 1.00 | 1.62 O |
| ATOM | 696 | NE2 | GLN | E | 84 | 23.854 | 30.392 | 29.101 | 1.00 | 1.90 N |
| ATOM | 697 | C | GLN | E | 84 | 27.383 | 32.325 | 32.319 | 1.00 | 0.02 C |
| ATOM | 698 | O | GLN | E | 84 | 27.343 | 33.534 | 32.050 | 1.00 | 0.03 O |
| ATOM | 699 | N | THR | E | 85 | 27.247 | 31.856 | 33.542 | 1.00 | 0.02 N |
| ATOM | 700 | CA | THR | E | 85 | 26.799 | 32.725 | 34.623 | 1.00 | 0.02 C |
| ATOM | 701 | CB | THR | E | 85 | 25.507 | 32.108 | 35.162 | 1.00 | 0.01 C |
| ATOM | 702 | OG1 | THR | E | 85 | 24.553 | 32.025 | 34.108 | 1.00 | 0.02 O |
| ATOM | 703 | CG2 | THR | E | 85 | 24.886 | 32.925 | 36.283 | 1.00 | 0.02 C |
| ATOM | 704 | C | THR | E | 85 | 27.823 | 32.878 | 35.753 | 1.00 | 0.02 C |
| ATOM | 705 | O | THR | E | 85 | 28.027 | 34.001 | 36.223 | 1.00 | 0.02 O |
| ATOM | 706 | N | LEU | E | 86 | 28.602 | 31.839 | 36.016 | 1.00 | 1.29 N |
| ATOM | 707 | CA | LEU | E | 86 | 29.427 | 31.812 | 37.243 | 1.00 | 1.82 C |
| ATOM | 708 | CB | LEU | E | 86 | 29.148 | 30.530 | 38.018 | 1.00 | 1.96 C |
| ATOM | 709 | CG | LEU | E | 86 | 27.748 | 30.409 | 38.623 | 1.00 | 2.93 C |
| ATOM | 710 | CD1 | LEU | E | 86 | 27.181 | 31.760 | 39.063 | 1.00 | 3.57 C |
| ATOM | 711 | CD2 | LEU | E | 86 | 26.782 | 29.645 | 37.728 | 1.00 | 3.69 C |
| ATOM | 712 | C | LEU | E | 86 | 30.942 | 31.877 | 37.024 | 1.00 | 1.44 C |
| ATOM | 713 | O | LEU | E | 86 | 31.498 | 32.940 | 36.727 | 1.00 | 1.68 O |
| ATOM | 714 | N | GLU | E | 87 | 31.550 | 30.699 | 37.131 | 1.00 | 1.98 N |
| ATOM | 715 | CA | GLU | E | 87 | 33.013 | 30.436 | 37.165 | 1.00 | 2.32 C |
| ATOM | 716 | CB | GLU | E | 87 | 33.377 | 29.353 | 36.152 | 1.00 | 3.37 C |
| ATOM | 717 | CG | GLU | E | 87 | 32.959 | 27.956 | 36.599 | 1.00 | 4.08 C |
| ATOM | 718 | CD | GLU | E | 87 | 33.583 | 26.915 | 35.670 | 1.00 | 4.73 C |
| ATOM | 719 | OE1 | GLU | E | 87 | 34.702 | 27.159 | 35.240 | 1.00 | 5.27 O |
| ATOM | 720 | OE2 | GLU | E | 87 | 32.937 | 25.906 | 35.398 | 1.00 | 4.98 O |
| ATOM | 721 | C | GLU | E | 87 | 33.951 | 31.617 | 36.931 | 1.00 | 2.43 C |
| ATOM | 722 | O | GLU | E | 87 | 34.047 | 32.530 | 37.757 | 1.00 | 2.58 O |
| ATOM | 723 | N | CYS | E | 88 | 34.813 | 31.436 | 35.942 | 1.00 | 2.78 N |
| ATOM | 724 | CA | CYS | E | 88 | 35.847 | 32.432 | 35.632 | 1.00 | 3.22 C |
| ATOM | 725 | CB | CYS | E | 88 | 37.198 | 31.728 | 35.622 | 1.00 | 3.41 C |
| ATOM | 726 | SG | CYS | E | 88 | 37.640 | 30.871 | 37.153 | 1.00 | 4.58 S |
| ATOM | 727 | C | CYS | E | 88 | 35.628 | 33.107 | 34.278 | 1.00 | 2.78 C |
| ATOM | 728 | O | CYS | E | 88 | 36.412 | 33.979 | 33.884 | 1.00 | 2.56 O |

TABLE 3-continued

| | | | | | | | | | | |
|---|---|---|---|---|---|---|---|---|---|---|
| ATOM | 729 | N | ILE | E | 89 | 34.617 | 32.665 | 33.549 | 1.00 | 2.87 N |
| ATOM | 730 | CA | ILE | E | 89 | 34.357 | 33.238 | 32.223 | 1.00 | 2.85 C |
| ATOM | 731 | CB | ILE | E | 89 | 34.102 | 32.092 | 31.239 | 1.00 | 3.27 C |
| ATOM | 732 | CG2 | ILE | E | 89 | 34.465 | 32.517 | 29.820 | 1.00 | 3.74 C |
| ATOM | 733 | CG1 | ILE | E | 89 | 34.922 | 30.865 | 31.622 | 1.00 | 3.86 C |
| ATOM | 734 | CD1 | ILE | E | 89 | 34.648 | 29.702 | 30.677 | 1.00 | 4.56 C |
| ATOM | 735 | C | ILE | E | 89 | 33.115 | 34.111 | 32.336 | 1.00 | 1.87 C |
| ATOM | 736 | O | ILE | E | 89 | 33.185 | 35.262 | 32.774 | 1.00 | 2.29 O |
| ATOM | 737 | N | SER | E | 90 | 32.002 | 33.537 | 31.914 | 1.00 | 0.02 N |
| ATOM | 738 | CA | SER | E | 90 | 30.661 | 34.038 | 32.195 | 1.00 | 0.03 C |
| ATOM | 739 | CB | SER | E | 90 | 30.466 | 33.901 | 33.689 | 1.00 | 0.02 C |
| ATOM | 740 | OG | SER | E | 90 | 30.719 | 32.530 | 33.972 | 1.00 | 0.02 O |
| ATOM | 741 | C | SER | E | 90 | 30.333 | 35.454 | 31.739 | 1.00 | 0.02 C |
| ATOM | 742 | O | SER | E | 90 | 30.848 | 36.456 | 32.255 | 1.00 | 0.02 O |
| ATOM | 743 | N | LYS | E | 91 | 29.180 | 35.486 | 31.101 | 1.00 | 0.02 N |
| ATOM | 744 | CA | LYS | E | 91 | 28.578 | 36.719 | 30.611 | 1.00 | 0.02 C |
| ATOM | 745 | CB | LYS | E | 91 | 27.496 | 36.302 | 29.625 | 1.00 | 0.28 C |
| ATOM | 746 | CG | LYS | E | 91 | 28.031 | 35.240 | 28.672 | 1.00 | 0.77 C |
| ATOM | 747 | CD | LYS | E | 91 | 26.917 | 34.620 | 27.845 | 1.00 | 0.79 C |
| ATOM | 748 | CE | LYS | E | 91 | 27.449 | 33.495 | 26.970 | 1.00 | 1.97 C |
| ATOM | 749 | NZ | LYS | E | 91 | 26.363 | 32.848 | 26.221 | 1.00 | 1.97 N |
| ATOM | 750 | C | LYS | E | 91 | 27.948 | 37.469 | 31.777 | 1.00 | 0.02 C |
| ATOM | 751 | O | LYS | E | 91 | 28.080 | 38.696 | 31.857 | 1.00 | 0.02 O |
| ATOM | 752 | N | ALA | E | 92 | 27.586 | 36.718 | 32.809 | 1.00 | 0.02 N |
| ATOM | 753 | CA | ALA | E | 92 | 27.086 | 37.324 | 34.047 | 1.00 | 0.02 C |
| ATOM | 754 | CB | ALA | E | 92 | 26.232 | 36.300 | 34.779 | 1.00 | 0.35 C |
| ATOM | 755 | C | ALA | E | 92 | 28.205 | 37.829 | 34.963 | 1.00 | 0.02 C |
| ATOM | 756 | O | ALA | E | 92 | 27.962 | 38.729 | 35.775 | 1.00 | 0.02 O |
| ATOM | 757 | N | LYS | E | 93 | 29.441 | 37.440 | 34.687 | 1.00 | 0.03 N |
| ATOM | 758 | CA | LYS | E | 93 | 30.593 | 38.021 | 35.383 | 1.00 | 0.02 C |
| ATOM | 759 | CB | LYS | E | 93 | 31.747 | 37.023 | 35.357 | 1.00 | 0.35 C |
| ATOM | 760 | CG | LYS | E | 93 | 33.064 | 37.670 | 35.780 | 1.00 | 1.21 C |
| ATOM | 761 | CD | LYS | E | 93 | 34.241 | 36.717 | 35.614 | 1.00 | 1.35 C |
| ATOM | 762 | CE | LYS | E | 93 | 34.174 | 35.566 | 36.608 | 1.00 | 2.56 C |
| ATOM | 763 | NZ | LYS | E | 93 | 34.409 | 36.048 | 37.977 | 1.00 | 3.03 N |
| ATOM | 764 | C | LYS | E | 93 | 31.023 | 39.302 | 34.670 | 1.00 | 0.03 C |
| ATOM | 765 | O | LYS | E | 93 | 31.378 | 40.291 | 35.322 | 1.00 | 0.03 O |
| ATOM | 766 | N | ASP | E | 94 | 30.704 | 39.355 | 33.385 | 1.00 | 0.02 N |
| ATOM | 767 | CA | ASP | E | 94 | 30.990 | 40.534 | 32.561 | 1.00 | 0.02 C |
| ATOM | 768 | CB | ASP | E | 94 | 30.969 | 40.101 | 31.097 | 1.00 | 0.27 C |
| ATOM | 769 | CG | ASP | E | 94 | 31.992 | 39.006 | 30.813 | 1.00 | 0.50 C |
| ATOM | 770 | OD1 | ASP | E | 94 | 31.692 | 38.164 | 29.975 | 1.00 | 0.76 O |
| ATOM | 771 | OD2 | ASP | E | 94 | 33.103 | 39.126 | 31.311 | 1.00 | 0.52 O |
| ATOM | 772 | C | ASP | E | 94 | 29.951 | 41.640 | 32.759 | 1.00 | 0.02 C |
| ATOM | 773 | O | ASP | E | 94 | 30.205 | 42.794 | 32.397 | 1.00 | 0.02 O |
| ATOM | 774 | N | ALA | E | 95 | 28.830 | 41.300 | 33.376 | 1.00 | 0.02 N |
| ATOM | 775 | CA | ALA | E | 95 | 27.790 | 42.285 | 33.679 | 1.00 | 0.02 C |
| ATOM | 776 | CB | ALA | E | 95 | 26.846 | 42.394 | 32.487 | 1.00 | 0.64 C |
| ATOM | 777 | C | ALA | E | 95 | 27.007 | 41.864 | 34.917 | 1.00 | 0.02 C |
| ATOM | 778 | O | ALA | E | 95 | 25.788 | 41.635 | 34.839 | 1.00 | 0.03 O |
| ATOM | 779 | N | SER | E | 96 | 27.708 | 41.823 | 36.043 | 1.00 | 0.03 N |
| ATOM | 780 | CA | SER | E | 96 | 27.131 | 41.359 | 37.316 | 1.00 | 0.03 C |
| ATOM | 781 | CB | SER | E | 96 | 28.193 | 41.422 | 38.403 | 1.00 | 1.65 C |
| ATOM | 782 | OG | SER | E | 96 | 28.434 | 42.790 | 38.690 | 1.00 | 2.08 O |
| ATOM | 783 | C | SER | E | 96 | 25.926 | 42.192 | 37.737 | 1.00 | 0.02 C |
| ATOM | 784 | O | SER | E | 96 | 25.887 | 43.419 | 37.574 | 1.00 | 0.02 O |
| ATOM | 785 | N | GLN | E | 97 | 24.927 | 41.482 | 38.225 | 1.00 | 0.02 N |
| ATOM | 786 | CA | GLN | E | 97 | 23.644 | 42.085 | 38.562 | 1.00 | 0.02 C |
| ATOM | 787 | CB | GLN | E | 97 | 22.879 | 42.279 | 37.263 | 1.00 | 1.35 C |
| ATOM | 788 | CG | GLN | E | 97 | 22.797 | 40.959 | 36.506 | 1.00 | 2.41 C |
| ATOM | 789 | CD | GLN | E | 97 | 22.005 | 41.149 | 35.231 | 1.00 | 3.21 C |
| ATOM | 790 | OE1 | GLN | E | 97 | 20.783 | 40.936 | 35.216 | 1.00 | 3.45 O |
| ATOM | 791 | NE2 | GLN | E | 97 | 22.713 | 41.553 | 34.190 | 1.00 | 4.08 N |
| ATOM | 792 | C | GLN | E | 97 | 22.830 | 41.172 | 39.472 | 1.00 | 0.03 C |
| ATOM | 793 | O | GLN | E | 97 | 23.333 | 40.176 | 40.003 | 1.00 | 0.02 O |
| ATOM | 794 | N | MET | E | 98 | 21.564 | 41.521 | 39.604 | 1.00 | 0.02 N |
| ATOM | 795 | CA | MET | E | 98 | 20.601 | 40.708 | 40.346 | 1.00 | 0.03 C |
| ATOM | 796 | CB | MET | E | 98 | 19.331 | 41.549 | 40.555 | 1.00 | 0.44 C |
| ATOM | 797 | CG | MET | E | 98 | 19.223 | 42.782 | 39.635 | 1.00 | 1.26 C |
| ATOM | 798 | SD | MET | E | 98 | 18.756 | 42.530 | 37.899 | 1.00 | 1.41 S |
| ATOM | 799 | CE | MET | E | 98 | 18.753 | 44.250 | 37.342 | 1.00 | 2.02 C |
| ATOM | 800 | C | MET | E | 98 | 20.281 | 39.373 | 39.658 | 1.00 | 0.03 C |
| ATOM | 801 | O | MET | E | 98 | 21.118 | 38.454 | 39.623 | 1.00 | 0.03 O |
| ATOM | 802 | N | ARG | E | 99 | 19.121 | 39.335 | 39.018 | 1.00 | 0.02 N |
| ATOM | 803 | CA | ARG | E | 99 | 18.528 | 38.119 | 38.450 | 1.00 | 0.02 C |
| ATOM | 804 | CB | ARG | E | 99 | 17.374 | 38.525 | 37.543 | 1.00 | 1.64 C |
| ATOM | 805 | CG | ARG | E | 99 | 16.409 | 39.473 | 38.232 | 1.00 | 2.02 C |
| ATOM | 806 | CD | ARG | E | 99 | 15.306 | 39.893 | 37.270 | 1.00 | 2.78 C |
| ATOM | 807 | NE | ARG | E | 99 | 14.484 | 40.969 | 37.842 | 1.00 | 4.09 N |

TABLE 3-continued

| ATOM | 808 | CZ | ARG | E | 99 | 14.399 | 42.179 | 37.284 | 1.00 | 4.97 | C |
| --- | --- | --- | --- | --- | --- | --- | --- | --- | --- | --- | --- |
| ATOM | 809 | NH1 | ARG | E | 99 | 13.592 | 43.103 | 37.813 | 1.00 | 5.86 | N |
| ATOM | 810 | NH2 | ARG | E | 99 | 15.082 | 42.450 | 36.169 | 1.00 | 5.20 | N |
| ATOM | 811 | C | ARG | E | 99 | 19.486 | 37.287 | 37.607 | 1.00 | 0.01 | C |
| ATOM | 812 | O | ARG | E | 99 | 19.971 | 36.253 | 38.079 | 1.00 | 0.02 | O |
| ATOM | 813 | N | PHE | E | 100 | 19.950 | 37.847 | 36.504 | 1.00 | 0.14 | N |
| ATOM | 814 | CA | PHE | E | 100 | 20.704 | 37.047 | 35.528 | 1.00 | 0.21 | C |
| ATOM | 815 | CB | PHE | E | 100 | 20.622 | 37.740 | 34.177 | 1.00 | 0.58 | C |
| ATOM | 816 | CG | PHE | E | 100 | 19.195 | 37.822 | 33.647 | 1.00 | 0.93 | C |
| ATOM | 817 | CD1 | PHE | E | 100 | 18.411 | 36.674 | 33.594 | 1.00 | 1.12 | C |
| ATOM | 818 | CE1 | PHE | E | 100 | 17.104 | 36.744 | 33.117 | 1.00 | 1.69 | C |
| ATOM | 819 | CZ | PHE | E | 100 | 16.587 | 37.963 | 32.693 | 1.00 | 2.30 | C |
| ATOM | 820 | CE2 | PHE | E | 100 | 17.372 | 39.104 | 32.742 | 1.00 | 2.50 | C |
| ATOM | 821 | CD2 | PHE | E | 100 | 18.673 | 39.035 | 33.216 | 1.00 | 1.84 | C |
| ATOM | 822 | C | PHE | E | 100 | 22.163 | 36.756 | 35.899 | 1.00 | 0.35 | C |
| ATOM | 823 | O | PHE | E | 100 | 22.845 | 36.051 | 35.147 | 1.00 | 0.74 | O |
| ATOM | 824 | N | ALA | E | 101 | 22.622 | 37.205 | 37.057 | 1.00 | 0.03 | N |
| ATOM | 825 | CA | ALA | E | 101 | 23.969 | 36.832 | 37.469 | 1.00 | 0.02 | C |
| ATOM | 826 | CB | ALA | E | 101 | 24.673 | 38.016 | 38.108 | 1.00 | 0.45 | C |
| ATOM | 827 | C | ALA | E | 101 | 23.960 | 35.661 | 38.447 | 1.00 | 0.03 | C |
| ATOM | 828 | O | ALA | E | 101 | 24.975 | 34.963 | 38.552 | 1.00 | 0.03 | O |
| ATOM | 829 | N | PHE | E | 102 | 22.842 | 35.401 | 39.111 | 1.00 | 0.03 | N |
| ATOM | 830 | CA | PHE | E | 102 | 22.849 | 34.294 | 40.077 | 1.00 | 0.01 | C |
| ATOM | 831 | CB | PHE | E | 102 | 23.204 | 34.843 | 41.452 | 1.00 | 0.02 | C |
| ATOM | 832 | CG | PHE | E | 102 | 24.692 | 35.096 | 41.628 | 1.00 | 0.03 | C |
| ATOM | 833 | CD1 | PHE | E | 102 | 25.585 | 34.031 | 41.587 | 1.00 | 0.02 | C |
| ATOM | 834 | CE1 | PHE | E | 102 | 26.945 | 34.256 | 41.741 | 1.00 | 0.03 | C |
| ATOM | 835 | CZ | PHE | E | 102 | 27.413 | 35.545 | 41.931 | 1.00 | 0.01 | C |
| ATOM | 836 | CE2 | PHE | E | 102 | 26.530 | 36.612 | 41.964 | 1.00 | 0.02 | C |
| ATOM | 837 | CD2 | PHE | E | 102 | 25.167 | 36.389 | 41.809 | 1.00 | 0.02 | C |
| ATOM | 838 | C | PHE | E | 102 | 21.571 | 33.465 | 40.182 | 1.00 | 0.02 | C |
| ATOM | 839 | O | PHE | E | 102 | 21.627 | 32.369 | 40.757 | 1.00 | 0.02 | O |
| ATOM | 840 | N | TYR | E | 103 | 20.505 | 33.852 | 39.502 | 1.00 | 0.02 | N |
| ATOM | 841 | CA | TYR | E | 103 | 19.239 | 33.110 | 39.624 | 1.00 | 0.02 | C |
| ATOM | 842 | CB | TYR | E | 103 | 18.130 | 33.927 | 38.970 | 1.00 | 0.55 | C |
| ATOM | 843 | CG | TYR | E | 103 | 16.831 | 33.153 | 38.751 | 1.00 | 0.93 | C |
| ATOM | 844 | CD1 | TYR | E | 103 | 16.432 | 32.829 | 37.460 | 1.00 | 1.87 | C |
| ATOM | 845 | CE1 | TYR | E | 103 | 15.262 | 32.115 | 37.255 | 1.00 | 2.82 | C |
| ATOM | 846 | CZ | TYR | E | 103 | 14.491 | 31.730 | 38.342 | 1.00 | 2.98 | C |
| ATOM | 847 | OH | TYR | E | 103 | 13.389 | 30.922 | 38.148 | 1.00 | 4.01 | O |
| ATOM | 848 | CE2 | TYR | E | 103 | 14.877 | 32.065 | 39.633 | 1.00 | 2.47 | C |
| ATOM | 849 | CD2 | TYR | E | 103 | 16.049 | 32.781 | 39.837 | 1.00 | 1.55 | C |
| ATOM | 850 | C | TYR | E | 103 | 19.282 | 31.721 | 38.985 | 1.00 | 0.02 | C |
| ATOM | 851 | O | TYR | E | 103 | 18.803 | 30.766 | 39.611 | 1.00 | 0.02 | O |
| ATOM | 852 | N | HIS | E | 104 | 20.135 | 31.559 | 37.986 | 1.00 | 0.02 | N |
| ATOM | 853 | CA | HIS | E | 104 | 20.273 | 30.263 | 37.308 | 1.00 | 0.02 | C |
| ATOM | 854 | CB | HIS | E | 104 | 21.136 | 30.471 | 36.061 | 1.00 | 0.29 | C |
| ATOM | 855 | CG | HIS | E | 104 | 20.763 | 31.653 | 35.183 | 1.00 | 1.03 | C |
| ATOM | 856 | ND1 | HIS | E | 104 | 21.622 | 32.506 | 34.587 | 1.00 | 1.52 | N |
| ATOM | 857 | CE1 | HIS | E | 104 | 20.919 | 33.433 | 33.902 | 1.00 | 2.51 | C |
| ATOM | 858 | NE2 | HIS | E | 104 | 19.606 | 33.152 | 34.053 | 1.00 | 2.89 | N |
| ATOM | 859 | CD2 | HIS | E | 104 | 19.493 | 32.053 | 34.831 | 1.00 | 2.10 | C |
| ATOM | 860 | C | HIS | E | 104 | 20.998 | 29.261 | 38.207 | 1.00 | 0.02 | C |
| ATOM | 861 | O | HIS | E | 104 | 20.574 | 28.105 | 38.337 | 1.00 | 0.02 | O |
| ATOM | 862 | N | SER | E | 105 | 21.828 | 29.818 | 39.070 | 1.00 | 0.02 | N |
| ATOM | 863 | CA | SER | E | 105 | 22.693 | 29.018 | 39.923 | 1.00 | 0.02 | C |
| ATOM | 864 | CB | SER | E | 105 | 23.903 | 29.879 | 40.239 | 1.00 | 0.14 | C |
| ATOM | 865 | OG | SER | E | 105 | 24.232 | 30.583 | 39.052 | 1.00 | 0.90 | O |
| ATOM | 866 | C | SER | E | 105 | 21.969 | 28.686 | 41.216 | 1.00 | 0.02 | C |
| ATOM | 867 | O | SER | E | 105 | 21.979 | 27.532 | 41.661 | 1.00 | 0.01 | O |
| ATOM | 868 | N | GLU | E | 106 | 21.134 | 29.619 | 41.644 | 1.00 | 0.02 | N |
| ATOM | 869 | CA | GLU | E | 106 | 20.357 | 29.430 | 42.867 | 1.00 | 0.02 | C |
| ATOM | 870 | CB | GLU | E | 106 | 19.819 | 30.783 | 43.316 | 1.00 | 0.14 | C |
| ATOM | 871 | CG | GLU | E | 106 | 19.028 | 30.664 | 44.614 | 1.00 | 0.19 | C |
| ATOM | 872 | CD | GLU | E | 106 | 18.371 | 31.998 | 44.948 | 1.00 | 1.03 | C |
| ATOM | 873 | OE1 | GLU | E | 106 | 18.248 | 32.299 | 46.125 | 1.00 | 1.38 | O |
| ATOM | 874 | OE2 | GLU | E | 106 | 18.029 | 32.707 | 44.008 | 1.00 | 1.80 | O |
| ATOM | 875 | C | GLU | E | 106 | 19.190 | 28.481 | 42.634 | 1.00 | 0.02 | C |
| ATOM | 876 | O | GLU | E | 106 | 18.889 | 27.667 | 43.514 | 1.00 | 0.02 | O |
| ATOM | 877 | N | GLU | E | 107 | 18.703 | 28.417 | 41.407 | 1.00 | 0.01 | N |
| ATOM | 878 | CA | GLU | E | 107 | 17.628 | 27.477 | 41.099 | 1.00 | 0.02 | C |
| ATOM | 879 | CB | GLU | E | 107 | 16.971 | 27.919 | 39.797 | 1.00 | 0.14 | C |
| ATOM | 880 | CG | GLU | E | 107 | 15.771 | 27.050 | 39.442 | 1.00 | 1.12 | C |
| ATOM | 881 | CD | GLU | E | 107 | 15.125 | 27.577 | 38.165 | 1.00 | 1.48 | C |
| ATOM | 882 | OE1 | GLU | E | 107 | 15.328 | 28.748 | 37.873 | 1.00 | 1.96 | O |
| ATOM | 883 | OE2 | GLU | E | 107 | 14.484 | 26.794 | 37.479 | 1.00 | 1.73 | O |
| ATOM | 884 | C | GLU | E | 107 | 18.170 | 26.057 | 40.964 | 1.00 | 0.02 | C |
| ATOM | 885 | O | GLU | E | 107 | 17.573 | 25.125 | 41.522 | 1.00 | 0.01 | O |
| ATOM | 886 | N | HIS | E | 108 | 19.401 | 25.939 | 40.493 | 1.00 | 0.02 | N |

TABLE 3-continued

| | | | | | | | | | | | |
|---|---|---|---|---|---|---|---|---|---|---|---|
| ATOM | 887 | CA | HIS | E | 108 | 20.012 | 24.617 | 40.367 | 1.00 | 0.02 | C |
| ATOM | 888 | CB | HIS | E | 108 | 21.232 | 24.723 | 39.457 | 1.00 | 0.27 | C |
| ATOM | 889 | CG | HIS | E | 108 | 21.936 | 23.400 | 39.227 | 1.00 | 0.70 | C |
| ATOM | 890 | ND1 | HIS | E | 108 | 21.624 | 22.479 | 38.297 | 1.00 | 0.85 | N |
| ATOM | 891 | CE1 | HIS | E | 108 | 22.470 | 21.434 | 38.399 | 1.00 | 1.41 | C |
| ATOM | 892 | NE2 | HIS | E | 108 | 23.327 | 21.699 | 39.411 | 1.00 | 1.84 | N |
| ATOM | 893 | CD2 | HIS | E | 108 | 23.010 | 22.907 | 39.931 | 1.00 | 1.50 | C |
| ATOM | 894 | C | HIS | E | 108 | 20.435 | 24.078 | 41.729 | 1.00 | 0.02 | C |
| ATOM | 895 | O | HIS | E | 108 | 20.112 | 22.930 | 42.055 | 1.00 | 0.02 | O |
| ATOM | 896 | N | VAL | E | 109 | 20.903 | 24.958 | 42.598 | 1.00 | 0.02 | N |
| ATOM | 897 | CA | VAL | E | 109 | 21.329 | 24.522 | 43.930 | 1.00 | 0.02 | C |
| ATOM | 898 | CB | VAL | E | 109 | 22.318 | 25.551 | 44.465 | 1.00 | 0.05 | C |
| ATOM | 899 | CG1 | VAL | E | 109 | 22.603 | 25.357 | 45.947 | 1.00 | 0.15 | C |
| ATOM | 900 | CG2 | VAL | E | 109 | 23.611 | 25.510 | 43.659 | 1.00 | 0.13 | C |
| ATOM | 901 | C | VAL | E | 109 | 20.161 | 24.328 | 44.898 | 1.00 | 0.02 | C |
| ATOM | 902 | O | VAL | E | 109 | 20.204 | 23.389 | 45.706 | 1.00 | 0.01 | O |
| ATOM | 903 | N | PHE | E | 110 | 19.041 | 24.983 | 44.639 | 1.00 | 0.02 | N |
| ATOM | 904 | CA | PHE | E | 110 | 17.867 | 24.768 | 45.486 | 1.00 | 0.01 | C |
| ATOM | 905 | CB | PHE | E | 110 | 16.885 | 25.920 | 45.306 | 1.00 | 0.03 | C |
| ATOM | 906 | CG | PHE | E | 110 | 15.657 | 25.823 | 46.208 | 1.00 | 0.02 | C |
| ATOM | 907 | CD1 | PHE | E | 110 | 15.778 | 26.076 | 47.568 | 1.00 | 0.03 | C |
| ATOM | 908 | CE1 | PHE | E | 110 | 14.665 | 25.984 | 48.393 | 1.00 | 0.01 | C |
| ATOM | 909 | CZ | PHE | E | 110 | 13.431 | 25.636 | 47.859 | 1.00 | 0.02 | C |
| ATOM | 910 | CE2 | PHE | E | 110 | 13.310 | 25.381 | 46.499 | 1.00 | 0.02 | C |
| ATOM | 911 | CD2 | PHE | E | 110 | 14.424 | 25.473 | 45.673 | 1.00 | 0.02 | C |
| ATOM | 912 | C | PHE | E | 110 | 17.190 | 23.449 | 45.137 | 1.00 | 0.02 | C |
| ATOM | 913 | O | PHE | E | 110 | 16.865 | 22.675 | 46.047 | 1.00 | 0.02 | O |
| ATOM | 914 | N | THR | E | 111 | 17.236 | 23.081 | 43.866 | 1.00 | 0.03 | N |
| ATOM | 915 | CA | THR | E | 111 | 16.690 | 21.778 | 43.470 | 1.00 | 0.01 | C |
| ATOM | 916 | CB | THR | E | 111 | 16.354 | 21.781 | 41.981 | 1.00 | 0.36 | C |
| ATOM | 917 | OG1 | THR | E | 111 | 17.522 | 22.111 | 41.239 | 1.00 | 0.82 | O |
| ATOM | 918 | CG2 | THR | E | 111 | 15.277 | 22.809 | 41.654 | 1.00 | 1.28 | C |
| ATOM | 919 | C | THR | E | 111 | 17.664 | 20.647 | 43.797 | 1.00 | 0.01 | C |
| ATOM | 920 | O | THR | E | 111 | 17.217 | 19.562 | 44.185 | 1.00 | 0.01 | O |
| ATOM | 921 | N | LEU | E | 112 | 18.940 | 20.979 | 43.912 | 1.00 | 0.02 | N |
| ATOM | 922 | CA | LEU | E | 112 | 19.944 | 20.010 | 44.356 | 1.00 | 0.02 | C |
| ATOM | 923 | CB | LEU | E | 112 | 21.314 | 20.652 | 44.167 | 1.00 | 0.02 | C |
| ATOM | 924 | CG | LEU | E | 112 | 22.450 | 19.748 | 44.627 | 1.00 | 0.01 | C |
| ATOM | 925 | CD1 | LEU | E | 112 | 22.541 | 18.500 | 43.756 | 1.00 | 0.02 | C |
| ATOM | 926 | CD2 | LEU | E | 112 | 23.769 | 20.509 | 44.610 | 1.00 | 0.02 | C |
| ATOM | 927 | C | LEU | E | 112 | 19.750 | 19.659 | 45.829 | 1.00 | 0.01 | C |
| ATOM | 928 | O | LEU | E | 112 | 19.645 | 18.472 | 46.168 | 1.00 | 0.02 | O |
| ATOM | 929 | N | MET | E | 113 | 19.456 | 20.662 | 46.642 | 1.00 | 0.02 | N |
| ATOM | 930 | CA | MET | E | 113 | 19.211 | 20.403 | 48.060 | 1.00 | 0.02 | C |
| ATOM | 931 | CB | MET | E | 113 | 19.175 | 21.722 | 48.820 | 1.00 | 0.02 | C |
| ATOM | 932 | CG | MET | E | 113 | 20.518 | 22.436 | 48.786 | 1.00 | 0.01 | C |
| ATOM | 933 | SD | MET | E | 113 | 20.587 | 23.967 | 49.742 | 1.00 | 0.03 | S |
| ATOM | 934 | CE | MET | E | 113 | 19.290 | 24.902 | 48.903 | 1.00 | 0.02 | C |
| ATOM | 935 | C | MET | E | 113 | 17.887 | 19.685 | 48.274 | 1.00 | 0.02 | C |
| ATOM | 936 | O | MET | E | 113 | 17.893 | 18.607 | 48.887 | 1.00 | 0.02 | O |
| ATOM | 937 | N | ALA | E | 114 | 16.869 | 20.089 | 47.530 | 1.00 | 0.02 | N |
| ATOM | 938 | CA | ALA | E | 114 | 15.525 | 19.532 | 47.716 | 1.00 | 0.02 | C |
| ATOM | 939 | CB | ALA | E | 114 | 14.531 | 20.435 | 46.997 | 1.00 | 0.15 | C |
| ATOM | 940 | C | ALA | E | 114 | 15.357 | 18.100 | 47.210 | 1.00 | 0.01 | C |
| ATOM | 941 | O | ALA | E | 114 | 14.607 | 17.330 | 47.819 | 1.00 | 0.01 | O |
| ATOM | 942 | N | LYS | E | 115 | 16.136 | 17.705 | 46.217 | 1.00 | 0.02 | N |
| ATOM | 943 | CA | LYS | E | 115 | 16.040 | 16.335 | 45.708 | 1.00 | 0.02 | C |
| ATOM | 944 | CB | LYS | E | 115 | 16.190 | 16.379 | 44.193 | 1.00 | 0.02 | C |
| ATOM | 945 | CG | LYS | E | 115 | 15.117 | 17.260 | 43.565 | 1.00 | 0.01 | C |
| ATOM | 946 | CD | LYS | E | 115 | 15.305 | 17.384 | 42.058 | 1.00 | 0.02 | C |
| ATOM | 947 | CE | LYS | E | 115 | 14.276 | 18.332 | 41.454 | 1.00 | 0.01 | C |
| ATOM | 948 | NZ | LYS | E | 115 | 12.908 | 17.869 | 41.736 | 1.00 | 0.02 | N |
| ATOM | 949 | C | LYS | E | 115 | 17.097 | 15.404 | 46.299 | 1.00 | 0.02 | C |
| ATOM | 950 | O | LYS | E | 115 | 17.033 | 14.189 | 46.083 | 1.00 | 0.02 | O |
| ATOM | 951 | N | ASP | E | 116 | 18.043 | 15.949 | 47.046 | 1.00 | 0.02 | N |
| ATOM | 952 | CA | ASP | E | 116 | 19.098 | 15.103 | 47.610 | 1.00 | 0.02 | C |
| ATOM | 953 | CB | ASP | E | 116 | 20.443 | 15.662 | 47.157 | 1.00 | 0.02 | C |
| ATOM | 954 | CG | ASP | E | 116 | 21.605 | 14.847 | 47.715 | 1.00 | 0.02 | C |
| ATOM | 955 | OD1 | ASP | E | 116 | 21.754 | 13.706 | 47.302 | 1.00 | 0.01 | O |
| ATOM | 956 | OD2 | ASP | E | 116 | 22.372 | 15.415 | 48.482 | 1.00 | 0.02 | O |
| ATOM | 957 | C | ASP | E | 116 | 19.045 | 15.028 | 49.133 | 1.00 | 0.01 | C |
| ATOM | 958 | O | ASP | E | 116 | 18.713 | 13.979 | 49.698 | 1.00 | 0.02 | O |
| ATOM | 959 | N | SER | E | 117 | 19.284 | 16.152 | 49.786 | 1.00 | 0.02 | N |
| ATOM | 960 | CA | SER | E | 117 | 19.451 | 16.123 | 51.238 | 1.00 | 0.03 | C |
| ATOM | 961 | CB | SER | E | 117 | 20.534 | 17.116 | 51.635 | 1.00 | 0.01 | C |
| ATOM | 962 | OG | SER | E | 117 | 21.769 | 16.664 | 51.095 | 1.00 | 0.02 | O |
| ATOM | 963 | C | SER | E | 117 | 18.165 | 16.448 | 51.978 | 1.00 | 0.01 | C |
| ATOM | 964 | O | SER | E | 117 | 17.952 | 15.924 | 53.075 | 1.00 | 0.03 | O |
| ATOM | 965 | N | TYR | E | 118 | 17.244 | 17.122 | 51.314 | 1.00 | 0.02 | N |

TABLE 3-continued

| | | | | | | | | | | |
|---|---|---|---|---|---|---|---|---|---|---|
| ATOM | 966 | CA | TYR | E | 118 | 15.955 | 17.448 | 51.943 | 1.00 | 0.01 C |
| ATOM | 967 | CB | TYR | E | 118 | 15.130 | 18.308 | 50.998 | 1.00 | 0.02 C |
| ATOM | 968 | CG | TYR | E | 118 | 13.720 | 18.586 | 51.501 | 1.00 | 0.02 C |
| ATOM | 969 | CD1 | TYR | E | 118 | 13.526 | 19.156 | 52.753 | 1.00 | 0.02 C |
| ATOM | 970 | CE1 | TYR | E | 118 | 12.238 | 19.402 | 53.209 | 1.00 | 0.02 C |
| ATOM | 971 | CZ | TYR | E | 118 | 11.152 | 19.076 | 52.409 | 1.00 | 0.02 C |
| ATOM | 972 | OH | TYR | E | 118 | 9.888 | 19.437 | 52.802 | 1.00 | 0.03 O |
| ATOM | 973 | CE2 | TYR | E | 118 | 11.342 | 18.498 | 51.162 | 1.00 | 0.02 C |
| ATOM | 974 | CD2 | TYR | E | 118 | 12.629 | 18.251 | 50.708 | 1.00 | 0.02 C |
| ATOM | 975 | C | TYR | E | 118 | 15.136 | 16.232 | 52.419 | 1.00 | 0.03 C |
| ATOM | 976 | O | TYR | E | 118 | 14.843 | 16.212 | 53.622 | 1.00 | 0.02 O |
| ATOM | 977 | N | PRO | E | 119 | 14.866 | 15.198 | 51.620 | 1.00 | 0.02 N |
| ATOM | 978 | CA | PRO | E | 119 | 14.082 | 14.085 | 52.174 | 1.00 | 0.01 C |
| ATOM | 979 | CB | PRO | E | 119 | 13.755 | 13.207 | 51.006 | 1.00 | 0.20 C |
| ATOM | 980 | CG | PRO | E | 119 | 14.467 | 13.719 | 49.766 | 1.00 | 0.34 C |
| ATOM | 981 | CD | PRO | E | 119 | 15.184 | 14.985 | 50.194 | 1.00 | 0.16 C |
| ATOM | 982 | C | PRO | E | 119 | 14.824 | 13.295 | 53.259 | 1.00 | 0.03 C |
| ATOM | 983 | O | PRO | E | 119 | 14.201 | 12.948 | 54.268 | 1.00 | 0.03 O |
| ATOM | 984 | N | ARG | E | 120 | 16.148 | 13.301 | 53.216 | 1.00 | 0.03 N |
| ATOM | 985 | CA | ARG | E | 120 | 16.938 | 12.592 | 54.221 | 1.00 | 0.02 C |
| ATOM | 986 | CB | ARG | E | 120 | 18.292 | 12.291 | 53.594 | 1.00 | 0.01 C |
| ATOM | 987 | CG | ARG | E | 120 | 19.230 | 11.555 | 54.540 | 1.00 | 0.03 C |
| ATOM | 988 | CD | ARG | E | 120 | 20.473 | 11.082 | 53.797 | 1.00 | 0.02 C |
| ATOM | 989 | NE | ARG | E | 120 | 21.102 | 12.188 | 53.057 | 1.00 | 0.03 N |
| ATOM | 990 | CZ | ARG | E | 120 | 21.340 | 12.143 | 51.744 | 1.00 | 0.02 C |
| ATOM | 991 | NH1 | ARG | E | 120 | 20.969 | 11.075 | 51.034 | 1.00 | 0.01 N |
| ATOM | 992 | NH2 | ARG | E | 120 | 21.920 | 13.178 | 51.134 | 1.00 | 0.02 N |
| ATOM | 993 | C | ARG | E | 120 | 17.088 | 13.414 | 55.504 | 1.00 | 0.02 C |
| ATOM | 994 | O | ARG | E | 120 | 17.152 | 12.837 | 56.594 | 1.00 | 0.02 O |
| ATOM | 995 | N | PHE | E | 121 | 16.852 | 14.712 | 55.397 | 1.00 | 0.01 N |
| ATOM | 996 | CA | PHE | E | 121 | 16.797 | 15.593 | 56.565 | 1.00 | 0.03 C |
| ATOM | 997 | CB | PHE | E | 121 | 16.887 | 17.033 | 56.069 | 1.00 | 0.02 C |
| ATOM | 998 | CG | PHE | E | 121 | 16.510 | 18.091 | 57.100 | 1.00 | 0.02 C |
| ATOM | 999 | CD1 | PHE | E | 121 | 17.353 | 18.358 | 58.171 | 1.00 | 0.02 C |
| ATOM | 1000 | CE1 | PHE | E | 121 | 17.001 | 19.321 | 59.106 | 1.00 | 0.02 C |
| ATOM | 1001 | CZ | PHE | E | 121 | 15.807 | 20.017 | 58.973 | 1.00 | 0.02 C |
| ATOM | 1002 | CE2 | PHE | E | 121 | 14.964 | 19.749 | 57.904 | 1.00 | 0.01 C |
| ATOM | 1003 | CD2 | PHE | E | 121 | 15.315 | 18.787 | 56.967 | 1.00 | 0.02 C |
| ATOM | 1004 | C | PHE | E | 121 | 15.492 | 15.405 | 57.320 | 1.00 | 0.02 C |
| ATOM | 1005 | O | PHE | E | 121 | 15.517 | 15.300 | 58.551 | 1.00 | 0.01 O |
| ATOM | 1006 | N | VAL | E | 122 | 14.451 | 15.059 | 56.580 | 1.00 | 0.03 N |
| ATOM | 1007 | CA | VAL | E | 122 | 13.138 | 14.801 | 57.173 | 1.00 | 0.01 C |
| ATOM | 1008 | CB | VAL | E | 122 | 12.100 | 14.970 | 56.063 | 1.00 | 0.27 C |
| ATOM | 1009 | CG1 | VAL | E | 122 | 10.684 | 14.647 | 56.528 | 1.00 | 0.14 C |
| ATOM | 1010 | CG2 | VAL | E | 122 | 12.154 | 16.381 | 55.491 | 1.00 | 0.44 C |
| ATOM | 1011 | C | VAL | E | 122 | 13.063 | 13.398 | 57.784 | 1.00 | 0.02 C |
| ATOM | 1012 | O | VAL | E | 122 | 12.244 | 13.152 | 58.676 | 1.00 | 0.03 O |
| ATOM | 1013 | N | ARG | E | 123 | 13.995 | 12.536 | 57.411 | 1.00 | 0.02 N |
| ATOM | 1014 | CA | ARG | E | 123 | 14.084 | 11.206 | 58.020 | 1.00 | 0.03 C |
| ATOM | 1015 | CB | ARG | E | 123 | 14.541 | 10.224 | 56.949 | 1.00 | 0.29 C |
| ATOM | 1016 | CG | ARG | E | 123 | 13.632 | 10.232 | 55.730 | 1.00 | 0.95 C |
| ATOM | 1017 | CD | ARG | E | 123 | 14.219 | 9.356 | 54.630 | 1.00 | 1.08 C |
| ATOM | 1018 | NE | ARG | E | 123 | 13.417 | 9.429 | 53.401 | 1.00 | 0.69 N |
| ATOM | 1019 | CZ | ARG | E | 123 | 13.957 | 9.610 | 52.194 | 1.00 | 0.68 C |
| ATOM | 1020 | NH1 | ARG | E | 123 | 13.181 | 9.596 | 51.108 | 1.00 | 1.02 N |
| ATOM | 1021 | NH2 | ARG | E | 123 | 15.280 | 9.751 | 52.068 | 1.00 | 0.80 N |
| ATOM | 1022 | C | ARG | E | 123 | 15.109 | 11.166 | 59.152 | 1.00 | 0.02 C |
| ATOM | 1023 | O | ARG | E | 123 | 15.123 | 10.221 | 59.950 | 1.00 | 0.02 O |
| ATOM | 1024 | N | SER | E | 124 | 15.955 | 12.180 | 59.219 | 1.00 | 0.02 N |
| ATOM | 1025 | CA | SER | E | 124 | 17.040 | 12.186 | 60.202 | 1.00 | 0.02 C |
| ATOM | 1026 | CB | SER | E | 124 | 18.236 | 12.951 | 59.651 | 1.00 | 0.02 C |
| ATOM | 1027 | OG | SER | E | 124 | 17.909 | 14.333 | 59.663 | 1.00 | 0.02 O |
| ATOM | 1028 | C | SER | E | 124 | 16.625 | 12.836 | 61.509 | 1.00 | 0.02 C |
| ATOM | 1029 | O | SER | E | 124 | 15.723 | 13.683 | 61.558 | 1.00 | 0.01 O |
| ATOM | 1030 | N | GLN | E | 125 | 17.511 | 12.666 | 62.475 | 1.00 | 0.01 N |
| ATOM | 1031 | CA | GLN | E | 125 | 17.316 | 13.184 | 63.833 | 1.00 | 0.03 C |
| ATOM | 1032 | CB | GLN | E | 125 | 18.330 | 12.466 | 64.719 | 1.00 | 0.38 C |
| ATOM | 1033 | CG | GLN | E | 125 | 18.156 | 12.773 | 66.201 | 1.00 | 1.43 C |
| ATOM | 1034 | CD | GLN | E | 125 | 19.232 | 12.038 | 66.992 | 1.00 | 2.28 C |
| ATOM | 1035 | OE1 | GLN | E | 125 | 20.431 | 12.248 | 66.776 | 1.00 | 3.19 O |
| ATOM | 1036 | NE2 | GLN | E | 125 | 18.790 | 11.131 | 67.845 | 1.00 | 2.30 N |
| ATOM | 1037 | C | GLN | E | 125 | 17.505 | 14.703 | 63.942 | 1.00 | 0.01 C |
| ATOM | 1038 | O | GLN | E | 125 | 17.043 | 15.297 | 64.920 | 1.00 | 0.03 O |
| ATOM | 1039 | N | ILE | E | 126 | 17.899 | 15.352 | 62.856 | 1.00 | 0.01 N |
| ATOM | 1040 | CA | ILE | E | 126 | 18.065 | 16.802 | 62.888 | 1.00 | 0.01 C |
| ATOM | 1041 | CB | ILE | E | 126 | 19.004 | 17.185 | 61.746 | 1.00 | 0.31 C |
| ATOM | 1042 | CG2 | ILE | E | 126 | 19.341 | 18.668 | 61.795 | 1.00 | 0.72 C |
| ATOM | 1043 | CG1 | ILE | E | 126 | 20.298 | 16.379 | 61.813 | 1.00 | 0.82 C |
| ATOM | 1044 | CD1 | ILE | E | 126 | 21.140 | 16.765 | 63.026 | 1.00 | 1.53 C |

TABLE 3-continued

| ATOM | 1045 | C   | ILE | E | 126 | 16.697 | 17.475 | 62.721 | 1.00 | 0.03 | C |
|------|------|-----|-----|---|-----|--------|--------|--------|------|------|---|
| ATOM | 1046 | O   | ILE | E | 126 | 16.443 | 18.526 | 63.320 | 1.00 | 0.02 | O |
| ATOM | 1047 | N   | TYR | E | 127 | 15.773 | 16.766 | 62.089 | 1.00 | 0.01 | N |
| ATOM | 1048 | CA  | TYR | E | 127 | 14.395 | 17.249 | 61.982 | 1.00 | 0.02 | C |
| ATOM | 1049 | CB  | TYR | E | 127 | 13.920 | 16.977 | 60.561 | 1.00 | 0.02 | C |
| ATOM | 1050 | CG  | TYR | E | 127 | 12.449 | 17.270 | 60.290 | 1.00 | 0.02 | C |
| ATOM | 1051 | CD1 | TYR | E | 127 | 12.001 | 18.583 | 60.209 | 1.00 | 0.02 | C |
| ATOM | 1052 | CE1 | TYR | E | 127 | 10.660 | 18.841 | 59.963 | 1.00 | 0.01 | C |
| ATOM | 1053 | CZ  | TYR | E | 127 | 9.772  | 17.786 | 59.797 | 1.00 | 0.02 | C |
| ATOM | 1054 | OH  | TYR | E | 127 | 8.438  | 18.040 | 59.561 | 1.00 | 0.02 | O |
| ATOM | 1055 | CE2 | TYR | E | 127 | 10.218 | 16.475 | 59.875 | 1.00 | 0.02 | C |
| ATOM | 1056 | CD2 | TYR | E | 127 | 11.559 | 16.218 | 60.123 | 1.00 | 0.01 | C |
| ATOM | 1057 | C   | TYR | E | 127 | 13.494 | 16.534 | 62.986 | 1.00 | 0.01 | C |
| ATOM | 1058 | O   | TYR | E | 127 | 12.598 | 17.145 | 63.584 | 1.00 | 0.01 | O |
| ATOM | 1059 | N   | LYS | E | 128 | 13.877 | 15.312 | 63.317 | 1.00 | 0.02 | N |
| ATOM | 1060 | CA  | LYS | E | 128 | 13.112 | 14.492 | 64.266 | 1.00 | 0.03 | C |
| ATOM | 1061 | CB  | LYS | E | 128 | 13.450 | 13.028 | 64.006 | 1.00 | 0.23 | C |
| ATOM | 1062 | CG  | LYS | E | 128 | 12.916 | 12.555 | 62.660 | 1.00 | 1.16 | C |
| ATOM | 1063 | CD  | LYS | E | 128 | 11.393 | 12.600 | 62.632 | 1.00 | 1.39 | C |
| ATOM | 1064 | CE  | LYS | E | 128 | 10.849 | 12.077 | 61.309 | 1.00 | 2.20 | C |
| ATOM | 1065 | NZ  | LYS | E | 128 | 11.327 | 10.709 | 61.051 | 1.00 | 2.66 | N |
| ATOM | 1066 | C   | LYS | E | 128 | 13.380 | 14.792 | 65.743 | 1.00 | 0.02 | C |
| ATOM | 1067 | O   | LYS | E | 128 | 12.624 | 14.299 | 66.594 | 1.00 | 0.04 | O |
| ATOM | 1068 | N   | ALA | E | 129 | 14.306 | 15.691 | 66.041 | 1.00 | 0.04 | N |
| ATOM | 1069 | CA  | ALA | E | 129 | 14.668 | 15.978 | 67.435 | 1.00 | 0.02 | C |
| ATOM | 1070 | CB  | ALA | E | 129 | 15.855 | 16.935 | 67.433 | 1.00 | 0.43 | C |
| ATOM | 1071 | C   | ALA | E | 129 | 13.524 | 16.607 | 68.222 | 1.00 | 0.02 | C |
| ATOM | 1072 | O   | ALA | E | 129 | 13.183 | 16.124 | 69.307 | 1.00 | 0.02 | O |
| ATOM | 1073 | N   | VAL | E | 130 | 12.826 | 17.545 | 67.600 | 1.00 | 0.02 | N |
| ATOM | 1074 | CA  | VAL | E | 130 | 11.665 | 18.170 | 68.246 | 1.00 | 0.02 | C |
| ATOM | 1075 | CB  | VAL | E | 130 | 11.790 | 19.687 | 68.115 | 1.00 | 1.13 | C |
| ATOM | 1076 | CG1 | VAL | E | 130 | 10.878 | 20.411 | 69.104 | 1.00 | 1.60 | C |
| ATOM | 1077 | CG2 | VAL | E | 130 | 13.231 | 20.121 | 68.367 | 1.00 | 1.34 | C |
| ATOM | 1078 | C   | VAL | E | 130 | 10.358 | 17.641 | 67.638 | 1.00 | 0.02 | C |
| ATOM | 1079 | O   | VAL | E | 130 | 9.318  | 18.310 | 67.656 | 1.00 | 0.04 | O |
| ATOM | 1080 | N   | LEU | E | 131 | 10.421 | 16.436 | 67.098 | 1.00 | 0.01 | N |
| ATOM | 1081 | CA  | LEU | E | 131 | 9.262  | 15.860 | 66.422 | 1.00 | 0.02 | C |
| ATOM | 1082 | CB  | LEU | E | 131 | 9.290  | 16.320 | 64.964 | 1.00 | 1.51 | C |
| ATOM | 1083 | CG  | LEU | E | 131 | 7.970  | 16.030 | 64.260 | 1.00 | 2.24 | C |
| ATOM | 1084 | CD1 | LEU | E | 131 | 6.818  | 16.742 | 64.957 | 1.00 | 3.13 | C |
| ATOM | 1085 | CD2 | LEU | E | 131 | 8.033  | 16.435 | 62.793 | 1.00 | 2.99 | C |
| ATOM | 1086 | C   | LEU | E | 131 | 9.325  | 14.339 | 66.501 | 1.00 | 0.00 | C |
| ATOM | 1087 | O   | LEU | E | 131 | 8.307  | 13.643 | 66.354 | 1.00 | 0.02 | O |
| END  |      |     |     |   |     |        |        |        |      |      |   |

TABLE 4

| REMARK | 4 | Human RGS7 protein modeled on Rat RGS-4 (E. chain from PDB |
|--------|---|---|
| REMARK | 4 | entry 1AGR. See: Tesmer J.J., D.M. Berman, A.G. Gilman, S.R. Sprang |
| REMARK | 4 | Structure of G(I RGS4 Bound to ALF4 (−)-Activated Alpha1): |
| REMARK | 4 | Stabilization of the Transition State for GTP Hydrolysis, |
| REMARK | 4 | Cell(Cambridge, Mass.) V. 89 251 1997) |
| REMARK | 4 | |

HEADER seqmod.18424, Minimized 100 + 2 * 200

| ATOM | 1  | N   | GLY E 1 | −0.821 | 27.251 | 73.130 | 1.00 | 1.02 |
|------|----|-----|---------|--------|--------|--------|------|------|
| ATOM | 5  | CA  | GLY E 1 | −1.017 | 28.084 | 71.932 | 1.00 | 0.85 |
| ATOM | 6  | C   | GLY E 1 | 0.229  | 28.103 | 71.055 | 1.00 | 0.53 |
| ATOM | 7  | O   | GLY E 1 | 0.240  | 27.532 | 69.957 | 1.00 | 0.56 |
| ATOM | 8  | N   | LEU E 2 | 1.319  | 28.585 | 71.628 | 1.00 | 0.41 |
| ATOM | 10 | CA  | LEU E 2 | 2.568  | 28.728 | 70.871 | 1.00 | 0.33 |
| ATOM | 11 | CB  | LEU E 2 | 3.481  | 29.677 | 71.640 | 1.00 | 0.41 |
| ATOM | 12 | CG  | LEU E 2 | 4.741  | 30.020 | 70.853 | 1.00 | 1.13 |
| ATOM | 13 | CD1 | LEU E 2 | 4.392  | 30.672 | 69.518 | 1.00 | 1.51 |
| ATOM | 14 | CD2 | LEU E 2 | 5.658  | 30.926 | 71.666 | 1.00 | 1.25 |
| ATOM | 15 | C   | LEU E 2 | 3.267  | 27.385 | 70.658 | 1.00 | 0.30 |
| ATOM | 16 | O   | LEU E 2 | 3.900  | 27.185 | 69.615 | 1.00 | 0.28 |
| ATOM | 17 | N   | VAL E 3 | 2.970  | 26.415 | 71.506 | 1.00 | 0.29 |
| ATOM | 19 | CA  | VAL E 3 | 3.486  | 25.055 | 71.297 | 1.00 | 0.25 |
| ATOM | 20 | CB  | VAL E 3 | 3.274  | 24.223 | 72.560 | 1.00 | 0.37 |
| ATOM | 21 | CG1 | VAL E 3 | 3.839  | 22.815 | 72.395 | 1.00 | 0.52 |
| ATOM | 22 | CG2 | VAL E 3 | 3.903  | 24.907 | 73.768 | 1.00 | 0.41 |
| ATOM | 23 | C   | VAL E 3 | 2.871  | 24.385 | 70.049 | 1.00 | 0.25 |
| ATOM | 24 | O   | VAL E 3 | 3.659  | 24.046 | 69.155 | 1.00 | 0.20 |
| ATOM | 25 | N   | PRO E 4 | 1.547  | 24.262 | 69.903 | 1.00 | 0.31 |
| ATOM | 26 | CA  | PRO E 4 | 1.018  | 23.763 | 68.626 | 1.00 | 0.30 |
| ATOM | 27 | CB  | PRO E 4 | −0.459 | 23.617 | 68.822 | 1.00 | 0.41 |

TABLE 4-continued

| | | | | | | | | |
|---|---|---|---|---|---|---|---|---|
| ATOM | 28 | CG | PRO E 4 | −0.841 | 24.122 | 70.201 | 1.00 | 0.67 |
| ATOM | 29 | CD | PRO E 4 | 0.459 | 24.535 | 70.862 | 1.00 | 0.40 |
| ATOM | 30 | C | PRO E 4 | 1.310 | 24.663 | 67.418 | 1.00 | 0.26 |
| ATOM | 31 | O | PRO E 4 | 1.500 | 24.114 | 66.325 | 1.00 | 0.23 |
| ATOM | 32 | N | ARG E 5 | 1.503 | 25.963 | 67.613 | 1.00 | 0.27 |
| ATOM | 34 | CA | ARG E 5 | 1.906 | 26.834 | 66.501 | 1.00 | 0.23 |
| ATOM | 35 | CB | ARG E 5 | 1.928 | 28.285 | 66.962 | 1.00 | 0.50 |
| ATOM | 36 | CG | ARG E 5 | 0.526 | 28.844 | 67.153 | 1.00 | 1.05 |
| ATOM | 37 | CD | ARG E 5 | 0.603 | 30.281 | 67.651 | 1.00 | 1.48 |
| ATOM | 38 | NE | ARG E 5 | 1.499 | 31.069 | 66.788 | 1.00 | 2.28 |
| ATOM | 39 | CZ | ARG E 5 | 1.073 | 31.965 | 65.894 | 1.00 | 3.07 |
| ATOM | 40 | NH1 | ARG E 5 | −0.233 | 32.216 | 65.768 | 1.00 | 3.88 |
| ATOM | 41 | NH2 | ARG E 5 | 1.953 | 32.622 | 65.136 | 1.00 | 3.52 |
| ATOM | 42 | C | ARG E 5 | 3.286 | 26.456 | 65.982 | 1.00 | 0.15 |
| ATOM | 43 | O | ARG E 5 | 3.409 | 26.024 | 64.827 | 1.00 | 0.14 |
| ATOM | 44 | N | GLY E 6 | 4.237 | 26.382 | 66.897 | 1.00 | 0.03 |
| ATOM | 46 | CA | GLY E 6 | 5.615 | 25.999 | 66.575 | 1.00 | 0.02 |
| ATOM | 47 | C | GLY E 6 | 5.683 | 24.627 | 65.916 | 1.00 | 0.03 |
| ATOM | 48 | O | GLY E 6 | 6.220 | 24.509 | 64.809 | 1.00 | 0.03 |
| ATOM | 49 | N | SER E 7 | 4.962 | 23.666 | 66.475 | 1.00 | 0.03 |
| ATOM | 51 | CA | SER E 7 | 4.994 | 22.307 | 65.930 | 1.00 | 0.04 |
| ATOM | 52 | CB | SER E 7 | 4.323 | 21.354 | 66.916 | 1.00 | 0.42 |
| ATOM | 53 | OG | SER E 7 | 2.975 | 21.762 | 67.101 | 1.00 | 0.35 |
| ATOM | 54 | C | SER E 7 | 4.346 | 22.166 | 64.546 | 1.00 | 0.02 |
| ATOM | 55 | O | SER E 7 | 4.929 | 21.453 | 63.721 | 1.00 | 0.02 |
| ATOM | 56 | N | HIS E 8 | 3.363 | 22.982 | 64.186 | 1.00 | 0.04 |
| ATOM | 58 | CA | HIS E 8 | 2.817 | 22.836 | 62.830 | 1.00 | 0.03 |
| ATOM | 59 | CB | HIS E 8 | 1.327 | 23.184 | 62.745 | 1.00 | 0.45 |
| ATOM | 60 | CG | HIS E 8 | 0.909 | 24.638 | 62.874 | 1.00 | 0.78 |
| ATOM | 61 | ND1 | HIS E 8 | 0.188 | 25.165 | 63.879 | 1.00 | 1.80 |
| ATOM | 63 | CE1 | HIS E 8 | −0.009 | 26.478 | 63.652 | 1.00 | 2.59 |
| ATOM | 64 | NE2 | HIS E 8 | 0.589 | 26.784 | 62.478 | 1.00 | 2.35 |
| ATOM | 65 | CD2 | HIS E 8 | 1.145 | 25.658 | 61.980 | 1.00 | 1.43 |
| ATOM | 66 | C | HIS E 8 | 3.631 | 23.635 | 61.819 | 1.00 | 0.02 |
| ATOM | 67 | O | HIS E 8 | 3.708 | 23.227 | 60.654 | 1.00 | 0.01 |
| ATOM | 68 | N | ARG E 9 | 4.432 | 24.571 | 62.301 | 1.00 | 0.02 |
| ATOM | 70 | CA | ARG E 9 | 5.359 | 25.268 | 61.414 | 1.00 | 0.04 |
| ATOM | 71 | CB | ARG E 9 | 5.750 | 26.596 | 62.046 | 1.00 | 0.23 |
| ATOM | 72 | CD | ARG E 9 | 4.511 | 27.454 | 62.272 | 1.00 | 0.96 |
| ATOM | 73 | CD | ARG E 9 | 4.851 | 28.794 | 62.910 | 1.00 | 1.69 |
| ATOM | 74 | NE | ARG E 9 | 5.662 | 29.615 | 61.996 | 1.00 | 2.00 |
| ATOM | 75 | CZ | ARG E 9 | 6.745 | 30.291 | 62.386 | 1.00 | 2.66 |
| ATOM | 76 | NH1 | ARG E 9 | 7.163 | 30.206 | 63.650 | 1.00 | 3.47 |
| ATOM | 77 | NH2 | ARG E 9 | 7.421 | 31.034 | 61.506 | 1.00 | 3.00 |
| ATOM | 78 | C | ARG E 9 | 6.587 | 24.400 | 61.165 | 1.00 | 0.01 |
| ATOM | 79 | O | ARG E 9 | 7.055 | 24.343 | 60.024 | 1.00 | 0.02 |
| ATOM | 80 | N | VAL E 10 | 6.873 | 23.512 | 62.107 | 1.00 | 0.03 |
| ATOM | 82 | CA | VAL E 10 | 7.910 | 22.498 | 61.900 | 1.00 | 0.00 |
| ATOM | 83 | CB | VAL E 10 | 8.203 | 21.791 | 63.220 | 1.00 | 0.02 |
| ATOM | 84 | CG1 | VAL E 10 | 9.122 | 20.592 | 63.012 | 1.00 | 0.00 |
| ATOM | 85 | CG2 | VAL E 10 | 8.791 | 22.749 | 64.248 | 1.00 | 0.01 |
| ATOM | 86 | C | VAL E 10 | 7.450 | 21.468 | 60.874 | 1.00 | 0.02 |
| ATOM | 87 | O | VAL E 10 | 8.192 | 21.203 | 59.923 | 1.00 | 0.02 |
| ATOM | 88 | N | LYS E 11 | 6.160 | 21.163 | 60.878 | 1.00 | 0.01 |
| ATOM | 90 | CA | LYS E 11 | 5.606 | 20.239 | 59.881 | 1.00 | 0.02 |
| ATOM | 91 | CB | LYS E 11 | 4.180 | 19.895 | 60.288 | 1.00 | 0.02 |
| ATOM | 92 | CG | LYS E 11 | 4.144 | 19.259 | 61.670 | 1.00 | 0.01 |
| ATOM | 93 | CD | LYS E 11 | 2.718 | 19.146 | 62.192 | 1.00 | 0.01 |
| ATOM | 94 | CE | LYS E 11 | 2.696 | 18.664 | 63.638 | 1.00 | 0.00 |
| ATOM | 95 | NZ | LYS E 11 | 1.324 | 18.668 | 64.171 | 1.00 | 0.03 |
| ATOM | 96 | C | LYS E 11 | 5.597 | 20.861 | 58.487 | 1.00 | 0.03 |
| ATOM | 97 | O | LYS E 11 | 5.997 | 20.188 | 57.526 | 1.00 | 0.02 |
| ATOM | 98 | N | ARG E 12 | 5.482 | 22.179 | 58.433 | 1.00 | 0.02 |
| ATOM | 100 | CA | ARG E 12 | 5.538 | 22.903 | 57.159 | 1.00 | 0.03 |
| ATOM | 101 | CB | ARG E 12 | 5.029 | 24.320 | 57.376 | 1.00 | 0.15 |
| ATOM | 102 | CG | ARG E 12 | 3.538 | 24.347 | 57.672 | 1.00 | 1.14 |
| ATOM | 103 | CD | ARG E 12 | 3.071 | 25.776 | 57.915 | 1.00 | 1.50 |
| ATOM | 104 | NE | ARG E 12 | 1.606 | 25.847 | 58.008 | 1.00 | 2.77 |
| ATOM | 105 | CZ | ARG E 12 | 0.845 | 26.323 | 57.019 | 1.00 | 3.81 |
| ATOM | 106 | NH1 | ARG E 12 | −0.483 | 26.328 | 57.140 | 1.00 | 4.89 |
| ATOM | 107 | NH2 | ARG E 12 | 1.412 | 26.769 | 55.894 | 1.00 | 4.15 |
| ATOM | 108 | C | ARG E 12 | 6.942 | 22.994 | 56.565 | 1.00 | 0.02 |
| ATOM | 109 | O | ARG E 12 | 7.047 | 23.084 | 55.336 | 1.00 | 0.02 |
| ATOM | 110 | N | TRP E 13 | 7.973 | 22.717 | 57.350 | 1.00 | 0.03 |
| ATOM | 112 | CA | TRP E 13 | 9.340 | 22.720 | 56.813 | 1.00 | 0.03 |
| ATOM | 113 | CB | TRP E 13 | 10.345 | 22.869 | 57.953 | 1.00 | 0.01 |
| ATOM | 114 | CG | TRP E 13 | 10.191 | 24.083 | 58.847 | 1.00 | 0.02 |
| ATOM | 115 | CD1 | TRP E 13 | 9.558 | 25.273 | 58.554 | 1.00 | 0.01 |
| ATOM | 116 | NE1 | TRP E 13 | 9.636 | 26.079 | 59.642 | 1.00 | 0.03 |

TABLE 4-continued

| | | | | | | | | |
|---|---|---|---|---|---|---|---|---|
| ATOM | 118 | CE2 | TRP E 13 | 10.317 | 25.487 | 60.641 | 1.00 | 0.02 |
| ATOM | 119 | CZ2 | TRP E 13 | 10.655 | 25.896 | 61.920 | 1.00 | 0.02 |
| ATOM | 120 | CH2 | TRP E 13 | 11.391 | 25.049 | 62.743 | 1.00 | 0.01 |
| ATOM | 121 | CZ3 | TRP E 13 | 11.784 | 23.796 | 62.289 | 1.00 | 0.03 |
| ATOM | 122 | CE3 | TRP E 13 | 11.442 | 23.374 | 61.008 | 1.00 | 0.03 |
| ATOM | 123 | CD2 | TRP E 13 | 10.709 | 24.217 | 60.185 | 1.00 | 0.01 |
| ATOM | 124 | C | TRP E 13 | 9.635 | 21.400 | 56.106 | 1.00 | 0.02 |
| ATOM | 125 | O | TRP E 13 | 10.437 | 21.353 | 55.166 | 1.00 | 0.02 |
| ATOM | 126 | N | GLY E 14 | 8.835 | 20.396 | 56.426 | 1.00 | 0.00 |
| ATOM | 128 | CA | GLY E 14 | 8.977 | 19.069 | 55.824 | 1.00 | 0.00 |
| ATOM | 129 | C | GLY E 14 | 7.986 | 18.890 | 54.683 | 1.00 | 0.02 |
| ATOM | 130 | O | GLY E 14 | 8.148 | 18.000 | 53.840 | 1.00 | 0.02 |
| ATOM | 131 | N | PHE E 15 | 6.965 | 19.731 | 54.668 | 1.00 | 0.01 |
| ATOM | 133 | CA | PHE E 15 | 6.025 | 19.743 | 53.542 | 1.00 | 0.02 |
| ATOM | 134 | CB | PHE E 15 | 4.646 | 20.162 | 54.044 | 1.00 | 0.62 |
| ATOM | 135 | CG | PHE E 15 | 3.981 | 19.179 | 55.004 | 1.00 | 1.08 |
| ATOM | 136 | CD1 | PHE E 15 | 3.200 | 19.657 | 56.049 | 1.00 | 1.84 |
| ATOM | 137 | CE1 | PHE E 15 | 2.594 | 18.769 | 56.927 | 1.00 | 2.25 |
| ATOM | 138 | CZ | PHE E 15 | 2.763 | 17.401 | 56.760 | 1.00 | 1.96 |
| ATOM | 139 | CE2 | PHE E 15 | 3.536 | 16.921 | 55.711 | 1.00 | 1.56 |
| ATOM | 140 | CD2 | PHE E 15 | 4.143 | 17.809 | 54.832 | 1.00 | 1.19 |
| ATOM | 141 | C | PHE E 15 | 6.483 | 20.706 | 52.444 | 1.00 | 0.01 |
| ATOM | 142 | O | PHE E 15 | 6.033 | 20.599 | 51.297 | 1.00 | 0.01 |
| ATOM | 143 | N | GLY E 16 | 7.390 | 21.604 | 52.787 | 1.00 | 0.02 |
| ATOM | 145 | CA | GLY E 16 | 7.974 | 22.512 | 51.799 | 1.00 | 0.01 |
| ATOM | 146 | C | GLY E 16 | 9.338 | 23.012 | 52.263 | 1.00 | 0.00 |
| ATOM | 147 | O | GLY E 16 | 9.454 | 23.688 | 53.296 | 1.00 | 0.03 |
| ATOM | 148 | N | MET E 17 | 10.320 | 22.871 | 51.386 | 1.00 | 0.00 |
| ATOM | 150 | CA | MET E 17 | 11.694 | 23.241 | 51.749 | 1.00 | 0.01 |
| ATOM | 151 | CB | MET E 17 | 12.680 | 22.583 | 50.790 | 1.00 | 0.97 |
| ATOM | 152 | CG | MET E 17 | 14.106 | 22.721 | 51.313 | 1.00 | 1.67 |
| ATOM | 153 | SD | MET E 17 | 15.410 | 21.988 | 50.302 | 1.00 | 2.86 |
| ATOM | 154 | CE | MET E 17 | 15.289 | 23.064 | 48.858 | 1.00 | 3.38 |
| ATOM | 155 | C | MET E 17 | 11.902 | 24.752 | 51.729 | 1.00 | 0.02 |
| ATOM | 156 | O | MET E 17 | 12.708 | 25.264 | 52.512 | 1.00 | 0.02 |
| ATOM | 157 | N | ASP E 18 | 10.999 | 25.474 | 51.085 | 1.00 | 0.02 |
| ATOM | 159 | CA | ASP E 18 | 11.069 | 26.935 | 51.130 | 1.00 | 0.02 |
| ATOM | 160 | CB | ASP E 18 | 10.342 | 27.543 | 49.928 | 1.00 | 0.18 |
| ATOM | 161 | CG | ASP E 18 | 8.901 | 27.050 | 49.805 | 1.00 | 0.80 |
| ATOM | 162 | OD1 | ASP E 18 | 8.020 | 27.718 | 50.330 | 1.00 | 0.95 |
| ATOM | 163 | OD2 | ASP E 18 | 8.710 | 26.023 | 49.166 | 1.00 | 1.43 |
| ATOM | 164 | C | ASP E 18 | 10.495 | 27.475 | 52.438 | 1.00 | 0.03 |
| ATOM | 165 | O | ASP E 18 | 10.982 | 28.499 | 52.923 | 1.00 | 0.02 |
| ATOM | 166 | N | GLU E 19 | 9.720 | 26.666 | 53.143 | 1.00 | 0.01 |
| ATOM | 168 | CA | GLU E 19 | 9.205 | 27.083 | 54.445 | 1.00 | 0.00 |
| ATOM | 169 | CB | GLU E 19 | 7.916 | 26.328 | 54.781 | 1.00 | 0.36 |
| ATOM | 170 | CG | GLU E 19 | 6.677 | 26.894 | 54.079 | 1.00 | 1.11 |
| ATOM | 171 | CD | GLU E 19 | 6.337 | 26.194 | 52.758 | 1.00 | 2.06 |
| ATOM | 172 | OE1 | GLU E 19 | 5.191 | 26.300 | 52.349 | 1.00 | 3.03 |
| ATOM | 173 | OE2 | GLU E 19 | 7.219 | 25.561 | 52.186 | 1.00 | 2.42 |
| ATOM | 174 | C | GLU E 19 | 10.265 | 26.816 | 55.504 | 1.00 | 0.02 |
| ATOM | 175 | O | GLU E 19 | 10.451 | 27.638 | 56.412 | 1.00 | 0.02 |
| ATOM | 176 | N | ALA E 20 | 11.104 | 25.833 | 55.223 | 1.00 | 0.03 |
| ATOM | 178 | CA | ALA E 20 | 12.261 | 25.572 | 56.071 | 1.00 | 0.01 |
| ATOM | 179 | CB | ALA E 20 | 12.892 | 24.248 | 55.654 | 1.00 | 0.13 |
| ATOM | 180 | C | ALA E 20 | 13.281 | 26.690 | 55.917 | 1.00 | 0.02 |
| ATOM | 181 | O | ALA E 20 | 13.484 | 27.437 | 56.881 | 1.00 | 0.01 |
| ATOM | 182 | N | LEU E 21 | 13.603 | 27.012 | 54.673 | 1.00 | 0.01 |
| ATOM | 184 | CA | LEU E 21 | 14.678 | 27.972 | 54.377 | 1.00 | 0.02 |
| ATOM | 185 | CB | LEU E 21 | 15.125 | 27.761 | 52.936 | 1.00 | 0.19 |
| ATOM | 186 | CG | LEU E 21 | 15.669 | 26.358 | 52.701 | 1.00 | 0.28 |
| ATOM | 187 | CD1 | LEU E 21 | 16.085 | 26.180 | 51.245 | 1.00 | 0.37 |
| ATOM | 188 | CD2 | LEU E 21 | 16.837 | 26.055 | 53.631 | 1.00 | 0.47 |
| ATOM | 189 | C | LEU E 21 | 14.317 | 29.450 | 54.554 | 1.00 | 0.02 |
| ATOM | 190 | O | LEU E 21 | 15.229 | 30.279 | 54.656 | 1.00 | 0.02 |
| ATOM | 191 | N | LYS E 22 | 13.039 | 29.788 | 54.619 | 1.00 | 0.02 |
| ATOM | 193 | CA | LYS E 22 | 12.665 | 31.178 | 54.907 | 1.00 | 0.03 |
| ATOM | 194 | CB | LYS E 22 | 11.398 | 31.525 | 54.135 | 1.00 | 0.45 |
| ATOM | 195 | CG | LYS E 22 | 11.648 | 31.485 | 52.632 | 1.00 | 0.74 |
| ATOM | 196 | CD | LYS E 22 | 10.349 | 31.643 | 51.853 | 1.00 | 1.17 |
| ATOM | 197 | CE | LYS E 22 | 10.588 | 31.506 | 50.353 | 1.00 | 1.93 |
| ATOM | 198 | NZ | LYS E 22 | 9.323 | 31.601 | 49.609 | 1.00 | 3.00 |
| ATOM | 199 | C | LYS E 22 | 12.439 | 31.382 | 56.401 | 1.00 | 0.02 |
| ATOM | 200 | O | LYS E 22 | 12.401 | 32.516 | 56.892 | 1.00 | 0.02 |
| ATOM | 201 | N | ASP E 23 | 12.305 | 30.279 | 57.114 | 1.00 | 0.01 |
| ATOM | 203 | CA | ASP E 23 | 12.219 | 30.326 | 58.658 | 1.00 | 0.00 |
| ATOM | 204 | CB | ASP E 23 | 11.425 | 29.097 | 58.996 | 1.00 | 0.79 |
| ATOM | 205 | CG | ASP E 23 | 11.125 | 29.086 | 60.488 | 1.00 | 1.19 |
| ATOM | 206 | OD1 | ASP E 23 | 9.950 | 29.095 | 60.823 | 1.00 | 1.81 |

TABLE 4-continued

| | | | | | | | | |
|---|---|---|---|---|---|---|---|---|
| ATOM | 207 | OD2 | ASP E 23 | 12.059 | 28.874 | 61.251 | 1.00 | 1.63 |
| ATOM | 208 | C | ASP E 23 | 13.635 | 30.277 | 59.133 | 1.00 | 0.01 |
| ATOM | 209 | O | ASP E 23 | 14.391 | 29.357 | 58.807 | 1.00 | 0.03 |
| ATOM | 210 | N | PRO E 24 | 13.940 | 31.161 | 60.071 | 1.00 | 0.02 |
| ATOM | 211 | CA | PRO E 24 | 15.297 | 31.235 | 60.627 | 1.00 | 0.02 |
| ATOM | 212 | CB | PRO E 24 | 15.239 | 32.324 | 61.654 | 1.00 | 0.23 |
| ATOM | 213 | CG | PRO E 24 | 13.846 | 32.938 | 61.663 | 1.00 | 0.18 |
| ATOM | 214 | CD | PRO E 24 | 13.042 | 32.182 | 60.619 | 1.00 | 0.14 |
| ATOM | 215 | C | PRO E 24 | 15.761 | 29.909 | 61.235 | 1.00 | 0.01 |
| ATOM | 216 | O | PRO E 24 | 16.699 | 29.305 | 60.698 | 1.00 | 0.02 |
| ATOM | 217 | N | VAL E 25 | 14.937 | 29.318 | 62.086 | 1.00 | 0.02 |
| ATOM | 219 | CA | VAL E 25 | 15.309 | 28.064 | 62.750 | 1.00 | 0.02 |
| ATOM | 220 | CB | VAL E 25 | 14.340 | 27.835 | 63.903 | 1.00 | 0.22 |
| ATOM | 221 | CG1 | VAL E 25 | 14.667 | 26.547 | 64.651 | 1.00 | 0.23 |
| ATOM | 222 | CG2 | VAL E 25 | 14.351 | 29.024 | 64.858 | 1.00 | 0.32 |
| ATOM | 223 | C | VAL E 25 | 15.269 | 26.868 | 61.800 | 1.00 | 0.02 |
| ATOM | 224 | O | VAL E 25 | 16.223 | 26.080 | 61.804 | 1.00 | 0.02 |
| ATOM | 225 | N | GLY E 26 | 14.380 | 26.916 | 60.820 | 1.00 | 0.03 |
| ATOM | 227 | CA | GLY E 26 | 14.275 | 25.856 | 59.809 | 1.00 | 0.01 |
| ATOM | 228 | C | GLY E 26 | 15.524 | 25.788 | 58.934 | 1.00 | 0.02 |
| ATOM | 229 | O | GLY E 26 | 16.172 | 26.949 | 58.485 | 1.00 | 0.02 |
| ATOM | 230 | N | ARG E 27 | 15.973 | 26.949 | 58.485 | 1.00 | 0.02 |
| ATOM | 232 | CA | ARG E 27 | 17.163 | 27.042 | 57.639 | 1.00 | 0.01 |
| ATOM | 233 | CB | ARG E 27 | 17.158 | 28.445 | 57.029 | 1.00 | 0.18 |
| ATOM | 234 | CG | ARG E 27 | 18.198 | 28.676 | 55.931 | 1.00 | 0.52 |
| ATOM | 235 | CD | ARG E 27 | 19.543 | 29.138 | 56.477 | 1.00 | 1.05 |
| ATOM | 236 | NE | ARG E 27 | 19.363 | 30.333 | 57.313 | 1.00 | 2.02 |
| ATOM | 237 | CZ | ARG E 27 | 20.116 | 30.590 | 58.383 | 1.00 | 2.94 |
| ATOM | 238 | NH1 | ARG E 27 | 19.829 | 31.633 | 59.165 | 1.00 | 3.86 |
| ATOM | 239 | NH2 | ARG E 27 | 21.102 | 29.754 | 58.717 | 1.00 | 3.32 |
| ATOM | 240 | C | ARG E 27 | 18.434 | 26.784 | 58.447 | 1.00 | 0.03 |
| ATOM | 241 | O | ARG E 27 | 19.341 | 26.117 | 57.937 | 1.00 | 0.03 |
| ATOM | 242 | N | GLU E 28 | 18.390 | 27.049 | 59.744 | 1.00 | 0.02 |
| ATOM | 244 | CA | GLU E 28 | 19.529 | 26.739 | 60.618 | 1.00 | 0.02 |
| ATOM | 245 | CB | GLU E 28 | 19.305 | 27.411 | 61.965 | 1.00 | 0.14 |
| ATOM | 246 | CG | GLU E 28 | 19.442 | 28.923 | 61.891 | 1.00 | 0.41 |
| ATOM | 247 | CD | GLU E 28 | 18.765 | 29.539 | 63.108 | 1.00 | 0.96 |
| ATOM | 248 | OE1 | GLU E 28 | 18.277 | 30.655 | 62.987 | 1.00 | 1.43 |
| ATOM | 249 | OE2 | GLU E 28 | 18.576 | 28.808 | 64.072 | 1.00 | 1.42 |
| ATOM | 250 | C | GLU E 28 | 19.682 | 25.241 | 60.863 | 1.00 | 0.03 |
| ATOM | 251 | O | GLU E 28 | 20.807 | 24.734 | 60.792 | 1.00 | 0.03 |
| ATOM | 252 | N | GLN E 29 | 18.575 | 24.516 | 60.921 | 1.00 | 0.02 |
| ATOM | 254 | CA | GLN E 29 | 18.662 | 23.076 | 61.174 | 1.00 | 0.01 |
| ATOM | 255 | CB | GLN E 29 | 17.326 | 22.568 | 61.711 | 1.00 | 0.11 |
| ATOM | 256 | CG | GLN E 29 | 16.820 | 23.351 | 62.922 | 1.00 | 0.22 |
| ATOM | 257 | CD | GLN E 29 | 17.743 | 23.242 | 64.133 | 1.00 | 0.64 |
| ATOM | 258 | OE1 | GLN E 29 | 17.908 | 22.166 | 64.716 | 1.00 | 1.46 |
| ATOM | 259 | NE2 | GLN E 29 | 18.229 | 24.391 | 64.575 | 1.00 | 1.11 |
| ATOM | 262 | C | GLN E 29 | 19.006 | 22.333 | 59.888 | 1.00 | 0.02 |
| ATOM | 263 | O | GLN E 29 | 19.815 | 21.397 | 59.919 | 1.00 | 0.02 |
| ATOM | 264 | N | PHE E 30 | 18.629 | 22.913 | 58.758 | 1.00 | 0.02 |
| ATOM | 266 | CA | PHE E 30 | 18.998 | 22.307 | 57.477 | 1.00 | 0.02 |
| ATOM | 267 | CB | PHE E 30 | 18.062 | 22.807 | 56.383 | 1.00 | 0.02 |
| ATOM | 268 | CG | PHE E 30 | 18.237 | 22.077 | 55.053 | 1.00 | 0.01 |
| ATOM | 269 | CD1 | PHE E 30 | 18.452 | 20.705 | 55.037 | 1.00 | 0.01 |
| ATOM | 270 | CE1 | PHE E 30 | 18.610 | 20.038 | 53.830 | 1.00 | 0.02 |
| ATOM | 271 | CZ | PHE E 30 | 18.551 | 20.743 | 52.635 | 1.00 | 0.02 |
| ATOM | 272 | CE2 | PHE E 30 | 18.333 | 22.115 | 52.649 | 1.00 | 0.03 |
| ATOM | 273 | CD2 | PHE E 30 | 18.175 | 22.781 | 53.857 | 1.00 | 0.01 |
| ATOM | 274 | C | PHE E 30 | 20.442 | 22.643 | 57.117 | 1.00 | 0.02 |
| ATOM | 275 | O | PHE E 30 | 21.148 | 21.772 | 56.596 | 1.00 | 0.03 |
| ATOM | 276 | N | LEU E 31 | 20.994 | 23.753 | 57.632 | 1.00 | 0.02 |
| ATOM | 278 | CA | LEU E 31 | 22.351 | 24.101 | 57.430 | 1.00 | 0.02 |
| ATOM | 279 | CB | LEU E 31 | 22.534 | 25.589 | 57.710 | 1.00 | 0.21 |
| ATOM | 280 | CG | LEU E 31 | 23.953 | 26.055 | 57.400 | 1.00 | 1.03 |
| ATOM | 281 | CD1 | LEU E 31 | 24.316 | 25.781 | 55.944 | 1.00 | 1.18 |
| ATOM | 282 | CD2 | LEU E 31 | 24.120 | 27.536 | 57.722 | 1.00 | 1.18 |
| ATOM | 283 | C | LEU E 31 | 23.245 | 23.288 | 58.358 | 1.00 | 0.04 |
| ATOM | 284 | O | LEU E 31 | 24.325 | 22.867 | 57.934 | 1.00 | 0.02 |
| ATOM | 285 | N | LYS E 32 | 22.701 | 22.849 | 59.481 | 1.00 | 0.04 |
| ATOM | 287 | CA | LYS E 32 | 23.441 | 21.956 | 60.377 | 1.00 | 0.02 |
| ATOM | 288 | CB | LYS E 32 | 22.737 | 21.958 | 61.728 | 1.00 | 0.16 |
| ATOM | 289 | CG | LYS E 32 | 23.431 | 21.043 | 62.728 | 1.00 | 1.06 |
| ATOM | 290 | CD | LYS E 32 | 22.649 | 20.966 | 64.032 | 1.00 | 1.39 |
| ATOM | 291 | CE | LYS E 32 | 21.231 | 20.460 | 63.787 | 1.00 | 2.08 |
| ATOM | 292 | NZ | LYS E 32 | 20.506 | 20.302 | 65.056 | 1.00 | 2.62 |
| ATOM | 293 | C | LYS E 32 | 23.482 | 20.533 | 59.819 | 1.00 | 0.01 |
| ATOM | 294 | O | LYS E 32 | 24.543 | 19.892 | 59.843 | 1.00 | 0.03 |
| ATOM | 295 | N | PHE E 33 | 22.448 | 20.173 | 59.075 | 1.00 | 0.02 |

TABLE 4-continued

| | | | | | | | | |
|---|---|---|---|---|---|---|---|---|
| ATOM | 297 | CA | PHE E 33 | 22.428 | 18.873 | 58.405 | 1.00 | 0.01 |
| ATOM | 298 | CB | PHE E 33 | 20.993 | 18.573 | 57.998 | 1.00 | 0.02 |
| ATOM | 299 | CG | PHE E 33 | 20.828 | 17.222 | 57.318 | 1.00 | 0.03 |
| ATOM | 300 | CD1 | PHE E 33 | 21.116 | 16.059 | 58.019 | 1.00 | 0.02 |
| ATOM | 301 | CE1 | PHE E 33 | 20.976 | 14.824 | 57.400 | 1.00 | 0.04 |
| ATOM | 302 | CZ | PHE E 33 | 20.548 | 14.756 | 56.082 | 1.00 | 0.02 |
| ATOM | 303 | CE2 | PHE E 33 | 20.257 | 15.920 | 55.383 | 1.00 | 0.02 |
| ATOM | 304 | CD2 | PHE E 33 | 20.397 | 17.154 | 56.000 | 1.00 | 0.02 |
| ATOM | 305 | C | PHE E 33 | 23.333 | 18.871 | 57.172 | 1.00 | 0.03 |
| ATOM | 306 | O | PHE E 33 | 24.066 | 17.899 | 56.951 | 1.00 | 0.01 |
| ATOM | 307 | N | LEU E 34 | 23.472 | 20.025 | 56.543 | 1.00 | 0.02 |
| ATOM | 309 | CA | LEU E 34 | 24.417 | 20.166 | 55.436 | 1.00 | 0.02 |
| ATOM | 310 | CB | LEU E 34 | 24.013 | 21.390 | 54.628 | 1.00 | 0.03 |
| ATOM | 311 | CG | LEU E 34 | 22.711 | 21.174 | 53.867 | 1.00 | 0.02 |
| ATOM | 312 | CD1 | LEU E 34 | 22.148 | 22.492 | 53.361 | 1.00 | 0.02 |
| ATOM | 313 | CD2 | LEU E 34 | 22.894 | 20.198 | 52.714 | 1.00 | 0.02 |
| ATOM | 314 | C | LEU E 34 | 25.858 | 20.311 | 55.927 | 1.00 | 0.03 |
| ATOM | 315 | O | LEU E 34 | 26.783 | 19.892 | 55.220 | 1.00 | 0.03 |
| ATOM | 316 | N | GLU E 35 | 26.047 | 20.699 | 57.178 | 1.00 | 0.02 |
| ATOM | 318 | CA | GLU E 35 | 27.394 | 20.714 | 57.760 | 1.00 | 0.03 |
| ATOM | 319 | CB | GLU E 35 | 27.405 | 21.510 | 59.064 | 1.00 | 0.23 |
| ATOM | 320 | CG | GLU E 35 | 27.198 | 23.011 | 58.880 | 1.00 | 0.80 |
| ATOM | 321 | CD | GLU E 35 | 28.375 | 23.663 | 58.160 | 1.00 | 1.78 |
| ATOM | 322 | OE1 | GLU E 35 | 28.183 | 24.758 | 57.651 | 1.00 | 2.50 |
| ATOM | 323 | OE2 | GLU E 35 | 29.465 | 23.112 | 58.221 | 1.00 | 2.17 |
| ATOM | 324 | C | GLU E 35 | 27.844 | 19.294 | 58.072 | 1.00 | 0.03 |
| ATOM | 325 | O | GLU E 35 | 28.949 | 18.910 | 57.672 | 1.00 | 0.03 |
| ATOM | 326 | N | SER E 36 | 26.905 | 18.466 | 58.504 | 1.00 | 0.02 |
| ATOM | 328 | CA | SER E 36 | 27.227 | 17.066 | 58.815 | 1.00 | 0.01 |
| ATOM | 329 | CB | SER E 36 | 26.213 | 16.525 | 59.819 | 1.00 | 0.02 |
| ATOM | 330 | OG | SER E 36 | 24.933 | 16.508 | 59.204 | 1.00 | 0.01 |
| ATOM | 331 | C | SER E 36 | 27.259 | 16.171 | 57.572 | 1.00 | 0.02 |
| ATOM | 332 | O | SER E 36 | 27.652 | 15.003 | 57.664 | 1.00 | 0.02 |
| ATOM | 333 | N | GLU E 37 | 26.841 | 16.701 | 56.432 | 1.00 | 0.02 |
| ATOM | 335 | CA | GLU E 37 | 27.033 | 16.008 | 55.154 | 1.00 | 0.02 |
| ATOM | 336 | CB | GLU E 37 | 25.808 | 16.238 | 54.283 | 1.00 | 0.02 |
| ATOM | 337 | CG | GLU E 37 | 24.541 | 15.642 | 54.871 | 1.00 | 0.01 |
| ATOM | 338 | CD | GLU E 37 | 23.363 | 16.140 | 54.046 | 1.00 | 0.01 |
| ATOM | 339 | OE1 | GLU E 37 | 23.162 | 17.348 | 54.018 | 1.00 | 0.00 |
| ATOM | 340 | OE2 | GLU E 37 | 22.707 | 15.319 | 53.425 | 1.00 | 0.02 |
| ATOM | 341 | C | GLU E 37 | 28.242 | 16.545 | 54.389 | 1.00 | 0.02 |
| ATOM | 342 | O | GLU E 37 | 28.584 | 16.000 | 53.332 | 1.00 | 0.03 |
| ATOM | 343 | N | PHE E 38 | 28.860 | 17.591 | 54.924 | 1.00 | 0.03 |
| ATOM | 345 | CA | PHE E 38 | 29.927 | 18.344 | 54.248 | 1.00 | 0.03 |
| ATOM | 346 | CB | PHE E 38 | 31.179 | 17.479 | 54.143 | 1.00 | 0.97 |
| ATOM | 347 | CG | PHE E 38 | 32.455 | 18.264 | 53.857 | 1.00 | 1.85 |
| ATOM | 348 | CD1 | PHE E 38 | 33.454 | 17.710 | 53.066 | 1.00 | 2.66 |
| ATOM | 349 | CE1 | PHE E 38 | 34.615 | 18.429 | 52.812 | 1.00 | 3.84 |
| ATOM | 350 | CZ | PHE E 38 | 34.778 | 19.701 | 53.348 | 1.00 | 4.14 |
| ATOM | 351 | CE2 | PHE E 38 | 33.778 | 20.253 | 54.139 | 1.00 | 3.53 |
| ATOM | 352 | CD2 | PHE E 38 | 32.619 | 19.535 | 54.393 | 1.00 | 2.52 |
| ATOM | 353 | C | PHE E 38 | 29.449 | 18.812 | 52.870 | 1.00 | 0.02 |
| ATOM | 354 | O | PHE E 38 | 30.064 | 18.541 | 51.833 | 1.00 | 0.01 |
| ATOM | 355 | N | SER E 39 | 28.339 | 19.530 | 52.900 | 1.00 | 0.02 |
| ATOM | 357 | CA | SER E 39 | 27.662 | 20.011 | 51.696 | 1.00 | 0.01 |
| ATOM | 358 | CB | SER E 39 | 26.671 | 18.943 | 51.257 | 1.00 | 0.02 |
| ATOM | 359 | OG | SER E 39 | 25.756 | 18.767 | 52.331 | 1.00 | 0.02 |
| ATOM | 360 | C | SER E 39 | 26.897 | 21.291 | 52.008 | 1.00 | 0.03 |
| ATOM | 361 | O | SER E 39 | 25.926 | 21.645 | 51.323 | 1.00 | 0.00 |
| ATOM | 362 | N | SER E 40 | 27.408 | 22.036 | 52.975 | 1.00 | 0.02 |
| ATOM | 364 | CA | SER E 40 | 26.713 | 23.239 | 53.458 | 1.00 | 0.03 |
| ATOM | 365 | CB | SER E 40 | 27.167 | 23.546 | 54.877 | 1.00 | 1.37 |
| ATOM | 366 | OG | SER E 40 | 28.560 | 23.828 | 54.861 | 1.00 | 2.01 |
| ATOM | 367 | C | SER E 40 | 26.939 | 24.464 | 52.583 | 1.00 | 0.02 |
| ATOM | 368 | O | SER E 40 | 26.134 | 25.404 | 52.631 | 1.00 | 0.02 |
| ATOM | 369 | N | GLU E 41 | 27.825 | 24.324 | 51.611 | 1.00 | 0.02 |
| ATOM | 371 | CA | GLU E 41 | 28.142 | 25.413 | 50.685 | 1.00 | 0.02 |
| ATOM | 372 | CB | GLU E 41 | 29.429 | 25.087 | 49.910 | 1.00 | 0.02 |
| ATOM | 373 | CG | GLU E 41 | 29.311 | 24.045 | 48.787 | 1.00 | 0.02 |
| ATOM | 374 | CD | GLU E 41 | 29.334 | 22.599 | 49.279 | 1.00 | 0.02 |
| ATOM | 375 | OE1 | GLU E 41 | 29.694 | 22.433 | 50.441 | 1.00 | 0.02 |
| ATOM | 376 | OE2 | GLU E 41 | 28.625 | 21.804 | 48.680 | 1.00 | 0.03 |
| ATOM | 377 | C | GLU E 41 | 27.005 | 25.706 | 49.707 | 1.00 | 0.01 |
| ATOM | 378 | O | GLU E 41 | 26.829 | 26.873 | 49.346 | 1.00 | 0.02 |
| ATOM | 379 | N | ASN E 42 | 26.081 | 24.770 | 49.546 | 1.00 | 0.01 |
| ATOM | 381 | CA | ASN E 42 | 24.946 | 25.003 | 48.660 | 1.00 | 0.02 |
| ATOM | 382 | CB | ASN E 42 | 24.331 | 23.651 | 48.306 | 1.00 | 0.02 |
| ATOM | 383 | CG | ASN E 42 | 25.370 | 22.723 | 47.676 | 1.00 | 0.02 |
| ATOM | 384 | OD1 | ASN E 42 | 26.036 | 23.070 | 46.690 | 1.00 | 0.02 |

TABLE 4-continued

| | | | | | | | | |
|---|---|---|---|---|---|---|---|---|
| ATOM | 385 | ND2 | ASN E 42 | 25.529 | 21.562 | 48.288 | 1.00 | 0.02 |
| ATOM | 388 | C | ASN E 42 | 23.904 | 25.896 | 49.335 | 1.00 | 0.03 |
| ATOM | 389 | O | ASN E 42 | 23.426 | 26.850 | 48.708 | 1.00 | 0.00 |
| ATOM | 390 | N | LEU E 43 | 23.800 | 25.801 | 50.653 | 1.00 | 0.02 |
| ATOM | 392 | CA | LEU E 43 | 22.818 | 26.629 | 51.358 | 1.00 | 0.02 |
| ATOM | 393 | CB | LEU E 43 | 22.340 | 25.906 | 52.609 | 1.00 | 0.29 |
| ATOM | 394 | CG | LEU E 43 | 21.182 | 26.649 | 53.267 | 1.00 | 0.88 |
| ATOM | 395 | CD1 | LEU E 43 | 20.067 | 26.916 | 52.263 | 1.00 | 1.15 |
| ATOM | 396 | CD2 | LEU E 43 | 20.646 | 25.883 | 54.469 | 1.00 | 1.57 |
| ATOM | 397 | C | LEU E 43 | 23.422 | 27.976 | 51.732 | 1.00 | 0.02 |
| ATOM | 398 | O | LEU E 43 | 22.722 | 28.997 | 51.695 | 1.00 | 0.02 |
| ATOM | 399 | N | ARG E 44 | 24.741 | 28.017 | 51.821 | 1.00 | 0.01 |
| ATOM | 401 | CA | ARG E 44 | 25.407 | 29.296 | 52.049 | 1.00 | 0.03 |
| ATOM | 402 | CB | ARG E 44 | 26.802 | 29.041 | 52.602 | 1.00 | 0.17 |
| ATOM | 403 | CG | ARG E 44 | 26.713 | 28.416 | 53.990 | 1.00 | 0.48 |
| ATOM | 404 | CD | ARG E 44 | 28.083 | 28.249 | 54.636 | 1.00 | 0.81 |
| ATOM | 405 | NE | ARG E 44 | 28.908 | 27.253 | 53.934 | 1.00 | 0.67 |
| ATOM | 406 | CZ | ARG E 44 | 30.132 | 27.512 | 53.468 | 1.00 | 0.63 |
| ATOM | 407 | NH1 | ARG E 44 | 30.606 | 28.759 | 53.492 | 1.00 | 1.43 |
| ATOM | 408 | NH2 | ARG E 44 | 30.844 | 26.540 | 52.894 | 1.00 | 0.62 |
| ATOM | 409 | C | ARG E 44 | 25.467 | 30.113 | 50.762 | 1.00 | 0.02 |
| ATOM | 410 | O | ARG E 44 | 25.283 | 31.335 | 50.815 | 1.00 | 0.03 |
| ATOM | 411 | N | PHE E 45 | 25.431 | 29.433 | 49.628 | 1.00 | 0.02 |
| ATOM | 413 | CA | PHE E 45 | 25.319 | 30.124 | 48.345 | 1.00 | 0.02 |
| ATOM | 414 | CB | PHE E 45 | 25.718 | 29.155 | 47.241 | 1.00 | 0.03 |
| ATOM | 415 | CG | PHE E 45 | 25.400 | 29.666 | 45.843 | 1.00 | 0.02 |
| ATOM | 416 | CD1 | PHE E 45 | 26.153 | 30.691 | 45.287 | 1.00 | 0.02 |
| ATOM | 417 | CE1 | PHE E 45 | 25.852 | 31.161 | 44.016 | 1.00 | 0.02 |
| ATOM | 418 | CZ | PHE E 45 | 24.799 | 30.608 | 43.302 | 1.00 | 0.01 |
| ATOM | 419 | CE2 | PHE E 45 | 24.045 | 29.585 | 43.861 | 1.00 | 0.02 |
| ATOM | 420 | CD2 | PHE E 45 | 24.342 | 29.116 | 45.131 | 1.00 | 0.02 |
| ATOM | 421 | C | PHE E 45 | 23.894 | 30.606 | 48.099 | 1.00 | 0.02 |
| ATOM | 422 | O | PHE E 45 | 23.705 | 31.755 | 47.678 | 1.00 | 0.01 |
| ATOM | 423 | N | TRP E 46 | 22.922 | 29.852 | 48.587 | 1.00 | 0.01 |
| ATOM | 425 | CA | TRP E 46 | 21.522 | 30.256 | 48.446 | 1.00 | 0.03 |
| ATOM | 426 | CB | TRP E 46 | 20.634 | 29.103 | 48.906 | 1.00 | 0.02 |
| ATOM | 427 | CG | TRP E 46 | 19.149 | 29.390 | 48.807 | 1.00 | 0.01 |
| ATOM | 428 | CD1 | TRP E 46 | 18.354 | 29.208 | 47.696 | 1.00 | 0.02 |
| ATOM | 429 | NE1 | TRP E 46 | 17.094 | 29.604 | 48.001 | 1.00 | 0.03 |
| ATOM | 431 | CE2 | TRP E 46 | 17.009 | 30.033 | 49.274 | 1.00 | 0.02 |
| ATOM | 432 | CZ2 | TRP E 46 | 15.964 | 30.546 | 50.027 | 1.00 | 0.02 |
| ATOM | 433 | CH2 | TRP E 46 | 16.183 | 30.915 | 51.350 | 1.00 | 0.02 |
| ATOM | 434 | CZ3 | TRP E 46 | 17.443 | 30.772 | 51.920 | 1.00 | 0.02 |
| ATOM | 435 | CE3 | TRP E 46 | 18.498 | 30.263 | 51.170 | 1.00 | 0.01 |
| ATOM | 436 | CD2 | TRP E 46 | 18.286 | 29.899 | 49.848 | 1.00 | 0.03 |
| ATOM | 437 | C | TRP E 46 | 21.223 | 31.496 | 49.282 | 1.00 | 0.02 |
| ATOM | 438 | O | TRP E 46 | 20.467 | 32.459 | 48.757 | 1.00 | 0.02 |
| ATOM | 439 | N | LEU E 47 | 21.821 | 31.570 | 50.461 | 1.00 | 0.02 |
| ATOM | 441 | CA | LEU E 47 | 21.613 | 32.723 | 51.337 | 1.00 | 0.03 |
| ATOM | 442 | CB | LEU E 47 | 22.000 | 32.308 | 52.752 | 1.00 | 0.12 |
| ATOM | 443 | CG | LEU E 47 | 21.653 | 33.380 | 53.777 | 1.00 | 0.93 |
| ATOM | 444 | CD1 | LEU E 47 | 20.161 | 33.699 | 53.748 | 1.00 | 1.23 |
| ATOM | 445 | CD2 | LEU E 47 | 22.078 | 32.945 | 55.175 | 1.00 | 1.20 |
| ATOM | 446 | C | LEU E 47 | 22.446 | 33.925 | 50.892 | 1.00 | 0.03 |
| ATOM | 447 | O | LEU E 47 | 21.938 | 35.055 | 50.919 | 1.00 | 0.02 |
| ATOM | 448 | N | ALA E 48 | 23.546 | 33.658 | 50.208 | 1.00 | 0.01 |
| ATOM | 450 | CA | ALA E 48 | 24.376 | 34.738 | 49.673 | 1.00 | 0.02 |
| ATOM | 451 | CB | ALA E 48 | 25.724 | 34.159 | 49.260 | 1.00 | 0.05 |
| ATOM | 452 | C | ALA E 48 | 23.719 | 35.418 | 48.477 | 1.00 | 0.02 |
| ATOM | 453 | O | ALA E 48 | 23.702 | 36.655 | 48.432 | 1.00 | 0.01 |
| ATOM | 454 | N | VAL E 49 | 22.949 | 34.670 | 47.700 | 1.00 | 0.02 |
| ATOM | 456 | CA | VAL E 49 | 22.219 | 35.291 | 46.590 | 1.00 | 0.03 |
| ATOM | 457 | CB | VAL E 49 | 21.892 | 34.233 | 45.547 | 1.00 | 0.09 |
| ATOM | 458 | CG1 | VAL E 49 | 21.246 | 34.866 | 44.318 | 1.00 | 0.10 |
| ATOM | 459 | CG2 | VAL E 49 | 23.151 | 33.483 | 45.141 | 1.00 | 0.20 |
| ATOM | 460 | C | VAL E 49 | 20.940 | 35.974 | 47.080 | 1.00 | 0.02 |
| ATOM | 461 | O | VAL E 49 | 20.598 | 37.044 | 46.563 | 1.00 | 0.02 |
| ATOM | 462 | N | GLU E 50 | 20.445 | 35.549 | 48.235 | 1.00 | 0.03 |
| ATOM | 464 | CA | GLU E 50 | 19.328 | 36.260 | 48.877 | 1.00 | 0.02 |
| ATOM | 465 | CB | GLU E 50 | 18.840 | 35.486 | 50.099 | 1.00 | 0.02 |
| ATOM | 466 | CG | GLU E 50 | 18.260 | 34.117 | 49.769 | 1.00 | 0.01 |
| ATOM | 467 | CD | GLU E 50 | 16.978 | 34.240 | 48.955 | 1.00 | 0.02 |
| ATOM | 468 | OE1 | GLU E 50 | 17.013 | 33.813 | 47.809 | 1.00 | 0.01 |
| ATOM | 469 | OE2 | GLU E 50 | 15.951 | 34.501 | 49.564 | 1.00 | 0.03 |
| ATOM | 470 | C | GLU E 50 | 19.793 | 37.630 | 49.360 | 1.00 | 0.02 |
| ATOM | 471 | O | GLU E 50 | 19.144 | 38.640 | 49.063 | 1.00 | 0.02 |
| ATOM | 472 | N | ASP E 51 | 21.028 | 37.680 | 49.837 | 1.00 | 0.03 |
| ATOM | 474 | CA | ASP E 51 | 21.621 | 38.939 | 50.297 | 1.00 | 0.02 |
| ATOM | 475 | CB | ASP E 51 | 22.898 | 38.617 | 51.070 | 1.00 | 0.17 |

TABLE 4-continued

| | | | | | | | | |
|---|---|---|---|---|---|---|---|---|
| ATOM | 476 | CG | ASP E 51 | 22.627 | 37.683 | 52.248 | 1.00 | 0.59 |
| ATOM | 477 | OD1 | ASP E 51 | 21.603 | 37.861 | 52.895 | 1.00 | 0.77 |
| ATOM | 478 | OD2 | ASP E 51 | 23.518 | 36.905 | 52.567 | 1.00 | 0.92 |
| ATOM | 479 | C | ASP E 51 | 21.987 | 39.843 | 49.122 | 1.00 | 0.03 |
| ATOM | 480 | O | ASP E 51 | 21.710 | 41.048 | 49.173 | 1.00 | 0.02 |
| ATOM | 481 | N | LEU E 52 | 22.318 | 39.233 | 47.994 | 1.00 | 0.03 |
| ATOM | 483 | CA | LEU E 52 | 22.688 | 39.978 | 46.786 | 1.00 | 0.03 |
| ATOM | 484 | CB | LEU E 52 | 23.367 | 39.010 | 45.827 | 1.00 | 0.49 |
| ATOM | 485 | CG | LEU E 52 | 23.870 | 39.725 | 44.580 | 1.00 | 0.86 |
| ATOM | 486 | CD1 | LEU E 52 | 25.021 | 40.664 | 44.926 | 1.00 | 1.11 |
| ATOM | 487 | CD2 | LEU E 52 | 24.297 | 38.723 | 43.519 | 1.00 | 1.06 |
| ATOM | 488 | C | LEU E 52 | 21.483 | 40.607 | 46.084 | 1.00 | 0.02 |
| ATOM | 489 | O | LEU E 52 | 21.630 | 41.665 | 45.462 | 1.00 | 0.02 |
| ATOM | 490 | N | LYS E 53 | 20.286 | 40.131 | 46.391 | 1.00 | 0.03 |
| ATOM | 492 | CA | LYS E 53 | 19.075 | 40.764 | 45.863 | 1.00 | 0.01 |
| ATOM | 493 | CB | LYS E 53 | 17.960 | 39.735 | 45.738 | 1.00 | 0.02 |
| ATOM | 494 | CG | LYS E 53 | 18.252 | 38.771 | 44.594 | 1.00 | 0.03 |
| ATOM | 495 | CD | LYS E 53 | 17.030 | 37.924 | 44.258 | 1.00 | 0.01 |
| ATOM | 496 | CE | LYS E 53 | 16.689 | 36.945 | 45.374 | 1.00 | 0.02 |
| ATOM | 497 | NZ | LYS E 53 | 17.734 | 35.918 | 45.485 | 1.00 | 0.02 |
| ATOM | 498 | C | LYS E 53 | 18.609 | 41.970 | 46.687 | 1.00 | 0.02 |
| ATOM | 499 | O | LYS E 53 | 17.542 | 42.529 | 46.408 | 1.00 | 0.02 |
| ATOM | 500 | N | LYS E 54 | 19.392 | 42.365 | 47.679 | 1.00 | 0.02 |
| ATOM | 502 | CA | LYS E 54 | 19.103 | 43.579 | 48.450 | 1.00 | 0.02 |
| ATOM | 503 | CB | LYS E 54 | 19.252 | 43.255 | 49.936 | 1.00 | 0.02 |
| ATOM | 504 | CG | LYS E 54 | 18.442 | 42.025 | 50.341 | 1.00 | 0.03 |
| ATOM | 505 | CD | LYS E 54 | 16.941 | 42.234 | 50.167 | 1.00 | 0.02 |
| ATOM | 506 | CE | LYS E 54 | 16.168 | 40.960 | 50.487 | 1.00 | 0.03 |
| ATOM | 507 | NZ | LYS E 54 | 14.726 | 41.159 | 50.273 | 1.00 | 0.02 |
| ATOM | 508 | C | LYS E 54 | 20.073 | 44.712 | 48.091 | 1.00 | 0.03 |
| ATOM | 509 | O | LYS E 54 | 20.043 | 45.768 | 48.734 | 1.00 | 0.03 |
| ATOM | 510 | N | ARG E 55 | 20.902 | 44.499 | 47.081 | 1.00 | 0.02 |
| ATOM | 512 | CA | ARG E 55 | 22.030 | 45.401 | 46.790 | 1.00 | 0.03 |
| ATOM | 513 | CB | ARG E 55 | 22.857 | 44.774 | 45.667 | 1.00 | 2.33 |
| ATOM | 514 | CG | ARG E 55 | 22.081 | 44.477 | 44.385 | 1.00 | 3.12 |
| ATOM | 515 | CD | ARG E 55 | 21.984 | 45.663 | 43.430 | 1.00 | 4.25 |
| ATOM | 516 | NE | ARG E 55 | 21.497 | 45.229 | 42.114 | 1.00 | 4.96 |
| ATOM | 517 | CZ | ARG E 55 | 20.777 | 46.008 | 41.306 | 1.00 | 5.88 |
| ATOM | 518 | NH1 | ARG E 55 | 20.343 | 45.530 | 40.137 | 1.00 | 6.52 |
| ATOM | 519 | NH2 | ARG E 55 | 20.464 | 47.249 | 41.680 | 1.00 | 6.43 |
| ATOM | 520 | C | ARG E 55 | 21.689 | 46.848 | 46.438 | 1.00 | 0.03 |
| ATOM | 521 | O | ARG E 55 | 20.662 | 47.164 | 45.828 | 1.00 | 0.03 |
| ATOM | 522 | N | PRO E 56 | 22.523 | 47.731 | 46.962 | 1.00 | 0.02 |
| ATOM | 523 | CA | PRO E 56 | 22.876 | 48.956 | 46.243 | 1.00 | 0.03 |
| ATOM | 524 | CB | PRO E 56 | 23.742 | 49.727 | 47.188 | 1.00 | 1.92 |
| ATOM | 525 | CG | PRO E 56 | 24.147 | 48.807 | 48.327 | 1.00 | 2.37 |
| ATOM | 526 | CD | PRO E 56 | 23.457 | 47.480 | 48.056 | 1.00 | 1.91 |
| ATOM | 527 | C | PRO E 56 | 23.627 | 48.622 | 44.955 | 1.00 | 0.03 |
| ATOM | 528 | O | PRO E 56 | 24.429 | 47.678 | 44.915 | 1.00 | 0.03 |
| ATOM | 529 | N | ILE E 57 | 23.530 | 49.526 | 43.993 | 1.00 | 0.01 |
| ATOM | 531 | CA | ILE E 57 | 24.080 | 49.295 | 42.646 | 1.00 | 0.02 |
| ATOM | 532 | CB | ILE E 57 | 23.575 | 50.426 | 41.754 | 1.00 | 0.40 |
| ATOM | 533 | CG2 | ILE E 57 | 24.005 | 50.216 | 40.306 | 1.00 | 0.91 |
| ATOM | 534 | CG1 | ILE E 57 | 22.057 | 50.539 | 41.838 | 1.00 | 1.03 |
| ATOM | 535 | CD1 | ILE E 57 | 21.531 | 51.645 | 40.931 | 1.00 | 1.87 |
| ATOM | 536 | C | ILE E 57 | 25.613 | 49.264 | 42.595 | 1.00 | 0.02 |
| ATOM | 537 | O | ILE E 57 | 26.179 | 48.504 | 41.806 | 1.00 | 0.02 |
| ATOM | 538 | N | LYS E 58 | 26.272 | 49.903 | 43.548 | 1.00 | 0.03 |
| ATOM | 540 | CA | LYS E 58 | 27.737 | 49.861 | 43.576 | 1.00 | 0.03 |
| ATOM | 541 | CB | LYS E 58 | 28.249 | 51.182 | 44.131 | 1.00 | 0.17 |
| ATOM | 542 | CG | LYS E 58 | 27.861 | 52.339 | 43.219 | 1.00 | 1.06 |
| ATOM | 543 | CD | LYS E 58 | 28.407 | 53.665 | 43.733 | 1.00 | 1.21 |
| ATOM | 544 | CE | LYS E 58 | 28.050 | 54.807 | 42.788 | 1.00 | 1.95 |
| ATOM | 545 | NZ | LYS E 58 | 28.607 | 54.571 | 41.445 | 1.00 | 1.86 |
| ATOM | 546 | C | LYS E 58 | 28.285 | 48.704 | 44.411 | 1.00 | 0.02 |
| ATOM | 547 | O | LYS E 58 | 29.479 | 48.393 | 44.319 | 1.00 | 0.02 |
| ATOM | 548 | N | GLU E 59 | 27.422 | 48.012 | 45.137 | 1.00 | 0.02 |
| ATOM | 550 | CA | GLU E 59 | 27.910 | 46.915 | 45.969 | 1.00 | 0.02 |
| ATOM | 551 | CB | GLU E 59 | 27.212 | 46.962 | 47.321 | 1.00 | 0.29 |
| ATOM | 552 | CG | GLU E 59 | 27.863 | 46.010 | 48.317 | 1.00 | 1.18 |
| ATOM | 553 | CD | GLU E 59 | 27.117 | 46.057 | 49.644 | 1.00 | 1.75 |
| ATOM | 554 | OE1 | GLU E 59 | 25.908 | 46.242 | 49.604 | 1.00 | 2.15 |
| ATOM | 555 | OE2 | GLU E 59 | 27.763 | 45.922 | 50.672 | 1.00 | 2.09 |
| ATOM | 556 | C | GLU E 59 | 27.658 | 45.578 | 45.285 | 1.00 | 0.02 |
| ATOM | 557 | O | GLU E 59 | 28.402 | 44.613 | 45.513 | 1.00 | 0.02 |
| ATOM | 558 | N | VAL E 60 | 26.744 | 45.572 | 44.328 | 1.00 | 0.03 |
| ATOM | 560 | CA | VAL E 60 | 26.507 | 44.334 | 43.580 | 1.00 | 0.02 |
| ATOM | 561 | CB | VAL E 60 | 25.225 | 44.428 | 42.751 | 1.00 | 0.39 |
| ATOM | 562 | CG1 | VAL E 60 | 25.210 | 45.557 | 41.727 | 1.00 | 1.04 |

TABLE 4-continued

| | | | | | | | | |
|---|---|---|---|---|---|---|---|---|
| ATOM | 563 | CG2 | VAL E 60 | 24.895 | 43.099 | 42.087 | 1.00 | 0.78 |
| ATOM | 564 | C | VAL E 60 | 27.703 | 43.831 | 42.740 | 1.00 | 0.02 |
| ATOM | 565 | O | VAL E 60 | 27.964 | 42.635 | 42.920 | 1.00 | 0.02 |
| ATOM | 566 | N | PRO E 61 | 28.544 | 44.624 | 42.062 | 1.00 | 0.03 |
| ATOM | 567 | CA | PRO E 61 | 29.681 | 43.994 | 41.377 | 1.00 | 0.03 |
| ATOM | 568 | CB | PRO E 61 | 30.381 | 45.089 | 40.632 | 1.00 | 0.17 |
| ATOM | 569 | CG | PRO E 61 | 29.695 | 46.412 | 40.913 | 1.00 | 0.22 |
| ATOM | 570 | CD | PRO E 61 | 28.542 | 46.084 | 41.841 | 1.00 | 0.09 |
| ATOM | 571 | C | PRO E 61 | 30.647 | 43.293 | 42.331 | 1.00 | 0.02 |
| ATOM | 572 | O | PRO E 61 | 30.868 | 42.090 | 42.144 | 1.00 | 0.01 |
| ATOM | 573 | N | SER E 62 | 30.896 | 43.891 | 43.487 | 1.00 | 0.03 |
| ATOM | 575 | CA | SER E 62 | 31.872 | 43.315 | 44.415 | 1.00 | 0.01 |
| ATOM | 576 | CB | SER E 62 | 32.308 | 44.380 | 45.420 | 1.00 | 0.13 |
| ATOM | 577 | OG | SER E 62 | 31.179 | 44.795 | 46.180 | 1.00 | 0.38 |
| ATOM | 578 | C | SER E 62 | 31.328 | 42.093 | 45.149 | 1.00 | 0.03 |
| ATOM | 579 | O | SER E 62 | 32.072 | 41.121 | 45.324 | 1.00 | 0.02 |
| ATOM | 580 | N | ARG E 63 | 30.023 | 42.021 | 45.356 | 1.00 | 0.02 |
| ATOM | 582 | CA | ARG E 63 | 29.488 | 40.829 | 46.010 | 1.00 | 0.02 |
| ATOM | 583 | CB | ARG E 63 | 28.252 | 41.177 | 46.821 | 1.00 | 0.27 |
| ATOM | 584 | CG | ARG E 63 | 28.633 | 42.085 | 47.981 | 1.00 | 0.98 |
| ATOM | 585 | CD | ARG E 63 | 27.522 | 42.149 | 49.017 | 1.00 | 1.31 |
| ATOM | 586 | NE | ARG E 63 | 26.269 | 42.632 | 48.423 | 1.00 | 2.08 |
| ATOM | 587 | CZ | ARG E 63 | 25.104 | 42.549 | 49.065 | 1.00 | 2.89 |
| ATOM | 588 | NH1 | ARG E 63 | 25.037 | 41.945 | 50.253 | 1.00 | 3.46 |
| ATOM | 589 | NH2 | ARG E 63 | 23.997 | 43.022 | 48.498 | 1.00 | 3.50 |
| ATOM | 590 | C | ARG E 63 | 29.194 | 39.715 | 45.016 | 1.00 | 0.03 |
| ATOM | 591 | O | ARG E 63 | 29.378 | 38.544 | 45.368 | 1.00 | 0.03 |
| ATOM | 592 | N | VAL E 64 | 29.039 | 40.063 | 43.749 | 1.00 | 0.03 |
| ATOM | 594 | CA | VAL E 64 | 28.936 | 39.034 | 42.714 | 1.00 | 0.02 |
| ATOM | 595 | CB | VAL E 64 | 28.452 | 39.665 | 41.412 | 1.00 | 0.06 |
| ATOM | 596 | CG1 | VAL E 64 | 28.719 | 38.764 | 40.213 | 1.00 | 0.14 |
| ATOM | 597 | CG2 | VAL E 64 | 26.977 | 40.037 | 41.484 | 1.00 | 0.07 |
| ATOM | 598 | C | VAL E 64 | 30.297 | 38.389 | 42.499 | 1.00 | 0.03 |
| ATOM | 599 | O | VAL E 64 | 30.398 | 37.156 | 42.519 | 1.00 | 0.03 |
| ATOM | 600 | N | GLN E 65 | 31.338 | 39.194 | 42.617 | 1.00 | 0.02 |
| ATOM | 602 | CA | GLN E 65 | 32.692 | 38.672 | 42.490 | 1.00 | 0.02 |
| ATOM | 603 | CB | GLN E 65 | 33.618 | 39.866 | 42.326 | 1.00 | 0.16 |
| ATOM | 604 | CG | GLN E 65 | 33.284 | 40.551 | 41.008 | 1.00 | 0.35 |
| ATOM | 605 | CD | GLN E 65 | 33.871 | 41.954 | 40.937 | 1.00 | 1.24 |
| ATOM | 606 | OE1 | GLN E 65 | 34.014 | 42.648 | 41.952 | 1.00 | 1.87 |
| ATOM | 607 | NE2 | GLN E 65 | 34.069 | 42.406 | 39.711 | 1.00 | 1.48 |
| ATOM | 610 | C | GLN E 65 | 33.070 | 37.820 | 43.693 | 1.00 | 0.02 |
| ATOM | 611 | O | GLN E 65 | 33.380 | 36.341 | 43.490 | 1.00 | 0.03 |
| ATOM | 612 | N | GLU E 66 | 32.677 | 38.247 | 44.883 | 1.00 | 0.02 |
| ATOM | 614 | CA | GLU E 66 | 32.994 | 37.463 | 46.085 | 1.00 | 0.02 |
| ATOM | 615 | CB | GLU E 66 | 32.658 | 38.287 | 47.323 | 1.00 | 0.18 |
| ATOM | 616 | CG | GLU E 66 | 33.752 | 39.500 | 47.461 | 1.00 | 0.66 |
| ATOM | 617 | CD | GLU E 66 | 35.027 | 39.065 | 47.607 | 1.00 | 0.69 |
| ATOM | 618 | OE1 | GLU E 66 | 35.402 | 38.713 | 48.717 | 1.00 | 1.39 |
| ATOM | 619 | OE2 | GLU E 66 | 35.748 | 39.120 | 46.620 | 1.00 | 1.13 |
| ATOM | 620 | C | GLU E 66 | 32.250 | 36.128 | 46.153 | 1.00 | 0.03 |
| ATOM | 621 | O | GLU E 66 | 32.900 | 35.101 | 46.392 | 1.00 | 0.02 |
| ATOM | 622 | N | ILE E 67 | 31.005 | 36.092 | 45.703 | 1.00 | 0.03 |
| ATOM | 624 | CA | ILE E 67 | 30.250 | 34.835 | 45.738 | 1.00 | 0.02 |
| ATOM | 625 | CB | ILE E 67 | 28.765 | 35.161 | 45.611 | 1.00 | 0.02 |
| ATOM | 626 | CG2 | ILE E 67 | 27.932 | 33.887 | 45.544 | 1.00 | 0.02 |
| ATOM | 627 | CG1 | ILE E 67 | 28.292 | 36.031 | 46.769 | 1.00 | 0.03 |
| ATOM | 628 | CD1 | ILE E 67 | 26.855 | 36.495 | 46.557 | 1.00 | 0.03 |
| ATOM | 629 | C | ILE E 67 | 30.675 | 33.895 | 44.611 | 1.00 | 0.01 |
| ATOM | 630 | O | ILE E 67 | 30.878 | 32.698 | 44.865 | 1.00 | 0.02 |
| ATOM | 631 | N | TRP E 68 | 31.095 | 34.464 | 43.492 | 1.00 | 0.02 |
| ATOM | 633 | CA | TRP E 68 | 31.540 | 33.646 | 42.365 | 1.00 | 0.02 |
| ATOM | 634 | CB | TRP E 68 | 31.590 | 34.524 | 41.120 | 1.00 | 0.15 |
| ATOM | 635 | CG | TRP E 68 | 31.962 | 33.799 | 39.841 | 1.00 | 0.21 |
| ATOM | 636 | CD1 | TRP E 68 | 31.104 | 33.158 | 38.974 | 1.00 | 0.38 |
| ATOM | 637 | NE1 | TRP E 68 | 31.831 | 32.648 | 37.948 | 1.00 | 0.44 |
| ATOM | 639 | CE2 | TRP E 68 | 33.141 | 32.917 | 38.100 | 1.00 | 0.42 |
| ATOM | 640 | CZ2 | TRP E 68 | 34.257 | 32.609 | 37.337 | 1.00 | 0.60 |
| ATOM | 641 | CH2 | TRP E 68 | 35.513 | 33.033 | 37.751 | 1.00 | 0.73 |
| ATOM | 642 | CZ3 | TRP E 68 | 35.656 | 33.766 | 38.926 | 1.00 | 0.72 |
| ATOM | 643 | CE3 | TRP E 68 | 34.542 | 34.078 | 39.695 | 1.00 | 0.50 |
| ATOM | 644 | CD2 | TRP E 68 | 33.288 | 33.654 | 39.287 | 1.00 | 0.33 |
| ATOM | 645 | C | TRP E 68 | 32.915 | 33.051 | 42.642 | 1.00 | 0.03 |
| ATOM | 646 | O | TRP E 68 | 33.085 | 31.838 | 42.482 | 1.00 | 0.02 |
| ATOM | 647 | N | GLN E 69 | 33.754 | 33.797 | 43.338 | 1.00 | 0.02 |
| ATOM | 649 | CA | GLN E 69 | 35.089 | 33.303 | 43.686 | 1.00 | 0.03 |
| ATOM | 650 | CB | GLN E 69 | 35.948 | 34.509 | 44.045 | 1.00 | 0.34 |
| ATOM | 651 | CG | GLN E 69 | 36.126 | 35.457 | 42.865 | 1.00 | 1.17 |
| ATOM | 652 | CD | GLN E 69 | 36.423 | 36.855 | 43.398 | 1.00 | 2.07 |

TABLE 4-continued

| | | | | | | | | |
|---|---|---|---|---|---|---|---|---|
| ATOM | 653 | OE1 | GLN E 69 | 36.271 | 37.860 | 42.691 | 1.00 | 2.43 |
| ATOM | 654 | NE2 | GLN E 69 | 36.740 | 36.904 | 44.680 | 1.00 | 3.04 |
| ATOM | 657 | C | GLN E 69 | 35.073 | 32.347 | 44.878 | 1.00 | 0.03 |
| ATOM | 658 | O | GLN E 69 | 36.022 | 31.573 | 45.050 | 1.00 | 0.02 |
| ATOM | 659 | N | GLU E 70 | 33.990 | 32.330 | 45.635 | 1.00 | 0.02 |
| ATOM | 661 | CA | GLU E 70 | 33.925 | 31.429 | 46.779 | 1.00 | 0.03 |
| ATOM | 662 | CB | GLU E 70 | 33.224 | 32.158 | 47.917 | 1.00 | 0.03 |
| ATOM | 663 | CG | GLU E 70 | 33.151 | 31.305 | 49.177 | 1.00 | 0.03 |
| ATOM | 664 | CD | GLU E 70 | 32.441 | 32.082 | 50.280 | 1.00 | 0.03 |
| ATOM | 665 | OE1 | GLU E 70 | 31.731 | 33.020 | 49.942 | 1.00 | 0.02 |
| ATOM | 666 | OE2 | GLU E 70 | 32.647 | 31.748 | 51.438 | 1.00 | 0.01 |
| ATOM | 667 | C | GLU E 70 | 33.185 | 30.136 | 46.458 | 1.00 | 0.03 |
| ATOM | 668 | O | GLU E 70 | 33.656 | 29.063 | 46.855 | 1.00 | 0.02 |
| ATOM | 669 | N | PHE E 71 | 32.125 | 30.217 | 45.670 | 1.00 | 0.02 |
| ATOM | 671 | CA | PHE E 71 | 31.300 | 29.030 | 45.419 | 1.00 | 0.02 |
| ATOM | 672 | CB | PHE E 71 | 29.853 | 29.356 | 45.795 | 1.00 | 0.03 |
| ATOM | 673 | CG | PHE E 71 | 29.584 | 29.788 | 47.236 | 1.00 | 0.02 |
| ATOM | 674 | CD1 | PHE E 71 | 29.568 | 28.846 | 48.256 | 1.00 | 0.01 |
| ATOM | 675 | CE1 | PHE E 71 | 29.315 | 29.240 | 49.564 | 1.00 | 0.02 |
| ATOM | 676 | CZ | PHE E 71 | 29.067 | 30.575 | 49.851 | 1.00 | 0.02 |
| ATOM | 677 | CE2 | PHE E 71 | 29.068 | 31.516 | 48.829 | 1.00 | 0.03 |
| ATOM | 678 | CD2 | PHE E 71 | 29.323 | 31.121 | 47.522 | 1.00 | 0.02 |
| ATOM | 679 | C | PHE E 71 | 31.280 | 28.540 | 43.968 | 1.00 | 0.01 |
| ATOM | 680 | O | PHE E 71 | 30.867 | 27.399 | 43.736 | 1.00 | 0.01 |
| ATOM | 681 | N | LEU E 72 | 31.670 | 29.355 | 43.003 | 1.00 | 0.01 |
| ATOM | 683 | CA | LEU E 72 | 31.439 | 28.959 | 41.604 | 1.00 | 0.02 |
| ATOM | 684 | CB | LEU E 72 | 30.612 | 30.026 | 40.886 | 1.00 | 0.77 |
| ATOM | 685 | CG | LEU E 72 | 29.141 | 30.081 | 41.296 | 1.00 | 0.45 |
| ATOM | 686 | CD1 | LEU E 72 | 28.897 | 31.051 | 42.477 | 1.00 | 0.32 |
| ATOM | 687 | CD2 | LEU E 72 | 28.306 | 30.523 | 40.104 | 1.00 | 1.01 |
| ATOM | 688 | C | LEU E 72 | 32.714 | 27.897 | 39.875 | 1.00 | 0.03 |
| ATOM | 689 | O | LEU E 72 | 32.713 | 27.897 | 39.875 | 1.00 | 0.03 |
| ATOM | 690 | N | ALA E 73 | 33.774 | 29.428 | 41.145 | 1.00 | 0.02 |
| ATOM | 692 | CA | ALA E 73 | 35.068 | 29.291 | 40.463 | 1.00 | 0.02 |
| ATOM | 693 | CB | ALA E 73 | 36.066 | 30.197 | 41.182 | 1.00 | 0.73 |
| ATOM | 694 | C | ALA E 73 | 35.560 | 27.844 | 40.483 | 1.00 | 0.02 |
| ATOM | 695 | O | ALA E 73 | 35.273 | 27.107 | 41.431 | 1.00 | 0.02 |
| ATOM | 696 | N | PRO E 74 | 36.368 | 27.468 | 39.500 | 1.00 | 0.02 |
| ATOM | 697 | CA | PRO E 74 | 36.809 | 26.066 | 39.356 | 1.00 | 0.02 |
| ATOM | 698 | CB | PRO E 74 | 37.439 | 25.998 | 37.998 | 1.00 | 0.48 |
| ATOM | 699 | CG | PRO E 74 | 37.516 | 27.396 | 37.402 | 1.00 | 0.55 |
| ATOM | 700 | CD | PRO E 74 | 36.839 | 28.318 | 38.401 | 1.00 | 0.24 |
| ATOM | 701 | C | PRO E 74 | 37.801 | 25.580 | 40.430 | 1.00 | 0.02 |
| ATOM | 702 | O | PRO E 74 | 38.112 | 24.386 | 40.483 | 1.00 | 0.02 |
| ATOM | 703 | N | GLY E 75 | 38.261 | 26.481 | 41.283 | 1.00 | 0.02 |
| ATOM | 705 | CA | GLY E 75 | 39.087 | 26.112 | 42.433 | 1.00 | 0.03 |
| ATOM | 706 | C | GLY E 75 | 38.586 | 26.858 | 43.669 | 1.00 | 0.02 |
| ATOM | 707 | O | GLY E 75 | 39.367 | 27.221 | 44.555 | 1.00 | 0.02 |
| ATOM | 708 | N | ALA E 76 | 37.284 | 27.098 | 43.699 | 1.00 | 0.03 |
| ATOM | 710 | CA | ALA E 76 | 36.663 | 27.856 | 44.788 | 1.00 | 0.02 |
| ATOM | 711 | CB | ALA E 76 | 35.236 | 28.181 | 44.370 | 1.00 | 0.02 |
| ATOM | 712 | C | ALA E 76 | 36.649 | 27.063 | 46.090 | 1.00 | 0.03 |
| ATOM | 713 | O | ALA E 76 | 36.309 | 25.874 | 46.102 | 1.00 | 0.03 |
| ATOM | 714 | N | PRO E 77 | 36.915 | 27.756 | 47.188 | 1.00 | 0.02 |
| ATOM | 715 | CA | PRO E 77 | 37.094 | 27.100 | 48.494 | 1.00 | 0.03 |
| ATOM | 716 | CB | PRO E 77 | 37.692 | 28.156 | 49.373 | 1.00 | 0.15 |
| ATOM | 717 | CG | PRO E 77 | 37.700 | 29.487 | 48.636 | 1.00 | 0.11 |
| ATOM | 718 | CD | PRO E 77 | 37.188 | 29.196 | 47.237 | 1.00 | 0.08 |
| ATOM | 719 | C | PRO E 77 | 35.796 | 26.574 | 49.118 | 1.00 | 0.03 |
| ATOM | 720 | O | PRO E 77 | 35.853 | 25.798 | 50.078 | 1.00 | 0.02 |
| ATOM | 721 | N | SER E 78 | 34.665 | 26.989 | 48.577 | 1.00 | 0.02 |
| ATOM | 723 | CA | SER E 78 | 33.367 | 26.486 | 49.009 | 1.00 | 0.02 |
| ATOM | 724 | CB | SER E 78 | 32.678 | 27.572 | 49.823 | 1.00 | 0.15 |
| ATOM | 725 | OG | SER E 78 | 33.556 | 27.947 | 50.875 | 1.00 | 0.16 |
| ATOM | 726 | C | SER E 78 | 32.530 | 26.153 | 47.781 | 1.00 | 0.02 |
| ATOM | 727 | O | SER E 78 | 31.328 | 26.440 | 47.756 | 1.00 | 0.01 |
| ATOM | 728 | N | ALA E 79 | 33.173 | 25.586 | 46.781 | 1.00 | 0.03 |
| ATOM | 730 | CA | ALA E 79 | 32.511 | 25.259 | 45.507 | 1.00 | 0.02 |
| ATOM | 731 | CB | ALA E 79 | 33.505 | 24.543 | 44.598 | 1.00 | 1.29 |
| ATOM | 732 | C | ALA E 79 | 31.251 | 24.409 | 45.664 | 1.00 | 0.02 |
| ATOM | 733 | O | ALA E 79 | 31.215 | 23.417 | 46.404 | 1.00 | 0.02 |
| ATOM | 734 | N | ILE E 80 | 30.202 | 24.881 | 45.015 | 1.00 | 0.01 |
| ATOM | 736 | CA | ILE E 80 | 28.907 | 24.200 | 45.002 | 1.00 | 0.01 |
| ATOM | 737 | CB | ILE E 80 | 27.816 | 25.259 | 44.892 | 1.00 | 1.88 |
| ATOM | 738 | CG2 | ILE E 80 | 27.805 | 26.153 | 46.125 | 1.00 | 2.48 |
| ATOM | 739 | CG1 | ILE E 80 | 27.998 | 26.091 | 43.629 | 1.00 | 2.64 |
| ATOM | 740 | CD1 | ILE E 80 | 27.007 | 27.245 | 43.575 | 1.00 | 3.61 |
| ATOM | 741 | C | ILE E 80 | 28.826 | 23.240 | 43.821 | 1.00 | 0.01 |
| ATOM | 742 | O | ILE E 80 | 29.706 | 23.225 | 42.949 | 1.00 | 0.02 |

TABLE 4-continued

| | | | | | | | | |
|---|---|---|---|---|---|---|---|---|
| ATOM | 743 | N | ASN E 81 | 27.818 | 22.388 | 43.828 | 1.00 | 0.01 |
| ATOM | 745 | CA | ASN E 81 | 27.662 | 21.463 | 42.701 | 1.00 | 0.02 |
| ATOM | 746 | CB | ASN E 81 | 26.991 | 20.181 | 43.174 | 1.00 | 0.02 |
| ATOM | 747 | CG | ASN E 81 | 26.761 | 19.252 | 41.986 | 1.00 | 0.02 |
| ATOM | 748 | OD1 | ASN E 81 | 25.617 | 19.007 | 41.586 | 1.00 | 0.02 |
| ATOM | 749 | ND2 | ASN E 81 | 27.851 | 18.756 | 41.428 | 1.00 | 0.01 |
| ATOM | 752 | C | ASN E 81 | 26.857 | 22.101 | 41.571 | 1.00 | 0.02 |
| ATOM | 753 | O | ASN E 81 | 25.630 | 22.231 | 41.645 | 1.00 | 0.01 |
| ATOM | 754 | N | LEU E 82 | 27.577 | 22.566 | 40.564 | 1.00 | 0.02 |
| ATOM | 756 | CA | LEU E 82 | 26.935 | 23.140 | 39.375 | 1.00 | 0.02 |
| ATOM | 757 | CB | LEU E 82 | 27.435 | 24.558 | 39.135 | 1.00 | 0.02 |
| ATOM | 758 | CG | LEU E 82 | 26.874 | 25.557 | 40.133 | 1.00 | 0.02 |
| ATOM | 759 | CD1 | LEU E 82 | 27.439 | 26.942 | 39.849 | 1.00 | 0.02 |
| ATOM | 760 | CD2 | LEU E 82 | 25.351 | 25.582 | 40.080 | 1.00 | 0.01 |
| ATOM | 761 | C | LEU E 82 | 27.229 | 22.341 | 38.117 | 1.00 | 0.02 |
| ATOM | 762 | O | LEU E 82 | 28.259 | 21.669 | 37.994 | 1.00 | 0.02 |
| ATOM | 763 | N | ASP E 83 | 26.282 | 22.394 | 37.199 | 1.00 | 0.02 |
| ATOM | 765 | CA | ASP E 83 | 26.538 | 21.915 | 35.840 | 1.00 | 0.02 |
| ATOM | 766 | CB | ASP E 83 | 25.229 | 21.487 | 35.175 | 1.00 | 0.01 |
| ATOM | 767 | CG | ASP E 83 | 24.286 | 22.671 | 34.983 | 1.00 | 0.01 |
| ATOM | 768 | OD1 | ASP E 83 | 23.156 | 22.953 | 35.886 | 1.00 | 0.02 |
| ATOM | 769 | OD2 | ASP E 83 | 24.464 | 23.361 | 33.987 | 1.00 | 0.01 |
| ATOM | 770 | C | ASP E 83 | 27.226 | 23.044 | 35.071 | 1.00 | 0.02 |
| ATOM | 771 | O | ASP E 83 | 26.974 | 24.226 | 35.344 | 1.00 | 0.02 |
| ATOM | 772 | N | SER E 84 | 27.975 | 22.698 | 34.037 | 1.00 | 0.02 |
| ATOM | 774 | CA | SER E 84 | 28.790 | 23.709 | 33.348 | 1.00 | 0.01 |
| ATOM | 775 | CB | SER E 84 | 29.778 | 23.007 | 32.426 | 1.00 | 0.02 |
| ATOM | 776 | OG | SER E 84 | 30.510 | 24.020 | 31.745 | 1.00 | 0.01 |
| ATOM | 777 | C | SER E 84 | 27.998 | 24.724 | 32.525 | 1.00 | 0.02 |
| ATOM | 778 | O | SER E 84 | 28.410 | 25.887 | 32.849 | 1.00 | 0.02 |
| ATOM | 779 | N | LYS E 85 | 26.773 | 24.407 | 32.140 | 1.00 | 0.02 |
| ATOM | 781 | CA | LYS E 85 | 25.987 | 25.367 | 31.359 | 1.00 | 0.02 |
| ATOM | 782 | CB | LYS E 85 | 24.804 | 24.633 | 30.745 | 1.00 | 0.11 |
| ATOM | 783 | CG | LYS E 85 | 25.278 | 23.497 | 29.849 | 1.00 | 1.06 |
| ATOM | 784 | CD | LYS E 85 | 24.100 | 22.757 | 29.230 | 1.00 | 0.76 |
| ATOM | 785 | CE | LYS E 85 | 24.571 | 21.631 | 28.318 | 1.00 | 1.78 |
| ATOM | 786 | NZ | LYS E 85 | 23.426 | 20.928 | 27.716 | 1.00 | 2.43 |
| ATOM | 787 | C | LYS E 85 | 25.486 | 26.513 | 32.232 | 1.00 | 0.02 |
| ATOM | 788 | O | LYS E 85 | 25.726 | 27.679 | 31.895 | 1.00 | 0.01 |
| ATOM | 789 | N | SER E 86 | 25.111 | 26.186 | 33.459 | 1.00 | 0.02 |
| ATOM | 791 | CA | SER E 86 | 24.650 | 27.210 | 34.401 | 1.00 | 0.02 |
| ATOM | 792 | CB | SER E 86 | 23.821 | 26.555 | 35.505 | 1.00 | 0.23 |
| ATOM | 793 | OG | SER E 86 | 24.640 | 25.631 | 36.213 | 1.00 | 0.75 |
| ATOM | 794 | C | SER E 86 | 25.824 | 27.970 | 35.012 | 1.00 | 0.02 |
| ATOM | 795 | O | SER E 86 | 25.709 | 29.182 | 35.237 | 1.00 | 0.03 |
| ATOM | 796 | N | TYR E 87 | 26.991 | 27.342 | 35.024 | 1.00 | 0.02 |
| ATOM | 798 | CA | TYR E 87 | 28.194 | 28.031 | 35.482 | 1.00 | 0.01 |
| ATOM | 799 | CB | TYR E 87 | 29.286 | 27.004 | 35.763 | 1.00 | 0.14 |
| ATOM | 800 | CG | TYR E 87 | 30.653 | 27.636 | 36.010 | 1.00 | 0.20 |
| ATOM | 801 | CD1 | TYR E 87 | 30.800 | 28.618 | 36.982 | 1.00 | 0.30 |
| ATOM | 802 | CE1 | TYR E 87 | 32.039 | 29.205 | 37.192 | 1.00 | 0.43 |
| ATOM | 803 | CZ | TYR E 87 | 33.130 | 28.806 | 36.433 | 1.00 | 0.48 |
| ATOM | 804 | OH | TYR E 87 | 34.352 | 29.405 | 36.631 | 1.00 | 0.66 |
| ATOM | 805 | CE2 | TYR E 87 | 32.989 | 27.820 | 35.465 | 1.00 | 0.48 |
| ATOM | 806 | CD2 | TYR E 87 | 31.748 | 27.235 | 35.254 | 1.00 | 0.36 |
| ATOM | 807 | C | TYR E 87 | 28.689 | 29.014 | 34.428 | 1.00 | 0.02 |
| ATOM | 808 | O | TYR E 87 | 29.903 | 30.184 | 34.758 | 1.00 | 0.02 |
| ATOM | 809 | N | ASP E 88 | 29.595 | 28.637 | 33.163 | 1.00 | 0.02 |
| ATOM | 811 | CA | ASP E 88 | 29.072 | 29.505 | 32.081 | 1.00 | 0.02 |
| ATOM | 812 | CB | ASP E 88 | 29.252 | 28.671 | 30.813 | 1.00 | 0.06 |
| ATOM | 813 | CG | ASP E 88 | 30.281 | 27.553 | 31.002 | 1.00 | 0.57 |
| ATOM | 814 | OD1 | ASP E 88 | 31.201 | 27.741 | 31.787 | 1.00 | 0.74 |
| ATOM | 815 | OD2 | ASP E 88 | 30.184 | 26.569 | 30.278 | 1.00 | 0.97 |
| ATOM | 816 | C | ASP E 88 | 28.087 | 30.637 | 31.801 | 1.00 | 0.02 |
| ATOM | 817 | O | ASP E 88 | 28.502 | 31.754 | 31.461 | 1.00 | 0.02 |
| ATOM | 818 | N | LYS E 89 | 26.824 | 30.413 | 32.125 | 1.00 | 0.02 |
| ATOM | 820 | CA | LYS E 89 | 25.829 | 31.477 | 32.003 | 1.00 | 0.03 |
| ATOM | 821 | CB | LYS E 89 | 24.438 | 30.866 | 32.105 | 1.00 | 0.16 |
| ATOM | 822 | CG | LYS E 89 | 23.360 | 31.939 | 32.022 | 1.00 | 0.84 |
| ATOM | 823 | CD | LYS E 89 | 23.442 | 32.716 | 30.713 | 1.00 | 1.52 |
| ATOM | 824 | CE | LYS E 89 | 22.416 | 33.842 | 30.677 | 1.00 | 2.77 |
| ATOM | 825 | NZ | LYS E 89 | 21.054 | 33.314 | 30.852 | 1.00 | 3.78 |
| ATOM | 826 | C | LYS E 89 | 26.022 | 32.506 | 33.109 | 1.00 | 0.02 |
| ATOM | 827 | O | LYS E 89 | 26.221 | 33.688 | 32.802 | 1.00 | 0.03 |
| ATOM | 828 | N | THR E 90 | 26.329 | 32.018 | 34.299 | 1.00 | 0.02 |
| ATOM | 830 | CA | THR E 90 | 26.550 | 32.907 | 35.437 | 1.00 | 0.02 |
| ATOM | 831 | CB | THR E 90 | 26.421 | 32.072 | 36.702 | 1.00 | 0.01 |
| ATOM | 832 | OG1 | THR E 90 | 25.060 | 31.668 | 36.801 | 1.00 | 0.02 |
| ATOM | 833 | CG2 | THR E 90 | 26.762 | 32.881 | 37.943 | 1.00 | 0.02 |

TABLE 4-continued

| | | | | | | | | |
|---|---|---|---|---|---|---|---|---|
| ATOM | 834 | C | THR E 90 | 27.909 | 33.607 | 35.382 | 1.00 | 0.02 |
| ATOM | 835 | O | THR E 90 | 28.000 | 34.763 | 35.803 | 1.00 | 0.02 |
| ATOM | 836 | N | THR E 91 | 28.831 | 33.058 | 34.615 | 1.00 | 0.02 |
| ATOM | 838 | CA | THR E 91 | 30.133 | 33.712 | 34.406 | 1.00 | 0.03 |
| ATOM | 839 | CB | THR E 91 | 31.114 | 32.674 | 33.870 | 1.00 | 0.15 |
| ATOM | 840 | OG1 | THR E 91 | 31.260 | 31.662 | 34.858 | 1.00 | 0.15 |
| ATOM | 841 | CG2 | THR E 91 | 32.490 | 33.274 | 33.308 | 1.00 | 0.29 |
| ATOM | 842 | C | THR E 91 | 30.016 | 34.881 | 33.426 | 1.00 | 0.02 |
| ATOM | 843 | O | THR E 91 | 30.598 | 35.942 | 33.684 | 1.00 | 0.02 |
| ATOM | 844 | N | GLN E 92 | 29.057 | 34.799 | 32.515 | 1.00 | 0.02 |
| ATOM | 846 | CA | GLN E 92 | 28.788 | 35.927 | 31.615 | 1.00 | 0.02 |
| ATOM | 847 | CB | GLN E 92 | 28.058 | 35.410 | 30.384 | 1.00 | 0.15 |
| ATOM | 848 | CG | GLN E 92 | 28.953 | 34.497 | 29.557 | 1.00 | 0.34 |
| ATOM | 849 | CD | GLN E 92 | 28.135 | 33.852 | 28.444 | 1.00 | 0.70 |
| ATOM | 850 | OE1 | GLN E 92 | 28.041 | 34.367 | 27.325 | 1.00 | 1.06 |
| ATOM | 851 | NE2 | GLN E 92 | 27.561 | 32.710 | 28.774 | 1.00 | 0.87 |
| ATOM | 854 | C | GLN E 92 | 27.931 | 36.975 | 32.317 | 1.00 | 0.02 |
| ATOM | 855 | O | GLN E 92 | 28.160 | 38.179 | 32.140 | 1.00 | 0.02 |
| ATOM | 856 | N | ASN E 93 | 27.205 | 36.528 | 33.328 | 1.00 | 0.02 |
| ATOM | 858 | CA | ASN E 93 | 26.441 | 37.441 | 34.180 | 1.00 | 0.02 |
| ATOM | 859 | CB | ASN E 93 | 25.369 | 36.638 | 34.902 | 1.00 | 0.02 |
| ATOM | 860 | CG | ASN E 93 | 24.353 | 35.981 | 33.970 | 1.00 | 0.03 |
| ATOM | 861 | OD1 | ASN E 93 | 24.181 | 36.374 | 32.809 | 1.00 | 0.03 |
| ATOM | 862 | ND2 | ASN E 93 | 23.628 | 35.031 | 34.536 | 1.00 | 0.02 |
| ATOM | 865 | C | ASN E 93 | 27.327 | 38.137 | 35.224 | 1.00 | 0.02 |
| ATOM | 866 | O | ASN E 93 | 26.949 | 39.194 | 35.741 | 1.00 | 0.02 |
| ATOM | 867 | N | VAL E 94 | 28.551 | 37.658 | 35.402 | 1.00 | 0.03 |
| ATOM | 869 | CA | VAL E 94 | 29.533 | 38.339 | 36.260 | 1.00 | 0.02 |
| ATOM | 870 | CB | VAL E 94 | 30.554 | 37.311 | 36.758 | 1.00 | 0.29 |
| ATOM | 871 | CG1 | VAL E 94 | 31.722 | 37.950 | 37.503 | 1.00 | 0.50 |
| ATOM | 872 | CG2 | VAL E 94 | 29.896 | 36.264 | 37.644 | 1.00 | 0.38 |
| ATOM | 873 | C | VAL E 94 | 30.240 | 39.457 | 35.490 | 1.00 | 0.03 |
| ATOM | 874 | O | VAL E 94 | 30.717 | 40.425 | 36.096 | 1.00 | 0.03 |
| ATOM | 875 | N | LYS E 95 | 30.099 | 39.434 | 34.172 | 1.00 | 0.02 |
| ATOM | 877 | CA | LYS E 95 | 30.636 | 40.511 | 33.333 | 1.00 | 0.02 |
| ATOM | 878 | CB | LYS E 95 | 30.840 | 39.966 | 31.923 | 1.00 | 0.23 |
| ATOM | 879 | CG | LYS E 95 | 31.510 | 40.984 | 31.010 | 1.00 | 0.39 |
| ATOM | 880 | CD | LYS E 95 | 31.673 | 40.439 | 29.597 | 1.00 | 0.34 |
| ATOM | 881 | CE | LYS E 95 | 32.344 | 41.470 | 28.699 | 1.00 | 1.25 |
| ATOM | 882 | NZ | LYS E 95 | 31.552 | 42.710 | 28.465 | 1.00 | 1.85 |
| ATOM | 883 | C | LYS E 95 | 29.666 | 41.696 | 33.316 | 1.00 | 0.02 |
| ATOM | 884 | O | LYS E 95 | 30.061 | 42.839 | 33.058 | 1.00 | 0.02 |
| ATOM | 885 | N | GLU E 96 | 28.419 | 41.428 | 33.670 | 1.00 | 0.02 |
| ATOM | 887 | CA | GLU E 96 | 27.474 | 42.514 | 33.955 | 1.00 | 0.02 |
| ATOM | 888 | CB | GLU E 96 | 26.512 | 42.673 | 32.781 | 1.00 | 0.03 |
| ATOM | 889 | CG | GLU E 96 | 25.654 | 43.930 | 32.910 | 1.00 | 0.03 |
| ATOM | 890 | CD | GLU E 96 | 26.532 | 45.180 | 32.953 | 1.00 | 0.02 |
| ATOM | 891 | OE1 | GLU E 96 | 26.884 | 45.586 | 34.053 | 1.00 | 0.03 |
| ATOM | 892 | OE2 | GLU E 96 | 26.801 | 45.723 | 31.892 | 1.00 | 0.02 |
| ATOM | 893 | C | GLU E 96 | 26.720 | 42.201 | 35.252 | 1.00 | 0.02 |
| ATOM | 894 | O | GLU E 96 | 25.548 | 41.802 | 35.215 | 1.00 | 0.03 |
| ATOM | 895 | N | PRO E 97 | 27.361 | 42.500 | 36.375 | 1.00 | 0.03 |
| ATOM | 896 | CA | PRO E 97 | 26.998 | 41.884 | 37.659 | 1.00 | 0.03 |
| ATOM | 897 | CB | PRO E 97 | 28.209 | 42.055 | 38.521 | 1.00 | 0.02 |
| ATOM | 898 | CG | PRO E 97 | 29.203 | 42.967 | 37.825 | 1.00 | 0.03 |
| ATOM | 899 | CD | PRO E 97 | 28.607 | 43.270 | 36.465 | 1.00 | 0.02 |
| ATOM | 900 | C | PRO E 97 | 25.778 | 42.514 | 38.329 | 1.00 | 0.02 |
| ATOM | 901 | O | PRO E 97 | 25.874 | 43.555 | 38.991 | 1.00 | 0.02 |
| ATOM | 902 | N | GLY E 98 | 24.638 | 41.870 | 38.143 | 1.00 | 0.02 |
| ATOM | 904 | CA | GLY E 98 | 23.403 | 42.266 | 38.832 | 1.00 | 0.02 |
| ATOM | 905 | C | GLY E 98 | 22.873 | 41.125 | 39.699 | 1.00 | 0.03 |
| ATOM | 906 | O | GLY E 98 | 23.540 | 40.097 | 39.870 | 1.00 | 0.02 |
| ATOM | 907 | N | ARG E 99 | 21.613 | 41.240 | 40.094 | 1.00 | 0.02 |
| ATOM | 909 | CA | ARG E 99 | 20.981 | 40.222 | 40.954 | 1.00 | 0.03 |
| ATOM | 910 | CB | ARG E 99 | 19.658 | 40.783 | 41.456 | 1.00 | 1.36 |
| ATOM | 911 | CG | ARG E 99 | 19.835 | 42.034 | 42.300 | 1.00 | 1.75 |
| ATOM | 912 | CD | ARG E 99 | 18.474 | 42.610 | 42.673 | 1.00 | 2.08 |
| ATOM | 913 | NE | ARG E 99 | 18.609 | 43.744 | 43.597 | 1.00 | 2.09 |
| ATOM | 914 | CZ | ARG E 99 | 17.991 | 44.912 | 43.418 | 1.00 | 2.46 |
| ATOM | 915 | NH1 | ARG E 99 | 18.128 | 45.884 | 44.323 | 1.00 | 3.38 |
| ATOM | 916 | NH2 | ARG E 99 | 17.219 | 45.101 | 42.347 | 1.00 | 2.32 |
| ATOM | 917 | C | ARG E 99 | 20.669 | 38.928 | 40.205 | 1.00 | 0.03 |
| ATOM | 918 | O | ARG E 99 | 20.750 | 37.837 | 40.784 | 1.00 | 0.03 |
| ATOM | 919 | N | TYR E 100 | 20.580 | 39.039 | 38.889 | 1.00 | 0.02 |
| ATOM | 921 | CA | TYR E 100 | 20.263 | 37.895 | 38.029 | 1.00 | 0.02 |
| ATOM | 922 | CB | TYR E 100 | 19.664 | 38.436 | 36.733 | 1.00 | 0.10 |
| ATOM | 923 | CG | TYR E 100 | 18.488 | 39.391 | 36.930 | 1.00 | 0.73 |
| ATOM | 924 | CD1 | TYR E 100 | 17.362 | 38.984 | 37.636 | 1.00 | 1.16 |
| ATOM | 925 | CE1 | TYR E 100 | 16.299 | 39.858 | 37.815 | 1.00 | 1.80 |

TABLE 4-continued

| | | | | | | | | |
|---|---|---|---|---|---|---|---|---|
| ATOM | 926 | CZ | TYR E 100 | 16.362 | 41.139 | 37.282 | 1.00 | 2.07 |
| ATOM | 927 | OH | TYR E 100 | 15.350 | 42.005 | 37.455 | 1.00 | 2.76 |
| ATOM | 928 | CE2 | TYR E 100 | 17.482 | 41.548 | 36.572 | 1.00 | 1.87 |
| ATOM | 929 | CD2 | TYR E 100 | 18.545 | 40.672 | 36.394 | 1.00 | 1.24 |
| ATOM | 930 | C | TYR E 100 | 21.491 | 37.043 | 37.699 | 1.00 | 0.01 |
| ATOM | 931 | O | TYR E 100 | 21.332 | 35.931 | 37.176 | 1.00 | 0.02 |
| ATOM | 932 | N | THR E 101 | 22.655 | 37.449 | 38.189 | 1.00 | 0.03 |
| ATOM | 934 | CA | THR E 101 | 23.903 | 36.747 | 37.883 | 1.00 | 0.02 |
| ATOM | 935 | CB | THR E 101 | 25.056 | 37.469 | 38.572 | 1.00 | 0.36 |
| ATOM | 936 | OG1 | THR E 101 | 25.217 | 38.728 | 37.938 | 1.00 | 0.41 |
| ATOM | 937 | CG2 | THR E 101 | 26.366 | 36.708 | 38.421 | 1.00 | 0.26 |
| ATOM | 938 | C | THR E 101 | 23.873 | 35.307 | 38.359 | 1.00 | 0.03 |
| ATOM | 939 | O | THR E 101 | 23.917 | 34.376 | 37.540 | 1.00 | 0.03 |
| ATOM | 940 | N | PHE E 102 | 23.497 | 35.151 | 39.615 | 1.00 | 0.03 |
| ATOM | 942 | CA | PHE E 102 | 23.476 | 33.833 | 40.234 | 1.00 | 0.01 |
| ATOM | 943 | CB | PHE E 102 | 23.924 | 33.964 | 41.679 | 1.00 | 0.02 |
| ATOM | 944 | CG | PHE E 102 | 25.347 | 34.484 | 41.815 | 1.00 | 0.03 |
| ATOM | 945 | CD1 | PHE E 102 | 26.396 | 33.780 | 41.242 | 1.00 | 0.02 |
| ATOM | 946 | CE1 | PHE E 102 | 27.694 | 34.259 | 41.349 | 1.00 | 0.03 |
| ATOM | 947 | CZ | PHE E 102 | 27.940 | 35.438 | 42.036 | 1.00 | 0.01 |
| ATOM | 948 | CE2 | PHE E 102 | 26.892 | 36.136 | 42.620 | 1.00 | 0.02 |
| ATOM | 949 | CD2 | PHE E 102 | 25.595 | 35.658 | 42.511 | 1.00 | 0.02 |
| ATOM | 950 | C | PHE E 102 | 22.109 | 33.175 | 40.185 | 1.00 | 0.02 |
| ATOM | 951 | O | PHE E 102 | 21.989 | 32.052 | 40.680 | 1.00 | 0.02 |
| ATOM | 952 | N | GLU E 103 | 21.172 | 33.727 | 39.431 | 1.00 | 0.02 |
| ATOM | 954 | CA | GLU E 103 | 19.800 | 33.208 | 39.450 | 1.00 | 0.02 |
| ATOM | 955 | CB | GLU E 103 | 18.934 | 34.193 | 38.675 | 1.00 | 0.44 |
| ATOM | 956 | CG | GLU E 103 | 17.455 | 33.837 | 38.726 | 1.00 | 0.96 |
| ATOM | 957 | CD | GLU E 103 | 16.668 | 34.859 | 37.915 | 1.00 | 1.34 |
| ATOM | 958 | OE1 | GLU E 103 | 17.257 | 35.881 | 37.590 | 1.00 | 1.84 |
| ATOM | 959 | OE2 | GLU E 103 | 15.507 | 34.607 | 37.625 | 1.00 | 1.75 |
| ATOM | 960 | C | GLU E 103 | 19.705 | 31.819 | 38.817 | 1.00 | 0.02 |
| ATOM | 961 | O | GLU E 103 | 19.091 | 30.921 | 39.409 | 1.00 | 0.02 |
| ATOM | 962 | N | ASP E 104 | 20.561 | 31.570 | 37.837 | 1.00 | 0.02 |
| ATOM | 964 | CA | ASP E 104 | 20.588 | 30.259 | 37.181 | 1.00 | 0.02 |
| ATOM | 965 | CB | ASP E 104 | 21.454 | 30.362 | 35.927 | 1.00 | 0.28 |
| ATOM | 966 | CG | ASP E 104 | 20.989 | 31.517 | 35.045 | 1.00 | 1.07 |
| ATOM | 967 | OD1 | ASP E 104 | 19.856 | 31.462 | 34.591 | 1.00 | 1.74 |
| ATOM | 968 | OD2 | ASP E 104 | 21.722 | 32.493 | 34.961 | 1.00 | 1.66 |
| ATOM | 969 | C | ASP E 104 | 21.192 | 29.202 | 38.103 | 1.00 | 0.02 |
| ATOM | 970 | O | ASP E 104 | 20.547 | 28.183 | 38.387 | 1.00 | 0.02 |
| ATOM | 971 | N | ALA E 105 | 22.245 | 29.597 | 38.800 | 1.00 | 0.02 |
| ATOM | 973 | CA | ALA E 105 | 22.960 | 28.661 | 39.664 | 1.00 | 0.02 |
| ATOM | 974 | CB | ALA E 105 | 24.355 | 29.222 | 39.909 | 1.00 | 0.02 |
| ATOM | 975 | C | ALA E 105 | 22.251 | 28.438 | 40.998 | 1.00 | 0.02 |
| ATOM | 976 | O | ALA E 105 | 22.234 | 27.303 | 41.486 | 1.00 | 0.01 |
| ATOM | 977 | N | GLN E 106 | 21.460 | 29.408 | 41.425 | 1.00 | 0.02 |
| ATOM | 979 | CA | GLN E 106 | 20.726 | 29.289 | 42.684 | 1.00 | 0.02 |
| ATOM | 980 | CB | GLN E 106 | 20.308 | 30.684 | 43.132 | 1.00 | 0.02 |
| ATOM | 981 | CG | GLN E 106 | 19.621 | 30.648 | 44.491 | 1.00 | 0.03 |
| ATOM | 982 | CD | GLN E 106 | 18.959 | 31.991 | 44.765 | 1.00 | 0.02 |
| ATOM | 983 | OE1 | GLN E 106 | 18.592 | 32.712 | 43.829 | 1.00 | 0.03 |
| ATOM | 984 | NE2 | GLN E 106 | 18.853 | 32.330 | 46.037 | 1.00 | 0.02 |
| ATOM | 987 | C | GLN E 106 | 19.482 | 28.431 | 42.515 | 1.00 | 0.02 |
| ATOM | 988 | O | GLN E 106 | 19.155 | 27.649 | 43.415 | 1.00 | 0.02 |
| ATOM | 989 | N | GLU E 107 | 18.959 | 28.381 | 41.301 | 1.00 | 0.01 |
| ATOM | 991 | CA | GLU E 107 | 17.819 | 27.505 | 41.035 | 1.00 | 0.02 |
| ATOM | 992 | CB | GLU E 107 | 17.128 | 27.991 | 39.770 | 1.00 | 0.15 |
| ATOM | 993 | CG | GLU E 107 | 16.478 | 29.347 | 40.011 | 1.00 | 0.61 |
| ATOM | 994 | CD | GLU E 107 | 16.077 | 29.977 | 38.683 | 1.00 | 1.24 |
| ATOM | 995 | OE1 | GLU E 107 | 16.148 | 29.281 | 37.681 | 1.00 | 1.81 |
| ATOM | 996 | OE2 | GLU E 107 | 15.868 | 31.183 | 38.673 | 1.00 | 1.66 |
| ATOM | 997 | C | GLU E 107 | 18.273 | 26.060 | 40.870 | 1.00 | 0.02 |
| ATOM | 998 | O | GLU E 107 | 17.636 | 25.156 | 41.428 | 1.00 | 0.01 |
| ATOM | 999 | N | HIS E 108 | 19.495 | 25.886 | 40.392 | 1.00 | 0.02 |
| ATOM | 1001 | CA | HIS E 108 | 20.055 | 24.540 | 40.285 | 1.00 | 0.02 |
| ATOM | 1002 | CB | HIS E 108 | 21.246 | 24.581 | 39.335 | 1.00 | 0.16 |
| ATOM | 1003 | CG | HIS E 108 | 21.925 | 23.238 | 39.160 | 1.00 | 1.11 |
| ATOM | 1004 | ND1 | HIS E 108 | 21.467 | 22.199 | 38.438 | 1.00 | 1.67 |
| ATOM | 1006 | CE1 | HIS E 108 | 22.342 | 21.176 | 38.524 | 1.00 | 2.49 |
| ATOM | 1007 | NE2 | HIS E 108 | 23.362 | 21.575 | 39.317 | 1.00 | 2.85 |
| ATOM | 1008 | CD2 | HIS E 108 | 23.116 | 22.843 | 39.719 | 1.00 | 2.23 |
| ATOM | 1009 | C | HIS E 108 | 20.499 | 24.020 | 41.651 | 1.00 | 0.02 |
| ATOM | 1010 | O | HIS E 108 | 20.213 | 22.863 | 41.979 | 1.00 | 0.02 |
| ATOM | 1011 | N | ILE E 109 | 20.925 | 24.923 | 42.519 | 1.00 | 0.02 |
| ATOM | 1013 | CA | ILE E 109 | 21.329 | 24.538 | 43.875 | 1.00 | 0.02 |
| ATOM | 1014 | CB | ILE E 109 | 22.237 | 25.635 | 44.417 | 1.00 | 0.02 |
| ATOM | 1015 | CG2 | ILE E 109 | 22.376 | 25.554 | 45.930 | 1.00 | 0.03 |
| ATOM | 1016 | CG1 | ILE E 109 | 23.603 | 25.568 | 43.746 | 1.00 | 0.02 |

TABLE 4-continued

| | | | | | | | | |
|---|---|---|---|---|---|---|---|---|
| ATOM | 1017 | CD1 | ILE E 109 | 24.260 | 24.211 | 43.966 | 1.00 | 0.02 |
| ATOM | 1018 | C | ILE E 109 | 20.137 | 24.312 | 44.805 | 1.00 | 0.02 |
| ATOM | 1019 | O | ILE E 109 | 20.169 | 23.365 | 45.603 | 1.00 | 0.01 |
| ATOM | 1020 | N | TYR E 110 | 19.018 | 24.953 | 44.509 | 1.00 | 0.02 |
| ATOM | 1022 | CA | TYR E 110 | 17.798 | 24.712 | 45.284 | 1.00 | 0.01 |
| ATOM | 1023 | CB | TYR E 110 | 16.802 | 25.829 | 44.983 | 1.00 | 0.33 |
| ATOM | 1024 | CG | TYR E 110 | 15.497 | 25.761 | 45.776 | 1.00 | 0.50 |
| ATOM | 1025 | CD1 | TYR E 110 | 15.410 | 26.379 | 47.017 | 1.00 | 1.45 |
| ATOM | 1026 | CE1 | TYR E 110 | 14.225 | 26.320 | 47.742 | 1.00 | 2.06 |
| ATOM | 1027 | CZ | TYR E 110 | 13.131 | 25.643 | 47.220 | 1.00 | 1.75 |
| ATOM | 1028 | OH | TYR E 110 | 11.970 | 25.541 | 47.956 | 1.00 | 2.40 |
| ATOM | 1029 | CE2 | TYR E 110 | 13.211 | 25.034 | 45.975 | 1.00 | 1.09 |
| ATOM | 1030 | CD2 | TYR E 110 | 14.394 | 25.096 | 45.251 | 1.00 | 0.69 |
| ATOM | 1031 | C | TYR E 110 | 17.201 | 23.361 | 44.906 | 1.00 | 0.02 |
| ATOM | 1032 | O | TYR E 110 | 16.864 | 22.570 | 45.797 | 1.00 | 0.02 |
| ATOM | 1033 | N | LYS E 111 | 17.362 | 22.999 | 43.644 | 1.00 | 0.03 |
| ATOM | 1035 | CA | LYS E 111 | 16.900 | 21.696 | 43.163 | 1.00 | 0.01 |
| ATOM | 1036 | CB | LYS E 111 | 16.909 | 21.754 | 41.642 | 1.00 | 0.14 |
| ATOM | 1037 | CG | LYS E 111 | 16.381 | 20.475 | 41.008 | 1.00 | 1.13 |
| ATOM | 1038 | CD | LYS E 111 | 16.475 | 20.567 | 39.490 | 1.00 | 1.61 |
| ATOM | 1039 | CE | LYS E 111 | 15.756 | 21.809 | 38.974 | 1.00 | 2.77 |
| ATOM | 1040 | NZ | LYS E 111 | 15.884 | 21.926 | 37.513 | 1.00 | 3.61 |
| ATOM | 1041 | C | LYS E 111 | 17.820 | 20.572 | 43.637 | 1.00 | 0.01 |
| ATOM | 1042 | O | LYS E 111 | 17.332 | 19.522 | 44.075 | 1.00 | 0.01 |
| ATOM | 1043 | N | LEU E 112 | 19.092 | 20.899 | 43.802 | 1.00 | 0.02 |
| ATOM | 1045 | CA | LEU E 112 | 20.076 | 19.944 | 44.314 | 1.00 | 0.02 |
| ATOM | 1046 | CB | LEU E 112 | 21.454 | 20.574 | 44.158 | 1.00 | 0.02 |
| ATOM | 1047 | CG | LEU E 112 | 22.555 | 19.675 | 44.704 | 1.00 | 0.01 |
| ATOM | 1048 | CD1 | LEU E 112 | 22.702 | 18.417 | 43.854 | 1.00 | 0.02 |
| ATOM | 1049 | CD2 | LEU E 112 | 23.873 | 20.432 | 44.769 | 1.00 | 0.02 |
| ATOM | 1050 | C | LEU E 112 | 19.842 | 19.631 | 45.789 | 1.00 | 0.01 |
| ATOM | 1051 | O | LEU E 112 | 19.763 | 18.450 | 46.155 | 1.00 | 0.02 |
| ATOM | 1052 | N | MET E 113 | 19.497 | 20.643 | 46.568 | 1.00 | 0.02 |
| ATOM | 1054 | CA | MET E 113 | 19.233 | 20.407 | 47.986 | 1.00 | 0.02 |
| ATOM | 1055 | CB | MET E 113 | 19.182 | 21.740 | 48.721 | 1.00 | 0.02 |
| ATOM | 1056 | CG | MET E 113 | 20.521 | 22.461 | 48.673 | 1.00 | 0.01 |
| ATOM | 1057 | SD | MET E 113 | 20.576 | 24.026 | 49.574 | 1.00 | 0.03 |
| ATOM | 1058 | CE | MET E 113 | 19.254 | 24.908 | 48.714 | 1.00 | 0.02 |
| ATOM | 1059 | C | MET E 113 | 17.912 | 19.677 | 48.185 | 1.00 | 0.02 |
| ATOM | 1060 | O | MET E 113 | 17.906 | 18.650 | 48.878 | 1.00 | 0.02 |
| ATOM | 1061 | N | LYS E 114 | 16.944 | 19.981 | 47.335 | 1.00 | 0.02 |
| ATOM | 1063 | CA | LYS E 114 | 15.612 | 19.383 | 47.447 | 1.00 | 0.02 |
| ATOM | 1064 | CB | LYS E 114 | 14.679 | 20.196 | 46.557 | 1.00 | 0.27 |
| ATOM | 1065 | CG | LYS E 114 | 13.236 | 19.716 | 46.638 | 1.00 | 1.16 |
| ATOM | 1066 | CD | LYS E 114 | 12.338 | 20.551 | 45.735 | 1.00 | 1.35 |
| ATOM | 1067 | CE | LYS E 114 | 10.889 | 20.081 | 45.799 | 1.00 | 2.33 |
| ATOM | 1068 | NZ | LYS E 114 | 10.035 | 20.894 | 44.919 | 1.00 | 2.92 |
| ATOM | 1069 | C | LYS E 114 | 15.576 | 17.918 | 47.014 | 1.00 | 0.01 |
| ATOM | 1070 | O | LYS E 114 | 14.912 | 17.106 | 47.668 | 1.00 | 0.01 |
| ATOM | 1071 | N | SER E 115 | 16.413 | 17.553 | 46.058 | 1.00 | 0.02 |
| ATOM | 1073 | CA | SER E 115 | 16.440 | 16.167 | 45.589 | 1.00 | 0.02 |
| ATOM | 1074 | CB | SER E 115 | 16.758 | 16.199 | 44.097 | 1.00 | 0.32 |
| ATOM | 1075 | OG | SER E 115 | 16.772 | 14.864 | 43.611 | 1.00 | 1.25 |
| ATOM | 1076 | C | SER E 115 | 17.473 | 15.303 | 46.315 | 1.00 | 0.02 |
| ATOM | 1077 | O | SER E 115 | 17.414 | 14.071 | 46.234 | 1.00 | 0.02 |
| ATOM | 1078 | N | ASP E 116 | 18.366 | 15.924 | 47.065 | 1.00 | 0.02 |
| ATOM | 1080 | CA | ASP E 116 | 19.412 | 15.150 | 47.736 | 1.00 | 0.02 |
| ATOM | 1081 | CB | ASP E 116 | 20.756 | 15.772 | 47.372 | 1.00 | 0.02 |
| ATOM | 1082 | CG | ASP E 116 | 21.912 | 15.035 | 48.040 | 1.00 | 0.02 |
| ATOM | 1083 | OD1 | ASP E 116 | 22.110 | 13.873 | 47.716 | 1.00 | 0.01 |
| ATOM | 1084 | OD2 | ASP E 116 | 22.647 | 15.688 | 48.768 | 1.00 | 0.02 |
| ATOM | 1085 | C | ASP E 116 | 19.251 | 15.121 | 49.252 | 1.00 | 0.01 |
| ATOM | 1086 | O | ASP E 116 | 18.941 | 14.074 | 49.833 | 1.00 | 0.02 |
| ATOM | 1087 | N | SER E 117 | 19.365 | 16.283 | 49.871 | 1.00 | 0.02 |
| ATOM | 1089 | CA | SER E 117 | 19.456 | 16.322 | 51.329 | 1.00 | 0.03 |
| ATOM | 1090 | CB | SER E 117 | 20.447 | 17.408 | 51.724 | 1.00 | 0.01 |
| ATOM | 1091 | OG | SER E 117 | 21.722 | 17.041 | 51.214 | 1.00 | 0.02 |
| ATOM | 1092 | C | SER E 117 | 18.114 | 16.585 | 51.991 | 1.00 | 0.01 |
| ATOM | 1093 | O | SER E 117 | 17.893 | 16.124 | 53.114 | 1.00 | 0.03 |
| ATOM | 1094 | N | TYR E 118 | 17.172 | 17.131 | 51.243 | 1.00 | 0.02 |
| ATOM | 1096 | CA | TYR E 118 | 15.842 | 17.411 | 51.800 | 1.00 | 0.01 |
| ATOM | 1097 | CB | TYR E 118 | 15.001 | 18.135 | 50.760 | 1.00 | 0.02 |
| ATOM | 1098 | CG | TYR E 118 | 13.647 | 18.589 | 51.283 | 1.00 | 0.02 |
| ATOM | 1099 | CD1 | TYR E 118 | 13.550 | 19.145 | 52.552 | 1.00 | 0.02 |
| ATOM | 1100 | CE1 | TYR E 118 | 12.317 | 19.560 | 53.034 | 1.00 | 0.02 |
| ATOM | 1101 | CZ | TYR E 118 | 11.188 | 19.419 | 52.241 | 1.00 | 0.02 |
| ATOM | 1102 | OH | TYR E 118 | 9.982 | 19.894 | 52.690 | 1.00 | 0.03 |
| ATOM | 1103 | CE2 | TYR E 118 | 11.280 | 18.865 | 50.972 | 1.00 | 0.02 |
| ATOM | 1104 | CD2 | TYR E 118 | 12.514 | 18.450 | 50.491 | 1.00 | 0.02 |

TABLE 4-continued

| ATOM | 1105 | C | TYR E 118 | 15.096 | 16.175 | 52.343 | 1.00 | 0.03 |
|---|---|---|---|---|---|---|---|---|
| ATOM | 1106 | O | TYR E 118 | 14.795 | 16.208 | 53.543 | 1.00 | 0.02 |
| ATOM | 1107 | N | PRO E 119 | 14.913 | 15.074 | 51.611 | 1.00 | 0.02 |
| ATOM | 1108 | CA | PRO E 119 | 14.197 | 13.943 | 52.224 | 1.00 | 0.01 |
| ATOM | 1109 | CB | PRO E 119 | 13.942 | 12.982 | 51.104 | 1.00 | 0.20 |
| ATOM | 1110 | CG | PRO E 119 | 14.649 | 13.461 | 49.848 | 1.00 | 0.33 |
| ATOM | 1111 | CD | PRO E 119 | 15.280 | 14.792 | 50.210 | 1.00 | 0.16 |
| ATOM | 1112 | C | PRO E 119 | 14.969 | 13.252 | 53.358 | 1.00 | 0.03 |
| ATOM | 1113 | O | PRO E 119 | 14.342 | 12.828 | 54.338 | 1.00 | 0.03 |
| ATOM | 1114 | N | ARG E 120 | 16.285 | 13.397 | 53.373 | 1.00 | 0.03 |
| ATOM | 1116 | CA | ARG E 120 | 17.094 | 12.786 | 54.423 | 1.00 | 0.02 |
| ATOM | 1117 | CB | ARG E 120 | 18.466 | 12.511 | 53.826 | 1.00 | 0.01 |
| ATOM | 1118 | CG | ARG E 120 | 19.371 | 11.726 | 54.764 | 1.00 | 0.03 |
| ATOM | 1119 | CD | ARG E 120 | 20.580 | 11.185 | 54.008 | 1.00 | 0.02 |
| ATOM | 1120 | NE | ARG E 120 | 21.231 | 12.241 | 53.217 | 1.00 | 0.03 |
| ATOM | 1121 | CZ | ARG E 120 | 21.394 | 12.159 | 51.893 | 1.00 | 0.02 |
| ATOM | 1122 | NH1 | ARG E 120 | 20.921 | 11.104 | 51.227 | 1.00 | 0.01 |
| ATOM | 1123 | NH2 | ARG E 120 | 21.997 | 13.148 | 51.231 | 1.00 | 0.02 |
| ATOM | 1124 | C | ARG E 120 | 17.168 | 13.684 | 55.661 | 1.00 | 0.02 |
| ATOM | 1125 | O | ARG E 120 | 17.311 | 13.188 | 56.784 | 1.00 | 0.02 |
| ATOM | 1126 | N | PHE E 121 | 16.801 | 14.941 | 55.478 | 1.00 | 0.01 |
| ATOM | 1128 | CA | PHE E 121 | 16.645 | 15.871 | 56.592 | 1.00 | 0.03 |
| ATOM | 1129 | CB | PHE E 121 | 16.696 | 17.285 | 56.024 | 1.00 | 0.02 |
| ATOM | 1130 | CG | PHE E 121 | 16.430 | 18.400 | 57.028 | 1.00 | 0.02 |
| ATOM | 1131 | CD1 | PHE E 121 | 17.205 | 18.508 | 58.175 | 1.00 | 0.02 |
| ATOM | 1132 | CE1 | PHE E 121 | 16.959 | 19.529 | 59.083 | 1.00 | 0.02 |
| ATOM | 1133 | CZ | PHE E 121 | 15.941 | 20.444 | 58.843 | 1.00 | 0.02 |
| ATOM | 1134 | CE2 | PHE E 121 | 15.170 | 20.339 | 57.693 | 1.00 | 0.01 |
| ATOM | 1135 | CD2 | PHE E 121 | 15.416 | 19.317 | 56.785 | 1.00 | 0.02 |
| ATOM | 1136 | C | PHE E 121 | 15.304 | 15.647 | 57.275 | 1.00 | 0.02 |
| ATOM | 1137 | O | PHE E 121 | 15.244 | 15.652 | 58.509 | 1.00 | 0.01 |
| ATOM | 1138 | N | ILE E 122 | 14.344 | 15.157 | 56.507 | 1.00 | 0.03 |
| ATOM | 1140 | CA | ILE E 122 | 13.019 | 14.848 | 57.051 | 1.00 | 0.01 |
| ATOM | 1141 | CB | ILE E 122 | 12.045 | 14.755 | 55.879 | 1.00 | 0.15 |
| ATOM | 1142 | CG2 | ILE E 122 | 10.646 | 14.367 | 56.345 | 1.00 | 0.37 |
| ATOM | 1143 | CG1 | ILE E 122 | 11.994 | 16.072 | 55.116 | 1.00 | 0.15 |
| ATOM | 1144 | CD1 | ILE E 122 | 11.059 | 15.976 | 53.917 | 1.00 | 0.13 |
| ATOM | 1145 | C | ILE E 122 | 13.024 | 13.535 | 57.836 | 1.00 | 0.02 |
| ATOM | 1146 | O | ILE E 122 | 12.281 | 13.398 | 58.813 | 1.00 | 0.03 |
| ATOM | 1147 | N | ARG E 123 | 13.956 | 12.649 | 57.522 | 1.00 | 0.02 |
| ATOM | 1149 | CA | ARG E 123 | 14.077 | 11.417 | 58.307 | 1.00 | 0.03 |
| ATOM | 1150 | CB | ARG E 123 | 14.377 | 10.248 | 57.374 | 1.00 | 0.24 |
| ATOM | 1151 | CG | ARG E 123 | 15.721 | 10.392 | 56.676 | 1.00 | 1.09 |
| ATOM | 1152 | CD | ARG E 123 | 15.921 | 9.312 | 55.623 | 1.00 | 1.06 |
| ATOM | 1153 | NE | ARG E 123 | 14.879 | 9.405 | 54.589 | 1.00 | 0.78 |
| ATOM | 1154 | CZ | ARG E 123 | 15.143 | 9.472 | 53.282 | 1.00 | 0.81 |
| ATOM | 1155 | NH1 | ARG E 123 | 14.143 | 9.554 | 52.403 | 1.00 | 1.03 |
| ATOM | 1156 | NH2 | ARG E 123 | 16.407 | 9.455 | 52.852 | 1.00 | 0.80 |
| ATOM | 1157 | C | ARG E 123 | 15.144 | 11.526 | 59.401 | 1.00 | 0.02 |
| ATOM | 1158 | O | ARG E 123 | 15.306 | 10.594 | 60.197 | 1.00 | 0.02 |
| ATOM | 1159 | N | SER E 124 | 15.856 | 12.641 | 59.449 | 1.00 | 0.02 |
| ATOM | 1161 | CA | SER E 124 | 16.876 | 12.825 | 60.485 | 1.00 | 0.02 |
| ATOM | 1162 | CB | SER E 124 | 18.069 | 13.593 | 59.928 | 1.00 | 0.02 |
| ATOM | 1163 | OG | SER E 124 | 17.662 | 14.931 | 59.685 | 1.00 | 0.02 |
| ATOM | 1164 | C | SER E 124 | 16.306 | 13.578 | 61.676 | 1.00 | 0.02 |
| ATOM | 1165 | O | SER E 124 | 15.393 | 14.405 | 61.540 | 1.00 | 0.01 |
| ATOM | 1166 | N | SER E 125 | 17.014 | 13.470 | 62.788 | 1.00 | 0.01 |
| ATOM | 1168 | CA | SER E 125 | 16.570 | 14.100 | 64.040 | 1.00 | 0.03 |
| ATOM | 1169 | CB | SER E 125 | 17.365 | 13.514 | 65.202 | 1.00 | 0.48 |
| ATOM | 1170 | OG | SER E 125 | 18.722 | 13.908 | 65.048 | 1.00 | 0.36 |
| ATOM | 1171 | C | SER E 125 | 16.734 | 15.623 | 64.053 | 1.00 | 0.01 |
| ATOM | 1172 | O | SER E 125 | 15.979 | 16.281 | 64.775 | 1.00 | 0.03 |
| ATOM | 1173 | N | ALA E 126 | 17.438 | 16.171 | 63.070 | 1.00 | 0.01 |
| ATOM | 1175 | CA | ALA E 126 | 17.621 | 17.623 | 62.970 | 1.00 | 0.01 |
| ATOM | 1176 | CB | ALA E 126 | 18.790 | 17.904 | 62.034 | 1.00 | 0.20 |
| ATOM | 1177 | C | ALA E 126 | 16.371 | 18.321 | 62.435 | 1.00 | 0.03 |
| ATOM | 1178 | O | ALA E 126 | 16.245 | 19.546 | 62.544 | 1.00 | 0.02 |
| ATOM | 1179 | N | TYR E 127 | 15.458 | 17.554 | 61.865 | 1.00 | 0.01 |
| ATOM | 1181 | CA | TYR E 127 | 14.142 | 18.095 | 61.544 | 1.00 | 0.02 |
| ATOM | 1182 | CB | TYR E 127 | 13.818 | 17.822 | 60.082 | 1.00 | 0.02 |
| ATOM | 1183 | CG | TYR E 127 | 12.341 | 18.000 | 59.756 | 1.00 | 0.02 |
| ATOM | 1184 | CD1 | TYR E 127 | 11.782 | 19.270 | 59.742 | 1.00 | 0.02 |
| ATOM | 1185 | CE1 | TYR E 127 | 10.432 | 19.423 | 59.471 | 1.00 | 0.01 |
| ATOM | 1186 | CZ | TYR E 127 | 9.642 | 18.309 | 59.218 | 1.00 | 0.02 |
| ATOM | 1187 | OH | TYR E 127 | 8.292 | 18.467 | 58.989 | 1.00 | 0.02 |
| ATOM | 1188 | CE2 | TYR E 127 | 10.198 | 17.039 | 59.225 | 1.00 | 0.02 |
| ATOM | 1189 | CD2 | TYR E 127 | 11.550 | 16.885 | 59.497 | 1.00 | 0.01 |
| ATOM | 1190 | C | TYR E 127 | 13.071 | 17.441 | 62.403 | 1.00 | 0.01 |
| ATOM | 1191 | O | TYR E 127 | 12.254 | 18.133 | 63.029 | 1.00 | 0.01 |

TABLE 4-continued

| ATOM | 1192 | N | GLN E 128 | 13.195 | 16.135 | 62.572 | 1.00 | 0.02 |
|---|---|---|---|---|---|---|---|---|
| ATOM | 1194 | CA | GLN E 128 | 12.090 | 15.361 | 63.139 | 1.00 | 0.03 |
| ATOM | 1195 | CB | GLN E 128 | 12.201 | 13.926 | 62.628 | 1.00 | 1.25 |
| ATOM | 1196 | CG | GLN E 128 | 10.929 | 13.131 | 62.917 | 1.00 | 2.29 |
| ATOM | 1197 | CD | GLN E 128 | 9.711 | 13.837 | 62.318 | 1.00 | 2.89 |
| ATOM | 1198 | OE1 | GLN E 128 | 9.656 | 14.096 | 61.109 | 1.00 | 2.82 |
| ATOM | 1199 | NE2 | GLN E 128 | 8.789 | 14.213 | 63.190 | 1.00 | 3.73 |
| ATOM | 1202 | C | GLN E 128 | 12.004 | 15.392 | 64.666 | 1.00 | 0.02 |
| ATOM | 1203 | O | GLN E 128 | 10.918 | 15.162 | 65.214 | 1.00 | 0.04 |
| ATOM | 1204 | N | GLU E 129 | 13.054 | 15.841 | 65.335 | 1.00 | 0.04 |
| ATOM | 1206 | CA | GLU E 129 | 12.976 | 16.024 | 66.787 | 1.00 | 0.02 |
| ATOM | 1207 | CB | GLU E 129 | 14.374 | 15.857 | 67.377 | 1.00 | 1.65 |
| ATOM | 1208 | CG | GLU E 129 | 14.352 | 15.596 | 68.879 | 1.00 | 2.63 |
| ATOM | 1209 | CD | GLU E 129 | 13.674 | 14.257 | 69.154 | 1.00 | 3.67 |
| ATOM | 1210 | OE1 | GLU E 129 | 14.226 | 13.254 | 68.721 | 1.00 | 4.45 |
| ATOM | 1211 | OE2 | GLU E 129 | 12.617 | 14.257 | 69.767 | 1.00 | 3.84 |
| ATOM | 1212 | C | GLU E 129 | 12.416 | 17.408 | 67.142 | 1.00 | 0.02 |
| ATOM | 1213 | O | GLU E 129 | 12.213 | 17.705 | 68.324 | 1.00 | 0.02 |
| ATOM | 1214 | N | LEU E 130 | 12.135 | 18.230 | 66.143 | 1.00 | 0.02 |
| ATOM | 1216 | CA | LEU E 130 | 11.589 | 19.561 | 66.419 | 1.00 | 0.02 |
| ATOM | 1217 | CB | LEU E 130 | 12.046 | 20.519 | 65.325 | 1.00 | 0.02 |
| ATOM | 1218 | CG | LEU E 130 | 13.565 | 20.572 | 65.203 | 1.00 | 0.03 |
| ATOM | 1219 | CD1 | LEU E 130 | 13.967 | 21.353 | 63.961 | 1.00 | 0.04 |
| ATOM | 1220 | CD2 | LEU E 130 | 14.214 | 21.166 | 66.450 | 1.00 | 0.02 |
| ATOM | 1221 | C | LEU E 130 | 10.064 | 19.513 | 66.457 | 1.00 | 0.02 |
| ATOM | 1222 | O | LEU E 130 | 9.429 | 20.229 | 67.239 | 1.00 | 0.04 |
| TER | | | | | | | | |

---

What is claimed is:

1. A method of screening to identify a candidate agent that agonizes interaction of a regulator of G protein signaling (RGS) polypeptide and a G protein subunit alpha q (Gαq) polypeptide, said method comprising:
   (a) contacting a RGS polypeptide and a Gαq polypeptide with a candidate agent, wherein said RGS polypeptide comprises an amino acid sequence having at least 95% sequence identity with the amino acid sequence of human RGS2 (SEQ ID NO.: 26), human RGS6 (SEQ ID NO.:27), human RGS7 (SEQ ID NO.:7), human RGS9 (SEQ ID NO.:11), or human RGS11 (SEQ ID NO.:9), and, wherein said Gαq polypeptide comprises an amino acid sequence having at least 95% sequence identity with the amino acid sequence of human Gαq (SEQ ID NO.:13);
   (b) detecting an amount of binding of said RGS polypeptide to said Gαq polypeptide in the presence of the candidate agent;
   (c) detecting a reference amount of binding of said RGS polypeptide to said Gαq polypeptide in the absence of the candidate agent; and
   (d) comparing the amount of binding of said RGS polypeptide to said Gαq polypeptide in the presence of the candidate agent to the reference amount of binding,
   wherein an increase in the amount of binding detected in the presence of the candidate agent relative to the reference amount of binding indicates that the candidate agent binds to said RGS polypeptide or Gαq polypeptide, and agonizes interaction of RGS and Gαq, and wherein said candidate agent is not a guanine nucleotide.

2. The method of claim 1 wherein said contacting in (a) comprises administering said candidate agent to cultured host cells that have been genetically engineered to express said RGS polypeptide and said Gαq polypeptide.

3. The method of claim 1 wherein said contacting in (a) comprises administering said candidate agent to a cell-free system comprising purified RGS and Gαq polypeptides.

4. The method of claim 1 wherein the method is used in a high throughput format to screen test agents in a compound library.

5. The method of claim 1 further comprising: testing the candidate agent in an animal model defective for RGS or Gαq, and detecting phenotypic changes relative to control animals.

6. A method for identifying an agent that modulates urinary incontinence, said method comprising:
   (a) contacting a RGS polypeptide and a Gαq polypeptide with a candidate agent, wherein said RGS polypeptide comprises an amino acid sequence having at least 95% sequence identity with the amino acid sequence of human RGS2 (SEQ ID NO.: 26), human RGS6 (SEQ ID NO.:27), human RGS7 (SEQ ID NO.:7), human RGS9 (SEQ ID NO.:11), or human RGS11 (SEQ ID NO.:9), and wherein said Gαq polypeptide comprises an amino acid sequence having at least 95% sequence identity with the amino acid sequence of human Gαq (SEQ ID NO.:13);
   (b) detecting an amount of binding of said RGS polypeptide to said Gαq polypeptide in the presence of the candidate agent;
   (c) detecting a reference amount of binding of said RGS polypeptide to said Gαq polypeptide in the absence of the candidate agent;
   (d) comparing the amount of binding of said RGS polypeptide to said Gαq polypeptide in the presence of the candidate agent to the reference amount of binding,
   wherein an increase in the amount of binding detected in the presence of the candidate agent relative to the reference amount of binding indicates that the candidate agent binds to said RGS polypeptide or αq polypeptide, and agonizes interaction of RGS and Gαq; and
   (e) testing if the candidate agent that agonizes interaction of RGS and Gαq modulates urinary incontinence, and wherein said candidate agent is not a guanine nucleotide.

* * * * *

SEQUENCE LISTING

<160> NUMBER OF SEQ ID NOS: 27

<210> SEQ ID NO 1
<211> LENGTH: 128
<212> TYPE: PRT
<213> ORGANISM: Rattus norvegicus

<400> SEQUENCE: 1

```
Val Ser Gln Glu Glu Val Lys Lys Trp Ala Glu Ser Leu Glu Asn Leu
1               5                   10                  15

Ile Asn His Glu Cys Gly Leu Ala Ala Phe Lys Ala Phe Leu Lys Ser
            20                  25                  30

Glu Tyr Ser Glu Glu Asn Ile Asp Phe Trp Ile Ser Cys Glu Glu Tyr
        35                  40                  45

Lys Lys Ile Lys Ser Pro Ser Lys Leu Ser Pro Lys Ala Lys Lys Ile
    50                  55                  60

Tyr Asn Glu Phe Ile Ser Val Gln Ala Thr Lys Glu Val Asn Leu Asp
65                  70                  75                  80

Ser Cys Thr Arg Glu Glu Thr Ser Arg Asn Met Leu Glu Pro Thr Ile
                85                  90                  95

Thr Cys Phe Asp Glu Ala Gln Lys Lys Ile Phe Asn Leu Met Glu Lys
            100                 105                 110

Asp Ser Tyr Arg Arg Phe Leu Lys Ser Arg Phe Tyr Leu Asp Leu Thr
            115                 120                 125
```

<210> SEQ ID NO 2
<211> LENGTH: 131
<212> TYPE: PRT
<213> ORGANISM: Caenorhabditis elegans

<400> SEQUENCE: 2

```
Thr Glu Lys Arg Val Lys Arg Trp Gly Leu Ser Val Gln Glu Leu Val
1               5                   10                  15
```

-continued

```
Lys Asp Pro Ile Gly Arg Gln Val Leu Glu Thr Phe Leu Glu Ser Glu
            20                  25                  30

Phe Ser Ser Glu Asn Ile Arg Phe Trp Ile Ala Ile Gln Asp Leu Lys
        35                  40                  45

Tyr Ala Pro Asn Glu Gln Ile Tyr Gln Lys Ala Glu Arg Ile Arg Glu
    50                  55                  60

Glu Phe Leu Ala Gln Gly Ala Pro Ala Gln Val Asn Val Asp Asn Arg
65                  70                  75                  80

Thr Leu Asp Gln Thr Leu Glu Cys Ile Ser Lys Ala Lys Asp Ala Ser
                85                  90                  95

Gln Met Arg Phe Ala Phe Tyr His Ser Glu Glu His Val Phe Thr Leu
            100                 105                 110

Met Ala Lys Asp Ser Tyr Pro Arg Phe Val Arg Ser Gln Ile Tyr Lys
        115                 120                 125

Ala Val Leu
    130
```

<210> SEQ ID NO 3
<211> LENGTH: 128
<212> TYPE: PRT
<213> ORGANISM: Rattus norvegicus

<400> SEQUENCE: 3

```
Val Ser Gln Glu Glu Val Lys Lys Trp Ala Glu Ser Leu Glu Asn Leu
1               5                   10                  15

Ile Asn His Glu Cys Gly Leu Ala Ala Phe Lys Ala Phe Leu Lys Ser
            20                  25                  30

Glu Tyr Ser Glu Glu Asn Ile Asp Phe Trp Ile Ser Cys Glu Glu Tyr
        35                  40                  45

Lys Lys Ile Lys Ser Pro Ser Lys Leu Ser Pro Lys Ala Lys Lys Ile
    50                  55                  60

Tyr Asn Glu Phe Ile Ser Val Gln Ala Thr Lys Glu Val Asn Leu Asp
65                  70                  75                  80

Ser Cys Thr Arg Glu Glu Thr Ser Arg Asn Met Leu Glu Pro Thr Ile
                85                  90                  95

Thr Cys Phe Asp Glu Ala Gln Lys Lys Ile Phe Asn Leu Met Glu Lys
            100                 105                 110

Asp Ser Tyr Arg Arg Phe Leu Lys Ser Arg Phe Tyr Leu Asp Leu Thr
        115                 120                 125
```

<210> SEQ ID NO 4
<211> LENGTH: 130
<212> TYPE: PRT
<213> ORGANISM: Homo sapiens

<400> SEQUENCE: 4

```
Gly Leu Val Pro Arg Gly Ser His Arg Val Lys Arg Trp Gly Phe Gly
1               5                   10                  15

Met Asp Glu Ala Leu Lys Asp Pro Val Gly Arg Glu Gln Phe Leu Lys
            20                  25                  30

Phe Leu Glu Ser Glu Phe Ser Ser Glu Asn Leu Arg Phe Trp Leu Ala
        35                  40                  45

Val Glu Asp Leu Lys Lys Arg Pro Ile Lys Glu Val Pro Ser Arg Val
    50                  55                  60

Gln Glu Ile Trp Gln Glu Phe Leu Ala Pro Gly Ala Pro Ser Ala Ile
65                  70                  75                  80
```

```
Asn Leu Asp Ser Lys Ser Tyr Asp Lys Thr Thr Gln Asn Val Lys Glu
            85                  90                  95

Pro Gly Arg Tyr Thr Phe Glu Asp Ala Gln Glu His Ile Tyr Lys Leu
           100                 105                 110

Met Lys Ser Asp Ser Tyr Pro Arg Phe Ile Arg Ser Ser Ala Tyr Gln
           115                 120                 125

Glu Leu
   130

<210> SEQ ID NO 5
<211> LENGTH: 131
<212> TYPE: PRT
<213> ORGANISM: Caenorhabditis elegans

<400> SEQUENCE: 5

Thr Glu Lys Arg Val Lys Arg Trp Gly Leu Ser Val Gln Glu Leu Val
1               5                   10                  15

Lys Asp Pro Ile Gly Arg Gln Val Leu Glu Thr Phe Leu Glu Ser Glu
            20                  25                  30

Phe Ser Ser Glu Asn Ile Arg Phe Trp Ile Ala Ile Gln Asp Leu Lys
        35                  40                  45

Tyr Ala Pro Asn Glu Gln Ile Tyr Gln Lys Ala Glu Arg Ile Arg Glu
50                  55                  60

Glu Phe Leu Ala Gln Gly Ala Pro Ala Gln Val Asn Val Asp Asn Arg
65                  70                  75                  80

Thr Leu Asp Gln Thr Leu Glu Cys Ile Ser Lys Ala Lys Asp Ala Ser
            85                  90                  95

Gln Met Arg Phe Ala Phe Tyr His Ser Glu His Val Phe Thr Leu
           100                 105                 110

Met Ala Lys Asp Ser Tyr Pro Arg Phe Val Arg Ser Gln Ile Tyr Lys
           115                 120                 125

Ala Val Leu
   130

<210> SEQ ID NO 6
<211> LENGTH: 130
<212> TYPE: PRT
<213> ORGANISM: Homo sapiens

<400> SEQUENCE: 6

Gly Leu Val Pro Arg Gly Ser His Arg Val Lys Arg Trp Gly Phe Gly
1               5                   10                  15

Met Asp Gly Ala Leu Lys Asp Pro Val Gly Arg Glu Gln Phe Leu Lys
            20                  25                  30

Phe Leu Glu Ser Glu Phe Ser Ser Glu Asn Leu Arg Phe Trp Leu Ala
        35                  40                  45

Val Glu Asp Leu Lys Lys Arg Pro Ile Lys Glu Val Pro Ser Arg Val
    50                  55                  60

Gln Glu Ile Trp Gln Glu Phe Leu Ala Pro Gly Ala Pro Ser Ala Ile
65                  70                  75                  80

Asn Leu Asp Ser Lys Ser Tyr Asp Lys Thr Thr Gln Asn Val Lys Glu
            85                  90                  95

Pro Gly Arg Tyr Thr Phe Glu Asp Ala Gln Glu His Ile Tyr Lys Leu
           100                 105                 110

Met Lys Ser Asp Ser Tyr Pro Arg Phe Ile Arg Ser Ser Ala Tyr Gln
           115                 120                 125
```

Glu Leu
    130

<210> SEQ ID NO 7
<211> LENGTH: 469
<212> TYPE: PRT
<213> ORGANISM: Homo sapiens

<400> SEQUENCE: 7

Met Ala Gln Gly Asn Asn Tyr Gly Gln Thr Ser Asn Gly Val Ala Asp
1               5                   10                  15

Glu Ser Pro Asn Met Leu Val Tyr Arg Lys Met Glu Asp Val Ile Ala
            20                  25                  30

Arg Met Gln Asp Glu Lys Asn Gly Ile Pro Ile Arg Thr Val Lys Ser
        35                  40                  45

Phe Leu Ser Lys Ile Pro Ser Val Phe Ser Gly Ser Asp Ile Val Gln
    50                  55                  60

Trp Leu Ile Lys Asn Leu Thr Ile Glu Asp Pro Val Glu Ala Leu His
65                  70                  75                  80

Leu Gly Thr Leu Met Ala Ala His Gly Tyr Phe Phe Pro Ile Ser Asp
                85                  90                  95

His Val Leu Thr Leu Lys Asp Asp Gly Thr Phe Tyr Arg Phe Gln Thr
            100                 105                 110

Pro Tyr Phe Trp Pro Ser Asn Cys Trp Glu Pro Glu Asn Thr Asp Tyr
        115                 120                 125

Ala Val Tyr Leu Cys Lys Arg Thr Met Gln Asn Lys Ala Arg Leu Glu
    130                 135                 140

Leu Ala Asp Tyr Glu Ala Glu Ser Leu Ala Arg Leu Gln Arg Ala Phe
145                 150                 155                 160

Ala Arg Lys Trp Glu Phe Ile Phe Met Gln Ala Glu Ala Gln Ala Lys
                165                 170                 175

Val Asp Lys Lys Arg Asp Lys Ile Glu Arg Lys Ile Leu Asp Ser Gln
            180                 185                 190

Glu Arg Ala Phe Trp Asp Val His Arg Pro Val Pro Gly Cys Val Asn
        195                 200                 205

Thr Thr Glu Val Asp Ile Lys Lys Ser Ser Arg Met Arg Asn Pro His
    210                 215                 220

Lys Thr Arg Lys Ser Val Tyr Gly Leu Gln Asn Asp Ile Arg Ser His
225                 230                 235                 240

Ser Pro Thr His Thr Pro Thr Pro Glu Thr Lys Pro Pro Thr Glu Asp
                245                 250                 255

Glu Leu Gln Gln Gln Ile Lys Tyr Trp Gln Ile Gln Leu Asp Arg His
            260                 265                 270

Arg Leu Lys Met Ser Lys Val Ala Asp Ser Leu Leu Ser Tyr Thr Glu
        275                 280                 285

Gln Tyr Leu Glu Tyr Asp Pro Phe Leu Leu Pro Pro Asp Pro Ser Asn
    290                 295                 300

Pro Trp Leu Ser Asp Asp Thr Thr Phe Trp Glu Leu Glu Ala Ser Lys
305                 310                 315                 320

Glu Pro Ser Gln Gln Arg Val Lys Arg Trp Gly Phe Gly Met Asp Glu
                325                 330                 335

Ala Leu Lys Asp Pro Val Gly Arg Glu Gln Phe Leu Lys Phe Leu Glu
            340                 345                 350

Ser Glu Phe Ser Ser Glu Asn Leu Arg Phe Trp Leu Ala Val Glu Asp

```
                355                 360                 365
Leu Lys Lys Arg Pro Ile Lys Glu Val Pro Ser Arg Val Gln Glu Ile
        370                 375                 380

Trp Gln Glu Phe Leu Ala Pro Gly Ala Pro Ser Ala Ile Asn Leu Asp
385                 390                 395                 400

Ser Lys Ser Tyr Asp Lys Thr Thr Gln Asn Val Lys Glu Pro Gly Arg
                405                 410                 415

Tyr Thr Phe Glu Asp Ala Gln Glu His Ile Tyr Lys Leu Met Lys Ser
                420                 425                 430

Asp Ser Tyr Pro Arg Phe Ile Arg Ser Ser Ala Tyr Gln Glu Leu Leu
                435                 440                 445

Gln Ala Lys Lys Gly Lys Ser Leu Thr Ser Lys Arg Leu Thr Ser
    450                 455                 460

Leu Ala Gln Ser Tyr
465

<210> SEQ ID NO 8
<211> LENGTH: 555
<212> TYPE: PRT
<213> ORGANISM: Caenorhabditis elegans

<400> SEQUENCE: 8

Met Ala Leu Pro Arg Leu Arg Val Asn Ala Ser Asn Glu Glu Arg Leu
1               5                   10                  15

Val His Pro Asn His Met Val Tyr Arg Lys Met Glu Met Leu Val Asn
            20                  25                  30

Gln Met Leu Asp Ala Glu Ala Gly Val Pro Ile Lys Thr Val Lys Ser
        35                  40                  45

Phe Leu Ser Lys Val Pro Ser Val Phe Thr Gly Gln Asp Leu Ile Gly
    50                  55                  60

Trp Ile Met Lys Asn Leu Glu Met Thr Asp Leu Ser Asp Ala Leu His
65                  70                  75                  80

Leu Ala His Leu Ile Ala Ser His Gly Tyr Leu Phe Gln Ile Asp Asp
                85                  90                  95

His Val Leu Thr Val Lys Asn Asp Gly Thr Phe Tyr Arg Phe Gln Thr
            100                 105                 110

Pro Tyr Phe Trp Pro Ser Asn Cys Trp Asp Pro Glu Asn Thr Asp Tyr
        115                 120                 125

Ala Val Tyr Leu Cys Lys Arg Thr Met Gln Asn Lys Ala His Leu Glu
    130                 135                 140

Leu Glu Asp Phe Glu Ala Glu Asn Leu Ala Lys Leu Gln Lys Met Phe
145                 150                 155                 160

Ser Arg Lys Trp Glu Phe Val Phe Met Gln Ala Glu Ala Gln Tyr Lys
                165                 170                 175

Val Asp Lys Lys Arg Asp Arg Gln Glu Arg Gln Ile Leu Asp Ser Gln
            180                 185                 190

Glu Arg Ala Phe Trp Asp Val His Arg Pro Val Pro Gly Cys Val Asn
        195                 200                 205

Thr Thr Glu Val Asp Phe Arg Lys Leu Ser Arg Ser Gly Arg Pro Lys
    210                 215                 220

Tyr Ser Ser Gly Gly His Ala Ala Leu Ala Ala Ser Thr Ser Gly Ile
225                 230                 235                 240

Gly Cys Thr Gln Tyr Ser Gln Ser Val Ala Ala His Ala Ser Leu
                245                 250                 255
```

```
Pro Ser Thr Ser Asn Gly Ser Ala Thr Ser Pro Arg Lys Asn Asp Gln
            260                 265                 270

Glu Pro Ser Thr Ser Gly Gly Glu Ser Pro Ser Thr Ser Ser Ala
        275                 280                 285

Ala Ala Gly Thr Ala Thr Thr Ser Ala Pro Ser Thr Ser Thr Pro Pro
        290                 295                 300

Val Thr Thr Ile Thr Ala Thr Ile Asn Ala Gly Ser Phe Arg Asn Asn
305                 310                 315                 320

Tyr Tyr Thr Arg Pro Gly Leu Arg Arg Cys Thr Gln Val Gln Asp Thr
                325                 330                 335

Leu Lys Leu Glu Ile Val Gln Leu Asn Ser Arg Leu Ser Lys Asn Val
            340                 345                 350

Leu Arg Thr Ser Lys Val Val Glu Asn Tyr Leu Ala Tyr Tyr Glu Gln
        355                 360                 365

Arg Arg Val Phe Asp Pro Leu Leu Thr Pro Gly Ser Gln Ala Asp
        370                 375                 380

Pro Phe Gln Ser Gln Pro Asn Pro Trp Ile Asn Asp Thr Val Asp Phe
385                 390                 395                 400

Trp Gln His Asp Lys Ile Thr Gly Asp Ile Gln Thr Arg Arg Leu Lys
                405                 410                 415

Leu Trp Glu Asp Ser Phe Glu Glu Leu Leu Ala Asp Ser Leu Gly Arg
            420                 425                 430

Glu Thr Leu Gln Lys Phe Leu Asp Lys Glu Tyr Ser Gly Glu Asn Leu
        435                 440                 445

Arg Phe Trp Trp Glu Val Gln Lys Leu Arg Lys Cys Ser Ser Arg Met
450                 455                 460

Val Pro Val Met Val Thr Glu Ile Tyr Asn Glu Phe Ile Asp Thr Asn
465                 470                 475                 480

Ala Ala Thr Ser Pro Val Asn Val Asp Cys Lys Val Met Glu Val Thr
                485                 490                 495

Glu Asp Asn Leu Lys Asn Pro Asn Arg Trp Ser Phe Asp Glu Ala Ala
            500                 505                 510

Asp His Ile Tyr Cys Leu Met Lys Asn Asp Ser Tyr Gln Arg Phe Leu
        515                 520                 525

Arg Ser Glu Ile Tyr Lys Asp Leu Val Leu Gln Ser Arg Lys Lys Val
        530                 535                 540

Ser Leu Asn Cys Ser Phe Ser Ile Phe Ala Ser
545                 550                 555

<210> SEQ ID NO 9
<211> LENGTH: 456
<212> TYPE: PRT
<213> ORGANISM: Homo sapiens

<400> SEQUENCE: 9

Met Ala Ala Gly Pro Ala Pro Pro Gly Arg Pro Arg Ala Gln Met
1               5                   10                  15

Pro His Leu Arg Lys Met Glu Arg Val Val Ser Met Gln Asp Pro
            20                  25                  30

Asp Gln Gly Val Lys Met Arg Ser Gln Arg Leu Leu Val Thr Val Ile
            35                  40                  45

Pro His Ala Val Thr Gly Ser Asp Val Val Gln Trp Leu Ala Gln Lys
        50                  55                  60

Phe Cys Val Ser Glu Glu Glu Ala Leu His Leu Gly Ala Val Leu Val
65                  70                  75                  80
```

```
Gln His Gly Tyr Ile Tyr Pro Leu Arg Asp Pro Arg Ser Leu Met Leu
                85                  90                  95

Arg Pro Asp Glu Thr Pro Tyr Arg Phe Gln Val Arg Leu Gly Gly Ala
            100                 105                 110

Ala Ile Tyr Leu Ala Lys Lys Asn Ile Arg Lys Arg Gly Thr Leu Val
        115                 120                 125

Asp Tyr Glu Lys Asp Cys Tyr Asp Arg Leu His Lys Lys Ile Asn His
    130                 135                 140

Ala Trp Asp Leu Val Leu Met Gln Ala Arg Glu Gln Leu Arg Ala Ala
145                 150                 155                 160

Lys Gln Arg Ser Lys Gly Asp Arg Leu Val Ile Ala Cys Gln Glu Gln
                165                 170                 175

Thr Tyr Trp Leu Val Asn Arg Pro Pro Gly Ala Pro Asp Val Leu
            180                 185                 190

Glu Gln Gly Pro Gly Arg Gly Ser Cys Ala Ala Ser Arg Val Leu Met
            195                 200                 205

Thr Lys Ser Ala Asp Phe His Lys Arg Glu Ile Glu Tyr Phe Arg Lys
    210                 215                 220

Ala Leu Gly Arg Thr Arg Val Lys Ser Ser Val Cys Leu Glu Ala Tyr
225                 230                 235                 240

Leu Ser Phe Cys Gly Gln Arg Gly Pro His Asp Pro Leu Val Ser Gly
                245                 250                 255

Cys Leu Pro Ser Asn Pro Trp Ile Ser Asp Asn Asp Ala Tyr Trp Val
            260                 265                 270

Met Asn Ala Pro Thr Val Ala Ala Pro Thr Lys Leu Arg Val Glu Arg
            275                 280                 285

Trp Gly Phe Ser Phe Arg Glu Leu Leu Glu Asp Pro Val Gly Arg Ala
            290                 295                 300

His Phe Met Asp Phe Leu Gly Lys Glu Phe Ser Gly Glu Asn Leu Ser
305                 310                 315                 320

Phe Trp Glu Ala Cys Glu Glu Leu Arg Tyr Gly Ala Gln Ala Gln Val
                325                 330                 335

Pro Thr Leu Val Asp Ala Val Tyr Glu Gln Phe Leu Ala Pro Gly Ala
            340                 345                 350

Ala His Trp Val Asn Ile Asp Ser Arg Thr Met Glu Gln Thr Leu Glu
        355                 360                 365

Gly Leu Arg Gln Pro His Arg Tyr Val Leu Asp Asp Ala Gln Leu His
    370                 375                 380

Ile Tyr Met Leu Met Lys Lys Asp Ser Tyr Pro Arg Phe Leu Lys Ser
385                 390                 395                 400

Asp Met Tyr Lys Ala Leu Leu Ala Glu Ala Gly Ile Pro Leu Glu Met
                405                 410                 415

Lys Arg Arg Val Phe Pro Phe Thr Trp Arg Pro Arg His Ser Ser Pro
            420                 425                 430

Ser Pro Ala Leu Leu Pro Thr Pro Val Glu Pro Thr Ala Ala Cys Gly
        435                 440                 445

Pro Gly Gly Gly Asp Gly Val Ala
450                 455
```

<210> SEQ ID NO 10
<211> LENGTH: 473
<212> TYPE: PRT
<213> ORGANISM: Caenorhabditis elegans

<400> SEQUENCE: 10

```
Met Met Pro Pro Leu Thr Lys Ile Glu Val Leu Ala Lys Arg Val Met
1               5                   10                  15

Glu Gly Ala Gln Leu Lys Thr His Lys Tyr Phe Arg Ile Ala Val Pro
            20                  25                  30

His Ala Ile Thr Gly Gln Gln Leu Ile Ala Leu Val Leu Glu Arg Gly
        35                  40                  45

Ala Pro Asp Asp Glu Ala Glu Ala Ser His Leu Ala Ser Leu Leu Leu
    50                  55                  60

His His Gly Tyr Met Phe Pro Val Ile Glu His Gly Gln Pro Phe Lys
65                  70                  75                  80

Asp Asp Gly Thr Leu Tyr Arg Leu Gln Arg Pro Tyr Phe Trp Pro Ser
                85                  90                  95

Gln Ala Glu Leu Val Pro Asp Val Gly Tyr Ala Ile Tyr Leu Asn Lys
            100                 105                 110

Arg Leu Leu Arg Asn Glu Gln Lys His Gly Leu Glu Glu Asp Glu Val
            115                 120                 125

Glu Ser Phe Asn Arg Leu Ala Asp Val Leu Ala His Met Trp Ala Phe
    130                 135                 140

Ile Val Gln Gln Ser Glu Leu Gln Leu Lys Gln Gln Lys Glu Lys Lys
145                 150                 155                 160

Lys Val Asp Lys Val Val Phe Asp Ser Glu Glu Arg Ala Phe Trp Lys
                165                 170                 175

Ile Arg Lys Pro Ser Arg Gly Gly Pro Asn Phe Leu Glu Asp Pro Tyr
            180                 185                 190

Met Lys Ile Glu Lys Lys Ile Arg Arg Gln Asn Ala Gln Gly Tyr Arg
            195                 200                 205

Cys Leu Met Asp Arg Leu Arg Phe Ala Ile Lys Thr Lys Pro Trp Leu
    210                 215                 220

Lys Ala Leu Lys Ala Ser Asp Thr Met Val Thr Trp Val Asp Gln Arg
225                 230                 235                 240

Ala Glu Phe Asp Pro Phe Leu His Pro Pro Gln Pro Ser Asn Pro Trp
                245                 250                 255

Ile Ser Asp Glu Ala Ser Phe Trp Asn Gln Pro Thr Asp Thr Ser Ser
            260                 265                 270

Ala Glu Ile Pro Thr Glu Lys Arg Val Lys Arg Trp Gly Leu Ser Val
            275                 280                 285

Gln Glu Leu Val Lys Asp Pro Ile Gly Arg Gln Val Leu Glu Thr Phe
    290                 295                 300

Leu Glu Ser Glu Phe Ser Ser Glu Asn Ile Arg Phe Trp Ile Ala Ile
305                 310                 315                 320

Gln Asp Leu Lys Tyr Ala Pro Asn Glu Gln Ile Tyr Gln Lys Ala Glu
                325                 330                 335

Arg Ile Arg Glu Glu Phe Leu Ala Gln Gly Ala Pro Ala Gln Val Asn
            340                 345                 350

Val Asp Asn Arg Thr Leu Asp Gln Thr Leu Glu Cys Ile Ser Lys Ala
            355                 360                 365

Lys Asp Ala Ser Gln Met Arg Phe Ala Phe Tyr His Ser Glu Glu His
    370                 375                 380

Val Phe Thr Leu Met Ala Lys Asp Ser Tyr Pro Arg Phe Val Arg Ser
385                 390                 395                 400

Gln Ile Tyr Lys Ala Val Leu Thr Ala Ala Gln His Gly Thr Lys
                405                 410                 415
```

-continued

Arg Leu Gly Trp Arg Asn Phe Val Phe Asn Met Gly Thr Thr Lys Lys
            420                 425                 430

Pro Ala Thr Ser Lys Pro Ala Lys Pro Gln Asp Ser Ile Gly Thr Gly
            435                 440                 445

Gln Val Leu Pro Lys Gln Leu Ser Ser Asp Ser Leu Pro Val Arg Gln
        450                 455                 460

Ala His Gly Val Lys Pro Asp Pro Glu
465                 470

<210> SEQ ID NO 11
<211> LENGTH: 674
<212> TYPE: PRT
<213> ORGANISM: Homo sapiens

<400> SEQUENCE: 11

Met Thr Ile Arg His Gln Gly Gln Gln Tyr Arg Pro Arg Met Ala Phe
1               5                   10                  15

Leu Gln Lys Ile Glu Ala Leu Val Lys Asp Met Gln Asn Pro Glu Thr
            20                  25                  30

Gly Val Arg Met Gln Asn Gln Arg Val Leu Val Thr Ser Val Pro His
        35                  40                  45

Ala Met Thr Gly Ser Asp Val Leu Gln Trp Ile Val Gln Arg Leu Trp
    50                  55                  60

Ile Ser Ser Leu Glu Ala Gln Asn Leu Gly Asn Phe Ile Val Arg Tyr
65                  70                  75                  80

Gly Tyr Ile Tyr Pro Leu Gln Asp Pro Lys Asn Leu Ile Leu Lys Pro
                85                  90                  95

Asp Gly Ser Leu Tyr Arg Phe Gln Thr Pro Tyr Phe Trp Pro Thr Gln
            100                 105                 110

Gln Trp Pro Ala Glu Asp Thr Asp Tyr Ala Ile Tyr Leu Ala Lys Arg
        115                 120                 125

Asn Ile Lys Lys Lys Gly Ile Leu Glu Glu Tyr Glu Lys Glu Asn Tyr
130                 135                 140

Asn Phe Leu Asn Gln Lys Met Asn Tyr Lys Trp Asp Phe Val Ile Met
145                 150                 155                 160

Gln Ala Lys Glu Gln Tyr Arg Ala Gly Lys Glu Arg Asn Lys Ala Asp
                165                 170                 175

Arg Tyr Ala Leu Asp Cys Gln Glu Lys Ala Tyr Trp Leu Val His Arg
            180                 185                 190

Cys Pro Pro Gly Met Asp Asn Val Leu Asp Tyr Gly Leu Asp Arg Val
        195                 200                 205

Thr Asn Pro Asn Glu Val Lys Val Asn Gln Lys Gln Thr Val Val Ala
    210                 215                 220

Val Lys Lys Glu Ile Met Tyr Tyr Gln Gln Ala Leu Met Arg Ser Thr
225                 230                 235                 240

Val Lys Ser Ser Val Ser Leu Gly Gly Ile Val Lys Tyr Ser Glu Gln
                245                 250                 255

Phe Ser Ser Asn Asp Ala Ile Met Ser Gly Cys Leu Pro Ser Asn Pro
            260                 265                 270

Trp Ile Thr Asp Asp Thr Gln Phe Trp Asp Leu Asn Ala Lys Leu Val
        275                 280                 285

Glu Ile Pro Thr Lys Met Arg Val Glu Arg Trp Ala Phe Asn Phe Ser
    290                 295                 300

Glu Leu Ile Arg Asp Pro Lys Gly Arg Gln Ser Phe Gln Tyr Phe Leu

```
                305                 310                 315                 320
Lys Lys Glu Phe Ser Gly Glu Asn Leu Gly Phe Trp Glu Ala Cys Glu
                    325                 330                 335
Asp Leu Lys Tyr Gly Asp Gln Ser Lys Val Lys Glu Lys Ala Glu Glu
                340                 345                 350
Ile Tyr Lys Leu Phe Leu Ala Pro Gly Ala Arg Arg Trp Ile Asn Ile
            355                 360                 365
Asp Gly Lys Thr Met Asp Ile Thr Val Lys Gly Leu Lys His Pro His
        370                 375                 380
Arg Tyr Val Leu Asp Ala Ala Gln Thr His Ile Tyr Met Leu Met Lys
385                 390                 395                 400
Lys Asp Ser Tyr Ala Arg Tyr Leu Lys Ser Pro Ile Tyr Lys Asp Met
                405                 410                 415
Leu Ala Lys Ala Ile Glu Pro Gln Glu Thr Thr Lys Lys Ser Ser Thr
                420                 425                 430
Leu Pro Phe Met Arg Arg His Leu Arg Ser Ser Pro Ser Pro Val Ile
                435                 440                 445
Leu Arg Gln Leu Glu Glu Glu Ala Lys Ala Arg Glu Ala Ala Asn Thr
            450                 455                 460
Val Asp Ile Thr Gln Pro Gly Gln His Met Ala Pro Ser Pro His Leu
465                 470                 475                 480
Thr Val Tyr Thr Gly Thr Cys Met Pro Pro Ser Ser Ser Pro Phe
                    485                 490                 495
Ser Ser Ser Cys Arg Ser Pro Arg Lys Pro Phe Ala Ser Pro Ser Arg
                500                 505                 510
Phe Ile Arg Arg Pro Ser Thr Thr Ile Cys Pro Ser Pro Ile Arg Val
                515                 520                 525
Ala Leu Glu Ser Ser Ser Gly Leu Glu Gln Lys Gly Glu Cys Ser Gly
                530                 535                 540
Ser Met Ala Pro Arg Gly Pro Ser Val Thr Glu Ser Ser Glu Ala Ser
545                 550                 555                 560
Leu Asp Thr Ser Trp Pro Arg Ser Arg Pro Arg Ala Pro Pro Lys Ala
                    565                 570                 575
Arg Met Ala Leu Ser Phe Ser Arg Phe Leu Arg Arg Gly Cys Leu Ala
                580                 585                 590
Ser Pro Val Phe Ala Arg Leu Ser Pro Lys Cys Pro Ala Val Ser His
                595                 600                 605
Gly Arg Val Gln Pro Leu Gly Asp Val Gly Gln Leu Pro Arg Leu
            610                 615                 620
Lys Ser Lys Arg Val Ala Asn Phe Phe Gln Ile Lys Met Asp Val Pro
625                 630                 635                 640
Thr Gly Ser Gly Thr Cys Leu Met Asp Ser Glu Asp Ala Gly Thr Gly
                    645                 650                 655
Glu Ser Gly Asp Arg Ala Thr Glu Lys Glu Val Ile Cys Pro Trp Glu
                660                 665                 670
Ser Leu

<210> SEQ ID NO 12
<211> LENGTH: 355
<212> TYPE: PRT
<213> ORGANISM: Caenorhabditis elegans

<400> SEQUENCE: 12

Met Ala Cys Cys Leu Ser Glu Glu Ala Arg Glu Gln Lys Arg Ile Asn
```

```
              1               5                  10                 15
Gln Glu Ile Glu Lys Gln Leu Gln Arg Asp Lys Arg Asn Ala Arg Arg
                20                 25                 30

Glu Leu Lys Leu Leu Leu Gly Thr Gly Glu Ser Gly Lys Ser Thr
            35                 40                 45

Phe Ile Lys Gln Met Arg Ile Ile His Gly Gln Gly Tyr Ser Glu Glu
            50                 55                 60

Asp Lys Arg Ala His Ile Arg Leu Val Tyr Gln Asn Val Phe Met Ala
65                  70                 75                 80

Ile Gln Ser Met Ile Arg Ala Met Asp Thr Leu Asp Ile Lys Phe Gly
                85                 90                 95

Asn Glu Ser Glu Glu Leu Gln Glu Lys Ala Ala Val Val Arg Glu Val
            100                105                110

Asp Phe Glu Ser Val Thr Ser Phe Glu Glu Pro Tyr Val Ser Tyr Ile
            115                120                125

Lys Glu Leu Trp Glu Asp Ser Gly Ile Gln Glu Cys Tyr Asp Arg Arg
            130                135                140

Arg Glu Tyr Gln Leu Thr Asp Ser Ala Lys Tyr Tyr Leu Ser Asp Leu
145                 150                155                160

Arg Arg Leu Ala Val Pro Asp Tyr Leu Pro Thr Glu Gln Asp Ile Leu
                165                170                175

Arg Val Arg Val Pro Thr Thr Gly Ile Ile Glu Tyr Pro Phe Asp Leu
                180                185                190

Glu Gln Ile Ile Phe Arg Met Val Asp Val Gly Gly Gln Arg Ser Glu
                195                200                205

Arg Arg Lys Trp Ile His Cys Phe Glu Asn Val Thr Ser Ile Met Phe
210                 215                220

Leu Val Ala Leu Ser Glu Tyr Asp Gln Val Leu Val Glu Cys Asp Asn
225                 230                235                240

Glu Asn Arg Met Glu Glu Ser Lys Ala Leu Phe Arg Thr Ile Ile Thr
                245                250                255

Tyr Pro Trp Phe Thr Asn Ser Ser Val Ile Leu Phe Leu Asn Lys Lys
                260                265                270

Asp Leu Leu Glu Glu Lys Ile Leu Tyr Ser His Leu Ala Asp Tyr Phe
            275                280                285

Pro Glu Tyr Asp Gly Pro Pro Arg Asp Pro Ile Ala Ala Arg Glu Phe
            290                295                300

Ile Leu Lys Met Phe Val Asp Leu Asn Pro Asp Ala Asp Lys Ile Ile
305                 310                315                320

Tyr Ser His Phe Thr Cys Ala Thr Asp Thr Glu Asn Ile Arg Phe Val
                325                330                335

Phe Ala Ala Val Lys Asp Thr Ile Leu Gln His Asn Leu Lys Glu Tyr
                340                345                350

Asn Leu Val
        355
```

<210> SEQ ID NO 13
<211> LENGTH: 353
<212> TYPE: PRT
<213> ORGANISM: Artificial
<220> FEATURE:
<223> OTHER INFORMATION: G-protein of the invention

<400> SEQUENCE: 13

Met Ala Cys Cys Leu Ser Glu Glu Ala Lys Glu Ala Arg Arg Ile Asn

-continued

```
                1               5                   10                  15
Asp Glu Ile Glu Arg Gln Leu Arg Arg Asp Lys Arg Asp Ala Arg Arg
                20                  25                  30

Glu Leu Lys Leu Leu Leu Gly Thr Gly Glu Ser Gly Lys Ser Thr
        35                  40                  45

Phe Ile Lys Gln Met Arg Ile Ile His Gly Ser Gly Tyr Ser Asp Glu
    50                  55                  60

Asp Lys Arg Gly Phe Thr Lys Leu Val Tyr Gln Asn Ile Phe Thr Ala
65                  70                  75                  80

Met Gln Ala Met Ile Arg Ala Met Asp Thr Leu Lys Ile Pro Tyr Lys
                85                  90                  95

Tyr Glu His Asn Lys Ala His Ala Gln Leu Val Arg Glu Val Asp Val
                100                 105                 110

Glu Lys Val Ser Ala Phe Glu Asn Pro Tyr Val Asp Ala Ile Lys Ser
            115                 120                 125

Leu Trp Asn Asp Pro Gly Ile Gln Glu Cys Tyr Asp Arg Arg Arg Glu
130                 135                 140

Tyr Gln Leu Ser Asp Ser Thr Lys Tyr Tyr Leu Asn Asp Leu Asp Arg
145                 150                 155                 160

Val Ala Asp Pro Ala Tyr Leu Pro Thr Gln Gln Asp Val Leu Arg Val
                165                 170                 175

Arg Val Pro Thr Thr Gly Ile Ile Glu Tyr Pro Phe Asp Leu Gln Ser
                180                 185                 190

Val Ile Phe Arg Met Val Asp Val Gly Gly Gln Arg Ser Glu Arg Arg
            195                 200                 205

Lys Trp Ile His Cys Phe Glu Asn Val Thr Ser Ile Met Phe Leu Val
        210                 215                 220

Ala Leu Ser Glu Tyr Asp Gln Val Leu Val Glu Ser Asp Asn Glu Asn
225                 230                 235                 240

Arg Met Glu Glu Ser Lys Ala Leu Phe Arg Thr Ile Ile Thr Tyr Pro
                245                 250                 255

Trp Phe Gln Asn Ser Ser Val Ile Leu Phe Leu Asn Lys Lys Asp Leu
            260                 265                 270

Leu Glu Glu Lys Ile Met Tyr Ser His Leu Val Asp Tyr Phe Pro Glu
        275                 280                 285

Tyr Asp Gly Pro Gln Arg Asp Ala Gln Ala Ala Arg Glu Phe Ile Leu
290                 295                 300

Lys Met Phe Val Asp Leu Asn Pro Asp Ser Asp Lys Ile Ile Tyr Ser
305                 310                 315                 320

His Phe Thr Cys Ala Thr Asp Thr Glu Asn Ile Arg Phe Val Phe Ala
                325                 330                 335

Ala Val Lys Asp Thr Ile Leu Gln Leu Asn Leu Lys Glu Tyr Asn Ala
                340                 345                 350

Val
```

<210> SEQ ID NO 14
<211> LENGTH: 354
<212> TYPE: PRT
<213> ORGANISM: Artificial
<220> FEATURE:
<223> OTHER INFORMATION: G-protein of the invention

<400> SEQUENCE: 14

```
Met Gly Cys Thr Leu Ser Ala Glu Asp Lys Ala Ala Val Glu Arg Ser
1               5                   10                  15
```

```
Lys Met Ile Asp Arg Asn Leu Arg Glu Asp Gly Glu Lys Ala Ala Arg
            20                  25                  30

Glu Val Lys Leu Leu Leu Gly Ala Gly Glu Ser Gly Lys Ser Thr
        35                  40                  45

Ile Val Lys Gln Met Lys Ile Ile His Glu Ala Gly Tyr Ser Glu Glu
        50                  55                  60

Glu Cys Lys Gln Tyr Lys Ala Val Val Tyr Ser Asn Thr Ile Gln Ser
 65                  70                  75                  80

Ile Ile Ala Ile Ile Arg Ala Met Gly Arg Leu Lys Ile Asp Phe Gly
                85                  90                  95

Asp Ser Ala Arg Ala Asp Asp Ala Arg Gln Leu Phe Val Leu Ala Gly
            100                 105                 110

Ala Ala Glu Glu Gly Phe Met Thr Ala Glu Leu Ala Gly Val Ile Lys
            115                 120                 125

Arg Leu Trp Lys Asp Ser Gly Val Gln Ala Cys Phe Asn Arg Ser Arg
        130                 135                 140

Glu Tyr Gln Leu Asn Asp Ser Ala Ala Tyr Tyr Leu Asn Asp Leu Asp
145                 150                 155                 160

Arg Ile Ala Gln Pro Asn Tyr Ile Pro Thr Gln Gln Asp Val Leu Arg
                165                 170                 175

Thr Arg Val Lys Thr Thr Gly Ile Val Glu Thr His Phe Thr Phe Lys
            180                 185                 190

Asp Leu His Phe Lys Met Phe Asp Val Gly Gly Gln Arg Ser Glu Arg
        195                 200                 205

Lys Lys Trp Ile His Cys Phe Glu Gly Val Thr Ala Ile Ile Phe Cys
210                 215                 220

Val Ala Leu Ser Asp Tyr Asp Leu Val Leu Ala Glu Asp Glu Glu Met
225                 230                 235                 240

Asn Arg Met His Glu Ser Met Lys Leu Phe Asp Ser Ile Cys Asn Asn
                245                 250                 255

Lys Trp Phe Thr Asp Thr Ser Ile Ile Leu Phe Leu Asn Lys Lys Asp
            260                 265                 270

Leu Phe Glu Glu Lys Ile Lys Lys Ser Pro Leu Thr Ile Cys Tyr Pro
        275                 280                 285

Glu Tyr Ala Gly Ser Asn Thr Tyr Glu Glu Ala Ala Tyr Ile Gln
            290                 295                 300

Cys Gln Phe Glu Asp Leu Asn Lys Arg Lys Asp Thr Lys Glu Ile Tyr
305                 310                 315                 320

Thr His Phe Thr Cys Ala Thr Asp Thr Lys Asn Val Gln Phe Val Phe
                325                 330                 335

Asp Ala Val Thr Asp Val Ile Ile Lys Asn Asn Leu Lys Asp Cys Gly
            340                 345                 350

Leu Phe

<210> SEQ ID NO 15
<211> LENGTH: 350
<212> TYPE: PRT
<213> ORGANISM: Artificial
<220> FEATURE:
<223> OTHER INFORMATION: G-protein of the invention

<400> SEQUENCE: 15

Met Gly Ala Gly Ala Ser Ala Glu Glu Lys His Ser Arg Glu Leu Glu
 1               5                  10                  15
```

```
Lys Lys Leu Lys Glu Asp Ala Glu Lys Asp Ala Arg Thr Val Lys Leu
            20                  25                  30

Leu Leu Leu Gly Ala Gly Glu Ser Gly Lys Ser Thr Ile Val Lys Gln
            35                  40                  45

Met Lys Ile Ile His Gln Asp Gly Tyr Ser Leu Glu Glu Cys Leu Glu
 50                  55                  60

Phe Ile Ala Ile Ile Tyr Gly Asn Thr Leu Gln Ser Ile Leu Ala Ile
65                   70                  75                  80

Val Arg Ala Met Thr Thr Leu Asn Ile Gln Tyr Gly Asp Ser Ala Arg
                85                  90                  95

Gln Asp Asp Ala Arg Lys Leu Met His Met Ala Asp Thr Ile Glu Glu
            100                 105                 110

Gly Thr Met Pro Lys Glu Met Ser Asp Ile Ile Gln Arg Leu Trp Lys
            115                 120                 125

Asp Ser Gly Ile Gln Ala Cys Phe Glu Arg Ala Ser Glu Tyr Gln Leu
130                 135                 140

Asn Asp Ser Ala Gly Tyr Tyr Leu Ser Asp Leu Glu Arg Leu Val Thr
145                 150                 155                 160

Pro Gly Tyr Val Pro Thr Glu Gln Asp Val Leu Arg Ser Arg Val Lys
            165                 170                 175

Thr Thr Gly Ile Ile Glu Thr Gln Phe Ser Phe Lys Asp Leu Asn Phe
            180                 185                 190

Arg Met Phe Asp Val Gly Gly Gln Arg Ser Glu Arg Lys Lys Trp Ile
            195                 200                 205

His Cys Phe Glu Gly Val Thr Cys Ile Ile Phe Ile Ala Ala Leu Ser
            210                 215                 220

Ala Tyr Asp Met Val Leu Val Glu Asp Asp Glu Val Asn Arg Met His
225                 230                 235                 240

Glu Ser Leu His Leu Phe Asn Ser Ile Cys Asn His Arg Tyr Phe Ala
            245                 250                 255

Thr Thr Ser Ile Val Leu Phe Leu Asn Lys Lys Asp Val Phe Phe Glu
            260                 265                 270

Lys Ile Lys Lys Ala His Leu Ser Ile Cys Phe Pro Asp Tyr Asp Gly
            275                 280                 285

Pro Asn Thr Tyr Glu Asp Ala Gly Asn Tyr Ile Lys Val Gln Phe Leu
            290                 295                 300

Glu Leu Asn Met Arg Arg Asp Val Lys Glu Ile Tyr Ser His Met Thr
305                 310                 315                 320

Cys Ala Thr Asp Thr Gln Asn Val Lys Phe Val Phe Asp Ala Val Thr
                325                 330                 335

Asp Ile Ile Ile Lys Glu Asn Leu Lys Asp Cys Gly Leu Phe
            340                 345                 350

<210> SEQ ID NO 16
<211> LENGTH: 354
<212> TYPE: PRT
<213> ORGANISM: Artificial
<220> FEATURE:
<223> OTHER INFORMATION: G-protein of the invention

<400> SEQUENCE: 16

Met Gly Cys Thr Leu Ser Ala Glu Glu Arg Ala Ala Leu Glu Arg Ser
1               5                   10                  15

Lys Ala Ile Glu Lys Asn Leu Lys Glu Asp Gly Ile Ser Ala Ala Lys
            20                  25                  30
```

```
Asp Val Lys Leu Leu Leu Gly Ala Gly Glu Ser Gly Lys Ser Thr
            35                  40                  45

Ile Val Lys Gln Met Lys Ile Ile His Glu Asp Gly Phe Ser Gly Glu
            50                  55                  60

Asp Val Lys Gln Tyr Lys Pro Val Val Tyr Ser Asn Thr Ile Gln Ser
65                  70                  75                  80

Leu Ala Ala Ile Val Arg Ala Met Asp Thr Leu Gly Ile Glu Tyr Gly
                85                  90                  95

Asp Lys Glu Arg Lys Ala Asp Ala Lys Met Val Cys Asp Val Val Ser
            100                 105                 110

Arg Met Glu Asp Thr Glu Pro Phe Ser Ala Glu Leu Leu Ser Ala Met
            115                 120                 125

Met Arg Leu Trp Gly Asp Ser Gly Ile Gln Glu Cys Phe Asn Arg Ser
            130                 135                 140

Arg Glu Tyr Gln Leu Asn Asp Ser Ala Lys Tyr Tyr Leu Asp Ser Leu
145                 150                 155                 160

Asp Arg Ile Gly Ala Ala Asp Tyr Gln Pro Thr Glu Gln Asp Ile Leu
                165                 170                 175

Arg Thr Arg Val Lys Thr Thr Gly Ile Val Glu Thr His Phe Thr Phe
            180                 185                 190

Lys Asn Leu His Phe Arg Leu Phe Asp Val Gly Gly Gln Arg Ser Glu
            195                 200                 205

Arg Lys Lys Trp Ile His Cys Phe Glu Asp Val Thr Ala Ile Ile Phe
            210                 215                 220

Cys Val Ala Leu Ser Gly Tyr Asp Gln Val Leu His Glu Asp Glu Thr
225                 230                 235                 240

Thr Asn Arg Met His Glu Ser Leu Met Leu Phe Asp Ser Ile Cys Asn
                245                 250                 255

Asn Lys Phe Phe Ile Asp Thr Ser Ile Ile Leu Phe Leu Asn Lys Lys
            260                 265                 270

Asp Leu Phe Gly Glu Lys Ile Lys Lys Ser Pro Leu Thr Ile Cys Phe
            275                 280                 285

Pro Glu Tyr Thr Gly Pro Asn Thr Tyr Glu Asp Ala Ala Ala Tyr Ile
            290                 295                 300

Gln Ala Gln Phe Glu Ser Lys Asn Arg Ser Pro Asn Lys Glu Ile Tyr
305                 310                 315                 320

Cys His Met Thr Cys Ala Thr Asp Thr Asn Asn Ile Gln Val Val Phe
                325                 330                 335

Asp Ala Val Thr Asp Ile Ile Ile Ala Asn Asn Leu Arg Gly Cys Gly
            340                 345                 350

Leu Tyr

<210> SEQ ID NO 17
<211> LENGTH: 355
<212> TYPE: PRT
<213> ORGANISM: Artificial
<220> FEATURE:
<223> OTHER INFORMATION: G-protein of the invention

<400> SEQUENCE: 17

Met Gly Cys Arg Gln Ser Ser Glu Glu Lys Glu Ala Ala Arg Arg Ser
1               5                   10                  15

Arg Arg Ile Asp Arg His Leu Arg Ser Glu Ser Gln Arg Gln Arg Arg
            20                  25                  30

Glu Ile Lys Leu Leu Leu Leu Gly Thr Ser Asn Ser Gly Lys Ser Thr
```

-continued

```
            35                  40                  45
Ile Val Lys Gln Met Lys Ile Ile His Ser Gly Gly Phe Asn Leu Glu
    50                  55                  60

Ala Cys Lys Glu Tyr Lys Pro Leu Ile Ile Tyr Asn Ala Ile Asp Ser
65                  70                  75                  80

Leu Thr Arg Ile Ile Arg Ala Leu Ala Ala Leu Arg Ile Asp Phe His
                85                  90                  95

Asn Pro Asp Arg Ala Tyr Asp Ala Val Gln Leu Phe Ala Leu Thr Gly
            100                 105                 110

Pro Ala Glu Ser Lys Gly Glu Ile Thr Pro Glu Leu Leu Gly Val Met
        115                 120                 125

Arg Arg Leu Trp Ala Asp Pro Gly Ala Gln Ala Cys Phe Ser Arg Ser
130                 135                 140

Ser Glu Tyr His Leu Glu Asp Asn Ala Ala Tyr Tyr Leu Asn Asp Leu
145                 150                 155                 160

Glu Arg Ile Ala Ala Ala Asp Tyr Ile Pro Thr Val Glu Asp Ile Leu
                165                 170                 175

Arg Ser Arg Asp Met Thr Thr Gly Ile Val Glu Asn Lys Phe Thr Phe
            180                 185                 190

Lys Glu Leu Thr Phe Lys Met Val Asp Val Gly Gly Gln Arg Ser Glu
        195                 200                 205

Arg Lys Lys Trp Ile His Cys Phe Glu Gly Val Thr Ala Ile Ile Phe
    210                 215                 220

Cys Val Glu Leu Ser Gly Tyr Asp Leu Lys Leu Tyr Glu Asp Asn Gln
225                 230                 235                 240

Thr Ser Arg Met Ala Glu Ser Leu Arg Leu Phe Asp Ser Ile Cys Asn
                245                 250                 255

Asn Asn Trp Phe Ile Asn Thr Ser Leu Ile Leu Phe Leu Asn Lys Lys
            260                 265                 270

Asp Leu Leu Ala Glu Lys Ile Arg Ile Pro Leu Thr Ile Cys Phe
        275                 280                 285

Pro Glu Tyr Lys Gly Gln Asn Thr Tyr Glu Glu Ala Ala Val Tyr Ile
    290                 295                 300

Gln Arg Gln Phe Glu Asp Leu Asn Arg Asn Lys Glu Thr Lys Glu Ile
305                 310                 315                 320

Tyr Ser His Phe Thr Cys Ala Thr Asp Thr Ser Asn Ile Gln Phe Val
                325                 330                 335

Phe Asp Ala Val Thr Asp Val Ile Ile Gln Asn Asn Leu Lys Tyr Ile
            340                 345                 350

Gly Leu Cys
        355

<210> SEQ ID NO 18
<211> LENGTH: 394
<212> TYPE: PRT
<213> ORGANISM: Artificial
<220> FEATURE:
<223> OTHER INFORMATION: G-protein of the invention

<400> SEQUENCE: 18

Met Gly Cys Leu Gly Asn Ser Lys Thr Glu Asp Gln Arg Asn Glu Glu
1               5                   10                  15

Lys Ala Gln Arg Glu Ala Asn Lys Lys Ile Glu Lys Gln Leu Gln Lys
            20                  25                  30

Asp Lys Gln Val Tyr Arg Ala Thr His Arg Leu Leu Leu Leu Gly Ala
```

```
                35                  40                  45
Gly Glu Ser Gly Lys Ser Thr Ile Val Lys Gln Met Arg Ile Leu His
 50                  55                  60

Val Asn Gly Phe Asn Gly Glu Gly Gly Glu Glu Asp Pro Gln Ala Ala
 65                  70                  75                  80

Arg Ser Asn Ser Asp Gly Glu Lys Ala Thr Lys Val Gln Asp Ile Lys
                 85                  90                  95

Asn Asn Leu Lys Glu Ala Ile Glu Thr Ile Val Ala Ala Met Ser Asn
                100                 105                 110

Leu Val Pro Pro Val Glu Leu Ala Asn Pro Glu Asn Gln Phe Arg Val
            115                 120                 125

Asp Tyr Ile Leu Ser Val Met Asn Val Pro Asp Phe Asp Phe Pro Pro
        130                 135                 140

Glu Phe Tyr Glu His Ala Lys Ala Leu Trp Glu Asp Glu Gly Val Arg
145                 150                 155                 160

Ala Cys Tyr Glu Arg Ser Asn Glu Tyr Gln Leu Ile Asp Cys Ala Gln
                165                 170                 175

Tyr Phe Leu Asp Lys Ile Asp Val Ile Lys Gln Ala Asp Tyr Val Pro
            180                 185                 190

Ser Asp Gln Asp Leu Leu Arg Cys Arg Val Leu Thr Ser Gly Ile Phe
        195                 200                 205

Glu Thr Lys Phe Gln Val Asp Lys Val Asn Phe His Met Phe Asp Val
210                 215                 220

Gly Gly Gln Arg Asp Glu Arg Arg Lys Trp Ile Gln Cys Phe Asn Asp
225                 230                 235                 240

Val Thr Ala Ile Ile Phe Val Val Ala Ser Ser Tyr Asn Met Val
                245                 250                 255

Ile Arg Glu Asp Asn Gln Thr Asn Arg Leu Gln Glu Ala Leu Asn Leu
            260                 265                 270

Phe Lys Ser Ile Trp Asn Asn Arg Trp Leu Arg Thr Ile Ser Val Ile
        275                 280                 285

Leu Phe Leu Asn Lys Gln Asp Leu Leu Ala Glu Lys Val Leu Ala Gly
    290                 295                 300

Lys Ser Lys Ile Glu Asp Tyr Phe Pro Glu Phe Ala Arg Tyr Thr Thr
305                 310                 315                 320

Pro Glu Asp Ala Thr Pro Glu Pro Gly Glu Asp Pro Arg Val Thr Arg
                325                 330                 335

Ala Lys Tyr Phe Ile Arg Asp Glu Phe Leu Arg Ile Ser Thr Ala Ser
            340                 345                 350

Gly Asp Gly Arg His Tyr Cys Tyr Pro His Phe Thr Cys Ala Val Asp
        355                 360                 365

Thr Glu Asn Ile Arg Arg Val Phe Asn Asp Cys Arg Asp Ile Ile Gln
370                 375                 380

Arg Met His Leu Arg Gln Tyr Glu Leu Leu
385                 390

<210> SEQ ID NO 19
<211> LENGTH: 377
<212> TYPE: PRT
<213> ORGANISM: Artificial
<220> FEATURE:
<223> OTHER INFORMATION: G-protein of the invention

<400> SEQUENCE: 19

Met Ala Asp Phe Leu Pro Ser Arg Ser Val Leu Ser Val Cys Phe Pro
```

```
                1               5                   10                  15
        Gly Cys Leu Leu Thr Ser Gly Glu Ala Glu Gln Gln Arg Lys Ser Lys
                        20                  25                  30

Glu Ile Asp Lys Cys Leu Ser Arg Glu Lys Thr Tyr Val Lys Arg Leu
                        35                  40                  45

Val Lys Ile Leu Leu Leu Gly Ala Gly Glu Ser Gly Lys Ser Thr Phe
                50                      55                  60

Leu Lys Gln Met Arg Ile Ile His Gly Gln Asp Phe Asp Gln Arg Ala
        65                      70                  75                  80

Arg Glu Glu Phe Arg Pro Thr Ile Tyr Ser Asn Val Ile Lys Gly Met
                                85                  90                  95

Arg Val Leu Val Asp Ala Arg Glu Lys Leu His Ile Pro Trp Gly Asp
                        100                 105                 110

Asn Ser Asn Gln Gln His Gly Asp Lys Met Met Ser Phe Asp Thr Arg
                        115                 120                 125

Ala Pro Met Ala Ala Gln Gly Met Val Glu Thr Arg Val Phe Leu Gln
                        130                 135                 140

Tyr Leu Pro Ala Ile Arg Ala Leu Trp Ala Asp Ser Gly Ile Gln Asn
        145                     150                 155                 160

Ala Tyr Asp Arg Arg Arg Glu Phe Gln Leu Gly Glu Ser Val Lys Tyr
                                165                 170                 175

Phe Leu Asp Asn Leu Asp Lys Leu Gly Glu Pro Asp Tyr Ile Pro Ser
                        180                 185                 190

Gln Gln Asp Ile Leu Leu Ala Arg Arg Pro Thr Lys Gly Ile His Glu
                        195                 200                 205

Tyr Asp Phe Glu Ile Lys Asn Val Pro Phe Lys Met Leu Asp Val Gly
        210                     215                 220

Gly Gln Arg Ser Glu Arg Lys Arg Trp Phe Glu Cys Phe Asp Ser Val
        225                     230                 235                 240

Thr Ser Ile Leu Phe Leu Val Ser Ser Glu Phe Asp Gln Val Leu
                        245                 250                 255

Met Glu Asp Arg Leu Thr Asn Arg Leu Thr Glu Ser Leu Asn Ile Phe
                        260                 265                 270

Glu Thr Ile Val Asn Asn Arg Val Phe Ser Asn Val Ser Ile Ile Leu
                        275                 280                 285

Phe Leu Asn Lys Thr Asp Leu Leu Glu Glu Lys Val Gln Ile Val Ser
                        290                 295                 300

Ile Lys Asp Tyr Phe Leu Glu Phe Glu Gly Asp Pro His Cys Leu Arg
        305                     310                 315                 320

Asp Val Gln Lys Phe Leu Val Glu Cys Phe Arg Asn Lys Arg Arg Asp
                        325                 330                 335

Gln Gln Gln Lys Pro Leu Tyr His His Phe Thr Thr Ala Ile Asn Thr
                        340                 345                 350

Glu Asn Ile Arg Leu Val Phe Arg Asp Val Lys Asp Thr Ile Leu His
                        355                 360                 365

Asp Asn Leu Lys Gln Leu Met Leu Gln
        370                     375

<210> SEQ ID NO 20
<211> LENGTH: 1603
<212> TYPE: DNA
<213> ORGANISM: Caenorhabditis elegans

<400> SEQUENCE: 20
```

-continued

```
gtacacacac acccgccacc accacatttc caccaacaga gaggcatccc tgtgcgttgt      60
tgtgttgttg ttttttttgtg atgtttataa cttgacgccc tcaatcgtcc caccgaaata    120
caaaaattgc atcgaacttc tatcctcgct ctagcgtgtt cttcttgttc tattcgctgg    180
cttcatctgc ggccttggtg gcaccttttc ggccgccatg gcctgctgtt tatccgaaga    240
ggctcgcgag cagaagcgaa taaatcaaga aattgagaag cagcttcagc gtgacaaaag    300
aaatgctcga cgagaactca aacttctttt attggggact ggagagtccg gcaagtcaac    360
gttcatcaag cagatgcgaa ttatccacgg tcagggatat tcggaagagg acaagcgagc    420
acacattcga cttgtctatc agaacgtgtt tatggccata cagtctatga tacgagcgat    480
ggacacatta gatataaagt ttggtaacga atcagaggag ctgcaggaga aggcggctgt    540
ggtgcgggaa gtggatttcg agtcggtgac gtctttcgag aaccctacg  tgtcgtatat    600 caaagagcta tgggaggatt ctggtattca ggaatgttat gataggaggc gagaatatca    660
gctcaccgat tcagccaaat actatctctc cgatctccga cggctggcgg tgccagacta    720
tctgccaacc gagcaggaca ttctgcgtgt tcgtgtgcca accactggta tcattgaata    780
tccatttgat ttggagcaga tcatctttcg aatggtggac gtcggaggtc agcgatcaga    840
aaggcggaag tggatccact gtttcgaaaa tgtcacctca atcatgttcc tggtggcgct    900
ttccgagtat gatcaggtgt tggtcgagtg tgacaacgag aaccgaatgg aagaatcgaa    960
agctctgttc cgaacgatca tcacgtaccc atggttcacc aactcatcgg tcattctatt   1020
cctgaacaag aaggatctgc tcgaggagaa gattctgtac tcgcatctcg ctgactactt   1080
tcccgaatat gacggacccc cacgcgatcc gatcgccgcc cgcgagttta ttctcaaaat   1140
gtttgtcgac ttgaatccgg acgccgacaa gattatctac tctcatttta cgtgcgcgac   1200
tgatacggaa aacattcggt tcgtgttcgc cgccgtcaaa gacacaattc tacagcataa   1260
tctgaaggag tacaacttgg tgtaagaaga aagtcgcatg tcggattgga tgatgatgat   1320
gatgatccat ctctctctct ctctctctct cactgggtcg agtgagacac caccacctaa   1380
acctaggaaa catttcttg  tactccttct aattttttgtt tttttttttgc aaaaaactttt  1440 ctctctctgt ctgtctctct ctccatctct tccttatttt cttattttct cattttcctc   1500
cctaaaacaa atgctcctcc cgaatattct ttccatataa gcactttttt cttctttttt   1560
tggatgtgct ttctgatata gctaatgcaa aaaaaaaaaa cgg                      1603
```

<210> SEQ ID NO 21
<211> LENGTH: 1603
<212> TYPE: DNA
<213> ORGANISM: Artificial
<220> FEATURE:
<223> OTHER INFORMATION: Mutant egl-30 nucleotide sequence

<400> SEQUENCE: 21

```
gtacacacac acccgccacc accacatttc caccaacaga gaggcatccc tgtgcgttgt      60
tgtgttgttg ttttttttgtg atgtttataa cttgacgccc tcaatcgtcc caccgaaata    120
caaaaattgc atcgaacttc tatcctcgct ctagcgtgtt cttcttgttc tattcgctgg    180
cttcatctgc ggccttggtg gcaccttttc ggccgccatg gcctgctgtt tatccgaaga    240
ggctcgcgag cagaagcgaa taaatcaaga aattgagaag cagcttcagc gtgacaaaag    300
aaatgctcga cgagaactca aacttctttt attggggact ggagagtccg gcaagtcaac    360
gttcatcaag cagatgcgaa ttatccacgg tcagggatat tcggaagagg acaagcgagc    420
acacattcga cttgtctatc agaacgtgtt tatggccata cagtctatga tacgagcgat    480
```

-continued

```
ggacacatta gatataaagt ttggtaacga atcagaggag ctgcaggaga aggcggctgt      540
ggtgcgggaa gtggatttcg agtcggtgac gtctttcgag gaaccctacg tgtcgtatat      600
caaagagcta tgggaggatt ctggtattca ggaatgttat gataggaggc gagaatatca      660
gctcaccgat tcagccaaat actatctctc cgatctccga cggctggcgg tgccagacta      720
tctgccaacc gagcaggaca ttctgcgtgt tcgtgtgcca accactggta tcattgaata      780
tccatttgat ttggagcaga tcatctttcg aatggtggac gtcggaggtc agcgatcaga      840
aaggcggaag tggatccact gtttcgaaaa tgtcacctca atcatgttcc tggtggcgct      900
ttccgagtat gatcaggtgt tggtcgagtg tgacaacgag aaccgaatag aagaatcgaa      960
agctctgttc cgaacgatca tcacgtaccc atggttcacc aactcatcgg tcattctatt     1020
cctgaacaag aaggatctgc tcgaggagaa gattctgtac tcgcatctcg ctgactactt     1080
tcccgaatat gacggacccc cacgcgatcc gatcgccgcc cgcgagttta ttctcaaaat     1140
gtttgtcgac ttgaatccgg acgccgacaa gattatctac tctcatttta cgtgcgcgac     1200
tgatacggaa acattcggt tcgtgttcgc cgccgtcaaa gacacaattc tacagcataa     1260
tctgaaggag tacaacttgg tgtaagaaga aagtcgcatg tcggattgga tgatgatgat     1320
gatgatccat ctctctctct ctctctctct cactgggtcg agtgagacac caccacctaa     1380
acctaggaaa cattttcttg tactccttct aattttttgtt ttttttttgc aaaaaacttt     1440
ctctctctgt ctgtctctct ctccatctct tccttatttt cttattttct cattttcctc     1500
cctaaaacaa atgctcctcc cgaatattct ttccatataa gcacttttt cttctttttt      1560 tggatgtgct ttctgatata gctaatgcaa aaaaaaaaaa cgg                        1603
```

<210> SEQ ID NO 22
<211> LENGTH: 1422
<212> TYPE: DNA
<213> ORGANISM: Caenorhabditis elegans

<400> SEQUENCE: 22

```
atgatgccac cgttgaccaa gatcgaggtg ctcgcgaagc gagtgatgga aggtgcgcaa       60
ttgaaaacgc ataaatactt ccggatcgcc gtgcctcatg ccatcaccgg tcagcaattg      120
atagctctcg ttcttgagcg aggtgctcct gacgatgagg ctgaagcgag tcatctggca      180
agtttgttac ttcaccacgg ttacatgttt ccagttatcg aacatggcca acctttcaaa      240
gacgatggaa cgttatacag gcttcaaagg ccgtattttt ggccttcaca ggctgaactg      300
gttccggatg ttgaatatgc catttacctc aacaagcgat tgctccgaaa tgagcaaaaa      360
cacgggttag aagaagatga agttgagtca ttcaacagac ttgccgatgt tctcgcacac      420
atgtgggctt tcatcgttca acagtctgag cttcaattga agcagcaaaa agaaaaaaag      480
aaagtggaca aggtagtgtt cgattcagaa gaacgagcgt tttggaagat acgaaaacca      540
agtcgtggtg gaccaaattt cctagaggac ccttatatga aaatagaaaa gaaaatacga      600
cggcagaatg cacaaggtta tagatgtctt atggatcgat tacgatttgc aatcaagaca      660
aagccatggc taaaagcatt aaaagcatcg gatacaatgg tgacgtgggt tgaccaaaga      720
gctgaattcg atccattcct tcaccctcca caaccatcca atccatggat cagtgatgaa      780
gcttcatttt ggaatcagcc tactgacacg tcaagtgccg agatccctac cgagaaacgg      840
gtaaaacgat ggggactttc tgttcaagag cttgtgaaag atcctatagg acggcaagtg      900
ctcgaaacat ttttagaatc cgaattttcg tcggaaaata tacggttctg gatagcgata      960
```

```
caagatttga aatatgcacc gaatgagcag atataccaga aagctgaaag aatacgagaa    1020
gaattttggg ctcaaggagc acctgcacaa gtaaatgtag acaatagaac cctcgatcag    1080
acattggagt gtatttcgaa agcgaaagat gcttcacaaa tgagattcgc attctatcat    1140
tctgaagagc acgtgttcac attgatggca aaggattcat atccacgttt cgtccgatcc    1200
caaatctaca aagcagtatt gacagcagcg caacagcacg gaacaaagcg actcgggtgg    1260
cgcaacttcg tattcaacat gggtacaact aaaaaaccag caacgagtaa accagcaaag    1320
ccgcaagatt ccatcgggac tggtcaagtt ctcccaaaac agctatcgtc gactcgctg     1380 ccagttcgac aggctcatgg ggtcaaaccg gatcccgaat ga                       1422
```

<210> SEQ ID NO 23
<211> LENGTH: 1422
<212> TYPE: DNA
<213> ORGANISM: Artificial
<220> FEATURE:
<223> OTHER INFORMATION: Mutant eat-16 nucleotide sequence

<400> SEQUENCE: 23

```
atgatgccac cgttgaccaa gatcgaggtg ctcgcgaagc gagtgatgga aggtgcgcaa      60
ttgaaaacgc ataaatactt ccggatcgcc gtgcctcatg ccatcaccgg tcagcaattg     120
atagctctcg ttcttgagcg aggtgctcct gacgatgagg ctgaagcgag tcatctggca     180
agtttgttac ttcaccacgg ttacatgttt ccagttatcg aacatggcca accttttcaaa    240 gacgatggaa cgttatacag gcttcaaagg ccgtattttt ggccttcaca ggctgaactg     300
gttccggatg ttgaatatgc catttacctc aacaagcgat tgctccgaaa tgagcaaaaa     360
cacgggttag aagaagatga agttgagtca ttcaacagac ttgccgatgt tctcgcacac     420
atgtgggctt tcatcgttca acagtctgag cttcaattga agcagcaaaa aaaaaaaaag     480
aaagtggaca aggtagtgtt cgattcagaa gaacgagcgt tttggaagat acgaaaacca     540
agtcgtggtg gaccaaattt cctagaggac ccttatatga aaatagaaaa gaaaatacga     600
cggcagaatg cacaaggtta tagatgtctt atggatcgat tacgatttgc aatcaagaca     660
aagccatggc taaaagcatt aaaagcatcg gataacaatgg tgacgtgggt tgaccaaaga    720
gctgaattcg atccattcct tcaccctcca caaccatcca atccatggat cagtgatgaa     780
gcttcatttt ggaatcagcc tactgacacg tcaagtgccg agatccctac cgagaaacgg     840
gtaaaacgat ggggactttc tgttcaagag cttgtgaaag atcctatagg acggcaagtg     900
ctcgaaacat ttttagaatc cgaattttcg tcggaaaata tacggttctg gatagcgata     960
caagatttga aatatgcacc gaatgagcag atataccaga aagctgaaag aatacgagaa    1020
gaattttggg ctcaaggagc acctgcacaa gtaaatgtag acaatagaac cctcgatcag    1080
acattggagt gtatttcgaa agcgaaagat gcttcacaaa tgagattcgc attctatcat    1140
tctgaagagc acgtgttcac attgatggca aaggattcat atccacgttt cgtccgatcc    1200
caaatctaca aagcagtatt gacagcagcg caacagcacg gaacaaagcg actcgggtgg    1260
cgcaacttcg tattcaacat gggtacaact aaaaaaccag caacgagtaa accagcaaag    1320
ccgcaagatt ccatcgggac tggtcaagtt ctcccaaaac agctatcgtc gactcgctg     1380 ccagttcgac aggctcatgg ggtcaaaccg gatcccgaat ga                       1422
```

<210> SEQ ID NO 24
<211> LENGTH: 13
<212> TYPE: PRT
<213> ORGANISM: Caenorhabditis elegans

```
<400> SEQUENCE: 24

Thr Glu Lys Arg Val Lys Arg Trp Gly Leu Ser Val Gln
1               5                   10

<210> SEQ ID NO 25
<211> LENGTH: 13
<212> TYPE: PRT
<213> ORGANISM: Homo sapiens

<400> SEQUENCE: 25

Ser Gln Gln Arg Val Lys Arg Trp Gly Arg Gly Met Asp
1               5                   10

<210> SEQ ID NO 26
<211> LENGTH: 211
<212> TYPE: PRT
<213> ORGANISM: Homo sapiens

<400> SEQUENCE: 26

Met Gln Ser Ala Met Phe Leu Ala Val Gln His Asp Cys Arg Pro Met
1               5                   10                  15

Asp Lys Ser Ala Gly Ser Gly His Lys Ser Glu Glu Lys Arg Glu Lys
            20                  25                  30

Met Lys Arg Thr Leu Leu Lys Asp Trp Lys Thr Arg Leu Ser Tyr Phe
        35                  40                  45

Leu Gln Asn Ser Ser Thr Pro Gly Lys Pro Lys Thr Gly Lys Lys Ser
    50                  55                  60

Lys Gln Gln Ala Phe Ile Lys Pro Ser Pro Glu Glu Ala Gln Leu Trp
65                  70                  75                  80

Ser Glu Ala Phe Asp Glu Leu Leu Ala Ser Lys Tyr Gly Leu Ala Ala
                85                  90                  95

Phe Arg Ala Phe Leu Lys Ser Glu Phe Cys Glu Glu Asn Ile Glu Phe
            100                 105                 110

Trp Leu Ala Cys Glu Asp Phe Lys Lys Thr Lys Ser Pro Gln Lys Leu
        115                 120                 125

Ser Ser Lys Ala Arg Lys Ile Tyr Thr Asp Phe Ile Glu Lys Glu Ala
    130                 135                 140

Pro Lys Glu Ile Asn Ile Asp Phe Gln Thr Lys Thr Leu Ile Ala Gln
145                 150                 155                 160

Asn Ile Gln Glu Ala Thr Ser Gly Cys Phe Thr Thr Ala Gln Lys Arg
                165                 170                 175

Val Tyr Ser Leu Met Glu Asn Asn Ser Tyr Pro Arg Phe Leu Glu Ser
            180                 185                 190

Glu Phe Tyr Gln Asp Leu Cys Lys Lys Pro Gln Ile Thr Thr Glu Pro
        195                 200                 205

His Ala Thr
    210

<210> SEQ ID NO 27
<211> LENGTH: 132
<212> TYPE: PRT
<213> ORGANISM: Homo sapiens

<400> SEQUENCE: 27

Met Gly Arg Pro Glu Arg Lys Ser Pro Gln Ser Leu Gly Trp Ala Arg
1               5                   10                  15

Trp Arg Leu Leu Phe Thr Ala Leu Ser Ser Leu Tyr Ser Cys Ile Pro
```

-continued

```
                 20                  25                  30
Thr Leu His Ser Leu Arg Gly Pro Asp Pro Ser Ser Phe Arg Gly Glu
        35                  40                  45

His Val Val Gly Phe Leu Ser Arg Leu Ser Leu Glu Ile Ile Leu Leu
    50                  55                  60

Ser Ser Leu Pro Arg Cys Leu Glu Thr Val Thr Pro Ser Gly Lys Phe
65                  70                  75                  80

Lys Arg His Glu Trp Thr Glu Ser Thr Ser Ser Ile Cys Ile Thr Ser
                85                  90                  95

Leu Ala Pro Pro Ile Val Thr Ala Thr Thr Ser Pro Pro Pro Pro Val
            100                 105                 110

Ile Pro His Val Ser Val Ala Thr Arg Val Ser Leu Pro Ala Pro Gly
        115                 120                 125

Thr Ala Phe Thr
        130
```